US009884860B2

(12) United States Patent
Bialy et al.

(10) Patent No.: US 9,884,860 B2
(45) Date of Patent: Feb. 6, 2018

(54) FUSED PYRROLEDICARBOXAMIDES AND THEIR USE AS PHARMACEUTICALS

(71) Applicant: SANOFI, Paris (FR)

(72) Inventors: Laurent Bialy, Frankfurt am Main (DE); Katrin Lorenz, Frankfurt am Main (DE); Klaus Wirth, Frankfurt am Main (DE); Klaus Steinmeyer, Frankfurt am Main (DE); Gerhard Hessler, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 15/041,541

(22) Filed: Feb. 11, 2016

(65) Prior Publication Data

US 2016/0159793 A1 Jun. 9, 2016

Related U.S. Application Data

(62) Division of application No. 14/375,273, filed as application No. PCT/EP2013/051996 on Feb. 1, 2013, now Pat. No. 9,284,333.

(30) Foreign Application Priority Data

Feb. 3, 2012 (EP) ..................................... 12305129

(51) Int. Cl.
*A61K 31/5383* (2006.01)
*C07D 471/04* (2006.01)
*C07D 498/04* (2006.01)
*C07D 513/04* (2006.01)

(52) U.S. Cl.
CPC ......... *C07D 471/04* (2013.01); *C07D 498/04* (2013.01); *C07D 513/04* (2013.01)

(58) Field of Classification Search
CPC ................................................ A61K 31/5383
See application file for complete search history.

(56) References Cited

U.S. PATENT DOCUMENTS

| | | | |
|---|---|---|---|
| 2004/0209886 A1 | 10/2004 | Salvati | |
| 2006/0183665 A1 | 8/2006 | Ellinghaus | |
| 2010/0197668 A1 | 8/2010 | Baudoin | |

FOREIGN PATENT DOCUMENTS

| | | |
|---|---|---|
| EP | 0447704 A1 | 9/1991 |
| GB | 2111056 B2 | 6/1983 |
| WO | 2006136304 A1 | 12/2006 |
| WO | 2006136305 A1 | 12/2006 |
| WO | 2007124849 A1 | 11/2007 |
| WO | 2008053319 A1 | 5/2008 |

OTHER PUBLICATIONS

Schmidt "Inhibition of cardiac two-pore-domain K+ (K2P) channels—an emerging antiarrhythmic concept" European Journal of Pharmacology 2014, 738, 250-255.*
Ravens, U., & Odening, K.E., Atrial fibrillation: Therapeutic potential of atrial K+ channel blockers, Pharmacology & Therapeutics (2016), Online "http://dx.doi.org/10.1016/j.pharmthera.2016.10.003".*
Rymer "Stroke service: How can we improve and measure outcomes? Consensus summary from a global stroke forum" Acta Neurol Scand 2014: 130: 73-80.*
Achuthan "A systematic review of the pharmacological approaches against snoring: can we count on the chickens that have hatched?" Sleep Breath (2015) 19:1035-1042.*
Evans "Postmortem review and genetic analysis in sudden infant death syndrome: an 11-year review" Human Pathology (2013) 44, 1730-1736.*
Babu "Emerging therapeutic strategies in COPD" Drug Discovery Today vol. 20, No. 3 Mar. 2015 371.*
Church, Andrew J. and Giovannoni, Gavin "Poststreptococcal movement disorders" in Neuroimmunology in Clinical Practice Eds. Bernadette Kalman and Thomas H. Brannagan III Blackwell: 2008 Chapter 21, 240-250.*
Fodstad et. al. "Intractable singultus: a diagnostic and therapeutic challenge" British Journal of Neurosurgery 1993, 7, 255-262.*
Kalviainen, R. "Clinical picture of EPM1-Unverricht-Lundborg disease" Epilepsia, 49(4):549-556, 2008.*
Adam, Octavian R. "Symptomatic Treatment of Huntington Disease" Neurotherapeutics: The Journal of the American Society for Experimental NeuroTherapeutics Apr. 2008, vol. 5, 181-197.*
Boyce Alimentary Tract: Clinical Review "Sialorrhea A Review of a Vexing, Often Unrecognized Sign of Oropharyngeal and Esophageal Disease" J Clin Gastroenterol vol. 39, No. 2, Feb. 2005 pp. 89-97.*
Julien, J.-P. "Transgenic mouse models of amyotrophic lateral sclerosis" Biochimica et Biophysica Acta 1762 (2006) 1013-1024.*

(Continued)

*Primary Examiner* — David K O'Dell
(74) *Attorney, Agent, or Firm* — McDonnell Boehnen Hulbert & Berghoff LLP

(57) ABSTRACT

The present invention relates in fused pyrroledicarboxamides of the formula (I), in which R1 to R9, X, m and n are as defined in claims. The compounds of the formula (I) are inhibitors of the acid-sensitive potassium channel TASK-1 and suitable for the treatment of TASK-1 channel-mediated diseases such as arrhythmias, in particular atrial arrhythmias like atrial fibrillation or atrial flutter, and respiratory disorders, in particular sleep-related respiratory disorders like sleep apnea, for example.

15 Claims, No Drawings

(56) References Cited

OTHER PUBLICATIONS

Mullard "Pharma pumps up anti-tau Alzheimer pipeline despite first Phase III failure" Nature Reviews Drug Discovery vol. 15 Sep. 2016, 591-592.*

Mancuso "Current and emerging treatment options in the management of Friedreich ataxia" Neuropsychiatric Disease and Treatment 2010:6 491-499.*

Georg Pilz, "Modern multiple sclerosis treatment—what is approved, what is on the horizon" Drug Discovery Today Dec. 2008, vol. 13, Nos. 23/24 1013-1025).*

Cowie "Sleep apnea: State of the art" Trends in Cardiovascular Medicine 2017, 27, 280-289.*

Mason "Drug therapy for obstructive sleep apnoea in adults (Review)" Cochrane Database of Systematic Reviews 2013, Issue 5. Art. No. CD003002.* de Godoy "Treatment of upper air way resistance syndrome in adults: Where do we stand?" Sleep Science 2015, 8, 42-48.*

Ingbir "The Incidence, Pathophysiology, Treatment and Prognosis of Cheyne-Stokes Breathing Disorder in Patients with Congestive Heart Failure" Herz 2002, 27, 107-112.*

Lazarenko, Roman M., et al. "Motoneuronal TASK Channels Contribute to Immobilizing Effects of Inhalational General Anesthetics" J. Neurosci., 30(22), 7691-7704 (Jun. 2, 2010).

Aller M.I. et al., "Modifying the Subunit Composition of TASK Channels Alters the Modulation of a Leak Conductance in Cerebellar Granule Neurons" J. Neuroscience (2005), vol. 25, p. 11455-11467 (Dec. 7, 2005).

Barth A.S. et al., "Functional profiling of human atrial and ventricular gene expression" Pflugers—Arch. Eur. J. Physiol. (2005), vol. 450, p. 201-208 (May 5, 2005).

Bayliss D.A. et al., "TASK-1 is a highly modulated pH-sensitive 'leak K+ channel expressed in brainstem respiratory neurons" Respiration Physiology (2001), vol. 129, p. 159-174 (Dec. 2001).

Bayliss D.A. et al., "Emerging roles for two-pore-domain potassium channels and their potential therapeutic impact" Trends Pharmacological Sciences (2008), vol. 29, p. 566-575 (Sep. 25, 2006).

Chemical Abstract 2009:440975 for El-Moghazy Aly "Synthesis and antitumor activity of some 5H-pyrrolizine, pyrimido [5,4-a]pyrrolizine pyrimido[4,5-b]pyrrolizine derivatives." Saudi Pharmaceutical Journal, 2009, vol. 17(1), pp. 3-18.

Berg A.P. et al., "Motoneurons Express Heteromeric TWIK-Related Acid-Sensitive K (TASK) Channels Containing TASK-1 (KCNK3) and TASK-3 (KCNK9) Subunits" J. Neuroscience (2004), vol. 24, p. 6693-6702 (Jul. 28, 2004).

Bittner S. et al., "TASK1 modulates inflammation and neurodegeneration in autoimmune inflammation of the central nervous system" Brain (2009), vol. 132, p. 2501-2516 (Jul. 1, 2009).

Brundel B.J.J.M. et al., "Alterations in Potassium Channel Gene Expression in Atria of Patients With Persistent and Paroxysmal Atrial Fibrillation: Differential Regulation of Protein and mRNA Levels for K1 Channels" J. Am. Coll. Cardiol. (2001), vol. 37, p. 926-932 (Mar. 1, 2001).

Buckler K.J. et al., "An oxygen, acid and anaesthetic-sensitive TASK-like background potassium channel in rat arterial chemoreceptor cells" J. Physiol. (2000), vol. 525.1, p. 135-142 (Jun. 15, 2000).

Coetzee W.J. et al., "Molecular Diversity of K+ Channels" Ann. New York Acad. Sci. (1999), vol. 868, p. 233-285 (Apr. 1999).

Colatsky T.J. et al., "Potassium Channels as Targets for Antiarrhythmic Drug Action" Drug Dev. Res. (1990), vol. 19, p. 129-149 (1990).

Cotten J.F. et al., "The Ventilatory Stimulant Doxapram Inhibits TASK Tandem Pore (K2p) Potassium Channel Function but Does Not Affect Minimum Alveolar Anesthetic Concentration" Anesth. Analg. (2006), vol. 102, p. 779-785 (Mar. 2006).

Dalisay D.S. et al., "Amplification of the Cotton Effect of a Single Chromophore through Liposomal Ordering—Stereochemical Assignment of Plakinic Acids I and J" Angew. Chem. Int. Ed. (2009), vol. 48, p. 4367-4371 (May 13, 2009).

Dobrev D. et al., "Remodeling of cardiomyocyte ion channels in human atrial fibrillation" Bas. Res. Cardiol. (2003), vol. 98, p. 137-148 (Apr. 16, 2003).

Donner B.C. et al., "Functional role of TASK-1 in the heart: studies in TASK-1-deficient mice show prolonged cardiac repolarization and reduced heart rate variability" Bas. Res. Cardiol. (2011), vol. 106, p. 75-87 (Oct. 27, 2010).

Duprat F. et al., "TASK, a human background KF channel to sense external pH variations near physiological pH" EMBO J. (1997), vol. 16, p. 5464-5471 (Jan. 9, 1997).

Ellinghaus P. et al., "Comparing the global mRNA expression profile of human atrial and ventricular myocardium with high-density oligonucleotide arrays" J. Tliorac. Cardiovasc. Surg. (2005), vol. 129, p. 1383-1390 (Jun. 2005).

Ellman J.A. et al., "N-tert-Butanesulfinyl [mines: Versatile Intermediates for the Asymmetric Synthesis of Amines" Acc. Chem. Res. (2002), vol. 35, p. 984-995 (Aug. 13, 2002).

Flanagan M.E. et al., "Discovery of CP-690,550: A Potent and Selective Janus Kinase (JAK) Inhibitor for the Treatment of Autoimmune Diseases and Organ Transplant Rejection" J. Med. Chem. (2010), vol. 53, p. 8468-8484 (Nov. 24, 2010).

Hewlett N.M. et al., "Total Synthesis of the Natural Product (+/−)-Dibromophakellin and Analogues" Organic Letters (2011), vol. 13, p. 4550-4553 (Jul. 28, 2011).

Kääb S. et al., "Global gene expression in human myocardium-oligonucleotide microarray analysis of regional diversity and transcriptional regulation in heart failure" J. Mol. Med. (2004), vol. 82, p. 308-316 (Apr. 23, 2004).

Knobloch K. et al., "Electrophysiological and antiarrhythmic effects of the novel IKur channel blockers, S9947 and S20951, on left vs. right pig atrium in vivo in comparison with the IKr blockers dofetilide, azimilide, d,l-sotalol and butilide" Naunyn Schmiedeberg's Arch. Pharmacol. (2002), vol. 366, p. 482-487 (Sep. 5, 2002).

Larrow J.F. et al., "(1S,2R)-1-Aminoindan-2-0L" Organic Syntheses (1999), vol. 76, p. 46 (1999).

Lauritzen I. et al., "K+-dependent Cerebellar Granule Neuron Apoptosis" J. Biol. Chem. (2003), vol. 278, p. 32068-32076 (Jun. 3, 2003).

Macdonald S.J.F. et al., "Synthesis of the Aglycones of the Ravidomycin Family of Antibiotics" J. Chem. Soc. Chem., Comm. (1987), p. 1528-1530 (Jan. 1, 1987).

Mahapatra T. et al., "Chemoenzymatic synthesis and resolution of compounds containing a quaternary stereocenters adjacent to a carbonyl group" Tetrahedron Asymmetry (2008), vol. 19, p. 1224-1232 (Dec. 12, 2008).

Maingret F. et al., "The endocannabinoid anandamide is a direct and selective blocker of the background K+ channel TASK-1" EMBO J. 2001, vol. 20, p. 47-54 (Jan. 15, 2001).

Maison W. et al., "Synthesis of novel pipecolic acid derivatives: a multicomponent approach from 3,4,5,6-tetrahydropyridines" J. Chem. Soc., Perkin Trans 1(1999), p. 3515-3525 (Jan. 1, 1999).

Medhurst A.D. et al., "Distribution analysis of human two pore domain potassium channels in tissues of the central nervous system and periphery" Mol. Brain Res. (2001), vol. 86, p. 101-114 (Jan. 31, 2001).

Meinzer A. et al., "Properties and Reactions of Substituted 1,2-Thiazetidine 1,1-Dioxides: Chiral Mono- and Bicyclic 1,2-Thiazetidine 1,1-Dioxides from alpha-Amino Acids" Hely. Chim. Acta (2004), vol. 87, p. 90-105 (Jan. 2004).

Meuth S.G. et al., "TWIK-related Acid-sensitive K+ Channel 1 (TASK1) and TASK3 Critically Influence T Lymphocyte Effector Functions" J. Biol. Chem. (2008), vol. 283, p. 14559-14570 (Mar. 28, 2008).

Mitsunobu 0. et al., "Preparation of Esters of Carboxylic and Phosphoric Acid via Quaternary Phosphonium Salts" Bull. Chem. Soc. Japan (1967), vol. 40, p. 2380-2382 (1967).

Miyaura N. et al., Stereoselective Synthesis of Arylated (E)-Alkenes by the Reaction of Alk-1-enylboranes with ArylHalides in the Presence of Palladium Catalyst J. Chem.Soc., Chem. Comm. (1979), p. 866-867 (Jan. 1, 1979).

(56) References Cited

OTHER PUBLICATIONS

Morton D et al, "Chiral non-racemic sulfinimines: versatile reagents for asymmetric synthesis" Tetrahedron (2006), vol. 62, p. 8869-8905 (Jul. 28, 2006).

Patel A.J. et al., "Inhalational anesthetics activate two-pore-domain background K+ channels" Nature Neurosci. (1999) vol. 2, p. 422-426 (May 1999).

Patel A.J. et al., "The 2P-domain K+ channels: role in apoptosis and tumorigenesis" Pflugers Arch.—Eur. J. Physiol. (2004), vol. 448, p. 261-273 (May 5, 2004).

Patel A.J. et al., "Properties and modulation of mammalian 2P domain K+ channels" Trends Neurosci. (2001), vol. 24, p. 339-346 (Jun. 2001).

Peukert S. et al., "Identification, Synthesis, and Activity of Novel Blockers of the Voltage-Gated Potassium Channel Kv1.5" J. Med. Chem. (2003), vol. 46, p. 486-498 (Jan. 21, 2003).

Pizzomo M.T. et al., "Novel Synthesis of 5,6,7,8-Tetrahydroindolizine" J. Org. Chem. (1977), vol. 42, p. 909-910 (Mar. 1977).

Putzke C. et al., "The acid-sensitive potassium channel TASK-1 in rat cardiac muscle" Cardiovasc. Res. (2007), vol. 75, p. 59-68 (Feb. 28, 2007).

Roden D.M., "Current Status of Class III Antiarrhythmic Drug Therapy" Am. J. Cardiol. (1993), vol. 72, p. 44B-49B (Aug. 26, 1993).

Shuman R.T. et al., "Shuman R.T. et al., J. Org. Chem. (1990), vol. 55, p. 738-741" J. Org. Chem. (1990), vol. 55, p. 738-741 (Jan. 1, 1990).

Staudacher K. et al., "Carvedilol targets human K2P3.1 (TASK1) K+ leak channels" Brit. J. Pharmacol (2011), vol. 165, p. 1099-1110 (Feb. 10, 2012).

Streit A.K et al., "A Specific Two-pore Domain Potassium Channel Blocker Defines the Structure of the TASK-1 Open Pore" J. Biol. Chem. (2011), vol. 286, p. 13977-13984 (Mar. 1, 2011).

Takahata H. et al., "Asymmetric synthesis of all stereoisomers of 6-methylpipecolic acids" Amino Acids (2003), vol. 24, p. 267-272 (Jan. 30, 2003).

Wakili R. et al., "Recent advances in the molecular pathophysiology of atrial fibrillation" J. Clin. Invest. (2011), vol. 121, p. 2955-2968 (Aug. 1, 2011).

Wannberg J. et al., Increasing Rates and Scope of Reactions: Sluggish Amines in Microwave-Heated Aminocarbonylation Reactions under Air I Org. Chem. (2003), vol. 68, p. 5750-5753 (Jun. 6, 2003).

Wood K et al., "Ring closing metathesis strategies towards functionalised 1,7-annulated 4,6-dimethoxyindoles" Tetrahedron (2011), vol. 67, p. 4093-4102 (Apr. 13, 2011).

European Search Report for European Patent Application No. EP 12 30 5129 dated May 10, 2012, dated May 25, 2012.

\* cited by examiner

FUSED PYRROLEDICARBOXAMIDES AND THEIR USE AS PHARMACEUTICALS

This application is divisional application of U.S. application Ser. No. 14/375,273, filed Jul. 29, 2014, which is a national stage application under 35 U.S.C. § 371 of International Application No. PCT/EP2013/051996, filed Feb. 1, 2013, which claims the priority of European Application No. 12305129.4 filed on Feb. 3, 2012.

The present invention relates to fused pyrroledicarboxamides of the formula I,

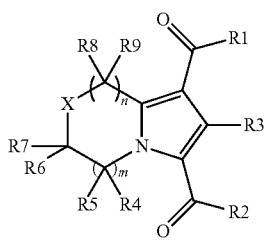

in which R1 to R9, X, m and n are as defined below. The compounds of the formula I are inhibitors of the acid-sensitive potassium channel TASK-1 and suitable for the treatment of TASK-1 channel-mediated diseases such as arrhythmias, in particular atrial arrhythmias like atrial fibrillation and atrial flutter, and respiratory disorders, in particular sleep-related respiratory disorders like sleep apnea, for example.

Potassium channels are widespread membrane proteins which, owing to their influences on cell membrane potentials, play an important role in many physiological processes. Within the various classes of the potassium channels; a distinction is drawn on the basis of their molecular structure between three large groups which are characterized by the number of transmembrane domains, which is 2, 4 or 6. The group of the potassium channels with four transmembrane segments is delimited from the two others in that their representatives each have two pore domains, which is why these channels are also referred to as $K_{2P}$ channels (Coetzee W. J. et al., Molecular diversity of $K^+$ channels, Ann. New York Acad. Sci. 1999, 868, 233-285). In functional terms, $K_{2P}$ channels are characterized in that the "leak" or "background" currents flow through them, which play an important role for the resting membrane potential and hence the excitability of nerve or muscle cells.

A family which is of particular interest among the $K_{2P}$ channels is that of the TASK channels (tandem of P domains in a weak inwardly rectifying $K^+$ channel-(TWIK-)-related acid-sensitive $K^+$ channels), which include the TASK-1, TASK-3, and TASK-5 subtype (Bayliss D. A. et al., Emerging roles for two-pore-domain potassium channels and their potential therapeutic impact, Trends in Pharmacological Sciences 2008, 29, 586-575), Other terms used in the literature for the underlying genes are KCNK3 or K2P3.1 (TASK-1), KCNK9 or K2P9.1 (TASK-3) and KCNK15 or K2P15.1 (TASK-5). The greatest homology within this family is possessed by the TASK-1 and TASK-3 channels with an amino acid identity of more than 50%. Dimerization of $K_{2P}$ channels forms functional potassium channels with a total of four pore units. The currents which flow through these channels are referred to in the literature as IKso current. In addition to a homodimerization of, for example, two TASK-1 or two TASK-3 proteins, heterodimerization of TASK-1 and TASK-3 is also possible in this context (Berg A. P. et al., Motoneurons express Heteromeric TWIK-related acid-sensitive $K^+$ (TASK) Channels containing TASK-1 (KCNK3) and TASK-3 (KCNK9) subunits, J. Neuroscience 2004, 24, 6693-6702).

The TASK channels are notable in particular for their very strong dependence upon the extracellular pH in the physiological range (ca. 6.5-7.5). The channels are inhibited at acidic pH and activated at alkaline pH. Owing to this pH dependence, the physiological function of a sensor which translates small changes in the extracellular pH to corresponding cellular signals is ascribed to the TASK channels (Duprat F. et al., TASK, a human background $K^+$ channel to sense external pH variations near physiological pH, EMBO J. 1997, 16, 5464-5471; Patel A. J. et al., Properties and modulation of mammalian 2P domain $K^+$ channels, Trends Neurosciences 2001, 24, 339-346).

TASK-1 knock-out mice show a mild phenotype and appear generally in good health and show normal breeding behavior (Aller M. I. et al., Modifying the Subunit Composition of TASK Channels Alters the Modulation of a Leak Conductance in Cerebellar Granule Neurons, J. Neuroscience 2005, 25, 11455-11467).

TASK-1 is expressed in the brain and also in spinal ganglia and some peripheral tissues, for example pancreas, placenta, uterus, lung, heart, kidney, small intestine and stomach. In addition, TASK-1 has been detected in the chemosensitive cells of the brainstem and of the carotid bodies, and also the motor neurons of the hypoglossal nerve (Medhurst A. D. et al., Distribution analysis of human two pore domain potassium channels in tissues of the central nervous system and periphery, Mol. Brain Res. 2001, 86, 101-114).

Electrical currents which are caused by TASK-1 potassium channel have been detected in motor neurons of the hypoglossal nerve, a motor cranial nerve which possesses the most important function for the maintenance and patency of the upper respiratory pathways, mastication, swallowing, phonation and speech, and locus coeruleus. Moreover, TASK-1 potassium channels have been found in other cranial and spinal motoneurons (Lazarenko R. M. et al., Motoneuronal TASK Channels Contribute to Immobilizing Effects of Inhalational General Anesthetics, J. Neuroscience 2010, 30, 7691-7704). It has been found that TASK-1 channels are involved in respiratory regulation in respiratory neurons of the brainstem, in carotid bodies and in motor neurons of the hypoglossal nerve, and also in neuroepithelial cells of the lung. In the event of inadequate respiration (hypoxia, hindered breathing) and in the event of physical stress, either via a rise in the carbon dioxide concentration and the resulting acidosis or via acidic metabolites, there is a lowering of the pH and hence a blockage of the pH-dependent TASK-1 channels. This depolarizes the cells, which leads to the activation of the neurons involved in the respiratory regulation (Buckler K. J. et al., An oxygen-, acid- and anesthetic-sensitive TASK-like background potassium channel in rat arterial chemoreceptor cells, J. Physiol. 2000, 525.1, 135-142; Bayliss D. A. et al., TASK-1 is a highly modulated pH-sensitive 'leak' $K^+$ channel expressed in brainstem respiratory neurons, Respiration Physiology 2001, 129, 159-174).

An increase in the activity of chemosensitive neurons in conjunction with an activation of the motor neurons of the hypoglossal nerve through blockage of the TASK-1 channel can stimulate respiration and simultaneously stabilize the upper airways to protect them from collapse and occlusion. Moreover, snoring can be inhibited by stabilizing the upper airway via an increase in pharyngeal muscle activity. The blockage of the TASK-1 ion channels is therefore useful in the treatment of respiratory disorders, for example of sleep apnea (WO 2007/124849).

Activation of the motor neurons of the hypoglossal nerve and other cranial motoneurons through blockage of the TASK-1 channel can also improve swallowing, and is therefore useful for the treatment of dysphagia and disturbed mastication, speech and facial muscles function in diseases where these functions are impaired, which is the case in many different neurodegenerative, neuromuscular and muscular diseases, dementia and in old age. Equally, in the diseases mentioned, blockage of the TASK-1 channel in spinal motoneurons can improve peripheral motor function of the limbs, for example in the case of paresis, and trunk reducing the degree of the motor disability.

In cultivated granulosa cells of the cerebellum, it has been shown that genetic inactivation of TASK channels brings about a neuroprotective action (Lauritzen I. et al., $K^+$—dependent cerebellar granule neuron apoptosis—Role of Task leak $K^+$ channels, J. Biol. Chem. 2003, 278, 32068-32076). It has also been shown that TASK-1 channels are responsible for programmed cell death (apoptosis) in granulosa cells, and that the cell death can be prevented by blocking the TASK-3. Thus, specific inhibitors of TASK-1 and/or TASK-3 channels are useful for the treatment of neurodegenerative disorders (Patel A. J. et al., The 2P-domain $K^+$ channels: role in apoptosis and tumorigenesis, Pflugers Arch.—Eur. J. Physiol. 2004, 448, 261-273).

TASK-1 has been identified as potassium conductance on T lymphocytes critically influencing T cell effector function, and identified as a possible molecular target for immunomodulation in T cell-mediated autoimmune disorders (Meuth S. G. et al., TWIK-related Acid-sensitive $K^+$ Channel 1 (TASK1) and TASK3 Critically Influence T Lymphocyte Effector Functions, J. Biol. Chem. 2008, 283, 14559-14570). It has been stated that TASK-1 is relevant for setting the resting membrane potential and balancing neuronal excitability that is expressed on T cells and neurons, and is a key modulator of T cell immunity and neurodegeneration in autoimmune central nervous system inflammation. After induction of experimental autoimmune encephalomyelitis, on experimental model mimicking multiple sclerosis, TASK-1(−/−) mice showed a significantly reduced clinical severity and markedly reduced axonal degeneration compared with wild-type controls. T cells from TASK-1(−/−) mice displayed impaired T cell proliferation and cytokine production, while the immune repertoire is otherwise normal. In addition to these effects on systemic T cell responses, TASK-1 exhibits an independent neuroprotective effect which was demonstrated using both a model of acutely prepared brain slices cocultured with activated T cells as well as in vitro cultivation experiments with isolated optic nerves. Preventive blockade of TASK-1 significantly ameliorated experimental autoimmune encephalomyelitis after immunization and significantly reduced disease severity and was capable of lowering progressive loss of brain parenchymal volume as assessed by magnetic resonance imaging. Thus, TASK-1 blockers are useful for the therapy of inflammatory and degenerative central nervous system disorders (Bittner S. et al., TASK1 modulates inflammation and neurodegeneration in autoimmune inflammation of the central nervous system, Brain: a journal of neurology 2009, 132, 2501-2516).

TASK-1, a member of two-pore-domain ($K_{2P}$) potassium channel family, has emerged as a target for the pharmacological treatment, of atrial fibrillation recently. Two-pore-domain ($K_{2P}$) potassium channels mediate background potassium currents, stabilizing resting membrane potential and expediting action potential repolarization. In the heart, TASK-1 channels have been shown to play a role in cardiac repolarization (Donner B. C. et al., Functional role of TASK-1 in the heart: studies in TASK-1-deficient mice show prolonged cardiac repolarization and reduced heart rate variability. Basic Res. Cardiol. 2011, 106, 75-87; Putzke C. et al., The acid-sensitive potassium channel TASK-1 in rat cardiac muscle, Cardiovascular Research 2007, 75, 59-68).

Atrial fibrillation (AF) and atrial flutter are very common cardiac rhythm disorders that cause substantial morbidity and contribute to mortality (Wakili R. et al., Recent advances in the molecular pathophysiology of atrial fibrillation, J. Clin. Invest. 2011: 121, 2955-2968). Presently available therapeutic approaches have major limitations, including limited efficacy and potentially serious side effects sued as malignant ventricular arrhythmia induction or negative inotropic effects. The occurrence of AF increases with age and frequently leads to fatal sequelae such as stroke. The class I and III antiarrhythmics which are in use at present reduce the rate of recurrence of AF but are used to only a limited extent because of their potential proarrhythmic side effects and limited efficacy. The growing incidence of AF emphasizes the importance of identifying appropriate treatments, particularly drugs, that are safe, effective, and associated with improved clinical outcomes.

It has been shown that in atrial fibrillation and atrial flutter re-entrant mechanisms play an important role in the induction and maintenance of the arrhythmia. Such reentries or re-entrant waves occur when the cardiac tissue has a low conduction velocity and, at the same time, short refractory periods, increasing the myocardial refractory period by prolonging the action potential is an acknowledged mechanism for terminating arrhythmias or for preventing them to develop (Colatsky T. J. et al., Potassium channels as targets for antiarrhythmic drug action, Drug Dev. Res. 1990, 19, 129-140). The length of the action potential is essentially determined by the extent of repolarizing $K^+$ currents which flow out of the cells through various $K^+$ channels. TASK-1 constitutes one of those repolarizing potassium currents. Its inhibition prolongs the action potential and thereby refractoriness.

Most of the known class III antiarrhythmics, for example dofetilide, E4031 and d-sotalol, block predominantly or exclusively the rapidly activating $I_{Kr}$ potassium channel which can be detected both in cells of the human ventricle and in the atrium. It has emerged that these compounds have an increased proarrhythmic risk at heart rates which are low or normal, and arrhythmias referred to as torsades de pointes have been observed in particular (Roden D. M., Current status of class III antiarrhythmic drug therapy. Am. J. Cardiol, 1993, 72, 44B-49B). Apart from this proarrhythmic risk, the therapeutic efficacy of the $I_{Kr}$ blockers has been found to decline under the conditions of tachycardia (electrical tachycardic atrial remodelling).

TASK-1 expression in the human heart has been shown to be restricted to the atria with no or very little expression in the ventricles. A further advantage is that TASK-1 expression is not decreased but even slightly Increased in atrial fibrillation patients compared with sinus rhythm parents. By contrast, a decreased expression of other atrial $K^+$ channels has been reported in atrial fibrillation patients compared with sinus rhythrn patients (Dobrev D. et al., Remodeling of cardiomyocyte ion channels in human atrial fibrillation, Basic Res. Cardiol. 2003, 98, 137-148; Brundel B. J. J. M. et al., Alterations in Potassium Channel Gene Expression in Atria of Patients With Persistent and Paroxysmal Atrial Fibrillation: Differential Regulation of Protein and mRNA Levels for K⁺ Channels, J. American College of Cardiology 2001, 37, 926-932). Thus, TASK-1 is still expressed in the larger patient population (Kääb S. et all, Global gene expression in human myocardium-oligonucleotide microarray analysis of regional diversity and transcriptional regulation in heart failure, J. Molecular Medicine 2004, 82, 308-316; Barth A. S. et al., Functional profiling of human atrial and ventricular gene expression, European J. Physiol. 2005, 450, 201-208; WO 2005/016965; Ellinghaus P. et al., Comparing the global mRNA expression profile of human atrial and ventricular myocardium with high-density oligonucleotide array, J. Thoracic Cardiovascular Surgery 2005, 129, 1383-1390).

In spite of the great physiological significance of the TASK channels, only very few pharmacological modulators of these channels are known to date in the literature. It has been stated that an activation of the TASK-1 channel can be achieved by therapeutic concentrations of the inhalative anesthetics halothane and isoflurane (Patel A. J. et al., Inhalational anesthetics activate two-pore-domain background K⁺ channels, Nature Neuroscience 1999, 2, 422-426). Furthermore, some Kv1.5 blockers which also inhibit the TASK-1 channel, are described in the state of the art (WO 2007/124849; WO 2006/136304). The compound A1899, a previously described Kv1.5 blocker (Peukert S. et al., Identification, Synthesis, and Activity of Novel Blockers of the Voltage-Gated Potassium Channel Kv1.5., J. Med. Chem. 2003, 46, 486-498) has been stated to be a TASK-1 blocker (Streit A. K. et al., A Specific Two-pore Domain Potassium Channel Blocker Defines the Structure of the TASK-1 Open Pore, J. Biol. Chem. 2011, 286, 13977-13984). Also the arachidonic acid amide anandamide, an endogenous ligand of the cannabinoid receptor, and its methanandamide homolog have been described as TASK-1 blockers (Maingret F. et al., The endocannabinoid anandamide is a direct and selective blocker of the background K⁺ channel TASK-1, EMBO J. 2001, 20, 47-54). Doxapram, which is used for the treatment of respiratory disorders, has been stated to be a TASK-1 blocker (Cotten J. F. et al.; The Ventilatory Stimulant Doxapram Inhibits TASK Tandem Pore ($K_{2P}$) Potassium Channel Function but Does Not Affect Minimum Alveolar Anesthetic Concentration, Anesth. Analg. 2006, 102, 779-785). Carvedilol has been found to be an unselective TASK-1 blocker at micromolar concentrations (Standaucher K. et al., Carvedilol targets human $K2P_{3.1}$ (TASK1) K⁺ leak channels, Brit. J. Pharmacol. 2011, 163, 1099-1110). There is a need for further compounds which are suitable for the treatment of TASK-1 related conditions, which are efficient TASK-1 inhibitors and preferably have further favorable properties, for example exhibit a favorable pharmacokinetic profile, are selective for TASK-1, or are devoid of proarrhythmic properties, in particular do not substantially inhibit the hERG channel. The present invention satisfies this need by providing the compounds of the formula I.

A subject of the present invention are the compounds of the formula I, in any of their stereoisomeric forms and mixtures of stereoisomers forms in any ratio, and the pharmaceutically acceptable salts thereof,

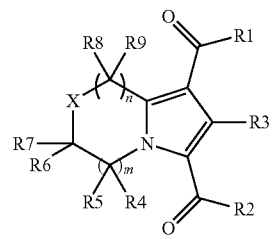

wherein
n is selected from the series consisting of 0 and 1;
m is selected from the series consisting of 0, 1 and 2, with the proviso that m and n cannot simultaneously be 0;
X is selected from the series consisting of oxygen, sulfur and (R10)(R11)C;
one of the groups R1 and R2 is the group R20—NH— and the other of the groups R1 and R2 is the group (R30)(R31)N—;
R3 is selected from the series consisting of hydrogen, halogen and ($C_1$-$C_4$)-alkyl;
R4, R5, R6, R7, R8, R9, R10 and R11 are independently of one another selected from the series consisting of hydrogen, fluorine and ($C_1$-$C_4$)-alkyl;
R20 is selected from the series consisting of ($C_5$-$C_7$)-cycloalkyl to which a benzene ring or a Het1 ring is fused, and (R21)(R22)(R23)C—, wherein the ($C_5$-$C_7$)-cycloalkyl is unsubstituted or substituted by one or more identical or different substituents selected from the series consisting of fluorine, ($C_1$-$C_4$)-alkyl and ($C_1$-$C_4$)-alkyl-O—, and the fused benzene ring and Het1 ring is unsubstituted or substituted by one or more identical or different substituents R24;
R21 is selected from the series consisting of phenyl and Het1, which are all unsubstituted or substituted by one or more identical or different substituents R24;
R22 is selected from the series consisting of hydrogen, ($C_1$-$C_4$)-alkyl, ($C_3$-$C_7$)-cycloalkyl, R25-($C_1$-$C_4$)-alkyl- and phenyl;
R23 is selected from the series consisting of hydrogen and ($C_1$-$C_4$)-alkyl;
R24 is selected from the series consisting of halogen, ($C_1$-$C_4$)-alkyl, ($C_3$-$C_7$)-cycloalkyl, HO—, ($C_1$-$C_4$)-alkyl-O—, ($C_1$-$C_4$)-alkyl-S(O)$_p$—, $F_5S$—, NC—, ($C_1$-$C_4$)-alkyl-O—C(O)—, —($C_3$-$C_5$)-alkanediyl-, —O—($C_1$-$C_4$)-alkanediyl-O— and —($C_1$-$C_4$)-alkanediyl-O—C(O)—;
R25 is selected from the series consisting of ($C_3$-$C_7$)-cycloalkyl, ($C_1$-$C_4$)-alkyl-O— and ($C_1$-$C_4$)-alkyl-S—;
R30 is selected from the series consisting of hydrogen, ($C_1$-$C_4$)-alkyl, ($C_3$-$C_7$)-cycloalkyl-($C_1$-$C_4$)-alkyl-, HO—($C_1$-$C_4$)-alkyl- and ($C_1$-$C_4$)-alkyl-O—($C_1$-$C_4$)-alkyl-;
R31 is selected from the series consisting of ($C_3$-$C_7$-cycloalkyl, ($C_5$-$C_7$)-cycloalkyl to which a benzene ring is fused, phenyl, Het2 and (R32)(R33)(R34)C—, wherein the ($C_3$-$C_7$)-cycloalkyl and ($C_5$-$C_7$)cycloalkyl are unsubstituted or substituted by one or more identical or different substituents selected from the series consisting of fluorine, ($C_1$-$C_4$)-alkyl, HO— and ($C_1$-$C_4$)-alkyl-O— and the fused benzene ring is unsubstituted or substituted by one or more identical or different substituents R35;
or the groups R30 and R31, together with the nitrogen atom carrying them, form a 4-membered to 10-membered, monocyclic or bicyclic, saturated or partially unsaturated heterocycle which, in addition to the nitrogen atom carrying R30 and R31; comprises 0 or 1 further ring heteroatom selected from the series consisting of nitrogen, oxygen and sulfur, and which is unsubstituted or substituted by one or more identical or different substituents R36;

R32 is selected from the series consisting of hydrogen and $(C_1-C_4)$-alkyl;

R33 is selected from the series consisting of hydrogen, $(C_1-C_4)$-alkyl, $(C_3-C_7)$-cycloalkyl, R37-$(C_1-C_4)$-alkyl- and $(C_1-C_4)$-alkyl-O—C(O)—;

or R32 and R33, together with the carbon atom carrying them, form a $(C_3-C_7)$-cycloalkane ring which, irrespective of the group R34, is unsubstituted or substituted by one or more identical or different substituents selected from the series consisting of fluorine and $(C_1-C_4)$-alkyl;

R34 is selected from the series consisting of hydrogen, $(C_1-C_6)$-alkyl, $(C_3-C_7)$-cycloalkyl, R38-$(C_3-C_7)$-cycloalkyl-, $(C_1-C_4)$-alkyl-O—C(O)—, (R39)(R40)N—C(O)—, phenyl and Het2, wherein the $(C_1-C_6)$-alkyl is unsubstituted or substituted by one or more identical or different substituents R41, and the phenyl is unsubstituted or substituted by one or more identical or different substituents R35;

R35 is selected from the series consisting of halogen, $(C_1-C_4)$-alkyl, HO—$(C_1-C_4)$-alkyl-, $(C_1-C_4)$-alkyl-O—$(C_1-C_4)$-alkyl-, $(C_1-C_4)$-alkyl-O—C(O)—$(C_1-C_4)$-alkyl-, NC—, HO—, $(C_1-C_4)$-alkyl-O—, $(C_1-C_4)$-alkyl—S(O)$_p$—, $(C_1-C_4)$-alkyl-S(O)$_2$—NH—, R42—O—C(O)—, (R43)(R44)N—C(O)— and (R45)(R46)N—S(O)$_2$—;

R36 is selected from the series consisting of fluorine, $(C_1-C_6)$-alkyl, $(C_2-C_4)$-alkenyl, $(C_2-C_4)$-alkynyl, $(C_3-C_7)$-cycloalkyl, phenyl, Het3, HO—, $(C_1-C_4)$-alkyl-O—, $(C_3-C_7)$-cycloalkyl-O—, $(C_3-C_7)$-cycloalkyl-($(C_1-C_4)$-alkyl-O—, phenyl-O—, $(C_1-C_4)$-alkyl-S(O)$_p$—, NC— and R47O—OC(O)—, wherein the $(C_1-C_6)$-alkyl is unsubstituted or substituted by one or more identical or different substituents R48;

R37 is selected from the series consisting of $(C_3-C_7)$-cycloalkyl, $(C_1-C_4)$-alkyl-O— and $(C_1-C_4)$-alkyl-S—;

R38 is selected from the series consisting of phenyl, HO— and $(C_1-C_4)$-alkyl-O—;

R39, R40, R42, R47, R49, R50 and R51 are independently of one another selected from the series consisting of hydrogen and $(C_1-C_4)$-alkyl;

R41 is selected from the series consisting of $(C_3-C_7)$-cycloalkyl, phenyl, Het1, HO—, $(C_1-C_4)$-alkyl-O— and $(C_1-C_4)$-alkyl-S—;

R43, R44, R45 and R46 are independently of one another selected from the series consisting of hydrogen, $(C_1-C_4)$-alkyl, HO—$(C_1-C_4)$-alkyl- and $(C_1-C_4)$-alkyl-O—$(C_1-C_4)$-alkyl;

R48 is selected from the series consisting $(C_3-C_7)$-cycloalkyl, phenyl, Het3, HO—, $(C_1-C_4)$-alkyl-O—, $(C_1-C_4)$-alkyl-C(O)—O—, $(C_1-C_4)$-alkyl-S(O)$_p$—, $(C_1-C_4)$-alkyl-C(O)—(R49)N—, (R50)(R51)N—C(O)— and $(C_1-C_4)$-alkyl-O—C(O)—;

p is selected from the series consisting of 0, 1 and 2, wherein all numbers p are independent of one another;

Het1 is a 5-membered or 6-membered, monocyclic, aromatic heterocycle comprising 1 or 2 identical or different ring heteroatoms selected from the series consisting of nitrogen, oxygen and sulfur, which is bonded via a ring carbon atom and which is unsubstituted or substituted by one or more identical or different substituents selected from the series consisting of halogen, $(C_1-C_4)$-alkyl, $(C_3-C_7)$-cycloalkyl, NC—, HO—, $(C_1-C_4)$-alkyl-O— and $(C_1-C_4)$-alkyl-S(O)$_p$—, unless specified otherwise;

Het2 is a 4-membered to 10-membered, monocyclic or bicyclic, saturated, partially unsaturated or aromatic heterocycle comprising 1, 2, 3 or 4 identical or different ring heteroatoms selected from the series consisting of nitrogen, oxygen and sulfur, which is bonded via a ring carbon atom and which is unsubstituted or substituted by one or more identical or different substituents selected from the series consisting of halogen, $(C_1-C_4)$-alkyl, NC—, HO— and $(C_1-C_4)$-alkyl-O—;

Het3 is a 4-membered to 7-membered, monocyclic, saturated partially unsaturated or aromatic heterocycle comprising 1, 2 or 3 identical or different ring heteroatoms selected from the series consisting of nitrogen, oxygen and sulfur, which is unsubstituted or substituted by one or more identical or different substituents selected from the series consisting of halogen, $(C_1-C_4)$-alkyl, $(C_3-C_7)$-cycloalkyl, NC—, HO—, $(C_1-C_4)$-alkyl-O— and $(C_1-C_4)$-alkyl-S(O)$_p$—;

wherein all phenyl groups are unsubstituted or substituted by one or more identical or different substituents selected from the series consisting of halogen, $(C_1-C_4)$-alkyl, NC—, HO— and $(C_1-C_4)$-alkyl-O—, unless specified otherwise;

wherein all cycloalkyl groups, independently of any other substituents which can be present on a cycloalkyl group, can be substituted by one or more identical or different substituents selected from the series consisting of fluorine and $(C_1-C_4)$-alkyl, unless specified otherwise.

wherein all alkyl groups, alkanediyl groups, alkenyl groups and alkynyl groups, independently of any other substituents which can be present on an alkyl group, can be substituted by one or more fluorine substituents.

if structural elements such as groups, substituents or numbers, for example, can occur several times in the compounds of the formula I, they are all independent of one another and can in each case have any of the indicated meanings, and they can in each case be identical to or different from any other such element. In a dialkylamino group, for example, the alkyl groups can be identical or different.

Alkyl groups, i.e. saturated hydrocarbon residues, can be straight-chain (linear) or branched. This also applies if these groups are substituted or part of another group, for example in a fluorinated alkyl group or an alkoxy group (alkyloxy group, alkyl-O-group, wherein the terminal hyphen in the latter group, and likewise in all other groups where it occurs, denotes the free bond via which the group is bonded, and thus indicates via which atom or subgroup a group composed of several subunits is bonded). Depending on the respective definition, the number of carbon atoms of an alkyl group can be 1, 2, 3, 4, 5 or 6, or 1, 2, 3 or 4, or 1, 2 or 3, or 1 or 2, or 1, for example. In one embodiment of the invention, the number of carbon atoms of an alkyl group occurring in the compounds of the formula I is, independent of any other occurrence, 1, 2, 3, or 4, in another embodiment 1, 2 or 3, in another embodiment 1 or 2, in another embodiment 1. Examples of alkyl groups are methyl, ethyl, propyl including n-propyl and isopropyl, butyl including n-butyl, isobutyl, sec-butyl and tert-butyl, pentyl and hexyl. One or more, for example 1, 2, 3, 4, 5, 6, 7, 8 or 9, hydrogen atoms in alkyl groups in the compounds of the formula I can in general be replaced by fluorine atoms, unless specified otherwise. Examples of fluorinated alkyl groups are $CF_3$ (trifluoromethyl), $CF_2H$, $CFH_2$, $CF_3$—$CH_2$—, $CF_2H$—$CH_2$—, $CFH_2$—$CH_2$—, $CH_3CF_2$—, $CH_3$—$CFH$—, $CF_3$—$CF_2$—, $CF_3$—$CH_2$—$CH_2$—, $CF_2H$—$CH_2$—$CH_2$, $CF_3$—$CF_2$—$CF_2$—, $CFR_3$—$CF_2$—$CH_2$—, $CF_3$—$CFH$—$CH_2$— and $CF_2H$—$CF_2$—$CH_2$—. With respect to all groups or substituents in the compounds of the formula I which can be an alkyl group which can generally contain one or more fluorine substituents, as an example of groups or substituents containing fluorine-substituted alkyl, which may be included in the definition of the group or substituent, any one or more of the mentioned groups, for example the group $CF_3$ (trifluoromethyl), may be mentioned in the definition besides any alkyl groups not substituted by fluorine. In one embodiment of the invention, an alkyl group in any occurrence in the compound of the formula I is, independently of any other substituents which may be present on it and independently of any other occurrences of alkyl groups, unsubstituted by fluorine, in another embodiment it is unsubstituted or substituted by fluorine, and in another embodiment it is substituted by fluorine.

Examples of alkyl-O— groups are methoxy, ethoxy, n-propoxy, isopropoxy, n-butoxy, sec-butoxy, isobutoxy, tert-butoxy, which can in general, and irrespective of any other substituents, also be substituted by one or more fluorine substituents as outlined above with respect to the comprised alkyl subunits. Examples of fluorinated alkyl-O— groups are $CF_3$—O—, $CF_2H$—O—, $CF_3$—$CH_2$—O— and $CF_2H$—$CH_2$—O—. An example of a substituted alkyl-O— group is cyclopropylmethoxy- (cyclopropyl-$CH_2$—O—). Examples of alkyl-S(O)$_p$— groups are methylsulfanyl ($CH_3$—S—), methylsulfinyl ($CH_3$—S(O)—), methanesulfonyl ($CH_3$—S(O)$_2$—), ethylsulfanyl ($CH_3$—$CH_2$—S—), methylsulfinyl ($CH_3$—S(O)—), methanesulfonyl ($CH_3$—S(O)$_2$—), ethanesulfonyl ($CH_3$—$CH_2$—S—), methylethylsulfanyl (($CH_3$)$_2$CH—S—), methylethylsulfinyl (($CH_3$)$_2$CH—S(O)—) and methylethenesulfonyl (($CH_3$)$_2$CH—S(O)$_2$—). In one embodiment of the invention, the number p is selected from the series consisting of 0 and 2, in another embodiment it is 0, and in another embodiment it is 2, wherein all numbers p are independent of one another and can be identical or different. An example of a fluorinated alkyl-S(O)$_p$— group is $CF_3$—S—.

A substituted alkyl group can be substituted in any positions by one or more identical or different substituents as specified in the definition of the respective group, provided that the resulting group or compound as a whole is sufficiently stable and is suitable as a pharmaceutically active compound. The prerequisite that a specific group and a compound or the formula I are sufficiently stable and suitable as a pharmaceutically active compound, applies in general with respect to the definitions of all groups in the compounds of the formula I. In one embodiment of the invention, a substituted alkyl group in any occurrence of the compounds of the formula I is, independent of any other occurrence, substituted by 1, 2 or 3 substituents, in another embodiment by 1 or 2 substituents, in another embodiment by 1 substituent. Examples of substituted alkyl groups are ($C_3$-$C_7$)-cycloalkyl-($C_1$-$C_6$)-alkyl-, phenyl-($C_1$-$C_6$)-alkyl-, Het1-($C_1$-$C_6$)-alkyl-, Het3-($C_1$-$C_6$)-alkyl-, HO—($C_1$-$C_6$)-alkyl-, ($C_1$-$C_4$)-alkyl-O—($C_1$-$C_6$)-alkyl-, ($C_1$-$C_4$)-alkyl-C(O)—O—($C_1$-$C_6$-alkyl-, ($C_1$-$C_4$)-alkyl-O—C(O)—($C_1$-$C_6$)-alkyl-, ($C_1$-$C_4$)-alkyl-S(O)$_p$—($C_1$-$C_6$)-alkyl-, ($C_1$-$C_4$)-alkyl-C(O)—(R49)N—($C_1$-$C_6$)-alkyl- and (R50)(R51)N—C(O)—($C_1$-$C_6$)-alkyl-. In one embodiment, the terminal ($C_1$-$C_6$)-alkyl group via which the substituted alkyl group as a whole is bonded, is a ($C_1$-$C_4$)-alkyl group, in another embodiment a ($C_1$-$C_2$)-alkyl group, in another embodiment a $C_1$-alkyl group.

Examples of ($C_3$-$C_7$)-cycloalkyl-($C_1$-$C_6$)-alkyl- groups are cyclopropyl-methyl, cyclopropyl-hydroxy-methyl-, cyclopropyl-phenyl-methyl-, 2-cyclopropyl-ethyl-,2-cyclopropyl-1-phenyl-ethyl-, cyclopentyl-methyl- and cyclohexyl-methyl-. Examples of ($C_1$-$C_4$)-alkyl-O—($C_1$-$C_6$)-alkyl- groups are methoxy-methyl-, ethoxy-methyl-, isopropoxy-methyl-, 1-methoxy-ethyl-, 1-ethoxy-ethyl-, 2-methoxy-ethyl- and 3-methoxy-propyl-. An example of a fluorinated ($C_1$-$C_4$)-alkyl-O—($C_1$-$C_6$)-alkyl- group is trifluoromethoxy-methyl-. Examples of ($C_1$-$C_4$)-alkyl-S(O)$_p$—($C_1$-$C_6$)-alkyl- groups are methyl-S-methyl-, ethyl-S-methyl-, methyl-S(O)$_2$-methyl- and ethyl-S(O)$_2$-methyl-. An examples of a fluorinated ($C_1$-$C_4$)-alkyl-S($C_1$-$C_6$)-alkyl-group is trifluoromethylsulfanyl-methyl-. Examples of HO—($C_1$-$C_6$)-alkyl- groups are hydroxy-methyl-, 1-hydroxy-ethyl-, 2-hydroxy-ethyl-, 1-hydroxy-1-methyl-ethyl- and 2-hydroxy-1-methyl-ethyl-. Examples of ($C_1$-$C_4$)-alkyl-C(O)—O—($C_1$-$C_6$)-alkyl- groups are methyl-C(O)—O-methyl-, ethyl-C(O)—O-methyl- and isopropyl-C(O)—O-methyl. Examples of ($C_1$-$C_4$)-alkyl-O—C(O)—($C_1$-$C_6$)-alkyl-groups are methyl-O—C(O)-methyl-, ethyl-O—C(O)-methyl-, isopropyl-O—C(O)-methyl, 2-(ethyl-O—C(O)—)-ethyl- and 2-(methyl-O-13C(O)—)-ethyl-. Examples of ($C_1$-$C_4$)-alkyl-C(O)-13 (R49)N—($C_1$-$C_6$)-alkyl- groups are methyl-C(O)—NH-methyl- and isopropyl-C(O)—NH-methyl-, An example of (R50)(R51)N—C(O)—(($C_1$-$C_6$)-alkyl- groups is methyl-NH—C(O)-methyl-. Examples of phenyl-($C_1$-$C_6$)-alkyl- groups are phenyl-methyl-(benzyl), 1-phenyl-ethyl-, 2-phenyl-ethyl-, 1-phenyl-propyl- and 1-phenyl-butyl-, in which the phenyl group can be unsubstituted or substituted and, for example, be a hydroxy-phenyl- group or a fluoro-phenyl- group and groups such as (hydroxy-phenyl)-methyl- and (fluoro-phenyl)-methyl-, including (3-fluoro-phenyl)-methyl and (4-fluoro-phenyl)-methyl, for example, can be present. Examples of Het1-($C_1$-$C_6$)-alkyl- groups are pyridin-2-yl-methyl-, pyridin-3-yl-methyl-, pyridin-4-yl-methyl-, pyrazin-2-yl-methyl-, pyrimidin-2-yl- methyl- and pyrimidin-4-yl-methyl-. Examples of Het3-($C_1$-$C_6$)-alkyl- groups are pyrrolidin-1-yl-methyl piperidin-1-yl-methyl-, morpholin-4yl-methyl-, pyridin-2-yl-methyl-, pyridin-3-yl-methyl-, pyridin-4-yl-methyl-, pyrazin-2-ylmethyl-, pyrimidin-2-yl -methyl-, pyrimidin-4-yl-methyl-, pyrazol-1-yl-methyl-and 1-pyrazol-1-yl-ethyl-.

The explanations with respect to a akyl groups apply correspondingly to alkyl groups which in the definition of a group in the compounds of the formula I are bonded to two adjacent groups, or linked to two groups, and may be regarded as divalent alkyl groups or alkanediyl groups, which may also be alkylene groups. Besides in the case of I he alkyl part of a substituted alkyl group, which may also be regarded as a divalent alkyl group, divalent alkyl groups occur in the groups —($C_3$-$C_5$)-alkanediyl-, —O—($C_1$-$C_4$)-alkanediyl-O— and —($C_1$-$C_4$)-alkanediyl-O—C(O)—, for example, in which groups the terminal hyphens denote the free bonds via which the group is bonded. Thus, such divalent alkyl groups can also be straight-chain or branched, the bonds to the adjacent groups can be located in any positions and can start from the same carbon atom or from different carbon atoms, and they can be unsubstituted or substituted by fluorine substituents independently of any other substituents. Examples of such divalent alkyl groups are methylene (—$CH_2$—), ethane, 1,1-diyl (1,1-ethylene, —$CH(CH_3)$—), ethane-1,2-diyl (1,2-ethylene, —$CH_2$—$CH_2$—), propane-1,1-diyl (1,1-propylene, —$CH(CH_2$—$CH_3$)—), propane-1,2-diyl (1,2-propylene, —$CH(CH_3)$—$CH_2$—, —$CH_2$—$CH(CH_3)$—), propane-2,2-diyl (2,2-propylene, —$C(CH_3)_2$—), propane-1,3-diyl (1,3-propylene, —$CH_2$—$CH_2$—$CH_2$—), butane-1,1-diyl (1,1-butylene, —CH($CH_2$—$CH_2$—$CH_3$)—), or butane-1,4-diyl (1,4-butylene, —$CH_2$—$CH_2$—$CH_2$—$CH_2$—). Examples of fluoro-substituted alkanediyl groups, which can contain 1, 2, 3, 4, 5 or 6 fluorine substituents, for example, are —CHF—, —CF$_2$—, —CF$_2$—CH$_2$—, —CH$_2$—CF$_2$—, —CF$_2$—CF$_2$—, —CF(CH$_3$)— or —C(CF$_3$)$_2$—, The explanations given with respect to alkyl groups apply correspondingly to alkenyl groups and alkynyl groups, i.e. unsaturated hydrocarbon residues which contain a double bond and a triple bond, respectively. Thus, they can also be straight-chain or branched, and can in general be substituted by fiuorine The double bond and triple bond can be present in any position. Examples of alkenyl groups and alkynyl groups are ethenyl (vinyl), prop-1-enyl, prop-2enyl (allyl), but-1-enyl, but-2-enyl, but-3-enyl, 2-methyl-prop-1-enyl, ethynyl, prop-1-ynyl, prop-2-ynyl (propargyl), but-2-ynyl. In one embodiment of the invention, an alkenyl group is an ethenyl group. In one embodiment of the invention, an alkynyl group is an ethynyl group.

The number of ring carbon atoms in a (C$_3$-C$_7$)-cycloalkyl group can be 3, 4, 5, 6 or 7. Examples of cycloalkyl are cyclopropyl, cyclobutyl, cyclopentyl, cyclohexyl and cycloheptyl. In one embodiment of the invention, a (C$_3$-C$_7$)-cycloalkyl group in any occurrence in the compounds of the formula I is independently of any other occurrence a (C$_3$-C$_6$)-cycloalkyl group, in another embodiment a C$_3$-C$_5$) cycloalkyl group, in another embodiment a (C$_3$-C$_4$-cycloalkyl group, in another embodiment a (C$_5$-C$_7$)-cycloalkyl group, in another embodiment a (C$_5$-C$_6$)-cycloalkyl group, in another embodiment a cyclopropyl group, in another embodiment a cyclohexyl group. Cycloalkyl groups can generally, independently of any other substituents, in any of their occurrences, independently of any other occurrence, be substituted by one or more fluorine substituents and/or (C$_1$-C$_4$)-alkyl substituents, for example by 1, 2, 3 or 4 identical or different substituents selected from the series consisting of fluorine and (C$_1$-C$_4$)-alkyl, such as fluorine and methyl substituents. which substituents can be located in any positions, or be unsubstituted by alkyl substituents and fluorine substituents, i.e. do not carry alkyl substituents and fluorine substituents, unless any other optional substitution is specified with respect to a cycloalkyl group in a specific position in the compounds of the formula I. Examples of alkyl-substituted and fluorine-substituted cycloalkyl groups are 1-methylcyclopropyl, 2,2-dimethylcyclopropyl-, 1-methylcyclopentyl-, 2,3-dimethylcyclopentyl-, 1-methylcyclohexyl, 4-methylcyclohexyl, 4-isopropylcyclohexyl-, 4-tert-butylcyclohexyl-, 3,3,5,5-tetramethylcyclohexyl-, 1-fluorocyclopropyl-, 2,2-difluorocyclopropyl-, 3,3-difluorocyclobutyl-, 1-fluorocyclohexyl-, 4,4-difluorocyclohexyl-, 3,3,4,4,5,5-hexafluorocyclohexyl-.

The number of ring carbon atoms in the cycloalkyl moiety of a (C$_5$-C$_7$)-cycloalkyl group to which a benzene ring or Het1 ring or another aromatic heterocyclic ring ss fused, which fused bicyclic group can represent R20 or R31 or in the case of a heterocyclic group is comprised by the group Het2, can be 5, 6 or 7, and the cycloalkyl moiety thus be derived from cyclopentane, cydohexane or cycloheptane. Since formally a double bond of the aromatic benzene dng or Het1 ring or another aromatic heterocyclic ring, which is present between the two ring atoms common to both fused rings, is regarded as belonging also to the cyclosikyl moiety, the latter can also be regarded as a cycloalkenyl moiety derived from cyclopentene, cyclohexene or cycloheptene. in case a benzene ring is fused to the (C$_5$-C7) cycloalkyl group, the resulting fused bicydic group is an mdanyl group, a 1,2,3,4tetrahydronaphthalenyl group or a 6,7,8,9-tetrahydro-5H-benzocycloheptenyl group, which can all be substituted as specified, in one embodiment of the invention a (C$_5$-C$_7$)-cycloalkyl group to which a benzene ring or ring Het1 or another aromatic heterocyclic ring is fused, which can represent R20 or R31 or in the case of a heterocyclic group is comprised by the group Het2, is a (C$_5$-C$_7$)-cycloalkyl group, and in the case of a fused benzene ring the resulting bicychc group is selected from the series consisting of indanyl and 1,2,3,4-tetrahydronaphthalenyl, and in another embodiment it is a C$_5$-cycloalkyl group, and in the case of a fused benzene ring the resulting bicyclic group is an indanyl group, which can all be substituted as specified, in one embodiment of the invention, a group Het1 which is fused to a (C$_5$-C$_7$)-cycloalkyl group to give a bicyclic group representing R20, is a 6-membered monocyclic aromatic heterocycle which comprises 1 or 2 nitrogen atoms as ring neieroatoms, in another embodiment it is a heterocycle selected from the series consisting of pyridine, pyrimidine, and pyrazine, in another embodiment it is a heterocycle selected from the series consisting of pyridine and pyrazine, in another embodiment it is a pyridine ring.

A (C$_5$-C$_7$)-cycloalkyl group to which a ring, such as a benzene ring or Het1 ring, is fused, is bonded via a ring carbon atom in the non-aromatic ring, for example via the 1-position or 2-position in the case of an indanyl or 1,2,3,4-tetrahydronaphthalenyl group, the 5-position, imposition or 7-position in the case of a 6,7,8,9-tetrahydro-5H-benzocycloheptenyl group, the 5-position, 6-position or 7-position in the case of a 6,7-dihydro-5H-[1]pyrindinyl (cyclopenta[b]pyndinyl) or 6,7-dihydro-5H[2]pyrindinyl (cyclopenta[c]pyridinyl) group, or the 5-position or 6-position in the case of a 5,6,7,8-tetrahydroquinoxalinyl group, in one embodiment of the invention, a (C$_5$-C$_7$)-cycloalkyl group to which a benzene ring or Het1 ring is fused, is bonded via a ring carbon atom in the non-aromatic ring which is adjacent to the aromatic ring, for example via the 1-iposition n the case of an indanyl or 1,2,3,4-tetrahydronapnthalenyl group, the 5-position in the case of a 6,7,8,9tetrahydro-5H-benzocycloheptenyl group, the 5-position or 7-position in the case of a 6,7-dihydro-5H-[1]pyrindinyl group or 6,7-dihydro-5H-[2]pyrindinyl group, or the 5-position in the case of a 5,6,7,8-tetrahydroquinoxalinyl group.

In one embodiment of the invention, the cycloalkyl subgroup in a (C$_5$-C$_7$)-cycloalkyl group to which a benzene ring or a Het1 ring is fused and which represents R20, is unsubstituted or substituted by 1, 2, 3 or 4, in another embodiment 1, 2 or 3, in another embodiment 1 or 2, in another embodiment 1, identical or different substituents selected from the series consisting of fluorene, (C$_1$-C$_4$)-alkyl and (C$_1$-C$_4$)-alkyl-O—, in another embodiment from the series consisting of fluorine and (C$_1$-C$_4$)-alkyl, in another embodiment by (C$_1$-C$_4$)-alkyl substituents, in another embodiment by fluorine substituents, and in another embodiment by (C$_1$-C$_4$)-alkyl-O— substituents. In one embodiment of the invention, the cycloalkyl subgroup in a (C$_5$-C$_7$)-cycloalkyl group to which a benzene ring is fused and which represents R31, is unsubstituted or substituted by 1, 2, 3 or 4, in another embodiment 1, 2 or 3, in another embodiment 1 or 2, in another embodiment 1, identical or different substituents selected from the series consisting of fluorine, (C$_1$-C$_4$)-alkyl, HO— and (C$_1$-C$_4$)-alkyl-O—, in another embodiment from the series consisting of fluorine and (C$_1$-C$_4$)-alkyl, in another embodiment by (C$_1$-C$_4$)-alkyl substituents, in another embodiment by fluorine substituents, and in another embodiment by substituents selected from the series consisting of HO— and (C$_1$-C$_4$)-alkyl-O—, in another embodiment by HO— (hydroxy) substituents, in another embodiment by (C$_1$-C$_4$)-alkyl-O— substituents. In one embodiment, the number of substituents R24 and R35, respectively, which can be present in a benzene ring and Het1 ring fused to the said ($C_5$-$C_7$)-cycloalkyl group representing R20 or R31, is 1, 2 or 3, in another embodiment 1 or 2, in another embodiment 1. In one embodiment, the substituents R24 and R35, respectively, which are can be present in a benzene ring and Het1 ring fused io the said ($C_5$-$C_7$)-cycloalkyl group representing R20 or R31, are independently of one another selected from the series consisting of halogen, ($C_1$-$C_4$)-alkyl, ($C_1$-$C_4$)-alkyl-O—, HO— and NC—, in another embodiment from the series consisting of halogen, ($C_1$-$C_4$)-alkyl, ($C_1$-$C_4$)-alkyl-O— and NC—, in another embodiment from the series consisting of halogen, ($C_1$-$C_4$)-alkyl and ($C_1$-$C_4$)-alkyl-O—, in another embodiment from the series consisting of halogen, ($C_1$-$C_4$)-alkyl and NC—, in another embodiment from the series consisting of halogen and ($C_1$-$C_4$)-alkyl, where all alkyl groups can be substituted by one or more fluorine substituents, as applies in general, and in another embodiment from the series consisting of fiuonne, chlorine, methyl, ethyl, isopropyl, methoxy, ethoxy. cyano (NC—), difluoromethyl and trifloromethyl.

Examples of alkyl ester groups, from any one or more of which a group ($C_1$-$C_4$)-alkyl-O—C(O)— in any occurrence in the compounds of the formula I is independently of any other occurrence selected in one embodiment of the invention, are methyl-O—C(O)—, ethyl-O—C(O)—, isopropyl—O—C(O)—, sec-butyl-O—C(O)—, tert-butyl-O—C(O)— and isobutyl-O—C(O)—.

Halogen is fluorine (F), chlorine (Cl), bromine (Br) or iodine (I). In one embodiment of the invention, halogen; is in any of its occurrences in the compounds of the formula I fluorine, chlorine or bromine, in another embodiment fluorine or chlorine, in another embodiment fluorine, in another embodiment chlorine, where all occurrences of halogen are independent of one another.

The present invention comprises all stereoisomeric forms of the compounds of the formula I, for example all enantiomers and diastereomers including cis/trans isomers.

The invention likewise comprises mixtures of two or more stereoisomeri forms, for example mixtures of enantiomers and/or diastereomers including cis/trans isomers. in all ratios. Asymmetric centers contained in the compounds of the formula I can all independently of one another have S configuration or R configuration. The invention relates to enantiomers, both the levorotatory and the dextrorotatory antipode, in enantiomencally pure form and essentially enantiomerically pure form, for example with a molar ratio of the two enantiomers of 98:2, or 99:1, or greater, and in the form of their racemate, i.e. a mixture of the two enantiomers in molar ratio of 1:1, and in the form of mixtures of the two enantiomers in all ratios. The invention likewise relates to diastereomers in the form of pure and essentially pure diastereomers and in the form of mixtures of two or more diastereomers in all ratios. The invention also comprises all cis/trans isomers of the compounds of the formula I in pure form and essentially pure form, for example with a molar ratio of the cis/trans isomers of 98:2, or 99:1, or greater, and in the form of rmxtures of the cis isomer and the trans isomer in all ratios. Cis/trans isomerism can occur in substituted rings, for example. The preparation of individual stereoisomers, if desired, can be carried out by resolution of a rmxture according to customary methods, for example, by chromatography or crystallization, or by use of stereochemically uniform starting compounds in the synthesis, or by stereoselective reactions. Optionally, before a separation of stereoisomers a derivatization can be carried out. The separation of a mixture of stereoisomers can be carried out at the stage of the compound of the formula I or at the stage of an intermediate in the course of the synthesis. For example, in the case of a compound of the formula I containing an asymmetric center the individual enantiomers can be prepared by preparing the racemate of the compound d the formula I and resolving it into the enantiomers by high pressure liquid chromatography on a chiral phase according to standard procedures, or resolving the racemate of any intermediate in the course of its synthesis by such chromatography or by crystallization of a salt thereof with an optically active amine or acid and converting the enantiomeric of the intermediate into the enantiomeric forms of the final compound of the formula I, or by performing an enantioselectlve reaction in the course of the synthesis. The invention also comprises all tautomeric forms of the compounds of the formula I.

If the compounds of the formula I comprise one or more acidic or basic groups, for example basic heterocyclic groups, the corresponding physiologically or lexicologically acceptable salts are also included in the invention, especially the pharmaceutically acceptable salts. The compounds of the formula I may thus be deprotonated on an acidic group and be used for example as alkali metal salts or as ammonium sails. Compounds of the formula I comprising at least one basic group may also be prepared and used in the form of their acid addition salts, for example in the form of pharmaceutically acceptable salts with inorganic acids and organic acids. Salts can in general be prepared from acidic and basse compounds of the formula I by reaction with an acid or base in a solvent or diluent according to customary procedures. If the compounds of the formula I simultaneously contain an acidic and a basic group in the molecule, the invention also includes internal salts (betaines, zwitterions) in addition to the salt forms mentioned. The present invention also comprises all salts of the compounds of the formula I which, because of low physiological tolerability, are not directly suitable for use as a pharmaceutical but are suitable as intermediates for chemical reactions or for the preparation of physiologically acceptable salts, for example by means of anion exchange or cation exchange.

In one embodiment of the invention, the number n is 0 (zero), and in this embodiment thus the group (R8)(R9)C is not present and the group X is bonded directly to the carbon atom in the pyrrole ring depicted in formula I. In another embodiment of the invention, n is 1.

In one embodiment of the invention, the number m is 0, and in this embodiment thus no groups (R4)(R5)C are present and the carbon atom carrying the groups R6 and R7 is bonded directly to the nitrogen atom of the pyrrole ring depicted in formula I. In another embodiment, m is 1, in another embodiment m is selected from the series consisting of 0 and 1, and in another embodiment m is selected from the series consisting of 1 and 2. In another embodiment, m is selected from the series consisting of 0 and 1 if X is sulfur or (R10)(R11)C, and m is 1 if X is oxygen.

In one embodiment of the invention, the divalent group X is selected from the series consisting of oxygen (—O—) and sulfur (—S—), in another embodiment from the series consisting of oxygen and (R10)(R11)C (—(R10)(R11)C—), in another embodiment from the series consisting of sulfur and (R10)(R11)C, in another embodiment X is oxygen, in another embodiment X is sulfur, and in another embodiment X is (R10)(R11)C.

In one embodiment of the present invention, the group R1 in the compounds of the formula I, as defined herein in general or in any embodiment, is the group R20—NH— and the group R2 is the group (R30)(R31)N—, and the compound of the formula I thus is a compound of the formula Ia.

in another embodiment of the present invention, the group R2 in the compounds of the formula I, as defined herein in general or in any embodiment, is the group R20—NH— and the group R1 is the group (R30)(R31)N—, and the compound of the formula I thus is a compound of the formula Ib. R3 to R9, R20, R30, R31, X, m and n in the compounds of the formulae Ia and Ib are defined as in the compounds of the formula I in general or in any embodiment.

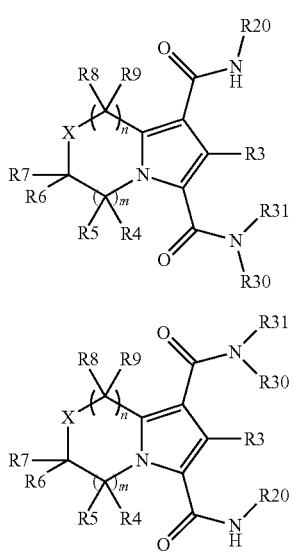

In one embodiment of the invention, a halogen atom representing the group R3 is selected from the series consisting of fluorine, chlorine and bromine, in another embodiment from the series consisting of fluorine and chlorine, in another embodiment from the series consisting of chlorine and bromine, in another embodiment n is fluorine, and in another embodiment it is chlorine. In one embodiment, a ($C_1$-$C_4$)-alkyl group representing R3 is ($C_1$-$C_3$)-alkyl group, in another embodiment a ($C_1$-$C_2$)-alkyl group, in another embodiment it is a methyl group. In one embodiment, R3 is selected from the series consisting of hydrogen and halogen, in another embodiment from the series consisting of hydrogen and ($C_1$-$C_4$)-alkyl, in another embodiment from the series consisting of hydrogen, fluorine, chlorine, methyl, ethyl and isopropyl, and in another embodiment R3 is hydrogen.

In one embodiment of the invention, a ($C_1$-$C_4$)-alkyl group representing any of the groups R4, R5, R6, R7, R8, R9, R10 and R11 is a ($C_1$-$C_3$)-alkyl group, in another embodiment a ($C_1$-$C_2$)-alkyl group, in another embodiment it is a methyl group, in one embodiment, the groups R4, R5, R6, R7, R8, R9, R10 and R11 are independently of one another selected from the series consisting of hydrogen and fluorine, in another embodiment from the series consisting hydrogen and ($C_1$-$C_4$)-alkyl, in another embodiment from the series consisting of hydrogen and methyl. In one embodiment, the groups R4 and R5 are hydrogen. In another embodiment, the groups R4, R5, R6, R7, R8, R9, R10 and R11 are independently of one another selected from the series consisting of hydrogen and methyl, with the proviso that at least six of these groups are hydrogen, in another embodiment, the groups R4, R5, R6, R7, R8, R9, R10 and R11 all are hydrogen.

In one embodiment of the invention, R20 is ($C_5$-$C_7$)-cycloalkyl to which a benzene ring or a Het1 ring is fused, wherein the ($C_5$-$C_7$-cycloalkyl is unsubstituted or substituted by one or more identical or different substituents selected from the series consisting of fluorine, ($C_1$-$C_4$)-alkyl and ($C_1$-$C_4$)-alkyl-O—, and the fused benzene ring and Het1 ring is unsubstituted or substituted by one or more identical or different substituents R24. In another embodiment, R20 is the group (R21)(R22)(R23)C—. In another embodiment, R20 is the group (R21)(R22)(R23)C— group, wherein R21 is selected from the series consisting of phenyl and Het1, which are all unsubstituted or substituted by one, two or three identical or different substituents R24, and wherein R22 is selected from the series consisting of hydrogen, methyl, ethyl, n-propyl, isopropyl, n-butyl, sec-butyl, isobutyl, tert-butyl and cyclopropyl, and wherein R23 is hydrogen.

In one embodiment of the invention, the number of substituents R24 which is present in a substituted phenyl group or Het1 group representing R21, is 1, 2, 3, or 4, in another embodiment it is 1, 2 or 3, in another embodiment it is 1 or 2, in another embodiment it is 1. In one embodiment, R21 is phenyl, and in another embodiment R21 is Het1, wherein phenyl and Het1 are all unsubstituted or substituted by one or more identical or different substituents R24. In another embodiment, R21 is selected from the series consisting of phenyl and Het1, which are all substituted by one or more identical or different substituents R24. In another embodiment, R21 is selected from the series consisting of phenyl and Het1, wherein Het1 is substituted by one or more identical or different, substituents R24, and phenyl is unsubsUtufed or substituted by one or more identical or different substituents R24. In another embodiment, R21 is selected from the series consisting of phenyl and Het1, wherein phenyl is unsubstituted and Het1 is unsubstituted or substituted by one or more identical or different substituents R24. In another embodiment, R21 is selected from the series consisting of phenyl and Het1, which are all unsubstituted.

In one embodiment of the invention, R22 is selected from the series consisting of hydrogen, ($C_1$-$C_4$)-alkyl, ($C_3$-$C_7$)-cycloalkyl and R25-($C_1$-$C_4$)-alkyl-, in another embodiment from the series consisting of hydrogen, ($C_1$-$C_4$)-alkyl, ($C_3$-$C_7$)-cycloalkyl and R25-(($C_1$-$C_4$)-alkyl- wherein R25 is ($C_3$-$C_7$)-cycloalkyl, in another embodiment from the series consisting of hydrogen, ($C_1$-$C_4$)-alkyl and ($C_3$-$C_7$)-cycloalkyl, in another embodiment from the series consisting of hydrogen, ($C_1$-$C_4$)-alkyl and cyclopropyl, in another embodiment from the series consisting of hydrogen and ($C_1$-$C_4$)-alkyl, in another embodiment from the series consisting of ($C_1$-$C_4$)-alkyl and ($C_3$-$C_7$)-cycloalkyl, in another embodiment from the series consisting of ($C_1$-$C_4$)-alkyl and cyclopropyl, in another embodiment from the series consisting of hydrogen, methyl, ethyl, n-propyl, isopropyl, n-butyl, sec-butyl, isobutyl, tert-bulyl and cyclopropyl. In another embodiment, R22 is ($C_1$-$C_4$)-alkyl, in another embodiment ($C_1$-$C_3$)-alkyl, in another embodiment ($C_1$-$C_2$)-alkyl, in another embodiment methyl.

In one embodiment of the invention, R23 is selected from the series consisting of hydrogen and ($C_1$-$C_2$)-alkyl, in another embodiment from the series consisting of hydrogen and methyl and in another embodiment R23 is hydrogen.

In one embodiment of the invention, R24 is selected from the series consisting of fluorine, chlorine, bromine, ($C_1$-$C_4$)-alkyl, ($C_3$-$C_7$)-cycloalkyl, HO—, ($C_1$-$C_4$)-alkyl-O—, ($C_1$-$C_4$)-alkyl-S(O)$_p$—, $F_5$S—, NC— and ($C_1$-$C_4$)-alkyl-O—C(O)—, in another embodiment from the series consisting of fluorine, chlorine, bromine, $(C_1-C_4)$-alkyl, $(C_3-C_7)$-cycloalkyl, $(C_1-C_4)$-alkyl-O—, $(C_1-C_4)$-alkyl-S—, $F_5S$— and NC—, in another embodiment from the series consisting of fluorine, chlorine, bromine, $(C_1-C_4)$-alkyl, $(C_3-C_7)$-cycloalkyl, $(C_1-C_4)$-alkyl-O—, $(C_1-C_4)$-alkyl-S— and NC—, in another embodiment from the series consisting of fluorine, chlorine, bromine, $(C_1-C_4)$-alkyl, $(C_1-C_4)$-alkyl-O—, $(C_1-C_4)$-alkyl-S— and NC—, in another embodiment from the series consisting of fluorine, chlorine, bromine, $(C_1-C_4)$-alkyl, $(C_1-C_4)$-alkyl-O— and NC—, in another embodiment from the series consisting of fluorine, chlorine, bromine, $(C_1-C_4)$-alkyl and $(C_1-C_4)$-alkyl-O—, in another embodiment from the series consisting of fluorine, chlorine, bromine and $(C_1-C_4)$-alkyl, and in another embodiment R24 is $(C_1-C_4)$-alkyl, wherein all $(C_1-C_4)$-alkyl groups can be substituted by one or more fluorine substituents. in another embodiment, R24 is selected from the series consisting of fluorine, chlorine, methyl, ethyl isopropyl, cyano, trifluoroethyl, difluoromethyl, 2,2,2-trifluoroethyl, 2,2-difluoroethyl, methoxy and ethoxy, in another embodiment from the series consisting of fluorine, chlorine, methyl, ethyl, cyano, trifluoromethyl. difluoromethyl, methoxy and ethoxy. In one embodiment, one substituent R24 on a substituted phenyl group or Het1 group representing R21 is selected from the series consisting of fluorine, chlorine, methyl, cyano, trifluoromethyl and methoxy, in another embodiment from the sehes consisting of fnjorine, chlorine, cyano, trifluoromethyl and methoxy, and one or two further identical or different substituents R24, which can be present or absent, i.e. a second and a third substituent if present, are selected from the series consisting of fluorine, chlorine, methyl and tnfluoromethyl. In one embodiment, one substituent R24 on a substituted phenyl group or Het1 group representing R21, i.e. a first substituent if present, and one further substituent R24 on a substituted phenyl group or Het1 group representing R21 which can be present, i.e. a second substituent if present are as defined in general or in any embodiment and any further substituents, i.e. a third substituent R24 and any further substituents R24 if present, are fluorine. In one embodiment, substituents R24 on a ring nitrogen atom in a substituted group Het1 representing R21 are selected from the series consisting of $(C_1-C_4)$-alkyl, $(C_3-C_7)$-cycloalkyl and $(C_1-C_4)$-alkyl-S(O)$_p$—, in another embodiment from the series consisting of $(C_1-C_4)$-alkyl and $(C_1-C_4)$-alkyl-S(O)$_p$—, in another embodiment from the series consisting of $(C_1-C_4)$-alkyl and $(C_3-C_7)$-cycloalkyl, and in another embodiment they are $(C_1-C_4)$-alkyl.

in one embodiment of the invention, R25 is selected from the series consisting of $(C_3-C_7)$-cycloalkyl and $(C_1-C_4)$-alkyl-O—, in another embodiment R25 is $(C_3-C_7)$-cycloalkyl.

In one embodiment of the invention, R30 is selected from the series consisting of hydrogen, $(C_1-C_4)$-alkyl, $(C_3-C_7)$-cycloalkyl-$(C_1-C_4)$-alkyl- and HO—($(C_1-C_4)$-alkyl, in another embodiment from the series consisting of hydrogen, $(C_1-C_4)$-alkyl and HO—$(C_1-C_4)$-alkyl-, in another embodiment from the series consisting of hydrogen, $(C_1-C_4)$-alkyl and $(C_3-C_7)$-cycloalkyl-$(C_1-C_4)$-alkyl-, in another embodiment from the series consisting of hydrogen and $(C_1-C_4)$-alkyl, in another embodiment from the series consisting of hydrogen and $(C_1-C_2)$-alkyl, in another embodiment from the series consisting of hydrogen and methyl, in another embodiment R30 is hydrogen, and in another embodiment R30 is $(C_1-C_2)$-alkyl.

In one embodiment, R31 is selected from the series consisting of $(C_3-C_7)$-cycloalkyl, $(C_5-C_7)$-cycloalkyl to which a benzene ring is fused, Het2 and (R32)(R33)(R34) C—, in another embodiment from the series consisting of $(C_5-C_7)$-cycloalkyl to which a benzene ring is fused, Het2 and (R32)(R33)(R34)C—. In another embodiment from the series consisting of $(C_5-C_7)$-cycloalkyl to which a benzene ring is fused, and (R32)(R33)(R34)C—, in another embodiment R31 is $(C_5-C_7)$-cycloalkyl to which a benzene ring is fused, and in another embodiment R31 is (R32)(R33)(R34)C—, wherein in all these embodiments the $(C_3-C_7)$-cycloalkyl and $(C_5-C_7)$-cycloalkyl are unsubstittued or substituted by one or more identical or different substituents selected from the series consisting of fluorine, $(C_1-C_4)$-alkyl, HO— and $(C_1-C_4)$-alkyl-O— and the fused benzene ring is unsubstituted or substituted by one or more identical or different substituents R35. In one embodiment, the number of substituents on a substituted $(C_3-C_7)$-cycloalkyl group representing R31 is 1, 2, 3 or 4, in another embodiment 1, 2 or 3, in another embodiment 1 or 2, in another embodiment 1. In one embodiment, the substituents on a substituted $(C_3-C_7)$-cycloalkyl group representing R31 are selected from the series consisting of fluorine, $(C_1-C_4)$-alkyl and $(C_1-C_4)$-alkyl-O—, in another embodiment from the series consisting of fluorine and $(C_1-C_4)$-alkyl, in another embodiment from the series consisting of HO— and $(C_1-C_4)$-alkyl-O—, in another embodiment from the series consisting of $(C_1-C_4)$-alkyl and $(C_1-C_4)$-alkyl-O—, and in another embodiment they are $(C_1-C_4)$-alkyl groups.

The heterocycle which can be formed by the groups R30 and R31 together with the nitrogen atom carrying them, can be 4-membered, 5-membered, 6-membered, 7-membered, 8-membered, 9-membered or 10-membered. In one embodiment of the invention, the heterocycle which can be formed by R30 and R31 together with the nitrogen atom carrying them, is a 4-membered to 7-membered monocyclic heterocycle or a 6-membered to 10-membered bioyclic, heterocycle, in another embodiment it is a 4-membered to 7-membered monocyclic heterocycle, in another embodiment it is a 4-membered to 6-membered monocyclic heterocycle, in another embodiment it is a 5-membered to 6-membered monocyclic heterocycle, in another embodiment it is a 5-membered monocyclic heterocycle, in another embodiment it is a 6-membered monocyclic heterocycle. In a bycyclic heterocycle which can be formed by R30 and R31 together with the nitrogen atom carrying them, and likewise in a bicyclic heterocycle representing Het2, the two rings can be bridged or fused or form a spirocyclic ring system. In one embodiment, the two rings in such a bycyclic heterocycle are bridged or fused. A partially unsaturated heterocycle which can be formed by R30 and R31 together with the nitrogen atom carrying them, and likewise a partially unsaturated group Het2 and Het3, contains one or more, for example one, two, three or four, or one, two or three, double bonds within the ring system, but is not aromatic, i.e., it does not comprise a cyclic system of six delocalized pi electrons in the case of a monocyclic ring system or ten delocalized pi electrons in the case of bicyclic ring system, wherein a partially unsaturated bicyclic ring system the double bonds can be present in one or both of the rings and one of the rings can also be aromatic, in one embodiment, a heterocycle which can be formed by R30 and R31 together with the nitrogen atom carrying them, is saturated. In one embodiment, the further ring heteroatom which can be present in a heterocycle which can be formed by R30 and R31 together with the nitrogen atom carrying them, is selected from the series consisting of nitrogen and oxygen, in another embodiment from the series consisting of oxygen and sulfur, and in another embodiment it is a nitrogen atom. In one embodiment, a heterocycle which can be formed by R30 and R31 together with the nitrogen atom carrying them, does not comprise a further ring heteroatom besides the nitrogen atom which carries R30 and R31 and via which the heterocycle is bonded. Examples of heterocyclic groups, from any one or more of which a heterocycle which can be formed by R30 and R31 together with the nitrogen atom carrying them is selected in one embodiment of the invention, are azetidin-1-yl, pyrrolidin-1-yl, piperidin-1-yl, azepan-1-yl, imidazolidin-1-yl, thiazolidin-3-yl, piperazin-1-yl, morpholin-4-yl, thiomorpholin-4-yl, 3-azqa-bicyclo[3.1.0]hex-3-yl, 1,3-dihydroisoindol-2-yl and 2,3-dihydroindol-1-yl, which are all unsubstituted or substituted by one ore more identical or different substituents R36. In one embodiment, the heterocyclic group which can be formed by R30 and R31 together with the nitrogen atom carrying them, is selected from the series consisting of pyrrolidin-1-yl, piperidin-1-yl, piperazin-1-yl and morpholin-4-yl, in another embodiment from the series consisting of pyrrolidin-1-yl and piperidin-1-yl, in another embodiment from the series consisting of pyrrolidin-1-yl and piperazin-1-yl, and in another embodiment it is a pyrrolidin-1-yl group, which are all unsubstituted or substituted by one ore more identical or different substituents R36 in one embodiment, the number of substituents R36 in a substituted heterocycle which can be formed by R30 and R31 together with the nitrogen atom carrying them, is 1, 2, 3 or 4, in another embodiment it is 1, 2 or 3, in another embodiment it is 1 or 2, in another embodiment it is 1. Substituents R36 can be present in any positions of the heterocycle which can be formed by R30 and R31 together with the nitrogen atom carrying them, provided that the resulting group or compound as a whole is sufficiently stable and is suitable as a pharmaoeutically active compound, as already mentioned above. For example, in a pyrrolidin-1-yl group representing the group (R30)(R31)N—, substituents can be present in any one or more of positions 2, 3, 4 and 5, and in a piperidin-1-yl group or a piperazin-1-yl group representing the group (R30)(R31)N— in any one or more of positions 2, 3, 4, 5 and 6. In one embodiment, the group (R30)(R31)N— is a pyrrolidin-1-yl group which carries a substituent in ring position 2, i.e. on a carbon atom adjacent to the ring nitrogen atom of the pyrrolidine ring, wherein in another embodiment such a substituent in position 2 is bonded via a carbon atom.

In one embodiment of the invention, R30 and R31 do not form a heterocycle together with the nitrogen atom carrying them, and only have their individual meanings, i.e., in this embodiment, the group R30 is selected from the series consisting of hydrogen, $(C_1-C_4)$-alkyl, $(C_3-C_7)$-cycloalkyl-$(C_1-C_4)$-alkyl-, HO—$(C_1-C_4)$-alkyl- and $(C_1-C_4)$-alkyl-O—13 $(C_1-C_4)$-alkyl-, or from any subseries thereof, for example a series mentioned in any embodiment herein, and the group R31 is selected from the series consisting of $(C_3-C_7)$-cycloalkyl, $C_5-C_7$-cycloalkyl to which a benzene ring is fused, phenyl, Het2 and (R32)(R33)(R34)C—, or from any subseries thereof, for example a series mentioned in any embodiment herein, wherein the $(C_3-C_7)$-cycloalkyl and $(C_5-C_7)$-cycloalkyl are unsubstituted or substituted by one or more identical or different substituents selected from the series consisting of fluorine, $(C_1-C_4)$-alkyl, HO— and $(C_1-C_4)$-alkyl-O— and the fused benzene ring is unsubstituted or substituted by one or more identical or different substituents R35. In another embodiment, R30 and R31 do not form a heterocycle together with the nitrogen atom carrying them, and the group R30 is selected from the series consisting of hydrogen and $(C_1-C_4)$-alkyl, and the group R31 is the group (R32)(R33)(R34)C—. In another embodiment, R30 and R31 do not have their individual meanings, and only form, together with the nitrogen atom carrying them, a 4-membered to 10-membered, monocyclic or bicyclic, saturated or partially unsaturated heterocyde which, in addition to the nitrogen atom carrying R30 and R31, comprises 0 or 1 further ring heteroatom selected from the series consisting of nitrogen, oxygen and sulfur, and which is unsubstituted or substituted by one ore more identical or different substituents R36.

The $(C_3-C_7)$-cycloalkane ring which can be formed by R32 and R33 together with the carbon atom carrying them, can be 3-membered, 4-membered, 5-membered, 6-membered or 7-membered. In one embodiment of the invention, it is a $(C_3-C_6)$-cycloalkane ring, in another embodiment a $(C_3-C_4)$-cycloalkane ring, i.e. a cyclopropane or cyclobutane ring, and in another embodiment it is a cyclopropane ring. Since the carbon atom, which together with R30 and R31 can form a cycloalkane ring and via which the cycloalkane ring is bonded, carries also the group R34, a group R34 different from hydrogen may be regarded as a substituent on such a cycloalkane ring, in one embodiment, the number of fluorine and $(C_1-C_4)$-alkyl substituents which can be present on a cycloalkane nny which can be formed by R32 and R33 together with the carbon atom carrying them, is 1, 2, 3 or in another embodiment it is 1 or 2, and in another embodiment such a cycloalkane ring does not carry fluorine or $(C_1-C_4)$-alkyl substituents, but only the group R34.

In one embodiment of the invention, R32 is selected from the series consisting of hydrogen and $(C_1-C_2)$-alkyl, in another embodiment from the series consisting of hydrogen and methyl, and in another embodiment R32 is hydrogen.

In one embodiment of the invention, R33 is selected from the series consisting of hydrogen, $(C_1-C_4)$-alkyl, $(C_3-C_7)$-cycloalkyl and R37—$(C_1-C_4)$-alkyl-, in another embodiment from the series consisting of hydrogen, $(C_1-C_4)$-alkyl, $(C_3-C_7)$-cycloalkyl and R37—$(C_1-C_4)$-alkyl, wherein R37 is $(C_3-C_7)$-cycloalkyl, in another embodiment from the series consisting of hydrogen, $(C_1-C_4)$-alkyl and $(C_3-C_7)$-cycloalkyl, in another embodiment from the series consisting of series consisting of hydrogen, $(C_1-C_4)$-alkyl, $(C_3-C_7)$-cycloalkyl and $(C_1-C_4)$-alkyl-O—C(O)—, in another embodiment from the series consisting of hydrogen, $(C_1-C_4)$-alkyl and cyclopropyl, in another embodiment from the series consisting of hydrogen and $(C_1-C_4)$-alkyl, in another embodiment from the series consisting of $(C_1-C_4)$-alkyl and $(C_3-C_7)$-cycloalkyl, in another embodiment from the series consisting of $(C_1-C_4)$-alkyl and cyclopropyl, in another embodiment from the series consisting of hydrogen, methyl, ethyl, n-propyl, isopropyl, n-butyl, sec-butyl, isobutyl, tert-butyl and cyclopropyl. In another embodiment, R33 is $(C_1-C_4)$-alkyl, in another embodiment $(C_1-C_3)$-alkyl, in another embodiment $(C_1-C_2)$-alkyl, in another embodiment methyl.

In one embodiment of the invention, R32 and R33 do not form a cycloalkane ring together with the carbon atom carrying them, and only have their individual meanings, i.e., in this embodiment the group R32 is selected from the series consisting of hydrogen and $(C_1-C_4)$-alkyl, or from a series mentioned in any embodiment herein, and the group R33 is selected from the series consisting of hydrogen, $(C_1-C_4)$-alkyl, $(C_3-C_7)$-cycloalkyl, R37—$(C_1-C_4)$-alkyl- and $(C_1-C_4)$-alkyl-O—C(O)—, or from a series mentioned in any embodiment herein. In another embodiment, R32 and R33 do not have their individual meanings, and only form, together with the carbon atom carrying them, a $(C_3-C_7)$-cycloalkane ring which, irrespective of the group R34, is unsubstituted or substituted by one or more identical or different substituents selected from the series consisting of fluorine and $(C_1-C_4)$-alkyl.

In one embodiment of the invention, R34 is selected from the series consisting of $(C_1-C_6)$-alkyl, $(C_3-C_7)$-cycloalkyl, R38—$(C_3-C_7)$-cycloalkyl-, $(C_1-C_4)$-alkyl-O—C(O)—, (R39)(R40)N—C(O)—, phenyl and Het2, in another embodiment from the series consisting of $(C_1-C_6)$-alkyl, $(C_3-C_7)$-cycloalkyl, $(C_1-C_4)$-alkyl-O—C(O)—, (R39)(R40)N—C(O)—, phenyl and Het2, in another embodiment from the series consisting of $(C_1-C_6)$-alkyl, $(C_3-C_7)$-cycloalkyl, $(C_1-C_4)$-alkyl-O—C(O)—, phenyl and Het2, in another embodiment, from the series consisting of $(C_3-C_7)$-cycloalkyl, $(C_1-C_4)$-alkyl-O—C(O)—, (R39)(R40)N—C(O)—, phenyl and Het2, in another embodiment from the series consisting of $(C_3-C_7)$-cycloalkyl, $(C_1-C_4)$-alkyl-O—C(O)—, phenyl and Het2, In another embodiment from the series consisting of $(C_1-C_4)$-alkyl-O—C(O)—, phenyl and Het2, in another embodiment from the series consisting of phenyl and Het2, in another embodiment R34 is $(C_1-C_4)$-alkyl-O—C(O)—, in another embodiment R34 is phenyl, and in another embodiment R34 is Het2, wherein in all these embodiments the $(C_1-C_6)$-alkyl is unsubstituted or substituted by one or more identical or different substituents R41, and the phenyl is unsubstituted or substituted by one or more identical or different substituents R35. In one embodiment, R34 is selected from the series consisting of $(C_1-C_4)$-alkyl-O—C(O)—, cyclopropyl, phenyl and Het2, wherein the phenyl and Het2 groups are unsubstituted or substituted by one or two identical or different substituents selected from the series consisting of fluorine, chlorine, cyano, $(C_1-C_4)$-alkyl and $(C_1-C_4)$-alkyl-O—. In one embodiment, the number of substituents R41 which is present on a substituted $(C_1-C_6)$-alkyl group representing R34, is 1, 2 or 3, in another embodiment it is 1 or 2, In another embodiment it is 1. In one embodiment, the number of substituents R35 which is present on a substituted phenyl group representing R34, is 1, 2 or 3, in another embodiment it is 1 or 2, in another embodiment it is 1.

In one embodiment of the invention, R30 is hydrogen and R31 is the group (R32)(R33)(R34)C—, i e., the group (R30)(R31)N— in the compounds of the formula I is the group (R32)(R33)(R34)C—NH—, wherein R32 is hydrogen, R33 is selected from the series consisting of hydrogen, methyl, ethyl, n-propyl, isopropyl, n-butyl, sec-butyl, isobutyl, tert-butyl and cyclopropyl, and R34 is selected from the series consisting of $(C_1-C_4)$-alkyl-O—C(O)—, cyclopropyl, phenyl and Het2, wherein the phenyl and Het2 groups are unsubstituted or substituted by one or two identical or different substituents selected from the series consisting of fluorine, chlorine, cyano, $(C_1-C_4)$-alkyl-and $(C_1-C_4)$-alkyl-O—.

In one embodiment of the invention, R35 is selected from the series consisting of halogen, $(C_1-C_4)$-alkyl, HO—$(C_1-C_4)$-alkyl-, NC—, HO—, $(C_1-C_4)$-alkyl-O—, $(C_1-C_4)$-alkyl-S(O)$_p$—, $(C_1-C_4)$-alkyl-S(O)$_2$—NH—, R42—O—C(O)—, (R43)(R44)N—C(O)— and (R45)(R46)N—S(O)$_2$—, in another embodiment from the series consisting of halogen, $(C_1-C_4)$-alkyl, HO—$(C_1-C_4)$-alkyl-, NC—, HO—, $(C_1-C_4)$-alkyl-O—, $(C_1-C_4)$-alkyl-S(O)$_p$— and $(C_1-C_4)$-alkyl-S(O)$_2$—NH—, in another embodiment from the series consisting of halogen, $(C_1-C_4)$-alkyl, NC—, in $(C_1-C_4)$-alkyl-O—, $(C_1-C_4)$-alkyl-S(O)$_p$— and $(C_1-C_4)$-alkyl-S(O)$_2$—NH—, in another embodiment from the series consisting of halogen, $(C_1-C_4)$-alkyl, NC— and $(C_1-C_4)$-alkyl-O—, in another embodiment from the series consisting of fluorine, chlorine, cyano, $(C_1-C_4)$-alkyl and $(C_1-C_4)$-alkyl-O—, in another embodiment from the series consisting of fluorine, chlorine, $(C_1-C_4)$-alkyl and $(C_1-C_4)$-alkyl-O—, wherein all alkyl groups can be substituted by one or more fluorine substituents, as applies in general. In another embodiment, R35 is selected from the series consisting of fluorine, chlorine, cyano, methyl, trifluoromeihyl and methoxy, and in another embodiment from the series consisting of fluorine, chlorine, methyl, trifluoromethyl and methoxy.

In one embodiment of the invention, the number of substituents R48, which is present in a substituted $(C_1-C_6)$-alkyl group representing R36, is 1, 2 or 3, in another embodiment it is 1 or 2, in another embodiment it is 1. In one embodiment, a $(C_1-C_6)$-alkyl group representing R36 which is unsubstituted or substituted by one or more identical or different substituents R48, is a $(C_1-C_4)$-alkyl group, in another embodiment a $(C_1-C_2)$-alkyl group, which are all unsubstituted or substituted by one or more identical or different substituents R48. In one embodiment, the total number of $(C_3-C_7)$-cycloalkyl, phenyl, Het3, $(C_3-C_7)$-cycloalkyl-O—, $(C_3-C_7)$-cycloalkyl-$(C_1-C_4)$-alkyl-O— and phenyl-O— groups representing the substituent R36 on a heterocycle formed by R30 and R31 together with the nitrogen atom carrying them, is 1 or 2, and in another embodiment it is 1. In one embodiment, R36 is selected from the series consisting of fluorine, $(C_1-C_4)$-alkyl, $(C_2-C_3)$-alkenyl, $(C_2-C_3)$-alkynyl, $(C_3-C_6)$-cycloalkyl, phenyl, Het3, HO—, $(C_1-C_4)$-alkyl-O—, $(C_3-C_6)$-cycloalkyl-O—, $(C_3-C_6)$-cycloalkyl-$(C_1-C_2)$-alkyl-O—, phenyl-O—, $(C_1-C_4)$-alkyl-S(O)$_p$—, NC— and R47—O—C(O)—, in another embodiment from the series consisting of fluorine, $(C_1-C_4)$-alkyl, ethenyl, ethynyl, $(C_3-C_6)$-cycloalkyl, phenyl, Het3, $(C_1-C_4)$-alkyl-O—, $(C_3-C_6)$-cycloalkyl-O—, $(C_3-C_6)$-cycloalkyl-$(C_1-C_2)$-alkyl-O—, phenyl-O—, $(C_1-C_4)$-alkyl-S(O)$_p$—; NC— and R47—O—C(O)—, in another embodiment from the series consisting of fluorine, $(C_1-C_4)$-alkyl, ethenyl, ethynyl, $(C_3-C_6)$-cycloalkyl, phenyl, Het3, $(C_1-C_4)$-alkyl-O—, $(C_3-C_6)$-cycloalkyl-O—, $(C_3-C_6)$-cycloalkyl-$(C_1-C_2)$-alkyl-O—, phenyl-O—, NC— and R47O—C(O)—, in another embodiment from the series consisting of fluorine, $(C_1-C_4)$-alkyl, ethenyl, ethynyl, $(C_3-C_6)$-cycloalkyl, phenyl, Het3, $(C_1-C_4)$-alkyl-O—, NC— and R47—O—C(O)—, in another embodiment from the series consisting of fluorine, $(C_1-C_4)$-alkyl, ethenyl, ethynyl, $(C_3-C_6)$-cycloalkyl, phenyl, Het3, NC— and R47—O—C(O)—, in another embodiment from the series consisting of fluorine, $(C_1-C_4)$-alkyl, $(C_3-C_6)$-cycloalkyl, phenyl, Het3, $(C_1-C_4)$-alkyl-O—, NC— and R47—O—C(O)—, in another embodiment from the series consisting of fluorine, $(C_1-C_4)$-alkyl, $(C_3-C_6)$-cycloalkyl, phenyl, Het3, NC— and R47—O—C(O)—, in another embodiment from the sereis consisting of fluorine, $(C_1-C_4)$-alkyl, $(C_3-C_6)$-cycloalkyl and R47—O—C(O)—, in another embodiment from the series consisting of fluorine, $(C_1-C_4)$-alkyl and R47—O—C(O)—, in another embodiment from the series consisting of fluorine and R47—O—C(O)—, in another embodiment from the series consisting of $(C_1-C_4)$-alkyl and R47—O—C(O)—, in another embodiment R36 is $(C_1-C_4)$-alkyl, alkyl, wherein in all these embodiments the $(C_1-C_4)$-alkyl group representing R36 is unsubstituted or substituted by one or more identical or different substituents R48 and, independently thereof, the $(C_1-C_4)$-alkyl group representing R36 can be substituted by one or more fluorine substituents, and in another embodiment R36 is unsubstituted $(C_1-C_4)$-alkyl. In another embodiment, R36 is selected from the series consisting of methyl, ethyl, isopropyl, cyclopropyl, trifluoromethyl, $(C_1-C_4)$-alkyl-O—C(O)-methyl-and $(C_1-C_4)$-alkyl-O—C(O)—, in another embodiment from the series consisting of methyl, ethyl, isopropyl, cyclopropyl and trifluoromethyl, in another embodiment from the series consisting of methyl and trifluoromethyl, in another embodiment R36 is methyl, in another embodiment R36 is selected from the series consisting of $(C_1-C_4)$-O—C(O)-methyl- and $(C_1-C_4)$-alkyl-O—C(O)—, and in another embodiment R38 is $(C_1-C_4)$-alkyl-O—C(O)—. In one embodiment, a substituent R36 on a further ring nitrogen atom in a substituted heterocycle formed by R30 and R31 together with the nitrogen atom carrying them, is selected from the series consisting of $(C_1-C_6)$-alkyl, $(C_2-C_4)$-alkenyl, $(C_2-C_4)$-alkynyl, $(C_3-C_7)$-cycloalkyl, phenyl, Het3, $((C_1-C_4)$-alkyl-S(O)$_p$— and R47—O—C(O)—, in another embodiment from the series consisting in $(C_1-C_6)$-alkyl, $(C_3-C_7)$-cycloalkyl, phenyl, Het3, $(C_1-C_4)$-alkyl-S(O)$_p$— and R47—O—C(O)—, in another embodiment from the series consisting of $(C_1-C_6)$-alkyl, $(C_3-C_7)$-cycloalkyl, phenyl, Het3 and R47—O—C(O)—, in another embodiment from the series consisting of $(C_1-C_6)$-alkyl, $(C_3-C_7)$-cycloalkyl, phenyl and Het3, in another embodiment from the series consisting of $(C_1-C_6)$-alkyl, $(C_3-C_7)$-cycloalkyl and R47—O—C(O)—, in another embodiment from the series consisting of $(C_1-C_6)$-alkyl and $(C_3-C_7)$-cycloalkyl, and in another embodiment it is $(C_1-C_6)$-alkyl, wherein the $(C_1-C_6)$-alkyl is unsubstituted or substituted by one or more identical or different substituents R48 and the Het3 is bonded via a ring carbon atom.

Examples of groups which can represent R36, and from any one or more of which R36 is selected in one embodiment of the invention, are fluorine, cyano, methyl, ethyl, isopropyl tertbutyl, trifluoromethyl, ethynyl, cyclopropyl, phenyl, methoxy, ethoxy, phenoxy, 4-fluoro-phenoxy-, cyclopropyl-methyl-O—, 2-methyl-propyl-O—, methyl-O—C(O)—, ethyl-O—C(O)—, isopropyl-O—C(O)—, methoxy-methyl-, trifluoromethoxy-methyl-, methyl-O—C(O)-methyl-, ethyl-O—C(O)-methyl, isopropyl-O—C(O)-methyl-, methyl-C(O)—O-methyl-, ethyl-C(O)—O-methyl-, methyl-C(O)—NH-methyl-, cyclopropyl-methyl-, hydroxy-methyl-, cyclopropyl-hydroxy-methyl-, phenyl-hydroxy-methyl-, 1-hydroxy-ethyl-, 1-methoxy-ethyl-, 1-hydroxy-1-methyl-ethyl-, 1-pyrazol-1-yl-ethyl- and a group Het3 which is selected from the series consisting of pyridin-2-yl, pyridin-3-yl, pyridin-4-yl, pyrimidin-2-yl, pyrimidin-4-yl, pyrimidin-5-yl, pyrazin-2-yl, isoxazol-3yl, isoxazol-4-yl, isoxazol-5-yl, pyrazol-3-yl and pyrazol-4-yl, wherein these groups Het3 are unsubstituted or substituted by one or two substituents which are independently of one another selected from the series consisting of methyl, trifluoromethyl and methoxy.

Examples of unsubstituted and substituted groups which can represent the group (R30)(R31)N— in which R30 and R31 together with the nitrogen atom carrying them form a heterocycle, and from any one or more of which a heterocycle formed by R30 and R31 together with the nitrogen atom carrying them is selected in one embodiment of the invention, are pyrrolidin-1-yl, 2-methyl-pyrrolidin-1-yl, ethyl-pyrrolidin-1-yl, 2-isopropyl-pyrrolidin-1-yl, 2-tert-butyl-pyrrolidin-1-yl, 2,2-dimethyl-pyrrolidin-1-yl, 2-fluoro-pyrrolidin-1-yl, 2-trifluoromethyl-pyrrolidin-1-yl, 2-cyano-pyrrolidin-1-yl, 2-ethynyl-pyrrolidin-1-yl, 2 - methoxy-pyrrolidin-1-yl, 2-ethoxy-pyrrolidin-1-yl, 2-trifluoromethoxy-pyrrolidin-1-yl, 2-cyclopropyl-pyrrolidin-1-yl, 2-phenyl-pyrrolidin-1-yl, 2-methoxymethyl-pyrrolidin-1-yl, 2-trifluoromethoxymethyl-pyrrolidin-1-yl, 2,5-bis-methoxymethyl-pyrrolidin-1-yl, 2-hydroxymethyl-pyrrolidin-1-yl, 2-(1-hydroxy-ethyl)-pyrrolidin-1-yl, 2-(2-hydroxy-ethyl)-pyrrlidin-1-yl, 2-(1-hydroxy-1-methyl-ethyl)-pyrrolidin-1-yl, 2-(1-methoxy-ethyl)-pyrrolidin-1-yl, 2-(1-hydroxy-1-phenyl-methyl)-pyrrolidin-1-yl, 2-(cyclopropyl-hydroxy-methyl-pyrrolidin-1-yl, 2-cyclopropyl-methoxy-pyrrolidin-1-yl, 2-methoxycarbonyl-pyrrolidin-1-yl, 2-ethoxycarbonyl-pyrrolidin-1-yl, 2-isopropoxycarbonyl-pyrrolidin-1-yl, 2-methoxycarbonyl-methyl-pyrrolidinyl-1-yl, 2-ethoxycarbonylmethyl-pyrrolidin-1-yl, 2-isopropoxycarbonylmethyl-pyrrolidin-1-yl, 2-(acetylamino-methyl)-pyrrolidin-1-yl-, 2-(3-methyl-isoxazol-5-yl)-pyrrolidin-1-yl, 2-(3,5-dimethyl-isoxazol-4-yl)-pyrrolidin-1-yl; 2-(1-methyl-1H-pyrazol-3-yl )-pyrrolidin-1-yl, 2-pyridin-2-yl-pyrrolidin-1-yl, 2-pyridin-3-yl-pyrrolidin-1-yl, 2-(6-methoxy-pyridin-3-yl)-pyrrolidin-1-yl, 2-(6-trifluoromethyl-pyridin-3-yl)-pyrrolidin-1-yl, 2-pyrazin-2-yl-pyrrolidin-1-yl, 2-pyrimidin-2-yl-pyrrolidin-1-yl, 2-(pyrazol-1-yl-methyl)-pyrrolidin-1-yl, 2-(1-pyrazol-1-yl-ethyl)-pyrrolidin-1-yl, 2-(morpholin-4-yl-methyl)-pyrrolidin-1-yl, 3-fluoro-pyrrolidin-1-yl, 3-cyano-pyrrolidin-1-yl, 3-methoxy-pyrrolidin-1-yl, 3-phenyl-pyrrolidin-1-yl, 3-(4-fluoro-phenoxy)-pyrrolidin-1-yl and 3-cyclopropyl-methoxy-pyrrolidin-1-yl.

In one embodiment of the invention, R37 is selected from the series consisting of $(C_3-C_7)$-cycloalkyl and $(C_1-C_4)$-alkyl-O—, in another embodiment R37 is $(C_3-C_7)$-cycloalkyl.

In one embodiment, of the invention, R38 is selected from the series consisting of phenyl and HO—, in another embodiment R38 is HO—.

In one embodiment of the invention, R39, R40, R49, R50 and R51 are independently of one another selected from the series consisting of hydrogen and $(C_1-C_2)$-alkyl, in another embodiment from the series consisting of hydrogen and methyl, and in another embodiment they are hydrogen.

In one embodiment of the invention, R41 is selected from the series consisting of $(C_3-C_7)$-cycloalkyl, phenyl Het1, HO— and $(C_1-C_4)$-alkyl-O—, in another embodiment from the series consisting of $(C_3-C_7)$-cycloalkyl, phenyl and Het1, in another embodiment from the series consisting of phenyl and Het1, and in another embodiment R41 is $(C_3-C_7)$-cycloalkyl.

In one embodiment of the invention, R42 and R47 are independently of one another selected from the series consisting of hydrogen and $(C_1-C_3)$-alkyl, in another embodiment from the series consisting of hydrogen and $(C_1-C_3)$-alkyl, in another embodiment they are hydrogen, in another embodiment they are $(C_1-C_4)$-alkyl, and in another embodiment they are $(C_1-C_3)$-alkyl In one embodiment of the invention, R43, R44, R45 and R46 are independently of one another selected from the series consisting of hydrogen and $(C_1-C_4)$-alkyl, in another embodiment from the series consisting of hydrogen and $(C_1-C_2)$-alkyl, in another embodiment from the series consisting of hydrogen and methyl, and in another embodiment they are hydrogen.

In one embodiment of the invention, R48 is selected from the series consisting of $(C_3-C_7)$-cycloalkyl, phenyl, Het3, HO—, $(C_1-C_4)$-alkyl-O—, $(C_1-C_4)$-alkyl-C(O)—O—, $(C_1-C_4)$-alkyl-C(O)-R49)N—, (R50)(R51)N—C(O)— and $(C_1-C_4)$-alkyl-O—C(O)—, in another embodiment from the series consisting of $(C_3-C_7)$-cycloalkyl, HO—, $(C_1-C_4)$-alkyl-O—, $(C_1-C_4)$-alkyl-C(O)—O—, $(C_1-C_4)$-alkyl-C(O)—(R49)N—, (R50)(R51)N—C(O)— and $(C_1-C_4)$-alkyl-O—C(O)—, in another embodiment from the series consisting of $(C_3-C_7)$-cycloalkyl, $(C_1-C_4)$-alkyl-O—, $(C_1-C_4)$-alkyl-C(O)—O—, $(C_1-C_4)$-alkyl-C(O)—(R49)N—, (R50)(R51)N—C(O)— and $(C_1-C_4)$-alkyl-O—C(O)—, in another rembodiment from the series consisting of $(C_3-C_7)$-cycloalkyl, $(C_1-C_4)$-alkyl-O—, $(C_1-C_4)$-alkyl-C(O)-13 O-13

, (R50)(R51)N—C(O)— and $(C_1-C_4)$-alkyl-O—C(O)—, in another embodiment from the series consisting of $(C_3-C_7)$-cycloalkyl, $(C_1-C_4)$-alkyl-O—, $(C_1-C_4)$-alkyl-C(O)—O— and $(C_1-C_4)$-alkyl-O—C(O)—, in another embodiment from the series consisting of $(C_1-C_4)$-alkyl-O—, $(C_1-C_4)$-alkyl-C(O)—O— and $(C_1-C_4)$-alkyl-O-13 C(O)—, in another embodiment from the series consisting of $(C_1-C_4)$-alkyl-O— and $(C_1-C_4)$-alkyl-C(O)—O—, in another embodiment R48 is $(C_3-C_7)$-cycloalkyl, and in another embodiment R48 is $(C_1-C_4)$-alkyl-O—C(O)—.

In one embodiment of the invention, the group Het1 is a 5-membered or 6-membered monocyclic, aromatic heterocycle, which is bonded via a ring carbon atom, and which comprises one ring heteroatom selected from the series consisting of nitrogen, oxygen and sulfur or one ring nitrogen atom and one further ring heteroatom which is selected from the series consisting of nitrogen, oxygen and sulfur, and in another embodiment Het1 is a 6-membered monocyclic, aromatic heterocycle which comprises one or two ring nitrogen atoms, wherein in all these embodiments Het1 is unsubstituted or substituted as specified. Examples of heterocyclic groups, from any one or more of which Het1 is selected in one embodiment of the invention, are pyridinyl, pyrimidinyl, pyrazinyl, pyridazinyl, pyrazolyl, imidazolyl, thiazolyl, isothiazolyl, oxazolyl, isoxazolyl, pyrrolyl, furanyl and thiophen-3-yl, including the more sepcific groups pyridin-2-yl, pyridin-3-yl, pyridin-4-yl, pyrimidin-2-yl, pyrimidin-4-yl, pyrimidin-5-yl, pyrazin-2-yl, pyridazin-3-yl, pyridazin-4-yl, pyrazol-3-yl, pyrazol-4-yl, imidazol-2-yl, imidazol-4-yl, thiazol-2-yl, thiazol-4-yl, thiazol-5-yl, isothiazol-3-yl, isothiazol-4-yl, isothiazol-5-yl, oxazol-2-yl, oxazol-4-yl, oxazol-5-yl, isoxazol-3-yl, osoxazol-4-yl, isoxazol-5-yl, pyrrol-2-yl, pyrrol-3-yl, furan-2-yl, furan-3-yl, thiophen-2-yl and thiophen-3-yl, which are all unsubstituted or substituted as specified. In one embodiment, Het1 is selected from the series consisting of pyridinyl, pyrimidinyl, thiazolyl and thiophenyl, in another embodiment from the series consisting of pyridinyl and pyrimidinyl, in another embodiment Het1 is pyridinyl, and in another embodiment Het1 is pyrimidinyl, these embodiments including the more specific groups pyridin-2-yl, pyridin-3-yl, pyridin-4-yl, pyrimidin-2-yl, pyrimidin-4-yl, pyrimidin-5-yl, thiazol-2-yl, thiazol-4-yl, thiazol-5-yl, thiophen-2-yl and thiophen-3-yl, which are all unsubstituted or substituted as specified. Unless specified otherwise, in one embodiment the number of substituents which is present on a substituted group Het1, is 1, 2 or 3, in another embodiment 1 or 2, in another embodiment 1. Unless specified otherwise, such as in the case of a group Het1 representing R21 which can be substituted by R24, in one embodiment the substituents in a substituted group Het1 are selected from the series consisting of halogen, $(C_1-C_4)$-alkyl, NC—, HO—, $(C_1-C_4)$-alkyl-O— and $(C_1-C_4)$-alkyl-S(O)$_p$—, in another embodiment from the series consisting of halogen, $(C_1-C_4)$-alkyl, NC—, HO— and $(C_1-C_4)$-alkyl-O—, in another embodiment from the series consisting of halogen, $(C_1-C_4)$-alkyl, NC— and $(C_1-C_4)$-alkyl-O—, in another embodiment from the series consisting of halogen, $(C_1-C_4)$-alkyl and $(C_1-C_4)$-alkyl-O—, in another embodiment from the series consisting of halogen and $(C_1-C_4)$-alkyl, wherein all alkyl groups can be substituted by one or more fluorine substituents. In case the substituents on a substituted group Het1 are selected from the series consisting of halogen $(C_1-C_4)$-alkyl, $(C_3-C_7)$-cycloalkyl, NC—, HO—, $(C_1-C_4)$-alkyl-O— and $(C_1-C_4)$-alkyl-S(O)$_p$—, in one embodiment substituents on a ring nitrogen atom in a substituted group Het1 are selected from the series consisting $(C_1-C_4)$-alkyl, $(C_3-C_7)$-cycloalkyl and $(C_1-C_4)$-alkyl-S(O)$_p$—, in another embodiment from the series consisting of $(C_1-C_4)$-alkyl and $(C_3-C_7)$-cycloalkyl, and in another embodiment they are $(C_1-C_4)$-alkyl.

Examples of unsubstituted and substituted heterocyclic groups, from any one or more of which Het1 is selected in one embodiment of the invention, are thiazol-2-yl, 5-trifluoromethyl-thiazol-2-yl, 4,5-dimethyl-thiazol-2-yl, thiophen-2-yl, 5-chloro-thiophen-2-yl, 5-bromo-thiophen-2-yl, 5-trifluoromethyl-thiophen-2-yl, 5-cyano-thiophen-2-yl, oxazol-2-yl, oxazol-5-yl, isoxazol-3-yl, isoxazol-5-yl, 3,5-dimethyl-isoxazol-4-yl, pyridin-2-yl, 6-methyl-pyridin-3-yl, 6-methoxy-pyridin-3-yl, 6-trifluoromethyl-pyridin-3-yl, 5-trifluoromethyl-pyridin-3-yl, 6-chloro-pyridin-3-yl, 6-bromo-pyridin-3-yl, 6-methylsulfanyl-pyridin-3-yl, 5-fluoro-pyridin-3-yl, 5-fluoro-pyridin-2-yl, 5-chloro-pyridin-3-yl, 2-trifluoromethyl-pyridin-3-yl, 6-hydroxy-pyridin-2-yl, 2-methoxy-pyridin-3-yl, 6-cyano-pyridin-3-yl, 5,6-dichloro-pyridin-3-yl, 5-chloro-6-methoxy-pyridin-3-yl, 4-chloro-6-trifluoromethyl-pyridin-3-yl, 5-chloro-6-methoxy-pyridin-3-yl, 4-chloro-6-trifluoromethyl-pyridin-3-yl, 5-fluoro-6-trifluoromethyl-ppyridin-2-yl, 4,6-bis-trifluoromethyl-pyridin-3-yl, 2-methyl-6-trifluoromethyl-pyridin-3-yl, 2-chloro-6-trifluoromethyl-pyridin-3-yl, 6-methoxy-5-trifluoromethyl-pyridin-3-yl, 5-methoxy-6-trifluoromethyl-pyridin-3-yl, 5-chloro-6-cyano-pyridin-3-yl, 3-methoxy-pyridin-2-yl, 6-methoxy-pyridin-2-yl, 6-cyano-pyridin-2-yl, 6-trifluoromethyl-pyridin-2-yl, 5-fluoro-pyridin-2-yl, 5-trifluoromethyl-pyridin-2-yl, 3-methoxy-pyridin-2-yl, 3-chloro-pyridin-2-yl, 3-chloro-pyridin-4-yl, 3-fluoro-2-trifluoromethyl-pyridin-4-yl, 3,5-dichloro-pyridin-4-yl, pyrimidin-2-yl, 5-trifluoromethyl-pyrimidin-2-yl, 2-trifluoromethyl-pyrimidin-5-yl, 2-methoxy-pyrimidin-5-yl, pyrazin-2-yl, 5-methoxy-pyrazin-2-yl and pyridazin-3-yl.

The group Het2 can be 4-membered, 5-membered, 6-membered, 7-membered, 8-membered, 9-membered or 10-membered. In one embodiment of the invention, Het2 is a 5-membered to 9-membered monocyclic or bicyclic heterocycle, in another embodiment it is a 4-membered to 7-membered monocyclic heterocycle or a 6-membered to 10-membered bicyclic heterocycle, in another embodiment it is a 4-membered to 7-membered monocyclic heterocycle, in another embodiment it is a 4-membered to 6-membered monocyclic heterocycle, in another embodiment it is a 5-membered to 6-membered monocyclic heterocycle, in another embodiment it is a 5-membered monocyclic heterocycle, in another embodiment it is a 6-membered monocyclic heterocycle, in another embodiment it is a 9-membered to 10-membered bicyclic heterocycle. In one embodiment, Het2 comprises 1, 2 or 3, in another embodiment 1 or 2, in another embodiment 1 ring heteroatom. In one embodiment, the ring heteroatoms in Het2 are selected from the series consisting of nitrogen and oxygen, in another embodiment from the series consisting of nitrogen and sulfur, in another embodiment from the series consisting of oxygen and sulfur, and in another embodiment they are nitrogen atoms. In one embodiment, Het2 comprises 1, 2, 3 or 4 ring nitrogen atoms, or 1 ring oxygen atom or 1 ring sulfur atom, or 1 or 2 ring nitrogen atoms and 1 ring oxygen atom or 1 ring sulfur atom. Examples of heterocyclic groups, from any one or more of which Het2 is selected in one embodiment, are pyridin2-yl, pyridin-3-yl, pyridin-4-yl, pyrimidin-2-yl, pyrimidin-4-yl, pyrimidin-5-yl, pyrazin-2-yl, pyridazin-3-yl, pyridazin-4-yl, pyrazol-3-yl, pyrazol-4-yl, imidazol-2-yl, imidazol-4-yl, [1,2,4]triazol-3yl, [1,2,4]triazol-5-yl, [1,2,4]oxadiazol-3-yl, [1,2,4]oxadiazol-5-yl, [1,2,4]thiadiazol-3-yl, [1,2,4]thiadiazol-5-yl, tetrazol-5-yl, thiazol-2-yl, thiazol- 4-yl, thiazol-5-yl, isothiazol-3-yl, isothiazol-4-yl, isothiazol-5-yl, oxazol-2-yl, oxazol-4-yl, oxazol-5-yl, isoxazol-3-yl, isoxazol-4-yl, isoxazol-5-yl, pyrrol-2-yl, pyrrol-3-yl, furan-2-yl, furan-3-yl, thiophen-2-yl, thiophen-3-yl, oxetan-2-yl, oxetan-3-yl, tetrahydrofuran-2-yl, tetrahydrofuran-3yl, pyrrolidin-2-yl, pyrrolidin-3-yl, tetrahydropyran-2-yl, tetrahydropyran-3-yl, tetrahydropyran-4-yl, piperidin-2-yl, piperidin-3-yl, piperidin-4-yl, piperazin-2-yl, thiazolidin-2-yl, thiazolidin-4-yl, thiazolidin-5-yl, morpholin-2-yl, morpholin-3-yl, thiomorpholin-2-yl, thiomorpholin-3-yl, indol-2-yl, indol-3-yl, indol-4-yl, indol-5-yl, indol-6-yl, indol-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinoiin-7-yl, isoquinolin-8-yl, quinoxalin-2-yl, quinoxalin-5-yl, quinoxalin-6-yl and cyclopenta-fused pyridinyl, pyrazinyl and pyrimidinyl groups and cyclohexa-fused pyridinyl, pyrazinyl and pyrimidinyl groups, which are all unsubstituted or substituted by one or more identical or different substituents selected from the series consisting of halogen, $(C_1-C_4)$-alkyl, NC—, HO— and $(C_1-C_4)$-alkyl-O—. In one embodiment the substituents on a substituted group Het2 are selected from the series consisting of halogen, $(C_1-C_4)$-alkyl, HO— and $(C_1-C_4)$-alkyl-O—, in another embodiment from the series consisting of halogen, $(C_1-C_4)$-alkyl, NC— and $(C_1-C_4)$-alkyl-O—, in another embodiment from the series consisting of halogen, $(C_1-C_4)$-alkyl and $(C_1-C_4)$-alkyl-O—, in another embodiment from the series consisting of halogen and $(C_1-C_4)$-alkyl, wherein all alkyl groups can be substituted by one or more fluorine substituents. In one embodiment substituents on a ring nitrogen atom in a substituted group Het2 are $(C_1-C_4)$-alkyl. In one embodiment, the number of substituents which is present on a substituted group Het2, is 1,2, 3 or 4, in another embodiment it is 1, 2 or 3, in another embodiment it is 1 or 2, in another embodiment it is 1.

In one embodiment, a group Het2 representing R31 is a 4-membered to 6-membered, monocyclic, saturated heterocycle which comprises one ring heteroatom which is an oxygen atom, or is $(C5-C_6)$-cycloalkyl to which a pyridine, pyrazine or pyrimidine ring is fused, which is bonded via a ring carbon atom, wherein the $(C_5-C_6)$-cycloalkyl is unsubstituted or substituted by one or two identical or different substituents selected from the series consisting of fluorine, $(C_1-C_4)$-alkyl and $(C_1-C_4)$-alkyl-O—, and the fused pyridine, pyrasine and pyrimidine rings all are unsubstituted or substituted by one or two identical or different substituents selected from the series consisting of halogen, $(C_1-C_4)$-alkyl, NC—, HO— and $(C_1-C_4)$-alkyl-O—. Examples of heterocyclic groups, from any one or more of which a group Het2 representing the group R31 is selected in another embodiment, are pyridin-2-yl, pyridin-3-yl, pyridin-4-yl, pyrimidin-2-yl, pyrimidin-4-yl, pyrimidin-5-yl, pyrazin-2-yl, pyrazol-3-yl, pyrazol-4-yl, imidazol-2-yl, imidazol-4yl, [1,2,4]triazol-3-yl, [1,2,4]triazol-5-yl, thiazol-2yl, thiazol-yl, thiazol-5-yl, isothiazol-3-yl, isothiazol-4-yl, isothiazol-5-yl, oxazol-2-yl, oxazol-4-yl, oxazol-5-yl, ilsoxazol-3-yl, isoxazol-4-yl, isoxazol-5-yl, pyrrol-2-yl, pyrrol-3-yl, thiophen-2-yl, thiophen-3-yl, oxetan-2-yl, oxetan-3-yl, tetrahydrofuran-2-yl, tetrahydrofuran-3-yl, tetrahydropyran-2-yl, tetrahydropyran-3-yl, tetrahydropyran-4-yl, cyclopenta-fused pyridinyl, pyrimidinyl and pyrazinyl groups, and cyclohexa-fused pyridinyl, pyrimidinyl and pyrazinyl groups including 5,6,7,8-tetrahydroquinolinyl, 5,6,7,8-tetrahydroisoquinolinyl, 5,6,7,8-tetrahydroquinoxalinyl and 5,6, 7,8-tetrahydroquinazolinyl, which are all unsubstituted or substituted as specified. In another embodiment, a group Het2 representing the group R31 is selected from the series consisting of isoxazol-4-yl, 3,5-dimethyl-isoxazol-4-yl, thiazol-2-yl, 4,5-dimethyl-thiazol-2-yl, pyridin-2-yl, 5-fluoro-pyridin-2-yl, pyridin-3-yl and 5-fluoro-pyridin-3-yl. In one embodiment a group Het2 representing R34 is 5-membered to 6-membered, monocyclic, saturated, partially unsaturated or aromatic heterocycle comprising 1, 2, 3 or 4 nitrogen atoms, or 1 oxygen atom or sulfur atoms, or 1 or 2 nitrogen atoms and 1 oxygen atom or sulfur atom, as ring heteroatoms, which is bonded via a ring carbon atom and which is unsubstituted or substituted by one or more identical or different substituents selected from the series consisting of halogen, $(C_1-C_4)$-alkyl, NC—HO— and $(C_1-C_4)$-alkyl-O—. Examples of heterocyclic groups, from any one or more of which a group Het2 representing the group R34 is selected in another embodiment, are thiazol-2-yl, 5-trifluoromethyl-thiazol-2-yl, 4,5-dimethyl-thiazol-2-yl, thiophen-2-yl, 5-chloro-thiophen-2-yl, 5-bromo-thiophen-2-yl, 5-trifluoromethyl-thiophen-2-yl, 5-cyano-thiophen-2-yl, oxazol-2-yl, oxazol-2-yl, benzoxazol-2-yl, isoxazol-3-yl, isoxazol-5-yl, 3,5-dimethyl-isoxazol-4-yl, 2H-[1,2,4]thazol-3-yl, 1-methyl-1H-tetrazol-5-yl, 1-ethyl-1H-tetrazol-5-yl, 2-methyl-2H-tetrazol-5-yl, 2-ethyl-2H-tetrazol-3-yl, pyridin-2-yl, 6-methyl-pyridin-3-yl, 6-methoxy-pyridin-3-yl, 6-trifluoromethyl-pyridin-3-yl, 5-trifluoromethyl-pyridin-3-yl, 6-chloro-pyridin-3-yl, 6-bromo-pyridin-3-yl, 6-methylsulfanyl-pyridin-3-yl, 5-fluoro-pyridin-3-yl, 5-fluoro-pyridin-2-yl, 5-chloro-pyridin-3-yl, 2-trifluoromethyl-pyridin-3-yl, 2-methoxy-pyridin-3-yl, 6-cyano-pyridin-3-yl, 5,6-dichloro-pyridin-3-yl, 5-chloro-6-methoxy-pyridin-3-yl, 4-chloro-5-trifluoromethyl-pyridin-35-fluoro-6-trifluoromethyl-pyridin-2-yl, 4,6-bis-trifluoromethyl-pyridin-3-yl, 2-methyl-6-trifluoromethyl-pyridin-3-yl, 2-chloro-6-trifluoromethyl-pyridin-3-yl, 6-methoxy-5-trifluoromethyl-pyridin-3-yl, 5-methoxy-6-trifluoromethyl-pyridin-3yl, 5-chloro-6-cyano-pyridin3-yl, 3-methoxy-pyridin-2-yl, 6-methoxy-pyridin-2-yl, 6-cyano-pyridin-2-yl, 6-trifluoromethyl-pyridin-2yl, 5-fluoro-pyridin-2yl, 5-trifluoromethyl-pyridin-2-yl, 3-methoxy-pyridin-2-yl, 3-chloro-pyridin-2-yl, 3-chloro-pyridin-4-yl, 3-fluoro-2-trifluoromethyl-pyridin-4-yl 3,5-dichloro-pyridin-4-yl, pyrimidin-2-yl, 5-trifluoromethyl-pyrimidin-2-yl, 2-trifluoromethyl-pyrimidin-5-yl, 2-methoxy-pyrimidin-5-yl, pyrazin-2-yl, 5-methoxy-pyrazin-2-yl, pyridazin-3-yl, 6-hydroxy-pyridin-2-yl (6-oxo-1,6-dihydro-pyridin-2-yl) and 1H-indol-6-yl.

The group Het3 can be 4-membered, 5-membered, 6-membered or 7-membered. In one embodiment of the invention, Het3 is a 5-membered to 7-membered heterocycle, in another embodiment in another embodiment it is a 4-membered to 6-membered heterocycle, in another embodiment a 5-membered to 6-membered heterocycle, in another embodiment 5-membered heterocycle, in another embodiment a 6-membered heterocycle. In one embodiment, Het3 is a saturated or aromatic heterocycle, in another embodiment it is a saturated heterocycle, in another embodiment it is an aromatic heterocycle. In one embodiment, Het3 comprises 1 or 2 identical or different ring heteroatoms, in another embodiment 1 ring heteroatom. In one embodiment, the ring heteroatoms in Het3 are selected from the series consisting of nitrogen and oxygen, in another embodiment from the series consisting of nitrogen and sulfur, in another embodiment from the series consisting of oxygen and sulfur, and in another embodiment they are nitrogen atoms. In one embodiment, Het3 comprises 1, 2 or 3 ring nitrogen atoms, or 1 ring sulfur atom or 1 ring oxygen atom, or 1 ring nitrogen atom and 1 one ring sulfur atom or 1 ring oxygen atom. Het3 can be bondad via any suitable ring carbon atom or ring nitrogen atom, in one embodiment, Het3 is bonded via a ring carbon atom, in another embodiment Het3 is bonded via a ring nitrogen atom. Examples of heterocyclic groups, from any one or more of which Het3 is selected in one embodiment of the invention, are pyridinyl, pyrimidinyl, pyrazinyl, pyridazinyl, pyrazolyl, imidazolyl, thiazolyl, isothiazolyl, oxazolyl, isoxazolyl, pyrrolyl, furanyl, thiophenyl, tetrahydropyranyl, piperidinyl, piperazinyl, morpholinyl and thiomorpholinyl, which are all unsubstituted or substituted as specified. Examples of more specific heterocyclic groups, from any one or more of which Het3 is selected in another embodiment, are pyridin-2-yl, pyridin-3-yl, pyridin-4-yl, pyrimidin-2-yl, pyrimidin-4-yl, pyrimidin-5-yl, pyrazin-2-yl, pyrazol-1-yl pyrazol-3-yl, pyrazol-4-yl, isoxazol-3-yl, isoxazol-4-yl, isoxazol-5-yl, oxazol-2-yl, oxazol-4yl, oxazol-5-yl, isothiazol-3-yl, isothiazol-4-yl, isothiazol-5-yl, thiazol-2-yl, thiazol-4-yl, thiazol5-yl, thiophen-2-yl, thiophen-3-yl, tetrahydropyran-2-yl, tetrahydropyran-3-yl, tetrahydropyran-4-yl, piperidin-2-yl, piperidin-3-yl, piperidin-4-yl, piperazin-2-yl, morpholin-2-yl, morpholin-3-yl, morpholin-4-yl, thiomorpholin-2-yl, thiomorpholin-3-yl and thiomorpholin-4-yl and partially unsaturated and saturated forms of pyridin-1-yl, pyrimidin-1-yl, pyrazin-1-yl, isoxazol-2-yl, oxazol-3-yl, isothiazol-2-yl and thiazol-3-yl including piperidin-1-yl and piperazin-1-yl, which are all unsubstituted or substituted as specified, in one embodiment, the number of substituents on a substituted group Het3 is 1, 2, 3 or 4, in another embodiment it is 1, 2 or 3, in another embodiment it is 1 or 2, in another embodiment it is 1. In one embodiment, substituents on a group Het3 are selected from the series consisting of halogen, $(C_1-C_4)$-alkyl, $(C_3-C_7)$-cycloalkyl, NC—, HO— and $(C_1-C_4)$-alkyl-O, in another embodiment from the series consisting of halogen, $(C_1-C_4)$-alkyl, $(C_3-C_7)$-cycloalkyl, NC—, $(C_1-C_4)$-alkyl-O— and $(C_1-C_4)$-alkyl-S(O)$_p$—, in another embodiment from the series consisting of halogen, $(C_1-C_4)$-alkyl, $(C_3-C_7)$-cycloalkyl, NC— and $(C_1-C_4)$-alkyl-O—, in another embodiment from the series consisting of halogen, $(C_1-C_4)$-alkyl, NC— and $(C_1-C_4)$-alkyl-O—. in another embodiment from the series consisting of halogen, $(C_1-C_4)$-alkyl and $(C_1-C_4)$-alkyl-O—, In another embodiment from the series consisting of halogen and $(C_1-C_4)$-alkyl, wherein all alkyl groups can be substituted by one or more fluorine substituents. In one embodiment substituents on a ring nitrogen atom in a substituted group Het3 are selected from the series consisting of $(C_1-C_4)$-alkyl, $(C_3-C_7)$-cycloalkyl and $(C_1-C_4)$-alkyl-S(O)$_p$—, in another embodiment from the series consisting of $(C_1-C_4)$-alkyl and $(C_3-C_7)$-cycloalkyl, and in another embodiment they are $(C_1-C_4)$-alkyl.

Phenyl groups in compounds of the formula I, with respect to which no other substitution is specified such as phenyl groups representing the group R21 which are unsubstituted or substituted by one or more identical or different substituents R24 or phenyl groups representing the group R34 which are unsubstiuted or substituted by one or more identical or different substituents R35, are unsubstituted or substituted by one or more identical or different substituents selected from the series consisting of halogen, $(C_1-C_4)$-alkyl, NC—, HO— and $(C_1-C_4)$-alkyl-O—, in one embodiment from the series consisting of halogen, $(C_1-C_4)$-alkyl, NC— and $(C_1-C_4)$-alkyl-O—, in another embodiment from the series consisting of halogen, $(C_1-C_4)$-alkyl and $(C_1-C_4)$-alkyl-O—, in another embodiment from the series consisting of halogen and $(C_1-C_4)$-alkyl, wherein an alkyl groups can be substituted by one or more fluorine substituents, and wherein all phenyl groups are independent of one another.

Examples of groups, from any one or more of which phenyl groups occurring in the compounds of the formula, including a phenyl group representing R21 and a phenyl group representing R34, are independently of one another selected in one embodiment of the invention, are phenyl, 2-fluoro-phenyl, 3-fluoro-phenyl, 4-fluoro-phenyl, 2,4-difluoro-phenyl, 3,4-difluoro-phenyl, 2,6-difluoro-phenyl, 2,4,6-trifluoro-phenyl, 2-chloro-phenyl, 3-chloro-phenyl, 4-chloro-phenyl, 2,4-dichloro-phenyl, 3,4-dichloro-phenyl, 2,6-dichloro-phenyl, 2-chloro-4-cyano-phenyl, 2-chloro-5-cyano-phenyl, 3-chloro-4-cyano-phenyl, 3-chloro-5-cyano-phenyl, 2-chloro-4-fluoro-phenyl, 2-chloro-5-fluoro-phenyl, 2-chloro-6-fluoro-phenyl, 3-chloro-4-fluoro-phenyl, 2-chloro-4-trifluoromethyl-phenyl, 2-chloro-5-trifluoromethyl-phenyl, 2-chloro-6-trifluoromethyl-phenyl, 3-chloro-4-trifluoromethyl-phenyl, 3-chloro-5-trifluoromethyl-phenyl, 4-chloro-3-trifluoromethyl-phenyl; 2-cyano-phenyl, 3-cyano-phenyl, 4-cyano-phenyl, 3-cyano-4-fluoro-phenyl, 4-cyano-2fluoro-pheny, 3-cyano-4-trifluoromethyl-phenyl, 4-cyano-2,6-difluoro-phenyl, 4-cyano-3,5-drifluoro-phenyl, 2-fluoro-4-trifluoromethyl-phenyl, 3-fluoro-4-trifluoromethyl-phenyl, 4-fluoro-3-trifluoromethyl-phenyl, 2,6-difluoro-4-trifluoromethyl-phenyl, 2-hydroxy-phenyl, 3-hydroxy-phenyl, 4-hydroxy-phenyl, 2-methyl-phenyl, 3-methyl-phenyl, 4-methyl-phenyl, 4-difluoromethyl-phenyl, 1,1-difluoroethyl-phenyl, 2-trifluoromethyl-phenyl, 3-trifluoromethyl-phenyl, 4-trifluoromethyl-phenyl, 2,4-bis-trifluoromethyl-phenyl, 3,5-bis-trifluoromethyl-phenyl, indan-4-yl, indan-5-yl, 2-methoxy-phenyl, 3-methoxy-phenyl, 4-methoxy-phenyl, 3,5-dimethoxy-phenyl, 2-difluoromethoxy-phenyl, 2-trifluoromethoxy-phenyl, 4-difluoromethoxy-phenyl, 4-trifluoromethoxy-phenyl, 2,3-methylenedioxy-phenyl (benzo[1,3]dioxol-4-yl), 3,4-methylenedioxy-phenyl (benzo[1,3]dioxol-5yl), 2,3-(difluoromethylenedioxy)-phenyl (2,2-difluoro-benzo[1,3]dioxol-4-yl), 3,4-(difluoromethylenedioxy)-phenyl (2,2-difluoro-benzo[1,3]dioxol-5-yl), 1-oxo-1,3-dihydro-isobenzofuran-5-yl, 2-pentafluorosulfanyl-phenyl, 3-pentafluorosulfanyl-phenyl, 4-pentafluorosulfanyl-phenyl, 2-methylsulfanyl-phenyl, 3-methylsulfanyl-phenyl, 4-methylsulfanyl-phenyl, 2-methylsulfanyl-phenyl, 3-ethylsulfanyl-phenyl, 4-ethylsulfanyl-phenyl, 2-trifluoromethylsulfanyl -phenyl, 3-trifluoromethylsulfanyl-phenyl, 4-trifluoromethylsulfanyl-phenyl, 2-methanesulfonyl-phenyl, 3-methanesulfonyl-phenyl, 4-methanesulfonyl-phenyl, 2-ethanesulfonyl-phenyl, 3-ethanesulfonyl-phenyl, 4-ethanesulfonyl-phenyl, 3-methanesulfonylamino-phenyl, 3-sulfamoyl-phenyl, 3-dimethylsulfamoyl-phenyl, 3-carboxyphenyl, 4-carboxyphenyl, 3-methoxycarbonylphenyl, 4-methoxycarbonylphenyl, 3-ethoxycarbonylphenyl and 4-ethoxycarbonylphenyl.

In one embodiment of the invention, the group R20—NH— is the group (R21)(R22) (R23)C—NH— wherein R23 is hydrogen and wherein the resulting group (R21)(R22)CH—NH— has the stereo isomeric structure depicted in the following formula, in which the Une crossed by the dashed line denotes the bond by which the group (R21)(R22)CH—NH— is bonded to the C(O) group depicted in formula I

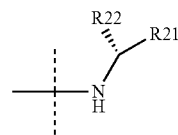

In another embodiment of the invention, the group R20—NH— is the group (R21)(R22)(R23)C—NH— wherein R23 is hydrogen and wherein the resulting group (R21)(R22)CH—NH— has the stereoisomers structure depicted in the following formula, in which the line crossed by the dashed line denotes the bond by which the group (R21)(R22)CH—NH— is bonded to the C(O) group depicted in formula I.

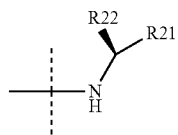

In one embodiment: of the invention, the groups R30 and R31 together with the nitrogen atom carrying them form a saturated heterocycle, which carries a substituent R36 on a ring carbon atom adjacent to the ring nitrogen atom via which the heterocycle is bonded, and one or two further substituents R36 in any other ring positions which further substituents can be presenter absent, wherein the resuming groups have wsth respect, to the ring carbon atom adjacent, to the said ring nitrogen atom the stereoisomeric structure depicted in the following formulae, in which the line crossed by the dashed line denotes the bond by which the heterocyclic group representing the group (R30)(R31)N— is bonded to the C(O) group depicted in formula I.

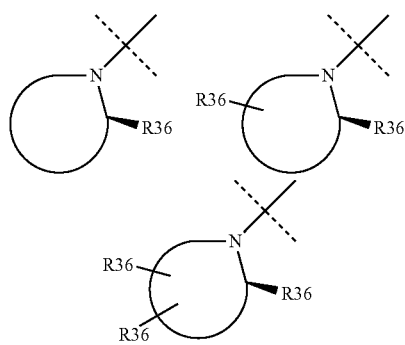

In another embodiment, the groups R30 and R31 together with the nitrogen atom carrying them form a pyrrolidine ring, which cames a substituent R36 on a ring carbon atom in position 2, and one further substituem R36 in any other ring position which further substituent can be present; or absent, wherein the resulting groups have with respect to the ring carbon atom in position 2 the stereoisomeric structure depicted in the following formulae, in which the line crossed by the dashed line denotes the bond by which the pyrrolidinyl group representing the group (R30)(R31)N— is bonded to the C(O) group depicted in formula I.

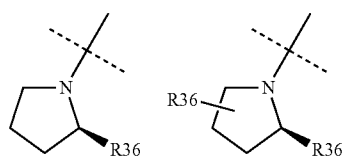

A subject of the invention are all compounds of the formula I wherein any one or more structural elements such as groups, residues, substituents and numbers are defined as in any of the specified embodiments or definitions of the elements, or have one or more of the specific meanings which are mentioned herein as examples of elements, wherein all combinations of one or more definitions of compounds or elements and/or specified embodiments and/or specific meanings of elements are a subject of the present invention. Also with respect to all such compounds of the formula I, all their stereoisomeric forms and mixtures of stereoisomeric forms in any ratio, and their pharmaceutically acceptable salts are a subject of the present invention. Examples of such combinations of one or more definitions of compounds or elements and/or specified embodiments and/or specific meanings of elements have already been given above.

Another example of such compounds of the invention, which with respect to any structural elements are defined as in one or more specified embodiments of the invention or definitions of such elements or have meanings mentioned as examples of elements, are compounds of the formula I, in any of their stereoisomeric forms and mixtures of stereoisomeric forms in any ratio, and the pharmaceutically acceptable salts thereof, wherein the number n is 1 and the number m is selected from the series consisting of 0 and 1. Another example of such compounds are compounds of the formula I, in any of their stereoisomeric forms and mixtures of stereoisomeric forms in any ratio, and the pharmaceutioally acceptable salts thereof, wherein the number n is 1 and the number m is 1. Another example of such compounds are compounds of the formula I, in any of their stereoisomeric forms and mixtures of stereoisomeric forms in any ratio, and the pharmaceutically acceptable salts thereof, wherein n is 1;

m is selected from the series consisting of 0 and 1 if X is sulfur or (R10)(R11)C, and m is 1 if X is oxygen;

R3 is selected from the series consisting of hydrogen, Huonne. chlonne, bromine and $(C_1$-$C_4)$-alkyl;

R4, R5, R6, R7, R8, R9, R10 and R11 are independently of one another selected from the series consisting of hydrogen and $(C_1$-$C_4)$-alkyl, with the proviso that at least six of these groups are hydrogen.

Another example of such compounds are compounds of the formula I, in any of their stereoisomersc forms and mixtures of stereoisomeric forms in any ratio, and the pharmaceutical acceptable salts thereof, wherein n is 1;

m is 1;

X is selected from the series consisting of oxygen, sulfur and (R10)(R11)C;

one of the groups R1 and R2 is the group R20—NH— and the other of the groups R1 and R2 is the group (R30)(R31)N—;

R3, R4, R5, R6, R7, R8, R9, R10 and R11 are hydrogen;

R20 is (R21)(R22)(R23)C—;

R21 is selected from the series consisting of phenyl and Het1, which are all unsubstituted or substituted by one. two or three identical or different substituents R24;

R22 is selected from the series consisting of hydrogen, $(C_1$-$C_4)$ -alkyl and cyclopropyl; R23 is hydrogen;

R24 is selected from the series consisting of fluorine, chlorine, bromine, $(C_1$-$C_4)$-alkyl, $(C_3$-$C_7)$-cycloalkyl-, HO—, $(C_1$-$C_4)$-alkyl-O—, $(C_1$-$C_4)$-alkyl-S(O)$_p$—, $F_5S$—, NC— and $(C_1$-$C_4)$-alkyl-O—C(O)—;

R30 is selected from the series consisting of hydrogen, $(C_1$-$C_4)$-alkyl, cyclopropyl-$(C_1$-$C_4)$-alkyl-, HO—$(C_1$-$C_2)$-alkyl- and $(C_1$-$C_2)$-alkyl-O—$(C_1$-$C_2)$-alkyl-;

R31 is selected from the series consisting of $(C_3-C_6)$-cycloalkyl, $(C_5-C_6)$-cycloalkyl to which a benzene ring is fused, phenyl, Het2 and $(R32)(R33)(R34)C—$, wherein the $(C_3-C_6)$-cycloalkyl and $(C_5-C_6)$-cycloalkyl are unsubstituted or substituted by one or two identical or different substituents selected from the series consisting of fluorine, $(C_1-C_4)$-alkyl, HO— and $(C_1-C_4)$-alkyl-O— and the fused benzene ring is unsubstituted or substituted by one or two identical or different substituents R35;

or the groups R30 and R31, together with the nitrogen atom carrying them, form a 4-membered to 7-membered, monocyclic, saturated heterocycle which, in addition to the nitrogen atom carrying R30 and R31, composes 0 or 1 further ring heteroatom selected from the series consisting of nitrogen, oxygen and sulfur, and which is unsubstituted or substituted by one or two identical or different substituents R36;

R32 is selected from the series consisting of hydrogen and $(C_1-C_4)$-alkyl;

R33 is selected from the series cons-sting of hydrogen, $(C_1-C_4)$-alkyl, cyclopropyl and $R37-(C_1-C_2)$-alkyl-;

R34 is selected from the series consisting of hydrogen, $(C_1-C_6)$-alkyl, $(C_3-C_6)$-cycloalkyl, $R38-(C_3-C_6)$-cycloalkyl, $(C_1-C_4)$-alkyl-O—C(O)—, $(R39)(R40)N—C(O)—$, phenyl and Het2, wherein the $(C_1-C_6)$-alkyl is unsubstituted or substituted by one or two identical or different substituents R41, and the phenyl is unsubstituted or substituted by one or more identical or different substituents R35;

R35 is selected from the series of fluorine, chlorine, bromine, $(C_1-C_4)$-alkyl, HO—$(C_1-C_4)$-alkyl-, $(C_1-C_4)$-alkyl-O—$(C_1-C_4)$-alkyl-, $(C_1-C_4)$-alkyl-O—C(O)—$(C_1-C_4)$-alkyl-, NC—, HO—, $(C_1-C_4)$-alkyl-O—, $(C_1-C_4)$-alkyl-S(O)$_p$—, $(C_1-C_4)$-alkyl-S(O)$_2$—NH—, R42—O—C(O)—, $(R43)R44)N—C(O)—$ and $(R45)(R46)N—S(O)_2$—;

R36 is selected from the series consisting of fluorine, $(C_1-C_4)$-alkyl, ethenyl, ethynyl, $(C_3-C_6)$-cycloalkyl, phenyl, Het3, $(C_1-C_4)$-alkyl-O—, $(C_3-C_6)$-cycloalkyl-O—, $(C_3-C_6)$-cycloalkyl-$(C_1-C_2)$-alkyl-O—, phenyl-O—, $(C_1-C_2)$-alkyl-S(O)$_p$—, NC— and R47O—C(O)—, wherein the $(C_1-C_4)$-alkyl is unsubstituted or substituted by one or two identical or different substituents R48;

R37 is selected from the series consisting of cyclopropyl and $(C_1-C_2)$-alkyl-O—;

R38 is selected from the series consisting of phenyl, HO— and $(C_1-C_2)$-alkyl-O—;

R39, R40, R42, R47, R49, R50 and R51 are independently of one another selected from the series consisting of hydrogen and $(C_1-C_4)$-alkyl;

R41 is selected from the series consisting of $(C_3-C_6)$-cycloalkyl; phenyl, Het1, HO—, $(C_1-C_4)$-alkyl-O— and $(C_1-C_4)$-alkyl-S—;

R43, R44, R45 and R46 are independently of one another selected from the series consisting of hydrogen, $(C_1-C_4)$-alkyl, HO—$(C_1-C_4)$-alkyl- and $(C_1-C_4)$-alkyl-O—$(C_1-C_4)$-alkyl-;

R48 is selected from the series consisting of $C_3-C_6$-cycloalkyl, phenyl, Het3, HO—, $(C_1-C_4)$-alkyl-O—, $(C_1-C_4)$-alkyl-C(O)—O—, $(C_1-C_4)$-alkyl-S(O)$_p$—, $(C_1-C_4)$-alkyl-C(O)—(R49)N—, $(R50)(R51)N—C(O)—$ and $(C_1-C_4)$-alkyl-O—C(O)—$;

p is selected from the series consisting of 0 and 2, wherein all numbers p are independent of one another;

Het1 is a 5-membered or 8membered, monocyclic, aromatic heterocycle comprising one ring heteroatom selected from the series consisting of nitrogen, oxygen and sulfur or one ring nitrogen atom and one further ring heteroatom selected from the series consisting of nitrogen, oxygen and sulfur, which is bonded via a ring carbon atom and which is unsubstituted or substituted by one or more identical or different substituents selected from the series consisting of halogen, $(C_1-C_4)$-alkyl, $(C_3-C_7)$-cycloalkyl, NC—, HO—, $(C_1-C_4)$-alkyl-O— and $(C_1-C_4)$-alkyl-S(O)$_p$—, unless specified otherwise;

Het2 is a 5-membered to 10-membered, monocyclic or bicyclic, saturated, partially unsaturated or aromatic heterocycle comprising 1, 2, 3 or 4 nitrogen atoms, or 1 oxygen atom or sulfur atom, or 1 or 2 nitrogen atoms and 1 oxygen atom or sulfur atom, as ring heteroatoms, which is bonded via a ring carbon atom and which is unsubstituted or substituted by one or more identical or different substituents selected from the series consisting of halogen, $(C_1-C_4)$-alkyl, NC—, HO— and (C1-C4)-alkyl-O—;

Het3 is a 5-membered or 6-membered, monocyclic, saturated, partially unsaturated or aromatic heterocycle comprising 1, 2 or 3 nitrogen atoms, or 1 sulfur atom or oxygen atom, or one nitrogen atom and one oxygen atom or sulfur atom, as ring heteroatoms, which is unsubstituted or substituted by one or two identical or different substituents selected from the series consisting of halogen, $(C_1-C_4)$-alkyl and $(C_1-C_4)$-alkyl-O—;

wherein all phenyl groups are unsubstituted or substituted by one, two or three identical or different substituents selected from the series consisting of fluorine, chlorine, $(C_1-C_4)$-alkyl and $(C_1-C_2)$-alkyl-O—, unless specified otherwise;

wherein all cycloalkyl groups, independently of any other substituents which can be present on a cycloalkyl group, can be substituted by one or two identical or different substituents selected from the series consisting of fluorine and $(C_1-C_4)$-alkyl, unless specified otherwise;

wherein all alkyl groups, independently of any other substituents which can be present on an alkyl group, can be substituted by one or more fluorine substituents.

Another example of such compounds are compounds of the formula I, in any of their stereo isomeric forms and mixtures of stereoisomeric forms in any ratio, and the pharmaceutically acceptable salts thereof, wherein n is 1;

m is 1;

X is selected from the series consisting of oxygen, sulfur and (R10)(R11)C;

one of the groups R1 and R2 is the group R20—NH— and the other of the groups R1 and R2 is the group (R30)(R31)N—;

R3, R4, R5, R6, R7, R8, R9, R10 and R11 are hydrogen;

R20 is (R21)(R22)(R23)C—;

R21 is selected from the series consisting of phenyl and Het1, which are all unsubstituted or substituted by one, two or three identical or different substituents R24;

R22 is selected from the series consisting of hydrogen, $(C_1-C_4)$-alkyl and cyclopropyl;

R23 is hydrogen;

R24 is selected from the series consisting of fluorine, chlorine, bromine, $(C_1-C_4)$-alkyl, $(C_3-C_7)$-cycloalkyl-, $(C_1-C_4)$-alkyl-O—, $(C_1-C_4)$-alkyl-S—, $F_5S$— and NC—;

R30 is selected from the series consisting of hydrogen end $(C_1-C_4)$-alkyl;

R31 is selected from the series consisting of $(C_3-C_6)$-cycloalkyl, $(C_5-C_6)$-cycloalkyl to which a benzene ring is fused, Het2 and $(R32)(R33)(R34)C—$, wherein the Het2, which is bonded via a ring carbon atom, is a 4-membered to 6-membered, monocyclic, saturated heterocycle which comprises one ring heteroatom which is an oxygen atom, or is $(C_5-C_6)$-cycloalkyl to which a pyridine, pyrazine or pyrimidine ring is fused, and wherein the $(C_5-C_6)$-cycloalkyl and all $(C_5-C_6)$-cycloalkyl are unsubstituted or substituted by one or two identical or different substituents selected from the series consisting of fluorine, $(C_1-C_4)$-alkyl and $(C_1-C_4)$-alkyl-O—, and wherein the fused benzene, pyridine, pyrazine and pyrimidine rings all are unsubstituted or substituted by one or two identical or different substituents selected from the series consisting of halogen, $(C_1-C_4)$-alkyl, NC—, HO— and $(C_1-C_4)$-alkyl-O—;

or the groups R30 and R31, together with the nitrogen atom carrying them, form a 5-membered to 6-membered, monocyclic, saturated heterocycle which, in addition to the nitrogen atom carrying R30 and R31, comprises 0 or 1 further ring heteroatom selected from the series consisting of nitrogen, oxygen and sulfur, and which is unsubstituted or substituted by one or two identical or different substituents R35;

R32 is selected from the series consisting of hydrogen and $(C_1-C_4)$-alkyl;

R33 is selected from the series consisting of hydrogen, $(C_1-C_4)$-alkyl and cyclopropyl;

R34 is selected from the series consisting of $(C_1-C_6)$-alkyl, $(C_3-C_6)$-cycloalkyl, $(C_1-C_4)$-alkyl-O—C(O)—, (R39)(R40)N—C(O)—, phenyl and Het2, wherein the $(C_1-C_6)$-alkyl is unsubstituted or substituted by one or two identical or different substituents R41, and wherein the phenyl is unsubstituted or substituted by one or more identical or different substituents R35, and wherein the Het2, which is bonded via a ring carbon atom, is a 5-membered to 6-membered, monocyclic, saturated, partially unsaturated or aromatic heterocycle comprising 1, 2, 3 or 4 nitrogen atoms, or 1 oxygen atom or sulfur atom, or 1 or 2 nitrogen atoms and 1 oxygen atom or sulfur atom, as ring heteroatoms, and is unsubstituted or substituted by one or more identical or different substituents selected from the series consisting of halogen, $(C_1-C_4)$-alkyl, NC—, HO— and $(C_1-C_4)$-alkyl-O—;

R35 is selected from the series of fluorine, chlorine, bromine, $(C_1-C_4)$-alkyl, HO—$(C_1-C_4)$-alkyl-, $(C_1-C_4)$-alkyl-O—$(C_1-C_4)$-alkyl-, $(C_1-C_4)$-alkyl-O—C(O)—$(C_1-C_4)$-alkyl-, NC—, HO—, $(C_1-C_4)$-alkyl-O—, $(C_1-C_4)$-alkyl-S(O)$_p$—, $(C_1-C_4)$-alkyl-S(O)$_2$—NH—, R42—O—C(O)—, (R43)(R44)N—C(O)— and (R45)(R46)N—S(O)$_2$—;

R36 is selected from the series consisting of fluorine, $(C_1-C_4)$-alkyl ethenyl, ethynyl, $(C_3-C_6)$-cycloalkyl, phenyl, Het3, $(C_1-C_4)$-alkyl-O—, $(C_3-C_6$-cycloalkyl-O—, $(C_3-C_6)$-cycloalkyl—$(C_1-C_2)$-alkyl-O—, phenyl-O—, $(C_1-C_2)$-alkyl-S(O)$_p$—, NC— and R47—O—C(O)—, wherein the $(C_1-C_4)$-alkyl is unsubstituted or substituted by one or two identical or different substituents R48;

R39, R40, R42, R43, R44, R45, R46, R47, R49, R50 and R51 are independently of one another selected from the series consisting of hydrogen and $(C_1-C_4)$-alkyl;

R41 is selected from the series consisting of $(C_3-C_6)$-cycloalkyl, phenyl and Het1;

R48 is selected from the series consisting of $(C_3-C_6)$-cycloalkyl, phenyl, Het3, HO—, $(C_1-C_4)$-alkyl-O—, $(C_1-C_4)$-alkyl-C(O)—O—, $(C_1-C_4)$-alkyl-S(O)$_p$—, $(C_1-C_4)$-alkyl-C(O)—(R49)N—, (R50)R51)N—C(O)— and $(C_1-C_4)$-alkyl-O-13 C(O)—;

p is selected from the series consisting of 0 and 2, wherein all numbers p are independent of one another;

Het1 is a 5-membered or 6-membered, monocyclic, aromatic heterocycle comprising one ring heteroatom selected from the series consisting of nitrogen, oxygen and sulfur or one ring nitrogen atom and one further ring hetetoatom selected from the series consisting of nitrogen, oxygen and sulfur, which is bonded via a ring carbon atom and which is unsubstituted or substituted by one or more identical or different substituents selected from the series consisting of halogen, $(C_1-C_4)$-alkyl, $(C_3-C_7)$-cycloalkyl, NC—, HO—, $(C_1-C_4)$-alkyl-O— and $(C_1-C_4)$-alkyl-S(O)$_p$—, unless specified othenmse;

Het3 is a 5-membered or 6-membered, monocyclic, saturated, partially unsaturated or aromatic heterocycle comprising 1, 2 or 3 nitrogen atoms, or 1 sulfur atom or oxygen atom, or 1 nitrogen atom and 1 oxygen atom or sulfur atom, as ring heteroatoms, which is unsubstituted or substituted by one or two identical or different substituents selected from the series consisting of fluorine, chlorine, NC—, $(C_1-C_2)$-alkyl and $(C_1-C_2)$-alkyl-O—;

wherein all phenyl groups are unsubstituted or substituted by one, two or three identical or different substituents selected from the series consisting of fluorine, chlorine, $(C_1-C_2)$-alkyl and $(C_1-C_2)$-alkyl-O—, unless specified otherwise; wherein all cycloalkyl groups, independently of any other substituents which can be present on a cycloalkyl group, can be substituted by one or two identical or different substituents selected from the series consisting of fluorine and $(C_1-C_4)$-alkyl, unless specified otherwise;

wherein all alkyl groups, independently of any other substituents which can be present on an alkyl group, can be substituted by one or more fluorine substituents.

Another example of such compounds are compounds of the formula I, in any of their stereoisomers forms and mixtures of stereoisomeric forms in any ratio, and the pharmaceutically acceptable salts thereof, wherein n is 1;

m is 1;

X is selected from the series consisting of oxygen and (R10)(R11 )C;

one of the groups R1 and R2 is the group R20—NH— and the other of the groups R1 and R2 is the group (R30)(R31)N—;

R3, R4, R5, R6, R7, R8, R9, R10 and R11 are hydrogen;

R20 is (R21)(R22)(R23)C—;

R21 is selected from the series consisting of phenyl and Het1, wherein Het1 is selected from the series consisting of pyridinyl, pyrimidinyl, pyrazinyl, pyridazinyl, pyrazolyl, imidazolyl, thiazolyl, isothiazolyl, oxazolyl, isoxazolyl, pyrrolyl, furanyl and thiophenyl, which are all bonded via a ring carbon atom, and wherein the phenyl and Het1 are all unsubstituted or substituted by one, two or three identical or different substituents selected from the series consisting of fluorine, chlorine, cyano, $(C_1-C_4)$-alkyl and $(C_1-C_4)$-alkyl-O—, wherein the alkyl groups can be substituted by one or more fluorine substituents;

R22 is hydrogen, $(C_1-C_4)$-alkyl or cyctopropyl;

R23 is hydrogen;

R30 is hydrogen or $(C_1-C_4)$-alkyl;

R31 is (R32)(R33) (R34)C—;

or the groups R30 and R31, together with the nitrogen atom carrying them, form a pyrrolidine ring which is unsubstituted or substituted by one or two identical or different substituents R36, wherein one of the substituents R36 is selected from the series consisting of fluorine, cyano, $(C_1-C_4)$-alkyl cyclopropyl, $(C_1-C_4)$-alkyl-O—, phenyl, Het3 and $(C_1-C_4)$-alkyl-O—C(O)—, and a second of the substituents R36, if present, is selected from the series consisting of fluorine and $(C_1-C_4)$-alkyl, and wherein the $(C_1-C_4)$-alkyl groups representing R36 are independently of one another unsubstituted or substituted by one or two identical or different substituents R48, and wherein the alkyl groups can independently of one another be substituted by one or more fluorine substituents, and wherein the phenyl is unsubstituted or substituted by one, two or three identical or different substituents selected from the series consisting of fluorine, chlorine, (C$_1$-C$_2$)-alkyl, (C$_1$-C$_2$)-alkyl-O— and trifluoromethyl, and wherein the Het3 is selected from the series consisting of pyridinyl, pyrimidinyl, pyrazinyl, oxazolyl, isoxazolyl, thiophenyl and thiazolyl, which are all unsubstituted or substituted by one or two identical or different substituents selected from the series consisting of fluorine, chlorine, cyano, (C$_1$-C$_2$)-alkyl, (C$_1$-C$_2$)-alkyl-O— and trifluoromethyl;

R32 is hydrogen;

R33 is selected from the series consisting of hydrogen, (C$_1$-C$_4$)-alkyl and cyclopropyl;

R34 is selected from the series consisting of (C$_1$-C$_4$)-alkyl-O—C(O)—, cyclopropyl, phenyl and Het2, wherein Het2 is selected from the series consisting of pyridinyl, pyrimidinyl, pyrazinyl, pyridazinyl, pyrazolyl, imidazolyl, thiazolyl, isothiazolyl, oxazolyl, isoxazolyl, pyrrolyl, furanyl and thiophenyl, which are all bonded via a ring carbon atom, and wherein the phenyl and Het2 groups are unsubstituted or substituted by one or two identical or different substituents selected from the series consisting of fluorine, chlorine, cyano, (C$_1$-C$_4$)-alkyl- and (C$_1$-C$_4$)-alkyl-O—, wherein the alkyl groups cap be substituted by one or more fluorine substituents;

R48 is selected from the series consisting of cyclopropyl, (C$_1$-C4) -alkyl-O—, (C$_1$-C$_4$)-alkyl-C(O)—O— and (C$_1$-C$_4$)-alkyl-O—C(O)—.

Another example of such compounds are compounds of the formula I, in any of their stereoisomers forms and mixtures of stereoisomeric forms in any ratio, and the pharmaceutically acceptable salts thereof, wherein n is 1;

m is 1;

X is oxygen;

one of the groups R1 and R2 is the group R20—NH— and the other of the groups R1 and R2 is the group (R30)(R31)N—;

R3, R4, R5, R6, R7, R8 and R9 are hydrogen;

R20 is (R21)(R22)(R23)C—;

R21 is selected from the series consisting of phenyl and Het1, wherein Het1 is selected from the series consisting of pyridinyl, pynmidinyl, thiazolyl and thiophenyl, which are all bonded via a ring carbon atom, and wherein Het1 is unsubsistuted or substituted by one or two identical or different substituents one substituent of which is selected from the series consisting of fluorine, chlorine, cyano, methyl, trifluoromethyl and methoxy and a second substituent is selected from the series consisting of fluorine, chlorine, methyl and trifluoromethyl, and wherein phenyl is unsubstituted or substituted by one, two or three identical or different substituents one substituent of which is selected from the series consisting of fluorine, chlorine, cyano, methyl, trifluoromethyl and methoxy, and a second and third substituent are selected from the series consisting of fluorine, chlorine, methyl and trifluoromethyl;

R22 is selected from the series consisting of methyl, ethyl, n-propyl, isopropyl amd cyclopropyl;

R23 is hydrogen;

the groups R30 and R31, together with the nitrogen atom carrying them, form a pyrrolidine ring which is unsubstituted or substituted in ring position 2 by one substituem R36 selected from the series consisting of methyl, ethyl, isopropyl, cyclopropyl, (C$_1$-C$_4$)-alkyl-O—C(L)—, (C$_1$-C$_4$)-alkyl-O—C(L)—CH$_2$— and trifluoromethyl; or R30 is hydrogen; and R31 is (R32)(R33)(R34)C—; and R34 is selected from the series consisting of phenyl and Het2, wherein Het2 is selected from the series consisting of pyridinyl, pynmidinyl, pyrazinyl, oxazolyl, isoxazolyl, thiazolyl, isothiazolyl and thiophenyl, which are bonded via a ring carbon atom, and wherein phenyl and Het2 are unsubstituted or substituted by one or two identical or different substituents selected from the series consisting of fluorine, chlorine, cyano, methyl, trifluoromethyl and methoxy; or R30 is selected from the series consisting of hydrogen, methyl and ethyl; and R31 is (R32)(R33)(R34)C—; and R34 is (C$_1$-C$_4$)-alkyl-O—C(O)—.

R32 is hydrogen;

R33 is selected from the series consisting of hydrogen, methyl, ethyl, n-propyl and isopropyl.

Another example of such compounds are compounds of the formula I, in any of their stereoisomers forms and mixtures of stereoisomeric forms in any ratio, and the pharmaceutically acceptable salts thereof, wherein n is 1;

m is 1;

X is oxygen;

one of the groups R1 and R2 is the group R20—NH— and the other of the groups R1 and R2 is the group (R30)(R31)N—;

R3, R4, R5, R6, R7, R8 and R9 are hydrogen;

R20 is (R21)(R22)(R23)C—;

R21 is selected from the series consisting of phenyl and Het1, wherein Het1 is selected from the series consisting of pyridinyl, pyrimidinyl, thiazolyl and thiophenyl, which are all bonded via a ring carbon atom, and wherein Het1 is substituted by one or two identical or different substituents one substituent of which is selected from the series consisting of fluorine, chlorine, cyano, trifluoromethyl and methoxy and a second substituent is selected from the series consisting of fluorine, chlorine, methyl and trifluoromethyl, and wherein phenyl is unsubstituted or substituted by one, two or three identical or different substituents one substituent of which is selected from the series consisting of fluorine, chlorine, cyano, trifluoromethyl and methoxy and a second substituent is selected from the series consisting of fluorine, chlorine, methyl and trifluoromethyl and a third substituent is fluorine;

R22 is selected from the series consisting of methyl, ethyl, n-propyl and isopropyl;

R23 is hyddrogen;

the groups R30 and R31, together with the nitrogen atom carrying them, form a pyrrolidine ring which is unsubstituted or substituted in ring position 2 by one substituent R36 selected from the series consisting of methyl, ethyl, isopropyl, cyclopropyl and trifluoromethyl.

Another example of such compounds are compounds of the formula I, in any of their stereoisomers forms and mixtures of stereoisomers forms in any ratio, and the pharmaceutically acceptable salts thereof, wherein n is 1;

m is 1;

X is oxygen;

one of the groups R1 and R2 is the group R20—NH— and the other of the groups R1 and R2 is the group (R30)(R31)N—;

R3, R4, R5, R6, R7, R8 and R9 are hydrogen;

R20 is (R21)(R22)(R23)C—;

R21 is selected from the series consisting of phenyl and Het1, wherein Het1 is selected from the series consisting of pyridinyl, pyrimidinyl, thiazolyl and thiophenyl, which are bonded via a ring carbon atom, and wherein Het1 is substituted by one or two identical or different substituents one substituent of which is selected from the series consisting of fluorine, chlorine, cyano, trifluoromethyl and methoxy and a second substituent is selected from the series consisting of fluorine, chlorine, methyl and trifluoromettryl, and wherein phenyl is unsubstituted or substituted by one, two or three identical or different substituents one substituent of which is selected from the series consisting of fluorine, chlorine, cyano, trifluoromethyl and methoxy and a second substituent is selected from the series consisting of fluorine. chlorine, methyl and trifluoromethyl and a third substituent is fluorine;

R22 is selected from the series consisting of methyl, ethyl, n-propyl and isopropyl;

R23 is hydrogen;

R30 is hydrogen;

R31 is (R32)(R33)(R34)C—;

R32 is hydrogen;

R33 is selected from the series consisting of hydrogen, methyl, ethyl, n-propyl and isopropyl;

R34 is selected from the series consisting of phenyl and Het2, wherein Het2 is selected from the series consisting of pyridinyl, pynmidinyl, pyrazinyl, oxazolyl, isoxazolyl, thiazolyl, isothiazolyl and thiophenyl, which are bonded via a ring carbon atom, and wherein the phenyl and Het2 are unsubstituted or substituted by one or two identical or different substituents selected from the series consisting of fluorine, chlorine, cyano, methyl, trifluoromethyl and methoxy.

Another example of such compounds are compounds of the formula I, and the pharmaceutically acceptable salts thereof, wherein R2 is the group (R30)(R31)N—, R1 is the group R20—NH—, R20 is the group (R21)(R22)(R23)C—NH—, R23 is hydrogen, and the resulting group (R21)(R22)CH—NH— has the stereoisomeric structure depicted in formula Ic.

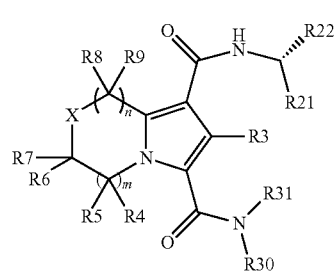

Ic

R3 to R9, R21, R22, R30, R31, X, m and n in the compounds of the formula Ic are defined as in the compounds of the formula I in general or in any embodiment. Apart from the stereoisomers structure at the carbon atom carrying the groups R21 and R22, the compounds of the formula Ic can be present in any of their stereoisomeric forms and as mixtures of stereoisomers forms in any ratio.

Another example of such compounds are compounds of the formula I, and the pharmaceutically acceptable saits thereof, wherein R2 is the group (R30)(R31)N—, R1 is the group R20—NH—, R20 is the group (R21)(R22)(R23)C—NH—, R23 is hydrogen, and the resulting group (R21)(R22)CH—NH— has the stereoisomers structure depicted in formula Id.

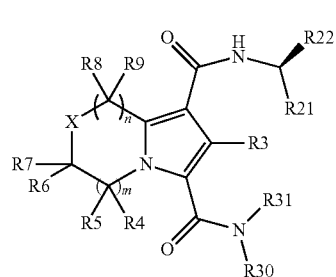

Id

R3 to R9, R21, R22, R30, R31, X, m and n in the compounds of the formula Id are defined as in the compounds of the formula I in general or in any embodiment. Apart from the stereoisomeric structure at the carbon atom carrying the groups R21 and R22, the compounds of the formula Id can be present in any of their stereoisomeric forms and as mixtures of stereoisomeric forms in any ratio.

Another example of such compounds are compounds of the formula I, and the pharmaceutically acceptable salts thereof, wherein R1 is the group (R30)(R31)N—, R2 is the group R20—NH—, R20 is the group (R21)(R22)(R23)C—NH—, R23 is hydrogen, end the resulting group (R21)(R22)CH—NH— has the stereoisomeric structure depicted in formula Ie.

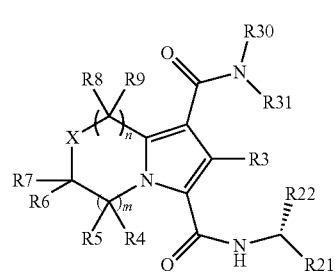

Ie

R3 to R9, R21, R22, R30, R31, X, m and n in the compounds of the formula Ie are defined as in the compounds of the formula I in general or in any embodiment. Apart from the stereoisomeric structure at the carbon atom carrying the groups R21 and R22, the compounds of the formula Ie can be present in any of their stereoisomeric forms and as mixtures of stereoisomeric forms in any ratio.

Another example of such compounds are cornpounds of the formula I, and the pharmaceutical acceptable salts thereof, wherein R1 is the group (R30)(R31)N—; R2 is the group R20—NH—, R20 is the group (R21)(R22)(R23)C—NH—, R23 is hydrogen, and the resulting group (R21)(R22)CH—NH— has the stereoisomeric structure depicted in formula If.

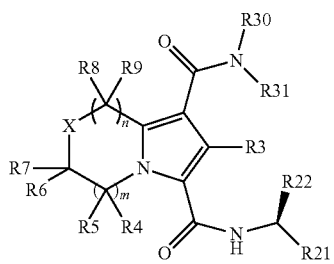

R3 to R9, R21, R22, R30, R31, X, m and n in the compounds of the formula If are defined as in the compounds of the formula I in general or in any embodiment. Apart from the stereoisomeric structure at the carbon atom carrying the groups R21 and R22, the compounds of the formula If can be present in any of their stereoisomeric forms and as mixtures of stereoisomers forms in any ratio.

Another example of such compounds are compounds of the formula Ig, and the pharmaceutically acceptable salts thereof, i.e. compounds of the formula I wherein R2 is the group (R30)(R31)N—, R30 and R31 together with the nitrogen atom carrying them form a pyrrolidine ring which carries a substituent R36 in ring position 2, R1 is the group R20—NH—, R20 is the group (R21)(R22)(R23)C—NH—, R23 is hydrogen, and the substituted pyrrolidine ring and the group (R21)(R22)CH—NH— have the stereoisomeric structure depicted in formula Ig,

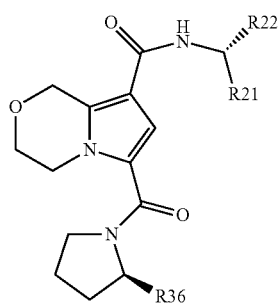

wherein
R21 is selected from the series consisting of phenyl and Het1, wherein Het1 is selected from the series consisting of pyridinyl, pyrimidinyl, thiazolyl and thiophenyl, which are bonded via a ring carbon atom, and Het1 is substituted by one or two identical or different substituents one substituent of which is selected from the series consisting of fluorine, chlorine, cyano, trifluoromethyl and methoxy and a second substituentis selected from the series consisting of fluorine, chlorine, methyl and trifluoromethyl, and phenyl is unsubstituted or substituted by one, two or three identical or different substituents one substituent of which is selected from the series consisting of fluorine, chlorine, cyano, trifluoromethyl and methoxy and a second substituent is selected from the series consisting of fluorine, chlorine, methyl and trifluoromethyl and a third substituent is fluorine;
R22 is selected from the series consisting of methyl ethyl, n-propyl and isopropyl;
R36 is selected from the series consisting of methyl, ethyl, isopropyl, cyclopropyl and trifluoromethyl.

A subject of the invention also is a compound of the formula I and the pharmaceutically acceptable salts thereof, which is selected from any of the specific compounds of the formula I which are disclosed herein, or is any one of the specific compounds of the formula I which are disclosed herein, wherein the compound of the formula I is a subject of the invention in any of its stereoisomers forms or a mixture of stereoisomers forms in any ratio, irrespective of the configuration in the specific compound disclosed herein, and, if a specific configuration is present on one or more carbon atoms in a specific compound which is disclosed herein, one embodiment of the invention relates to this compound with the disclosed specific configuration or configurations. For example, a subject of the invention is a compound of the formula I which is selected from the series consisting of
6-(pyrrolidine-1-carbonyl)-3,4-dihydro-1H-pyrrolo[2,1-c][1,4]oxazine-8-carboxylic acid ((R)-1-phenyl-propyl)-amide,
6-((S)-2-methyl-pyrrolidine-1-carbonyl)-3,4-dihydro-1H-pyrrolo[2,1-c][1,4]oxazine-8-carboxylic acid [(R)-1-(2-chloro-phenyl)-popyl]-amide,
6-((S)-2-methyl-pyrrolidine-1-carbonyl)-3,4-dihydro-1H-pyrrolo[2,1-c][1,4]oxazine-8-carboxylic acid ((R)-1-phenyl-propyl)-amide,
6-((S)-2-methyl-pyrrolidine-1-carbonyl)-3,4-dihydro-1H-pyrrolo[2,1-c][1,4]oxazine-8-carboxylic acid [(R)-1-(2,4-difluoro-phenyl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(6-cyano-pyridin-3-yl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(6-trifluoromethyl-pyridin-3-yl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(4-cyano-2,6-difluoro-phenyl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(4-cyano-phenyl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(4-trifluoromethyl-phenyl)-propyl]-amide,
6-((S)-2-ethyl-pyrrolidine-1-carbonyl)-3,4-dihydro-1H-pyrrolo[2,1-c][1,4]oxazine-8-carboxylic acid [(R)-1-(6-trifluoromethyl-pyridin-3-yl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(3-fluoro-4-trifluoromethyl-phenyl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(6-trifluoromethyl-pyridin-3-yl)-butyl]-amide,
6-((R)-2-trifluoromethyl-pyrrolidine-1-carbonyl)-3,4-dihydro-1H-pyrrolo[2,1-c][1,4]oxazine-8-carboxylic acid [(R)-1-(6-trifluoromethyl-pyridin-3-yl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(3-chloro-4-cyano-phenyl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(5-trifluoromethyl-thiazol-2-yl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(5-chloro-6-methoxy-pyridin-3-yl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(2-chloro-6-trifluoromethyl-pyridin-3-yl)-propyl]-amide, 6-((S)-2-methyl-pyrrolidine-1-carbonyl)-3,4-dihydro-1H-pyrrolo[2,1-c][1,4]oxazine-8-carboxylic acid [(R)-1-(5-trifluoromethyl-thiophen-2-yl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(3-chloro-4-trifluoromethyl-phenyl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(5-fluoro-6-trifluoromethyl-pyridin-3-yl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(3,4-dichloro-phenyl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(2,6-difluoro-4-trifluoromethyl-phenyl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(6-methoxy-5-trifluoromethyl-pyridin-3-yl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(-3-chloro-4-fluoro-phenyl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(3-chloro-4-methoxy-phenyl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(5-chloro-6-cyano-pyridin-3-yl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(2-fluoro-4-trifluoromethyl-phenyl)-propyl]-amide,
6-((S)-2-ethyl-pyrrolidine-1-carbonyl)-3,4-dihydro-1H-pyrrolo[2,1-c][1,4]oxazine-8-carboxylic acid ((R)-1-phenyl-propyl)-amide,
3-((S)-2-methylpyrrolidine-1-carbonyl)-5,6,7,8-tetrahydroindolizine-1-carboxylic acid [(R)-1-(6-cyano-pyridin-3-yl)-propyl]-amide,
3-((S)-2-methylpyrrolidine-1-carbonyl)-5,6,7,8-tetrahydroindolizine-1-carboxylic acid [(R)-1-(6-trifluoromethyl-pyridin-3-yl)-propyl]-amide,
6-((S)-2-methyl-pyrrolidine-1-carbonyl)-3,4-dihydro-1H-pyrrolo[2,1-c][1,4]oxazine-8-carboxylic acid [(R)-2-methyl-1-(6-trifluoromethyl-pyridin-3-yl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(4-chloro-phenyl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(4-fluoro-3-trifluoromethyl-phenyl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(3,5-dichloro-pyridin-4-yl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(2-chloro-5-fluoro-phenyl)-propyl]-amide,
6-((S)-2-methyl-pyrrolidine-1-carbonyl)-3,4-dihydro-1H-pyrrolo[2,1-c][1,4]oxazine-8-carboxylic acid [(R)-1-(2,6-difluoro-phenyl)-propyl]-amide,
6-(pyrrolidine-1-carbonyl)-3,4-dihydro-1H-pyrrolo[2,1-c][1,4]oxazine-8-carboxylic acid [(R)-1-(2,4-difluoro-phenyl)-propyl]-amide,
6-(pyrrolidine-1-carbonyl)-3,4-dihydro-1H-pyrrolo[2,1-c][1,4]oxazine-8-carboxylic acid [(R)-1-(2-chloro-4-fluoro-phenyl)-propyl]-amide;
or a compound of the formula I which is selected from the series consisting of
3,4-dihydro-1H-pyrrolo[2,1-c][1,4]oxazine-6,8-dicarboxylic acid bis-[((R)-1-phenyl-propyl)-amide],
3,4-dihydro-1H-pyrrolo[2,1-c][1,4]oxazine-6,8-dicarboxylic acid bis-{[(R)-1-(4-fluoro-propyl)-ethyl]amide},
3,4-dihydro-1H-pyrrolo[2,1-c][1,4]oxazine-6,8-dicarboxylic acid 6-{[(R)-1-(6-methoxy-pyridin-3-yl)propyl]-amide}8-[((R)-1-phenyl-propyl)-amide],
3,4-dihydro-1H-pyrrolo[2,1-c][1,4]oxazine-6,8-dicarboxylic acid 8-[((R)-1-phenylpropyl)-amide]6-[(pyrazin-2-ylmethyl)-amide],
3,4-dihydro-1H-pyrrolo[2,1-c][1,4]oxazine-6,8-dicarboxylic acid 6-{[(S)-1-(2-methoxy-pyrimidin-5-yl)-ropyl]-amide}8-[((R)-1-phenyl-propyl)-amide],
3,4-dihydro-1H-pyrrolo[2,1-c][1,4]oxazine-6,8-dicarboxylic acid 6-{[(R)-1-(6-cyano-pyridin-3-yl)-propyl]-amide} 8-[((R)-1-phenyl-propyl)-amide],
3,4-dihydro-1H-pyrrolo[2,1-c][1,4]oxazine-6,8-dicarboxylic acid 6-{[(R)-1-(5-methoxy-pyrazin-2-yl)-propyl]-amide} 8-[((R)-1-phenyl-propyl)-amide],
3,4-dihydro-1H-pyrrolo[2,1-c][1,4]oxazine-6,8-dicarboxylic acid 8-[((R)-1-phenyl-propyl)-amide]6-[(1-pyrazin-2-yl-ethyl)-amide],
3,4-dihydro-1H-pyrrolo[2,1-c][1,4]oxazine-6,8-dicarboxylic acid 6-{[(R)-1-(4-fluoro-phenyl)-2-methyl-propyl]-amide} 8-[(1-pyrimidin-2-yl-ethyl)-amide],
3,4-dihydro-1H-pyrrolo[2,1-c][1,4]oxazine-6,8-dicarboxylic acid 6-[(1-isoxazol-3-yl-ethyl)-amide] 8-[((R)-1-phenyl-propyl)-amide],
3,4-dihydro-1H-pyrrolo[2,1-c][1,4]oxazine-6,8-dicarboxylic acid 8-[((R)-1-phenyl-propyl)-amide] 6-[((S)-1-pyrazin-2-yl-propyl)-amide],
3,4-dihydro-1H-pyrrolo[2,1-c][1,4]oxazine-6,8-dicarboxylic acid 8-[((R)-1-phenyl-propyl)-amide] 6-[((S)-1-pyrazin-w-yl-ethyl)-amide],
3,4-dihydro-1H-pyrrolo[2,1-c][1,4]oxazine-6,8-dicarboxylic acid 6-{[(R)-1-(2,4-difluoro-phenyl)-propyl]-amide} 8-[((R)-1-pyrazin-2-yl-ethyl)-amide],
3,4-dihydro-1H-pyrrolo[2,1-c][1,4]oxazine-6,8-dicarboxylic acid 8-{[(R)-1-(2-chloro-4-fluoro-phenyl)-propyl]-amide} 6-[(1-primidin-2-yl-ethyl)-amide],
3,4-dihydro-1H-pyrrolo[2,1-c][1,4]oxazine-6,8-dicarboxylic acid 8-{[(R)-1-(2-chloro-phenyl)-propyl]-amide} 6-[(1-pyrimidin-2-yl-ethyl)-amide],
3,4-dihydro-1H-pyrrolo[2,1-c][1,4]oxazine-6,8-dicarboxylic acid 6-{[(R)-1-(4-fluoro-phenyl)-2-methyl-propyl]-amide} 8-[((S)-1-pyrimidin-2-yl-ethyl)-amide],
3,4-dihydro-1H-pyrrolo[2,1-c][1,4]oxazine-6,8-dicarboxylic acid 6-{[(R)-1-(4-fluoro-phenyl)-ethyl]-amide} 8-[((S)-1-pyrimidin-2-yl-ethyl)-amide],
3,4-dihydro-1H-pyrrolo[2,1-c][1,4]oxazine-6,8-dicarboxylic acid 6-{[(R)-1-(2,4-difluoro-phenyl)-propyl]-amide} 8-[((S)-1-pyrazin-2-yl-ethyl)-amide],
3,4-dihydro-1H-pyrrolo[2,1-c][1,4]oxazine-6,8-dicarboxylic acid 6-{[(R)-1-(4-fluoro-phenyl)-ethyl]-amide} 8-[((R)-1-pyrimidin-2-yl-ethyl)-amide],
3,4-dihydro-1H-pyrrolo[2,1-c][1,4]oxazine-6,8-dicarboxylic acid 6-{[(R)-1-(4-fluoro-phenyl)-ethyl]-amide} 8-[((R)-1-pyrimidin-2-yl-propyl)-amide],
3,4-dihydro-1H-pyrrolo[2,1-c][1,4]oxazine-6,8-dicarboxylic acid 8-[((R)-1-phenyl-propyl)-amide] 6-{[(R)-1-(6-trifluoromethyl-pyridin-3-yl)-propyl]-amide},
3,4-dihydro-1H-pyrrolo[2,1-c][1,4]oxazine-6,8-dicarboxylic acid 6-{[(R)-1-(4-fluoro-phenyl)-ethyl]-amide} 8-{[(R)-1-(5-trifluoromethyl-pyrimidin-2-yl)-propyl]-amide},
3,4-dihydro-1H-pyrrolo[2,1-c][1,4]oxazine-6,8-dicarboxylic acid 6-{[(R)-1-(4-fluoro-phenyl)-ethyl]-amide} 8-{[(R)-1-(4-trifluoromethyl-phenyl)-propyl]-amide}, 3,4-dihydro-1H-pyrrolo[2,1-c][1,4]oxazine-6,8-dicarboxylic acid 6-{[(R)-1-(4-fluoro-phenyl)-ethyl]-amide} 8-{[(R)-1-(6-trifluoromethyl-pyridin-3-yl)-propyl]-amide}, 3,4-dihydro-1H-pyrrolo[2,1-c][1,4]oxazine-6,8-dicarboxylic acid 6-{[(R)-1-(4-fluoro-phenyl)-ethyl]-amide} 8-{[(R)-1-(5-trifluoromethyl-pyridin-2-yl)-propyl]-amide}, 3,4-dihydro-1H-pyrrolo[2,1-c][1,4]oxazine-6,8-dicarboxylic acid 8-[((R)-1-pyrimidin-2-yl-propyl)-amide] 6-{[(R)-1-(4-trifluoromenthyl-phenyl)-propyl]-amide}, 3,4-dihydro-1H-pyrrolo[2,1-c][1,4]oxazine-6,8-dicarboxylic acid 6-[((R)-1-phenyl-propyl)-amide] 8-{[(R)-1-(6-trifluoromethyl-pyridin-3-yl)-propyl]-amide}, 3,4-dihydro-1H-pyrrolo[2,1-c][1,4]oxazine-6,8-dicarboxylic acid 6-{[(R)-1-(4-fluoro-phenyl)-ethyl]-amide} 8-{[(R)-1-(5-trifluoromethyl-pyridin-2-yl)-propyl]-amide}, 3,4-dihydro-1H-pyrrolo[2,1-c][1,4]oxazine-6,8-dicarboxylic acid 6-{[(R)-1-(4-fluoro-phenyl)-ethyl]-amide} 8-{[(R)-1-(5-trifluoromethyl-pyridin-2-yl)-propyl]-amide}, 5,6,7,8-tetrahydro-indolizine-1,3-dicarboxylic acid 3-[((S)-1-phenyl-propyl)-amide]1-[((R)-1-phenyl-propyl)-amide], 3,4-dihydro-1H-pyrrolo[2,1-c][1,4]oxazine-6,8-dicarboxylic acid 6-{[(R)-1-(6-methoxy-pyridin-2-yl)propyl]-amide} 8-[((R)-1-phenyl-propyl)-amide]

3,4-dihydro-1H-pyrrolo[2,1-c][1,4]oxazine-6,8-dicarboxylic acid 6-{[(R)-1-(4-fluoro-phenyl)-ethyl]-amide} 8-[((R)-1-phenyl-propyl)-amide]

5,6,7,8-tetrahydro-indolizine-1,3-dicarboxylic acid 3-[((S)-1-cyclopropyl-ethyl)-amide]1-[((R)-1-phenyl-propyl)-amide], 3,4-dihydro-1H-pyrrolo[2,1-c][1,4]oxazine-6,8-dicarboxylic acid 8-{[(R)-1-(4-fluoro-phenyl)-ethyl]-amide} 6-[((R)-1-phenyl-propyl)-amide], 3,4-dihydro-1H-pyrrolo[2,1-c][1,4]oxazine-6,8-dicarboxylic acid 6-{[(R)-1-(4-fluoro-phenyl)-ethyl]-amide} 8-{[(R)-1-(5-methoxy-pyrazin-2-yl)-propyl]-amide}, 3,4-dihydro-1H-pyrrolo[2,1-c][1,4]oxazine-6,8-dicarboxylic acid 6-(S)-indan-1-ylamide 8-[((R)-1-phenyl-propyl)-amide], 5,6,7,8-tetrahydro-indolizine-1,3-dicarboxylic acid 3-[((R)-cyclopropyl-phenyl-methyl)-amide] 1-[((R)-1-phenyl-propyl)-amide], 3,4-dihydro-1H-pyrrolo[2,1-c][1,4]oxazine-6,8-dicarboxylic acid 6-{[(R)-1-(4-fluoro-phenyl)-ethyl]-amide} 8-[((R)-1-phenyl-ethyl)-amide], 5,6,7,8-tetrahydro-indolizine-1,3-dicarboxylic acid bis-[((R)-1-phenyl-propyl)-amide], 5,6,7,8-tetrahydro-indolizine-1,3-dicarboxylic acid 3-{[(S)-1-(4-fluoro-phenyl)-ethyl]-amide} 1-[((R)-1-phenyl-propyl)-amide], 3,4-dihydro-1H-pyrrolo[2,1-c][1,4]oxazine-6,8-dicarboxylic acid 6-{[(S)-1-(4-fluoro-phenyl)-ethyl]-amide} 8-[((R)-1-phenyl-propyl)-amide], 5,6,7,8-tetrahydro-indolizine-1,3-dicarboxylic acid 3-[((R)-1-cyclopropyl-ethyl)-amide]1-[((R)-1-phenyl-propyl)-amide], 5,6,7,8-tetrahydro-indolizine-1,3-dicarboxylic acid 3-[(4-fluoro-benzyl)-methyl-amide]a-[((R)-1-phenyl-propyl)-amide], 3,4-dihydro-1H-pyrrolo[2,1-c][1,4]oxazine-6,8-dicarboxylic acid 8-{[(R)-1-(2-chloro-phenyl)-propyl]-amide} 6-cyclopropylmethyl-amide, and 5,6,7,8-tetrahydro-indolizine-1,3-dicarboxylic acid 3-[((R)-1-phenyl-propyl)-amide] 1-[(thiazol-2-ylmethyl)-amide];

or a compound of the formula I which is selected from the series consisting of

{[8-((R)-1-phenyl-propylcarbamoyl)-3,4-dihydro-1H-pyrrolo[2,1-c][1,4]oxazine-6-carbonyl]-amino}-acetic acid ethyl ester, (R)-[8-((R)-1-phenyl-propylcarbamoyl)-3,4-dihydro-1H-pyrrolo[2,1-c][1,4]oxazine-6-carbonyl]-pyrrolidine-2-carboxylic acid isopropyl ester, ((R)-1-{6-[(R)-1-(4-fluoro-phenyl)-ethylcarbamoyl]-3,4-dihydro-1H-pyrrolo[2,1-c][1,4]oxazine-8-carbonyl}-pyrrolidin-2-yl)-acetic acid ethyl ester, (R)-1-[8-((R)-1-phenyl-propylcarbamoyl)-3,4-dihydro-1H-pyrrolo[2,1-c][1,4]oxazine-6-carbonyl]-pyrrolidine-2-carboxylic acid ethyl ester, (S)-2-{[8-((R)-1-phenyl-propylcarbamoyl)-3,4-dihydro-1H-pyrrolo[2,1-c][1,4]oxazine-6-carbonyl]-amino}-propionic acid isopropyl ester, {methyl-[8-((R)-1-phenyl-propylcarbamoyl)-3,4-dihydro-1H-pyrrolo[2,1-c][1,4]oxazine-6-carbonyl]-amino}-acetic acid isopropyl ester, {methyl-[8-((R)-1-phenyl-propylcarbamoyl)-3,4-dihydro-1H-pyrrolo[2,1-c][1,4]oxazine-6-carbonyl]-amino}-acetic acid ethyl ester, (S)-2-{methyl-[8-((R)-1-phenyl-propylcarbamoyl)-3,4-dihydro-1H-pyrrolo[2,1-c][1,4]oxazine-6-carbonyl]-amino}-propionic acid ethyl ester, (S)-2-{methyl-[8-((R)-1-phenyl-propylcarbamoyl)-3,4-dihydro-1H-pyrrolo[2,1-c][1,4]oxazine-6-carbonyl]-amino}-propionic acid isopropyl ester, {(R)-1-[8-((R)-1-phenyl-propylcarbamoyl)-3,4-dihydro-1H-pyrrolo[2,1-c][1,4]oxazine-6-carbonyl]-pyrrolidin-2-yl}-acetic acid ethyl ester, {(R)-1-[8-((R)-1-phenyl-propylcarbamoyl)-3,4-dihydro-1H-pyrrolo[2,1-c][1,4]oxazine-6-carbonyl]-pyrrolidin-2-yl}acetic acid isopropyl ester, and (R)-1-{6-[(R)-1-(4-fluoro-phenyl)-2-methyl-propylcarbamoyl]-3,4-dihydro-1H-pyrrolo[2,1-c][1,4]oxazine-8-carbonyl}-pyrrolidine-2-carboxylic acid methyl ester;

or which is any one of these compounds, and its pharmaceutically acceptable salts, wherein the compound of the formula I is a subject of the invention in any of its stereoisomeric forms or a mixture of stereoisomers forms in any ratio, unless a specific configuration or stereoisomers form is specified with respect to any carbon atoms or structural element in the respective compound.

Another subject of the present invention are processes for the preparation of the compounds of the formula I which are outlined below and by which the compounds of the formula I and intermediates occurring in the course of their synthesis are obtainable. For example, one such process starts with the formation of fused pyrrolecarboxylic acid esters of the formula V from heterocyclic amino acids of the formula II by following a similar synthetic method as described in Pizzorno M. T. et al., J. Org. Chem. 1977, 42, 909-910. As shown in Scheme 1, in this process the compound of tine formula II is first formyiafed to give the compound of the formula III, for example by adding acetanhydride to a solution of the amino acid in formic acid, for example at temperatures from about 0° C. to about 25° C., followed by treatment with water. The obtained compound of the formula III is treated with an excess of acetanhydride and a propiohc acid ester of the formula IV, optionally in the presence of dimethylformamide, for example at temperatures from about 80° C. to about 120° C., to give a mixture of the isomeric fused pyrroiecarboxylic acid esters of the formulae V and VI, in which the desired compound of the formula V usually is the major isomer and from which the compound of the formula V can be isolated by standard techniques, for example by chromatography.

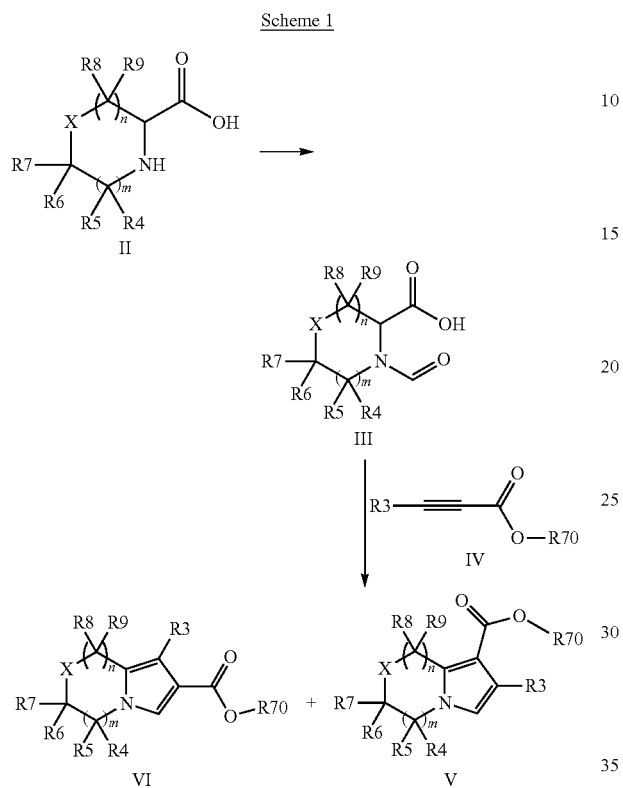

R4 to R9, X, m and n in the compounds of the formulae II, III, V and VI are defined as in the compounds of the formula I. The group R3 in the compounds of the formulae IV, V and VI is hydrogen or (C₁-C₄)-alkyl, in particular hydrogen, the group R70 in the compounds of Lhe formulae IV, V and V can be (C₁-C₄)-alkyl, for example (C₁-C₃)-alkyl such as ethyl. The method according to Scheme 1 is particularly suitable for the preparation of compounds of the formula V in which X is oxygen, sulfur or C(R10)(R11) and n and m are 1, and compounds in which X is sulfur and one of n and m is 0 and the other is 1. The heterocyclic amino acids of the formula II used as starting compounds are commercially available or have been described in the literature or can be synthesized according to various procedures described in the literature. For example, compounds of the formula II in which X is oxygen and n and m are 1, can be prepared according to the method described in Meinzer A. et al., Helv. Chim. Acta 2004, 87, 90-105 by reacting a 2-benzylamino-3-hydroxy-alkanoic acid with a 2-chloro-alkanoyl chloride to give, after esterification, the respective 4-benzyl-5-oxo-morpholine-3-carboxylic acid ester in which the lactam moiety can be reduced to the cyclic amine moiety, for example by means of a borane or complex hydride reducing agent, for example the complex of borane and dimethylsulfide, the benzyl protecting group then cleaved by catalytic hydrogenation, for example over palladium on charcoal, and the ester moiety saponified, for example with an alkali metal hydroxide like potassium hydroxide, to afford the respective rnorpholine-3-carboxylic acid. Compounds of the formula II in which X is sulfur and n and m are 1, can be prepared by the methods described in WO 82/03860, for example by reacting a 2-amino-3-mercapto-alkanoic acid derivative with a 2-halo-alkanone and reducing the cyclic imine intermediate by means of hydrogen in the presence of a catalyst such as palladium or a complex hydride. Methods for the preparation of compounds of the formula II In which X is (R10)(R11)C and n and m are 1, are described in Shuman R. T. et al., J. Org. Chem. 1990, 55, 738-741; Takahafa H. et al., Amino Acids 2003, 24, 267-272; Maison W. et al., J. Chem. Soc. Perkin Trans. 1 1999, 3515-3525; or EP 0447704, for example.

The fused pyrrolecarboxyllc acid esters of the formula V can then be reacted with 2,2,2-trichloroacetyl chloride in an inert solvent, such as a chlorinated hydrocarbon like dichloromethane, at temperatures from about 10° C. to about 30° C. to give compounds of the formula VII (Scheme 2).

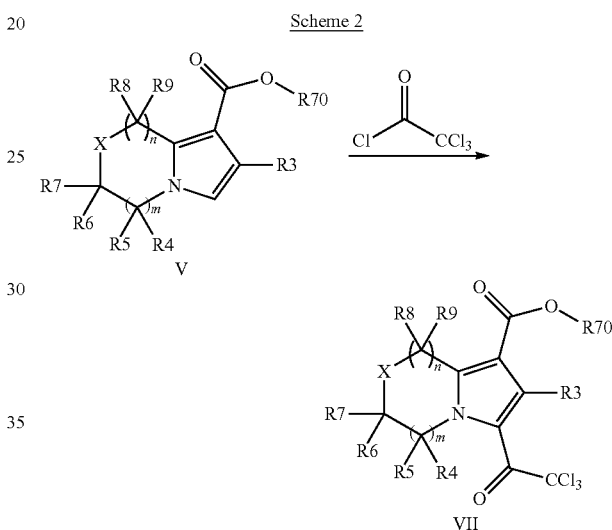

R3 to R9, R70, X, m and n in the compounds of the formula VII is defined as in the compounds of the formula V. The trichloroacetyl derivatives can be further reacted in different ways. In one of them, which is shown in Scheme 3 and can in the first step be performed according to the procedure described in Wood K. et al., Tetrahedron 2011, 87, 4093-4102, the trichloroacetyl group is directly converted into a carboxamide group by reaction of the compound of the formula VII either with an amine of the formula (R30)(R31)NH or with an amine of the formula R20—NH₂ in an

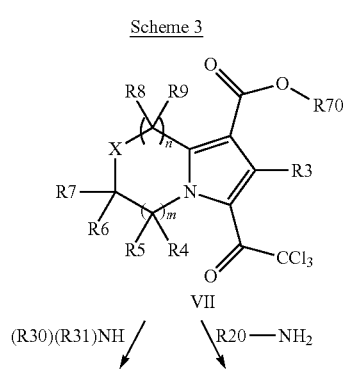

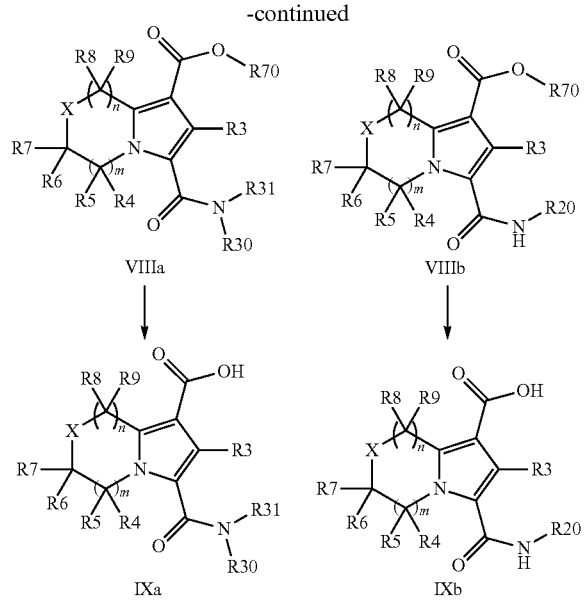

inert solvent such as an ether like tetrahydrofuran or dioxane, at temperatures from about 20° C. to about 80° C., for example at the reflux temperature of tetrahydrofuran, to give the compounds of the formulae VIIIa and VIIIb, respectively. The ester group R70—O—C(O)— in the compounds of the formulae VIIIa and VIIIb can then be hydrolyzed to the carboxylic acid group according to standard procedures, for example by treatment with an alkali metal hydroxide like sodium hydroxide or potassium hydroxide in an inert solvent such as water or a mixture of water and an organic solvent, for example a mixture of water and an alcohol like methanol or ethanol, at temperatures from about 50° C. to about 100° C., to give the compounds of the formulae IXa and IXb, respectively.

R3 to R9, R70, X, m and n in the compounds of the formulae VIIIa, VIIIb, IXa and IXb are defined as in the compounds of the formula V. R20, R30 and R31 in the compounds of the formulae VIIIa, VIIIb, IXa and IXb and the employed amines of the formulae (R30)(R31)NH and R20—NH$_2$ are defined as in the compounds of the formula I, and additionally can functional groups be present in protected form or in the form of a precursor group which are subsequently converted into the final groups.

In another way for further reacting the compounds of the formula VII, which is shown in Scheme 4, the trichloroacetyl group is first converted into a carboxylic acid group, which conversion has in general been described in the literature, for example in Hewlett N. M. et al., Organic Letters 2011, 13, 4550-4553, without interfering with the ester group R70—O—C(O)—. For example, by treatment with an alkali metal hydroxide like sodium hydroxide or potassium hydroxide in an inert solvent, such as a mixture of water and an organic solvent, for example a mixture of water and an ether like tetrahydrofuran, at temperatures of about 20° C. to about 30° C. chemoselective hydrolysis can be achieved to give the carboxylic acids of the formula X, in which R3 to R9, R70, X, m and n are defined as in the compounds of the formula V.

Scheme 4

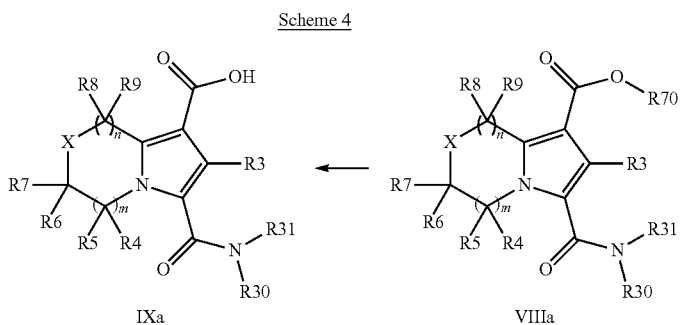

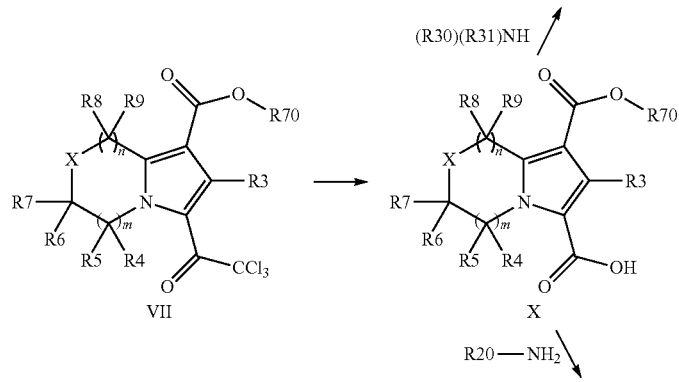

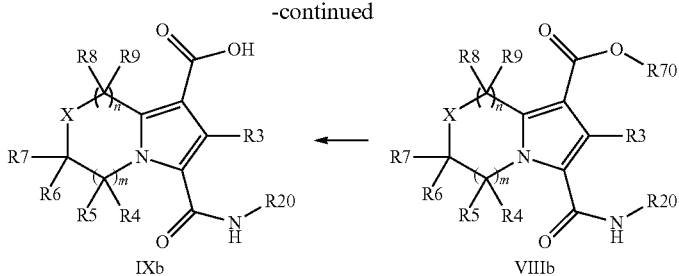

The carboxylic acids of the formula X can be convened into carboxamides of the formulae VIIIa and VIIIb by reaction either with an amine of the formula (R30)(R31)NH or with an amine of the formula R20—NH$_2$ according to the many methods for the formation of amides from carboxylic acids, for example by means of the various peptide coupling agents which are well known in the art, such as N,N'-carbonyldiazoles, carbodiimides or uronium-hased coupling agents, in an inert solvent, for example a hydrocarbon like toluene, a chlorinated hydrocarbon like dichloromethane, an ether like tetrahydrofuran, dioxane or 1,2-dimethoxyethane, or an amide like dimethylformamide or N-methylpyrrolidin-2-one, optionally in the presence of an auxiliary agent such as 1-hydroxy-benzotriazole and/or a base such as a tertiary amine, in a favorable manner for the formation of the carboxamides, a compound of the formula X is treated with a carbodiimide like 1-ethyl-3-(3-dimethylaminopropyl)carbodiimide hydrochloride (EDAC, EDC; EDCI) and 1-hydroxy-benzotriazole and then with an amine of the formula (R30)(R31)NH or R20—NH$_2$ in an amide like dimethylformamide as solvent at temperatures from about 20° C. to about 60° C. The ester group R70—O—C(O)— in the compounds of the formulae VIIIa and VIIIb can then be hydrolyzed according to standard procedures, for example by treatment with an alkali metal hydroxide like sodium hydroxide or potassium hydroxide as already outlined above, to give the carboxylic acids of the formulae IXa and IXb. The explanations given above with respect to the compounds of the formulae VIIIa, VIIIb, IXa and IXb and the amines of the formulae (R30)(R31)NH and R20—NH$_2$ occurring in the methods of Scheme 3 apply likewise to these compounds occurring in the methods of Scheme 4.

For the conversion into the final compounds of the formula I, the carboxylic acids of the formulae IXa and IXb, which have been obtained according to any of the methods outlined above, are then reacted with amines of the formulae (R30)(R31)NH and R20—NH$_2$ to give the compounds of the formulae Ia and Ib, respectively (Scheme 5). The explanations given above with respect to the conversion of the carboxylic acid group in the compounds of tbe formula X into a carboxamide group apply likewise to the conversion of the carboxylic acid group in the compounds of the Formulae IXa and IXb into a carboxarnlde group. Thus, for example, the carboxylic acid group can be activated by means of one of the various peptide coupling agents well known in the art, such as a N,N'-carbonyldiazole, a carbodiimide or a uronium-based coupling agent, optionally in the presence of an auxiliary agent such as 1-hydroxy-benzotriazole and/or a base such as a tertiary amine, and then treated with the amine of the formula (R30)(R31)NH or R20—NH$_2$. In this reaction, like in the reaction with the carboxylic acids of the formula X and in other reactions, the amines of the formulae (R30)(R31)NH and R20—Nh$_2$ can also be employed in the form of their salts, for example as hydrochloride or hydrobromide, and in such case a suitable auxiliary base be added for the liberation of the free amine, for example a tertiary amine like triethylamine, N,N-diisopropyl-ethylamine, or N-methyl-morpholine. It applies in general to the processes used in the preparation of the compounds of the formula I that starting compounds and

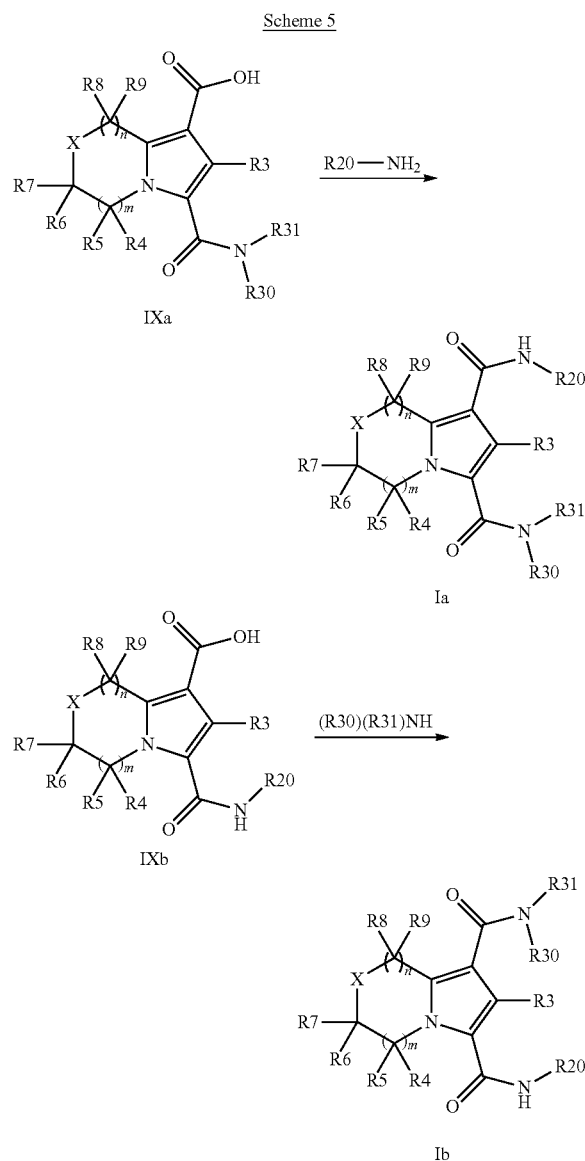

Scheme 5 intermediates can also be employed in the form of their salts, and intermediates as well as the compounds of the formula I can also be isolated in the form of their salts. Favorably, the carboxylic acid group in the compounds of the formula IXa and IXb is activated with a barbodiimide like 1-ethyl-3-(3-dimethylaminopropyl) carbodiimide hydrochloride and 1-hydroxy-benzotriazole and then treated with an amine of the formula (R30)(R31)NH or R20—NH$_2$ in an amide like dimethylformamide as solvent at temperatures from about 20° C. to about 60° C. The explanations given above with respect to the compounds of the formulae IXa and IXb and the amines of the formulae (R30)(R31)NH and R20—NH$_2$ occurring in the methods of Scheme 3 apply likewise to these compounds occurring in the methods of Scheme 5. In the compounds of the formulae Ia and Ib which are initially obtained in the reaction of the compounds of the formulae IXa and IXb with the amines of the formula (R30)(R31)NH and R20—NH$_2$, any functional groups may be present in protected form or in the form of a precursor group which are subsequently converted into the desired final groups to give the target compound of the formula Ia or Ib.

In another synthetic approach for the preparation of compounds of the formula I, which is outlined in Scheme 6, the compounds of the formula V, in which R3 to R9, R70, X, m and n are defined as above, are first converted into the carboxylic acids of the formula XI. Similarly as outlined above, the saponification of the carboxylic acid ester group R70—O—C(O)— can be performed, for example, by treatment with an alkali metal hydroxide like sodium hydroxide or potassium hydroxide in an inert solvent such as water or a mixture of water and an organic solvent, for example a mixture of water and an alcohol like methanol or ethanol, at temperatures from about 50° C. to about 80° C. For the subsequent reaction of the compound of the formula XI with the amines of the formulae R20—NH$_2$ and (R30)(R31)NH or their salts to give the compounds of the formulae XIIa and XIIb, respectively, likewise the methods outlined above can be used. Thus, for example, the compound of the formula XI can be activated with an activating agent such as a carbodiimide like 1-ethyl-3-(3-dimethylaminopropyl)carbodiimide hydrochloride and 1-hydroxy-benzotriazole and then treated with the amine in an inert solvent such as an amide like dimethylformamide at temperatures from about 20° C. to about 60° C. optionally in the presence of an auxiliary base such as a tertiary amine like triethylamine. Reaction of the obtained compounds of the formulae XIIa and XIIb with trichloroacetyl chloride, for example in a chlorinated hydrocarbon like dschloromethane at temperatures from about 10° C. to about 50° C., affords the compounds of the formulae XIIIa and XIIIb, Scheme 6

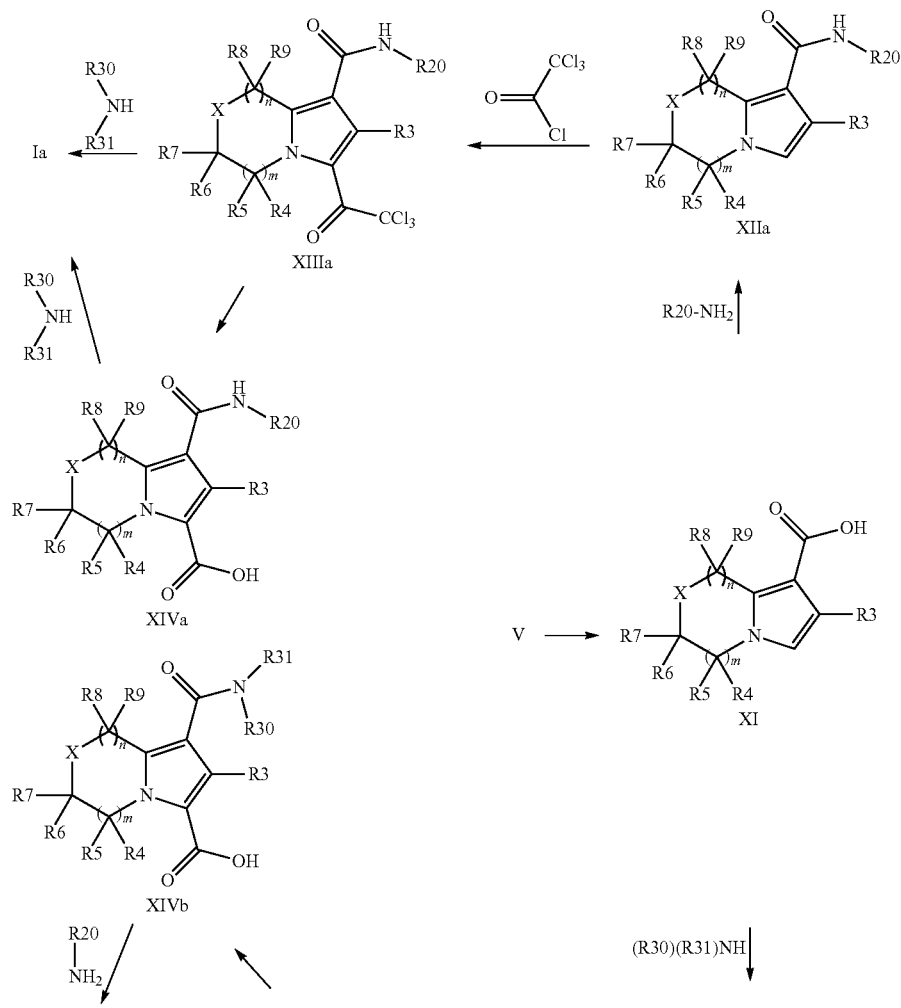

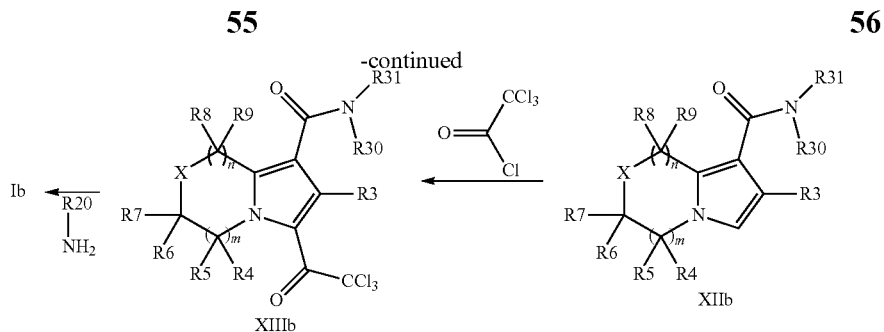

The compounds of the formulae XIIIa and XIIIb can be converted into the bisamides of the formulae Ia and Ib either by reacting them directly with the amine of the formula (R30)(R31)NH or R20—NH2, respectively, as outlined above with respect of tine reaction of the compounds of the formula VII with these amines, for example in an ether like tetrahydrofuran as solvent at temperatures from about 20° C. to about 80° C., or by first converting the trichloroacetyl group into a carboxylic acid group, for example by reaction with an alkali metal hydroxide like sodium hydroxide or potassium hydroxide in an inert solvent, such as a mixture of water and an organic solvent, for example a mixture of water and an ether like tetrahydrofuran, at temperatures from about 40° C. to about 80° C., to give the compounds of the formulae XIVa and XIVb, and then activating the compound of the formula XIVa or XIVb and treating it with the amine of the formula (R30)(R31)NH or R20—NH$_2$, respectively, for example by the carbodiimide methodology outlined above, such as by means of 1-ethyl-3-(3-dimethylaminopropyl)carbodiimide hydrochloride and 1-hydroxy-benzotriazole in a solvent like dimethyl formamide at temperatures from about 20° C. to about 60° C. R3 to R9, X, n and m in the compounds of the formulae XI, XIIa, XIIb, XIIIa, XIIIb, XIVa and XIVb are defined as in the compounds of the formula V. R20, R30 and R31 in the compounds of the formulae XIIa, XIIb, XIIIa, XIIIb, XIVa and XIVb, the initially obtained compounds of the formula Ia and Ib and the employed amines of the formulae (R30)(R31)NH and R20—NH$_2$ in the reactions depicted in Scheme 6 are defined as in the compounds of the formula I, and additionally can functional groups be present in protected form or in the form of a precursor group which are subsequently converted into the final groups.

In a further synthetic approach for the preparation of the compounds of the formula I, which is outlined in Scheme 7, the carboxamioes of the formulae XIIa and XIIb are first brominated with N-bromo-succinimide in an inert solvent such as a chlorinated hydrocarbon like dichloromethane at temperatures from about −80° C. to about 30° C. to give the brominated compounds of the formulae XVa and XVb, which are then subjected to a transition metal-catalyzed aminocarbonylation to give the compounds of the formulae Ia and Ib, respectively.

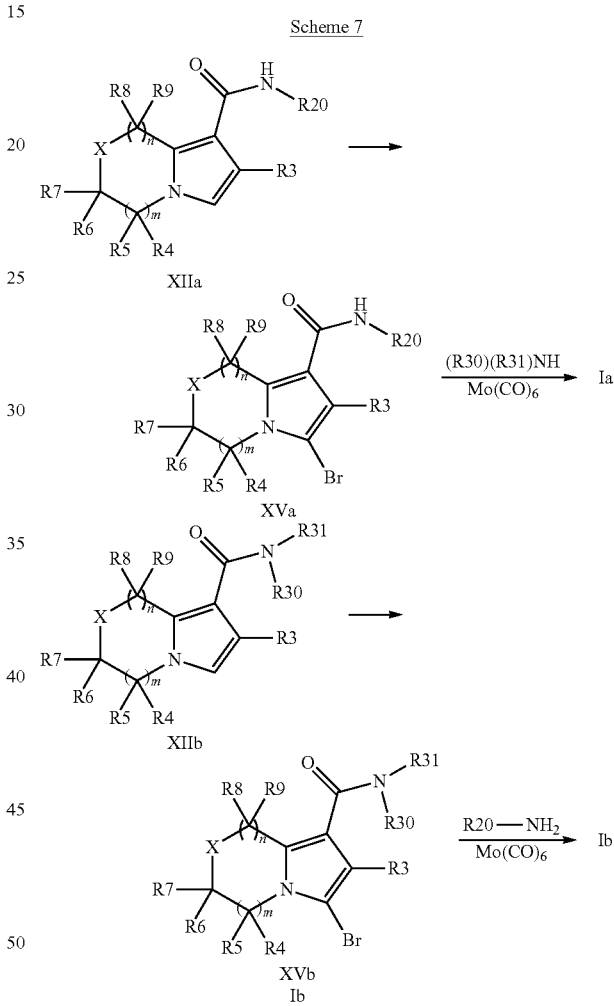

Scheme 7

R3 to R9, X, n and m in the compounds of the formulae XVa and XVb are defined as in the compounds of the formula V. R20, R30 and R31 in the compounds of the formulae XVa and XVb, the initially obtained compounds of the formula Ia and Ib and the employed amines of the formulae (R30)(R31)NH and R20—NH$_2$ in the reactions depicted in Scheme 7 are defined as in the compounds of the formula I, and additionally can functional groups be present in protected form or in the form of a precursor group which are subsequently converted into the final groups. The arrsinocarbonylation can favorably be carried out with a metal carbonyl as source of carbon monoxide, for example molybdenumhexacarbonyl Mo(CO)$_6$, and the amine of the formula R20—NH$_2$ or (R30)(R31)NH in the presence of a palladium catalyst like trans-di-(μ-acetato)bis[2-(di-o-tolylphosphino)benzyl]dipalladium(II) and a base like 1,8-diazabicyclo[5.4.0]undec-7-ene (DBU) in a solvent such as an ether like tetrahydrofuran or dioxane at temperatures from about 100° C. to about 150° C. under pressure and microwave irradiation, in analogy to the procedure described in Wannberg J. et al., J. Org. Chem. 2003, 68, 5750-5753.

An alternative synthesis of compounds of the formula I in which the number n is 0 and the group X is oxygen or sulfur, in particular oxygen, i.e. compounds of the formula Ih which is outlined in Scheme 8, starts from 5-halo-pyrrole-2,4-dicarboxylic

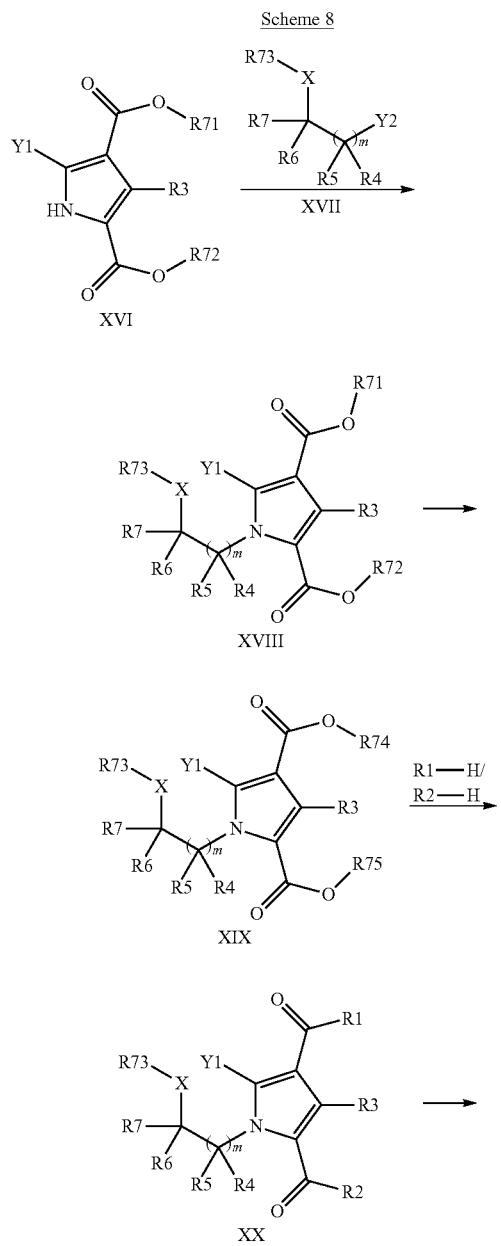

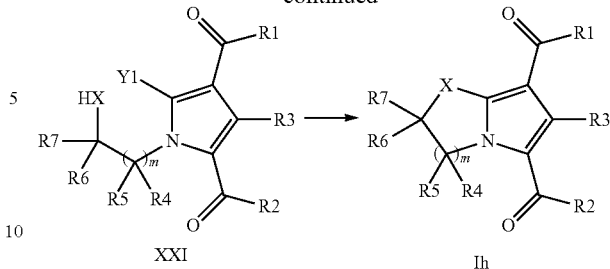

acid diesters of the formula XVI, which can be obtained from respective pyrrole-2,4-dicarboxylic acid diesters which are unsubstituted in ring position 5, by halogenation with N-chloro-succinimide or N-bromo-succinimide as described in US 2004/0209886. The compound of the formula XVI is alkylated at the ring nitrogen atom with a compound of the formula XVII under standard conditions for such allegations, for example in the presence of a base such as an alkali metal carbonate like cesium carbonate in an inert solvent such as a ketone like acetone or methyl ethyl ketone at temperatures from about 50° C. to about 80° C., to give a compound of the formula XVIII. The group Y2 in the compounds of the formula XVII is a nucleophliically substitutable leaving group, for example halogen such as bromine or a sulfonyloxy group such as methanesulfonyloxy in the compounds of the formulae XVI, XVII, XVIII, XIX, XX, XXI and Ih, the groups R4 to R7 are defined as in the compounds of the formula I, the group R3 is hydrogen or (C$_1$-C$_4$)-alkyl, the group X is oxygen or sulfur, in particular oxygen, the number m is 1 or 2, the group Y1 is chlorine or bromine, and the group R73 is a suitable protecting group, for example tert-butyl or a trialkylsilanyl group like trimethylsilanyl, triisopropylsllanyl or tert-butyl-dimethylsilanyl. The groups R71 and R72 in the compounds of the formulae XVI and XVIII can be alkyl groups such as (C$_1$-C$_4$)-alkyl like ethyl, for example, and can be identical or different. In particular for the synthesis of compounds of the formula Ih in which the two groups R1 and R2 are identical, the groups R71 and R72 can be identical and the ester groups R71—O—C(O)— and R72—O—C(O)— in the compound of the formula XVIII simultaneously be hydrolyzed, for example by treatment with an alkali metal hydroxide like sodium hydroxide or potassium hydroxide in an inert solvent such as wafer or a mixture of water and an organic solvent, for example a mixture of wafer and an alcohol like ethanol or isopropanol, at temperatures from about 20° C. to about 30° C. in the case of ethyl esters, to give a compound of the formula XIX in which the groups R74 and R75 are hydrogen, i.e. the groups R74—O—C(O)— and R75—O—C(O)— are carboxylic acid groups. Under suitable conditions, ester groups in compounds of the formula XVIII, in which R71 and R72 are identical or different, can be hydrolyzed sequentially or selectively, to give a compound of the formula XIX in which one of the groups R74 and R75 is hydrogen, i.e. one of the ester groups in the compound of the formula XVIII is converted into a carboxylic acid group, and the other is defined as the respective group in the compound of the formula XVIII, i.e. the other of the ester groups is maintained. The carboxylic acid group or groups in the compounds of the formula XIX are reacted with an amine of the formula R1—H and/or an amine of the formula R2—H to give the biscarboxamides of the formula XX. In the compounds of the formulae XX and XXI, the employed amines of the formulae R1—H and R2—H and in the initially obtained compounds of the formula Ih are the croups R1 and R2 defined as in the compounds of the formula I, i.e. one of the groups R1 and R2 is the group R20—NH— and the other is the group (R30)(R31)N—, and additionally can functional groups be present in protected form or in the form of a precursor group which are subsequently converted into the final groups, wherein the groups R1 and R2 can be identical or different, and in one embodiment of the invention are identical. For the conversion into the carboxamides, the carboxylic acid group or groups in the compounds of the formula XIX can be activated as outlined above for other amide formations, for example according to the carbodiimide methodology by treatment with 1-ethyl-3-(3-dimethylaminopropyl)carbodiimide hydrochloride and an N-hydroxy-triazole such as 1-hydroxy-benzotriazole or 1-hydroxy-7-azabenzotriazole in a solvent like dimethylformamide at temperatures from about 20° C. to about 30° C. In case one carboxylic acid and one ester group is present in the compound of the formula XIX, after the conversion of the carboxylic acid group info a carboxamicie group the ester can group can be hydrolyzed and the obtained carboxync acid group likewise reacted with an amine, which can be different from the amine employed in the first amide formation, to give a compound of the formula XX in which both groups R1—C(O)— and R2—C(O)— are amide groups. In case a mixture of compounds is obtained after the amidation reaction or reactions, the individual compounds can be separated by chromatography. De-protection of the moiety R73—X— in the compound of the formula XX, for example by treatment with an acid like hydrochloric acid at temperatures from about 20° C. to about 30° C. in the case of a trialkylsiianyl protecting group, affords a compound of the formula XXI, whose cyclization, for example by treatment with a base such as an alkali metal carbonate like cesium carbonate in an inert solvent such as an amide like dimethylformamide at temperatures from about 100° C. to about 150° C. under microwave irradiation, then provides the compound of the formula Ih.

The amines of the formulae R20—NH2 and (R30)(R31)NH, which are used as starting compounds in the synthesis of the compounds of the formula I, are commercially available or have been described in the literature or can be synthesized according to various procedures for the synthesis of such compounds described in the literature. By way of example, in the following some procedures are outlined by which such amines can be prepared. For example, chiral amines of the formulae XXIVa and XXIVa, which can be amines of the formula R20—NH2 in which R20 is (R21)(R22)(R23)C— and R23 is hydrogen, or amines of the formula (R30)(R31)NH in which R30 is hydrogen, R31 is (R32)(R33)(R34)C— and R32 is hydrogen, for example, can be prepared in analogy to the Ellman synthesis with the aid of enantiopure (R)- or (S)-tert-butyl sulfinamide of the formula (CH3)3C—S(O)—NH2 (cf. Ellman J. A. et al., Acc. Cham. Res 2002, 35, 984-995; Morton D. et al., Tetrahedron 2006, 82, 8869-8905), as outlined In Schemes 9 and 10. The groups R80 and R81 in the compounds

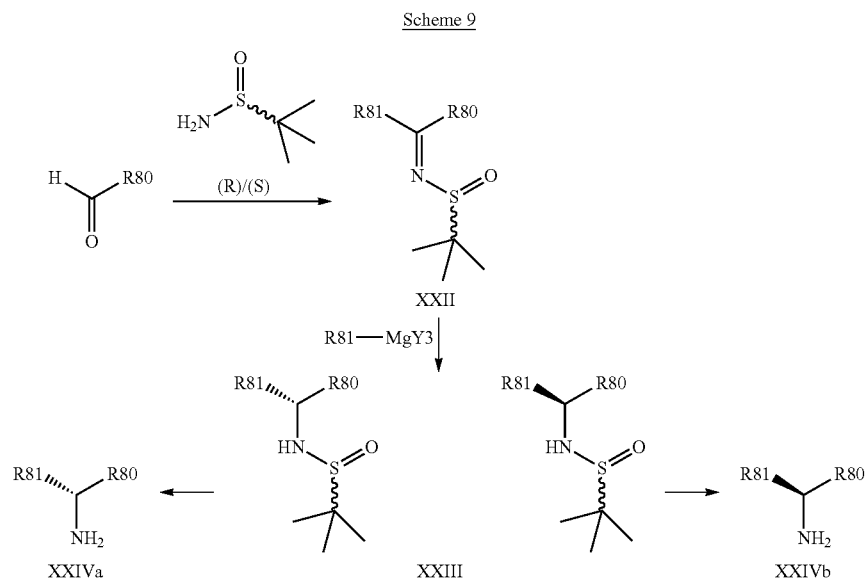

Scheme 9 of the formulae XXII, XXIII, XXIVa and XXIVb and the formulae R80—C(O)—H and R81—MgY3 are defined as R21 and R22, or as R33 and R34, wherein R21, R22, R33 and R34 are defined as in the compounds of the formula I and additionally can functional groups be present in protected form or in the form of a precursor group which are subsequently converted into the final groups.

For example, starting from an aldehyde of the formula R80—C(O)—H, in particular an anomatic aldehyde in which R80 is an unsubstituted or substituted phenyl group or aromatic heterocyclic group, by reaction with enantiopure (R)- or (S)-tert-butylsulfinamide in the presence of a catalyst such as an acidic compound like potassium hydrogensulfate in an inert solvent such as a hydrocarbon like toluene at temperatures from about 20° C. to about 80° C. enantiopure N-tert-butylsulfinyl imines of the formula XXII can be obtained, which can be reacted with Grignard reagents of the formula R81—MgY3, in which Y3 is halogen, for example chlorine or bromine, and R81 in particular is an aliphatic or alicyclic group, for example an alkyl, cycloalkyl or cycloalkyl-alkyl- group in an inert solvent such as an ether like tetrahydrofuran at low temperatures, for example at about −80° C., to give the intermediate of the formula XXIII, which can be a mixture of dsastereomers. The individual diastereomers of the formula XXIII, which can be separated by chromatography, can then be converted into the chiral amines of the formula XXIVa or XXIVb or their salts, for example their hydrochlorides, by treatment with an acid, for example hydrogen chloride in an alcohol like methanol or trifluoroacetic acid in a chlorinated hydrocarbon like dichloromethane, at temperatures from about 20° C. to about 30° (Scheme 9).

In another method, starting from an aldehyde of the formula R81—C(O)—H, in particular an aliphatic or alicyclic group aldehyde in which R81 is an alkyl, cycloalkyl or cycloalkyl-alkyl- group, for example, by reaction with enantiopure (R)- or (S)-tert-butylsulfinamide enantiopure N-tert-butylsulfinyl imines of the formula XXV can be obtained as outlined above with respect to the compounds of the formula XXII.

chlorine or bromine, in an inert solvent such as an ether like tetrahydrofuran at temperatures from about −80° C. to about 30° C., and in situ reduction of the imine intermediate of the formula (R80)(R81)C=NH with a complex hydride, for example sodium borohydride, at temperatures from about −80° C. to about 30° C. If desired, a mixture of stereoisomeric forms of an amine such as an racemate can be separated into the individual stereoisomers by conventional techniques, such as by chromatography, for example on a chiral phase, or by salt formation with an enantiopure carboxylic acid or sulfonic acid and fractional crystallization of diastereomeric salts.

Secondary amines of the formula (R30)(R31)NH, in which R30 is different from hydrogen, can be prepared from amines of the formula R31—NH$_2$, including enantiopure

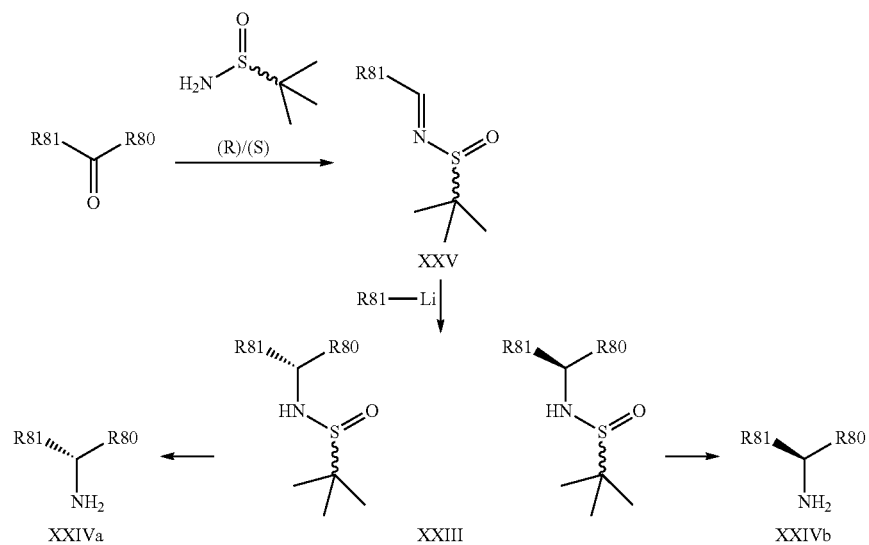

Scheme 10

Reaction of a compound of the formula XXV with an organolithium compound of the formula R80—Li, in which R80 is in particular an aromatic group like an unsubstituted or substituted phenyl group or aromatic heterocyclic group and which can be obtained from the respective halogemdes, for example compounds of the formula R80—Br, by treatment with an organolithium compound such as n-butyllithium in an inert solvent such as an ether like diethyl ether or tetrahydrofuran at temperatures from about −80° C. to about −° C., in an inert solvent such as an ether like tetrahydrofuran at low temperatures, for example at about −80° C., provides the intermediate of the formula XXIII, which can be a mixture of diastereomers. As in the case of its synthesis from the compound of the formula XXII, the individual diastereomers of the formula XXIII, which can be separated by chromatography, can then be converted into the chiral amines of the formula XXIVa or XXIVb or their salts, for example their hydrochlorides, by treatment with an acid such as hydrogen chloride or trifluoroacetic acid (Scheme 10).

Racemic amines of the formula (R80)(R81)CH—NH$_2$, in which R80 and R81 are defined as sn the compounds of the formula XXIVa and XXlVb, can be prepared from nitriles of the formula R80—CN or R81—CN by reaction with a Grignard reagent of the formula R81—MgY3 or R80—MgY3, respectively, in which Y3 is halogen, for example and racemic amines of the formula (R80)(R81)CH—NH$_2$, for example, by reaction with a compound of the formula R30—Y4, in which R30 is defined as in the compounds of the formula I except for the denotation hydrogen, and Y4 is a nucleophilically substitutable leaving group, for example halogen like bromine, in a solvent such as acetonitrlle in the presence of a base such as a tertiary amine like trlethylamine at temperatures from about 20° C. to about 80° C., or by any of the other methods for the alkylation of amines well known in the art, for example by reaction with an aldehyde and reduction of the imine that is initially obtained.

As another example of the preparation of amines which can be employed in the synthesis of compounds of the formula I, the formation of certain amines of the formula (R30)(R31)NH in which R30 and R31, together with the nitrogen atom carrying them, form a heterocycle substituted by R36, may be mentioned. For example, enantiopure amines of such type which are saturated heterocycles comprising no further ring heteroatom and carrying on a ring carbon atom in position 2 a substituent R36 which is an unsubstituted or substituted phenyl group or aromatic heterocyclic group Het3, i.e. compounds of the formula XXVI, in particular pyrrolidines carrying such a substituent R36 in ring position 2, can be obtained from the respective N-tert-butoxycarbonyl-protected heterocycle, for example N-tert-butoxycarbonyl-pyrrolidine, in analogy to the procedure described in WO 2008/053319 by deprotonation with sec-butyllithium in the presence of (−)-sparteine, treatment with zinc chloride, reaction with a compound of the formula R36—Y4, in which R36 is an unsubstituted or substituted phenyl group or aromatic Het3 group and Y4 is a nucleophilically substitutable leaving group, for example halogen like bromine, in the presence of a palladium compound such as palladium acetate and tri-tert-butylphosphonium tetrafluoroborate in an inert solvent such as an ether like tert-butyl methyl ether at temperatures from about −80° C. to about 30° C., and cleavage of the protecting group, for example by treatment with hydrogen chloride (Scheme 11).

Scheme 11

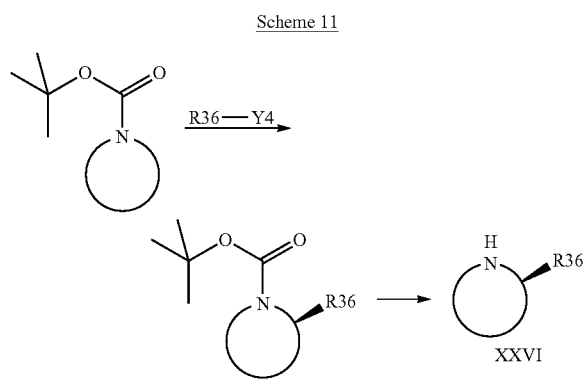

For obtaining further compounds of the formula I, including the compounds of the formulae Ia, Ib and Ih, whose synthesis is outlined above, various transformations of functional groups can be carried out under standard conditions in compounds of the formula I obtained as described above, and in intermediates and starting compounds of the synthesis of the compounds of the formula I. Such transformations can in particular be performed with functional groups present in the groups R20, R30 and R31, in case R20 occurs in R1 and R30 and R31 occur in R2 as well as in case R20 occurs in R2 and R30 and R31 occur in R1. Some examples of such transformations are briefly outlined in the following.

For the preparation of compounds of the formula I in which R3 is halogen, i.e. compounds of the formula Ij in which R3' is halogen, for example fluorine, chlorine or bromine, in particular chlorine or bromine, respective compounds of the formula I in which R3 is hydrogen, i.e. compounds of the formula Ii, can be halogenated, for example by treatment with an N-halo-succinimide like N-chloro-succinimide or N-bromo-succinimide in a chlorinated hydrocarbon like dichloromethane or chloroform at temperatures from about −80° C. to about 50° C., or by treatment with an N-fluoro-pyridinium salt like 2,6-dichloro-1-fluoro-pyridinium triflate (Scheme 12). R1, R2, R4 to R9, X, m and n in the compounds of the formulae Ii and Ij are defined as in the compounds of the formula I, and additionally can functional groups be present in protected form or in the form of a precursor group which are subsequently converted into the final groups.

Scheme 12

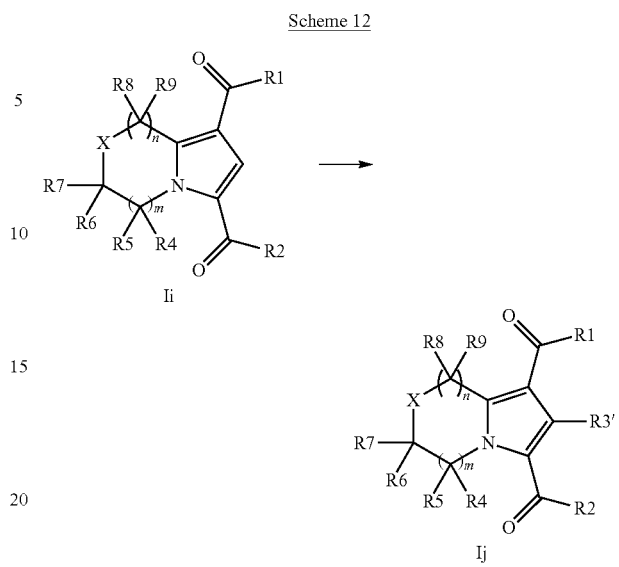

For the preparation of compounds of the formula I in which R3 is alkyl, i.e. compounds of the formula Im in which R3" is ($C_1$-$C_4$)-alkyl, for example ($C_1$-$C_3$)-alkyl, in particular methyl or ethyl, respective compounds of the formula Ik can be reacted with a tetraalkyltin reagent (Sn(($C_1$-$C_4$)-alkyl)$_4$) in the presence of a catalyst such as a palladium compound like tetrakis(triphenylphosphino)palladium(0) in an inert solvent such as dimethylformamide at temperatures from about 25° C. to about 150° C. (Scheme 13), analogously to the procedure for the replacement of bromine atoms on aromatic rings with alkyl groups described in Macdonald, S. J. F. et al., J. Chem. Soc., Chem. Comm. 1987, 1528-1530, for example, R1, R2, R4 to R9, X, m and n in the compounds of the formulae Ik and Ik are defined as in the compounds of the formula I, and additionally can functional groups be present in protected form or in the form of a precursor group which are subsequently converted into the final groups.

Scheme 13

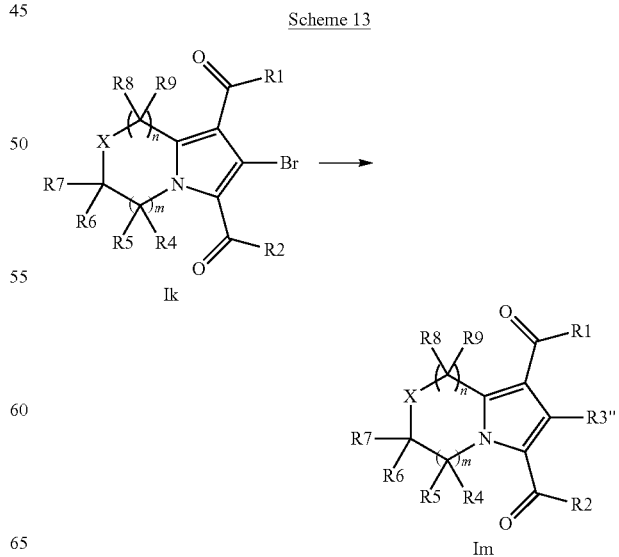

Hydroxy groups and amino groups, including ring nitrogen atoms in heterocyoles which can be acylated, in compounds of the formula I obtained as described above, and in intermediates and starting compounds can be acylated, i.e. converted into acyioxy groups and aoylamlno groups, respectively, which can also be termed as carboxylic acid ester groups and carboxamide groups, by treatment with a reactive carboxylic acid derivative like a carboxylic acid chloride, which may be obtained from carboxylic acid with thionyl chloride or oxalyl chloride, or with a carboxylic acid anhydride, or with a carboxylic acid in the presence of an activating agent similarly as already described above, for example in the presence of a coupling agent such as an N,N'-carbonyldiazole like N,N'-carbonyldiimidazole (CDI), a carbodiimide like 1,3-diisopropylcarbodiimide (DIC), 1,3-dicyclohexylcarbodiimide (DCC) or 1-(3-dimethylaminopropyl)-3-ethylcarbodiimide hydrochloride (EDAC), or a uroniom-based coupling agent like O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU) or O-(cyano(ethoxycarbonyl)methyeneamino)-N,N,N',N'-tetramethyluronium tetrafluoroborate (TOTU), in an inert solvent, for example a hydrocarbon like toluene, a chlorinated hydrocarbon like dichloromethane, an ether like tetrahydrofuran, dioxane or 1,2-dimethoxyethane, or an amide like dimethylformamide or N-methylpyrrolidin-2-one, generally in the presence of a base, such as a tertiary amine like triethylamine, diisopropylethylamine, N-methylmorphonine or pyridine, or an inorganic base. In such acylation reactions, an acylation catalyst like 4-dimethylaminopyridine may be added. Similarly, amino groups can be sulfonylated to give sulfonylamino groups by reaction with activated sulfonic acids derivatives such as sulfonic acid chlorides.

Hydroxy groups can be etherified, for example by alkylation or arylation with a halogen compound like a bromide or iodide or with a sulfonyloxy compound, generally in the presence of a base, such an alkali metal carbonate like potassium carbonate or cesium carbonate or an amide like sodium bis(trimethylsilyl)amide in an inert solvent such as an amide like dimethylformamide or N-methylpyrrolidin-2-one or a ketone like acetone or butan-2-one or an ether like tetrahydrofuran, or with an alcohol under the conditions of the Mitsunobu reaction in the presence of a phosphine like triphenylphosphine or tributylphosphine and an azodicarboxylic acid derivative like diethyl azodicardoxylate or diisopropyl azodicarboxylate. Ether groups can be converted into hydroxy groups by standard methods for ether cleavage, for example in the case of methoxy groups on phenyl rings and aromatic heterocyclic rings favorably by treatment with trimethylsilyl iodide in an inert solvent like acetonitrile.

By treatment with a suitable halogenating agent, hydrogen atoms on carbon atoms can be replaced with halogen atoms to give halides, and oxygen functional groups like hydroxy groups can be convened into halides. Halogen atoms can be replaced with a variety of groups in substitution reactions, which may also be transition-metal catalyzed reactions. For example, halides such as bromides can be converted into alkylmercapto compounds by treatment with alkylmercaptanes in the presence of a base, or with salts of alkylmercaptanes like their sodium salts, in an inert solvent such as an amide like dimethylformamide, or into nitriles by treatment with alkali metal cyanides, trimethylsilyl cyanide or, in the case of aromatic bromides, copper cyanide, which latter reaction can favorably be performed in an inert solvent such as dimethyl sulfoxide under microwave irradiation, or into other halides by halogen exchange. Instead of halides, in reactions for the preparation of such compounds also sulfonyloxy compounds can be employed which can be obtained from hydroxy compounds with sulfony chlorides such as methanesulfonyl chloride, for example.

Amino groups, including ring nitrogen atoms in heterocycles which can carry a hydrogen atom or substituent, such as ring nitrogen atoms in pyrrolidine rings and piperidine rings bonded via a ring carbon atom, or in piperazine rings or tetrazole rings, for example, can be modified under standard conditions for alkylation, for example by reaction with a halogen compound or by reductive amination with a carbonyl compound. Mixtures of products obtained in such reactions, can be separated by chromatography. Similarly, the nitrogen atom in a sulfonamide group $H_2N—S(O)_2$— can be alkylated, for example with a halide in the presence of a base such as an alkali metal hydroxide like potassium hydroxide, to give N-monosubstituted and N,N-disubstituted sulfonamides.

Carboxylic acid ester groups can be hydrolyzed under acidic or basic conditions, for example by treatment with an alkali metal hydroxide like sodium hydroxide or potassium hydroxide in an inert solvent such as water or an alcohol like methanol, ethanol or isopropanol or an ether like tetrahydrofuran or dioxane or mixtures thereof, to give carboxylic acids. Carboxylic acid groups can be activated or convened into a reactive derivative as outlined above, and reacted with an alcohol or with ammonia or an amine to give an ester or amide, respectively, Nitrile groups can be hydrolyzed to amide groups and carboxylic acid groups and reduced to aminomethyl- groups.

Carboxylic acid groups, carboxylic acid ester groups and ketone groups and aldehyde groups can be reduced, for example with complex hydrides such as lithium aluminum hydride, lithium borohydhde or sodium borohydride, and reacted with Grignard compounds and other organometal compounds to give hydroxy compounds. Hydroxy groups can be oxidized to oxo groups by means of pyridinium chlorochromate or the Dess-martin periodinane reagent, for example. Sulfur atoms in alkylmercapto compounds and sulfur heterocycles can be oxidized with a peroxide like hydrogen peroxide or a peracid to give sulfoxide ($S(O)$) or sulfone ($S(O)_2$) moieties.

All such reactions, which can be used in the preparation of the compounds of the formula I, are known per se and can be carried out in a manner familiar to a person skilled in the art according to, or analogously, to procedures which are described in the standard literature, for example in Houben-Weyl, Methods of Organic Chemistry, Thieme: or Organic Reactions, John Wiley & Sons, or R. C. Larock, Comprehensive Organic Transformations: A Guide to Functional Group Preparations, 2. ed. (1999), John Wiley & Sons, and the references quoted therein.

As already indicated, if can be advantageous or necessary in all reactions which are carried out in the course of the preparation of the compounds of the formula I, to temporarily protect functional groups or have them initially present in the form of precursor groups, and later deprotect them or convert them into the desired groups. Appropriate synthesis strategies and protective groups and precursor groups which are suitable for the respective case, are known to the person skilled in the art and can be found in P. G. M. Wuts and T. W. Greene, Greene's Protective Groups in Organic Synthesis, 4, ed. (2007), John Wiley & Sons, for example. Examples of protective groups which may be mentioned, are benzyl protective groups, for example benzyl ethers of hydroxy compounds and benzyl esters of carboxylic acids, from which the benzyl group can be removed by catalytic hydrogenation in the presence of a palladium catalyst, tert-butyl protective groups, for example tert-butyl esters of carboxylic acids, from which the tert-butyl group can be removed by treatment with trufluoroacetic acid, acyl protective groups, for example ester and amides of hydroxy compounds and amino compounds, which can be cleaved by acidic or basic hydrolysis, alkoxycarbonyl protective groups, for example tert-butoxycarbonyl derivatives of amino compounds, which can be cleaved by treatment with trifluoroacetic acid, or benzyloxycarbonyl derivatives of amino compounds, which can be cleaved by catalytic hydrogenation in the presence of a palladium catalyst. Examples of precursors which may be mentioned, are halogen atoms which can be replaced by many other groups as outlined above, or nitro groups which can be converted into amino groups, for example by catalytic hydrogenation.

As is usual and applies to all reactions performed in the course of the synthesis of a compound of the formula I, appropriate details of the conditions applied in a specific preparation process, including the solvent, a base or acid, the temperature, the order of addition, the molar ratios and other parameters, are routinely chosen by the skilled person in view of the characteristics of the starting compounds and the target compound and the other particularities of the specific case. As is also known to the skilled person, not all processes described herein will in the same way be suitable for the preparation of all compounds of the formula I and their intermediates, and adaptations have to be made. In all processes for the preparation of the compounds of the formula I, workup of the reaction mixture and the purification of the product is performed according to customary methods known to the skilled person which include, for example, quenching of a reaction mixture with water, adjustment to a certain pH, precipitation, extraction, drying, concentration, crystallization, distillation and chromatography including high performance liquid chromatography (HPLC). Also for the characterization of the products, customary methods are used such as NMR, IR and mass spectroscopy.

Another subject of the present invention are the novel starling compounds and intermediates occurring in the synthesis of the compounds of the formula I, including the compounds of the formulae II, III, IV, V, VII, VIIIa, VIIIb, IXa, IXb, X, XI, XIIa, XIIb, XIIIa, XIIIb, XIVa, XIVb, XVa, XVb, XVI, XVII, XVIII, XIX, XX, XXI, XXII, XXIII, XXXIVa, XXXIVb, XXV, XXVI and amines of the formulae R20—$NH_2$ and (R30)(R31)NH, wherein R1 to R9, R20, R30, R31, R36, R70 to R75, R80, R81, X, Y1 to Y4, m and n are defined as above, in any of their stereoisomeric forms or a mixture of stereoisomers forms in any ratio, and their salts, and their use as synthetic intermediates or starting compounds. All general explanations, specifications of embodiments and definitions of numbers and groups given above With respect to the compounds of the formula I apply correspondingly to the said intermediates and starting compounds. A subject of the invention are In particular the novel specific starting compounds and intermediates described herein, independently thereof whether they are described as a free compound and/or as a specific salt, they are a subject of the invention both in the form of the free compounds and in the form of their salts, and if a specific salt is described, additionally in the form of this specific salt.

The compounds of the formula I inhibit TASK ion channels, especially TASK-1, and in one embodiment of the invention have further favorable properties, for example exhibit a favorable pharmacokinetic profile, are selective for TASK-1, or are devoid of proarrhythmic properties, in particular do not substantially inhibit the hERG channel, as can be shown in the pharmacological tests described below and in other pharmacological tests which are known to a person skilled in the art, including animal models in which the effect of the compounds can be determined ex vivo or in vivo. The compounds of the formula I and their pharmaceutically acceptable salts therefore are valuable pharmaceutically active compounds. The compounds of the formula I and their pharmaceutically active salts can in particular be used for blocking TASK-1 channels with the aim of treating TASK-1 channel-mediated diseases, including disorders which are caused by activation of TASK-1 channels or by activated TASK-1 channels, and also disorders in which TASK-1-related damages appear secondary to another, primary cause, and more generally in disorders in which an inhibition of TASK-1 is intended by the physician for improving the patient's condition. The compounds of the formula I and their pharmaceutically acceptable salts can also be employed in cases where only a certain partial inhibition of TASK-1 activity is intended, for example by a low dosage. The treatment of diseases is to be understood as meaning both the therapy of existing pathological changes or malfunctions of the organism or of existing symptoms with the aim of relief, alleviation or cure, and the prophylaxis or prevention of pathological changes or malfunctions of the organism or of symptoms in humans or animals which are susceptible thereto and are in need of such a prophylaxis or prevention, with the aim of a prevention or suppression of their occurrence or of an attenuation in the case of their occurrence. For example, in patients who on account of their disease history are susceptible to cardiac arrhythmias, by means of the prophylactic or preventive medicinal treatment the occurrence or re-occurrence ol arrhythmias can be prevented or their extent and sequelae decreased. The treatment of diseases can occur both in acute cases and in chronic cases.

The compounds of the formula I and these pharmaceutical acceptable salts can be used for the treatment. Including therapy and prevention, of arrhythmias, in particular atrial arrhythmias, atrial tachyarrhythmias, atrial fibrillation and atrial flutter, and secondary damages thereof, for example stroke. More specifically, they can be used, for example, for the treatment of arrhythmias that respond to the changes in the shape of the action potential, mainly a prolongation of the action potential, which is induced by TASK-1 blockade. The compounds of the formula I and their pharmaceutically acceptable salts can be employed for terminating existent atrial fibrillation or atrial flutter and restoring the sinus rhythm. The compounds of the formula I and their pharmaceutical acceptable salts reduce the susceptibility for a new development of atrial fibrillation events, and thus are suitable for prophylactic treatment by maintenance of sinus rhythm (rhythm control). The substances are devoid of a ventricular proarrhythmic risk.

The compounds of the formula I and their pharmaceutically acceptable salts are also suitable for the treatment, including therapy and prevention, of respiratory disorders, in pedicular sleep-related respiratory dmoruerm sleep apnea, central sleep apnea, obstructive sleep apnea, upper airway resistance syndrome, Cheyne-Stokes respiration, snoring, disrupted central respiratory drive, sudden child death, postoperative hypoxia, postoperative apnea, muscle-related respiratory disorders, respiratory disorders after long-term mechanical ventilation, respiratory disorders during adaptation in high mountains, chronic lung disorders with hypoxia or hypercapnia, chronic obstructive pulmonary disease (COPD) and obesity hypoventilation syndrome. They can also be used as a respiratory stimulant for the treatment, including therapy and prevention, of respiratory depression, such as respiratory depression associated with anesthesia or procedural sedations for small interventions or for diagnostic purposes, for the treatment of respiratory depression caused by opioids in pain treatment, for example in cancer or palliative care, and for weaning from long-term mechanical ventilation.

The compounds of the formula I and their pharmaceutically acceptable salts are also suitable for the treatment, including therapy and prevention, of disturbed motor function and of diseases associated with impaired motor function. They can be used for the treatment of disturbances of cranial motor function, for example for the treatment of dysphagia, sialorrhea, dysarthria, facial paresis and hypomimia, as well as for the treatment of disturbances of peripheral motor function, in diseases such as stroke, Parkinson's disease, multiple sclerosis, amyotrophic lateral sclerosis, dementia and neuromuscular diseases.

The compounds of the formula I and their pharmaceutically acceptable salts are further suitable for the treatment, including therapy and prevention, of inflammatory disorders, inflammatory disorders of the central nervous system, immunomodulatory disorders, immunomodulatory disorders of the central nervous system, autoimmune diseases and multiple sclerosis.

The compounds of the formula I and their pharmaceutical acceptable salts can therefore be used in animals, in particular in mammals, specifically in humans, as a pharmaceutical or a medicament on their own, in mixtures with one another, or in the form of pharmaceutical compositions. A subject of the present invention also are the compounds of the formula I and their pharmaceutically acceptable salts for use as a pharmaceutical. A subject of the present invention also are pharmaceutical compositions and medicaments which comprise at least one compound of the formula I and/or a pharmaceutically acceptable salt thereof as an active ingredient, in an effective dose for the desired use, and a pharmaceutically acceptable carrier, i.e. one or more pharmaceutically innocuous, or nonhazardous, vehicles and/or excipients, and optionally one or more other pharmaceutically active compounds. A subject of the present invention also are the compounds of the formula I and their pharmaceutically acceptable salts for use in the treatment of the diseases mentioned above or below, including the treatment of any one or more of the mentioned diseases, for example arrhythmias, atrial arrhythmias, atrial fibrillation, atrial flutter, respiratory disorders, sleep-related respiratory disorders, sleep apnea, disturbed motor function, dysphagia, inflammatory disorders or immunomodulatory disorders, wherein treatment of diseases comprises their therapy and prophylaxis as mentioned above, or for use an inhibitor of TASK-1 channels. A subject of the present invention also are the use of the compounds of the formula I and their pharmaceutical acceptable salts for the manufacture of a medicament for the treatment of the diseases mentioned above or below, including the treatment of any one or more of the mentioned diseases, for example arrhythmias, atrial arrhythmias, atrial fibrillation, atrial flutter, respiratory disorders, sleep-related respiratory disorders, sleep apnea, disturbed motor function, dysphagia, inflammatory disorders or immunomodulatory disorders, wherein treatment of diseases comprises their therapy and prophylaxis as mentioned above, or a medicament for inhibition TASK-1 channels. A subject of the present invention also ere methods for the treatment of the diseases mentioned above or below, including the treatment of any one or more of the mentioned diseases, for example arrhythmias, atrial arrhythmias, atrial fibrillation, atrial flutter, respiratory disorders, sleep-related respiratory disorders, sleep apnea, disturbed motor function, dysphagia, inflammatory disorders or immunomodulatory disorders, wherein treatment of diseases comprises their therapy and prophylaxis as mentioned above, and a method for inhibiting TASK-1 channels, which comprise administering an efficacious amount of at least one compound of the formula I and/or a pharmaceutically acceptable salt thereof to a human or an animal which is in need thereof.

For example, a subject of the present invention is a compound of the formula I, in any of its stereoisomenc forms or a mixture of stereoisomerie forms in any ratio, or a pharmaceutically acceptable salt thereof, for use in the treatment of arrhythmias, atrial arrhythmias, atrial tachyarrhythmias, atrial fibrillation, atrial flutter, stroke, respiratory disorders, sleep-related respiratory disorders, sleep apnea, central sleep apnea, obstructive sleep apnea, upper airway resistance syndrome, Cheyne-Stokes respiration, snoring, disrupted central respiratory drive, sudden child death, postoperative hypoxia, postoperative apnea, muscle-related respiratory disorders, respiratory disorders after long-term mechanical ventilation, respiratory disorders during adaptation in high mountains, chronic lung disorders with hypoxia or hypercapnia, chronic obstructive pulmonary disease, obesity hypoventilation syndrome, disturbed motor function, dysphagia, sialorrhea, dysarthria, facial paresis, hypomimia, Parkinson's disease, amyotrophic lateral sclerosis, dementia, neuromuscular diseases, inflammatory disorders, inflammatory disorders of the central nervous system, immunomodulatory disorders, immunomodulatory disorders of the central nervous system, autoimmune diseases or multiple sclerosis, or as a respiratory stimulant for the treatment, of respiratory depression, a respiratory stimulant for the treatment of respiratory depression associated with anesthesia or procedural sedations or caused by opioids, or for weaning from long-term mechanical ventilation.

Another example of a subject of the invention is a compound of the formula I, in any of its stereoisomers forms or a mixture of stereoisomers forms in any ratio, or a pharmaceutically acceptable salt thereof, for use in the treatment of arrhythmias, atrial arrhythmias, atrial tachyarrhythmias, atrial fibrillation, atrial flutter, stroke, respiratory disorders, sleep-related respiratory disorders, sleep apnea, central sleep apnea, obstructive sleep apnea, upper airway resistance syndrome, Cheyne-Stokes respiration, snoring, disrupted central respiratory drive, sudden child death, postoperative hypoxia, postoperative apnea, muscle-related respiratory disorders, respiratory disorders after long-term mechanical ventilation, respiratory disorders during adaptation in high mountains, chronic lung disorders with hypoxia or hypercapnia, chronic obstructive pulmonary disease, obesity hypoventilation syndrome, inflammatory disorders, inflammatory disorders of the central nervous system, immunomodulatory disorders, immunomodulatory disorders of the central nervous system, autoimmune diseases or multiple sclerosis, or as a respiratory stimulant for the treatment of respiratory depression, a respiratory stimulant for the treatment of respiratory depression associated with anesthesia or procedural sedations or caused by opioids, or for weaning from long-term mechanical ventilation.

The compounds of the formula I and their pharmaceutically acceptable salts, and pharmaceutical compositions and medicaments comprising them, can be administered enterally, for example by oral or rectal administration, parenterally, for example by intravenous, intramuscular or subcutaneous injection or infusion, or by another type of administration such as topical, percutaneous, transcutaneous, nasal, pharyngal or inhalative administration, the preferred form of administration depending on the particulars of the specific case. The compounds of the formula I and their pharmaceutically acceptable salts can also be used in combination with other pharmaceutically active compounds.

The pharmaceutical compositions and medicaments according to the invention normally contain from about 0.5 to about 90 percent by weight of a compound or compounds of the formula I or pharmaceutically acceptable salt thereof, and an amount of active ingredient of the formula I and/or its pharmaceutically acceptable salt which in general is from about 0.1 mg to about 1 g, in particular from about 0.2 mg to about 500 mg, for example from about 1 mg to about 300 mg, per dose unit. Depending on the kind of the pharmaceutical composition and other particulars of the specific case, the amount may deviate from the indicated ones. The production of the pharmaceutical compositions and medicaments can be carried out in a manner known per se and familiar to the person skilled in the art. For this, the compounds of the formula I and/or their pharmaceutically acceptable salts are mixed together with one or more solid or liquid vehicles and/or excipients, if desired also in combination with one or more other pharmaceutically active compounds, and brought into a suitable form for dosage and administration, which can then be used in human medicine or veterinary medicine. In the production of solid pharmaceutical compositions, for example, dry granules or wet granules can be prepared. The compounds of the formula I and their pharmaceutically acceptable salts can also be lyophilized and the resulting lyophilizates be used, for example for producing medicaments for injection or infusion.

As vehicles, which may also be looked upon as diluents or solvents or bulking agents, and excipients suitable organic and inorganic substances can be used which do not react in an undesired manner with the compounds of the formula I. As examples of types of excipients, or additives, which can be contained in the pharmaceutical compositions and medicaments, lubricants, preservatives, gel formers, solubilizers, thickeners, stabilizers, disintegrants, wetting agents, emulsifiers, dispersants, antifoaming agents, salts, buffer substances, colorants, flavorings, antioxidants or agents for achieving a depot effect may be mentioned. Examples of vehicles and excipients are water, physiological saline, vegetable oils such as sunflower oil, animal oils such as fish liver oil, waxes, alcohols such as ethanol, isopropanoi, 1,2-propanediol, glycerol, polyols, polyethylene glycols, polypropylene glycols, polyvinylpyrrolidone, gelatin, gum arabic, cellulose, carbohydrates such as glucose, lactose or starch like corn starch, magnesium carbonate, potassium phosphate, sodium chloride, magnesia, stearic acid and its salts such as magnesium stearate, talc, lanolin, petroleum jelly, or mixtures thereof, for example mixtures of water or saline with one or more organic solvents such as mixtures of water with alcohols.

For oral and rectal use, pharmaceutical forms such as, for example, tablets, coated tablets, sugar-coated tablets, granules, hard and soft gelatin capsules, suppositories, solutions, including oily, alcoholic or agueous solutions, or drops, furthermore suspensions or emulsions, can be used. For parenteral use, for example by injection or infusion, pharmaceutical forms such as solutions, suspensions or emulsions, for example agueous solutions, can be used. For topical use, pharmaceutical forms such as ointments, creams, pastes, lotions, gels, sprays, foams, aerosols, solutions or powders can be used. Suitable as pharmaceutical compositions for administration in the form of aerosols or sprays are, for example, solutions, suspensions or emulsions of the active ingredient of the formula I or its pharmaceutically acceptable salt in a pharmaceutically acceptable solvent, such as ethanol or water or a mixture of such solvents, wherein the formulation may also comprise other pharmaceutical excipients such as surfactants, emulsifiers and stabilizers, and a propellant gas. Such a composition comprises the active ingredient normally in a concentration of about 0.1 percent to about 10 percent, in particular of about 0.3 percent to about 3 percent, by weight.

As usual, the dosage of the compounds of the formula I and the frequency of administration depend on the circumstances of the specific case and are adjusted by the physician according to the customary rules and procedures. They depend, for example, on the compound of the formula I administered and its potency and duration of action, on the nature and severity of the individual syndrome, on the gender, age, weight and the individual responsiveness of the human or animal to be treated, on whether the treatment is acute or chronic or prophylactic, or on whether further pharmaceutically active compounds are administered in addition to a compound of the formula I. Normally, in the case of administration to an adult weighing about 75 kg, a dose from about 0.01 mg to about 100 mg per kg per day, in particular from about 0.1 mg to about 20 mg per kg per day (in each case in mg per kg of body weight), is sufficient. The daily dose can be administered in the form of a single dose or divided into a number of individual doses, for example two, three or four individual doses. The administration can also be carried out continuously, for example by continuous injection or infusion. Depending on the individual behavior in a specific case, it may be necessary to deviate upward or downward from the indicated dosages, for example in acute episodes of a disease or in an intensive care unit. Especially in the treatment of acute cases of cardiac arrhythmias, for example in an intensive care unit, parenteral administration by continuous injection or infusion may be advantageous.

Besides as a pharmaceutically active compound in human medicine and veterinary medicine, the compounds of the formula I can also be employed as an aid in biochemical investigations or as a scientific tool or for diagnostic purposes, for example in in vitro diagnoses of biological samples, if an inhibition of TASK channels is intended. The compounds of the formula I and their salts can also be used as intermediates for the preparation of further pharmaceutical active substances.

The following examples illustrate the invention.

When example compounds containing a basic group were purified by preparative high performance liquid chromatography (HPLC) on reversed phase (RP) column material and, as customary, the eluent was a gradient mixture of water and acetonltnie containing trifluoroacetic acid, they were in part obtained in the form of acid addition salts with trifluoroacetic acid, depending on the details of the workup such as evaporation or lyophilization conditions. In the names and structural formulae of the example compounds such contained trifluoroacetic acid is not specified. The prepared compounds were in general characterized by spectroscopic data and chromatographic data, in particular mass spectra (MS) and HPLC retention times (Rt; in min) which were obtained by combined analytical HPLC/MS characterization (LC/MS), and/or nuclear magnetic resonance (NMR) spectra. Unless specified otherwise, $^1$H-NMR spectra were recorded at 500 MHz in $D_6$-dimethyl sulfoxide as solvent at room temperature. In the NMR characterization, the chemical shift δ (in ppm), the number of hydrogen atoms (H) and the multiplicity (s: singlet, bs: broad singlet, d: doublet, dd: double doublet, t: triplet, q: quartet, m: multiplet) of the peaks are given. In the MS characterization, in general the detected mass number (m/z) of the peak of the molecular ion (M), for example (M⁺), or of a related ion such as the ion (M+1), for example (M+1⁺), i.e. the protonated molecular ion (M+H⁺) (MH⁺), or the ion (M−1), for example (M−1)⁻, i.e. the deprotonated molecular ion (M−H)⁻, which was formed depending on the ionization method used, is given. The particulars of the LC/MS methods used were as follows. "ACN" means acetonitrile, "TFA" means trifluoroacetic acid, and "FA" means formic acid. Unless specified otherwise, the MS ionization method was electrospray ionization ES+.

LC/MS Method 1
  Column: Waters UPLC BEH C18, 2.1×50 mm. 1.7μ; temperature: 55° C.; eluent A: water+0.05% FA; eluent B: ACN+0.035% FA: flow: 0.9 ml/min; gradient: 95% A: 5% B (0 min) to 5% A: 95% B (1.1 min) to 5% A: 95% B (1.7 min) to 95% A: 5% B (1.9 min) to 95% A: 5% B (2 min)

LC/MS Method 2
  Column: Waters UPLC BEH C18, 2.1×50 mm. 1.7μ; temperature: 55° C.; eluent A: water+0.05% FA; eluent B: ACN+0.035% FA; flow: 0.9 ml/min; gradient: 95% A: 5% B (0 min) to 5% A: 95% B 1.1 min) to 5% A: 95% B (1.7 min) to 95% A: 5% B (1.8 min) to 95% A: 5% B (2 min)

LC/MS Method 3
  Column: Waters UPLC BEH C18. 2.1×50 mm, 1.7μ; temperature: 55° C.; eluent A: water+0.05% FA; eluent B: ACN+0.035% FA; flow: 0.9 ml/min; gradient: 95% A: 5% B (0 min) to 5% A: 95% B (2 min) to 5% A: 95% B (2.6 min) to 95% A: 5% B (2.7 min) to 95% A: 5% B (3 min)

LC/MS Method 4
  Column: Waters UPLC BEH C18, 2.1×50 mm, 1.7μ; temperature 55° C.; eluent A: water 0.1% FA; eluent B: ACN+0.08% FA; flow: 0.9 ml/min; gradient: 95% A: 5% B (0 min) to 5% A: 95% B (1.1 min) to 5% A: 95% B (1.7 min) to 95% A: 5% B (1.8 min) to 95% A: 5% B (2 min)

LC/MS Method 5
  Column: Waters XBridge C18. 4.6×50 mm, 2.5μ; temperature 30° C., eluent A: water+0.1% FA; eluent B: ACN+ 0.1% FA; flow: 1.3 ml/min; gradient: 97% A: 3% B (0 min) to 40% A: 60% B (3.5 min) to 2% A: 98% B (4 min) to 2% A: 98% B (5 min) to 97% A: 3% B (5.2 min) to 97% A: 3% B (6.5 min)

LC/MS Method 6
  Column: YMC-Pack Jsphere H80, 2.1×33 mm, 4μ; room temperature; eluent A: water+0.05% TFA; eluent B: methanol+0.05% TFA: flow 1.0 ml/min; gradient: 98% A: 2% B (0 min) to 98% A: 2% B (1 min) to 5% A: 95% B (5.0 min) to 5% A: 95% B (6.25 min)

LC/MS Method 7
  Column: YMC JSphere ODS H80, 2.1×20 mm: 4μ; temperature: 30° C.; eluent A: water+0.05% TFA; eluent B: ACN+0.05% TFA; flow: 1.0 ml/min; gradient: 96% A: 4% B (0 min) to 5% A: 95% B (2.0 min) to 5% A: 95% B (2,4 min) to 96% A: 4% B (2.45 min)

LC/MS Method 8
  Column: Luna C18, 2.0×10 mm, 3μ; room temperature; eluent A: water+0.05% TFA; eluent B ACN+0.05% TFA; flw: 1.1 ml/min; gradient: 93% A: 7% B (0 min) to 5% A: 95% B (1.2 min) to 5% A: 95% B (1.4 min) to 93% A: 7% B (1.45 min)

LC/MS Method 9
  Column: YMC JSphere ODS H80, 2.1×20 mm; 4μ; room temperature; eluent A: water+0.05% TFA, eluent B: ACN+ 0.05% TFA; flow: 1.0 ml/min; gradient: 96% A: 4% B (0 min) to 5% A: 95% B (2.4 min) to 98% A: 4% B (2.45 min)

EXAMPLE COMPOUNDS

4-Formyl-morpholine-3-carboxylic acid (comp. no. 1)

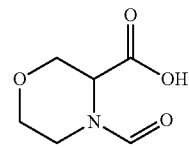 [SMILES: O=CN1CCOCC1C(=O)O]

To a mixture of morpholine-3-carboxylic acid (5 g, 38.1 mmol) and formic acid (46.6 g, 1.01 mol) cooled at 0-5° C. was added acetic anhydride (26.7 g, 262 mmol) dropwise. The resulting mixture was stirred at room temperature for 2 h. An excess of water was added while cooling the mixture. The resulting mixture was then concentrated under reduced pressure. The crude product 4-formyl-morpholine-3-carboxylic acid (6 g) was used in the next step without further purification. LC/MS (method 7): Rt=0.13 min; m/z=160.1 (M+H⁺).

3,4-Dihydro-1H-pyrrolo[2,1-c][1,4]oxazine-3-carboxylic acid ethyl ester (comp. no. 2a)

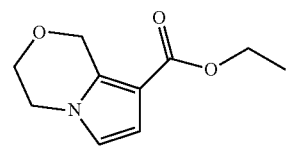

To a mixture of 4-formyl-morpholine-3-carboxylic acid (comp. no. 1) (43 g, 0.295 mol) and acetic anhydride (410 g, 4 mol) was added ethyl propiolate (190 g, 1.94 mol). The resulting mixture was heated slowly to 120° C. which was accompanied by gas evolution. After heating for 2 h at 120° C., the resulting mixture was concentrated under reduced pressure. The crude product was purified by silica gel chromatography (eluting with up to 25% ethyl acetate in heptane) to give 21.4 g (37%) of pure 3,4-dihydro-1H-pyrrolo[2,1-c][1,4]oxazine-8-carboxylic acid ethyl ester. LC/MS (method 4): Rt=1.10 min; m/z=196.1 (M+H⁺).

4-Benzyl-2-methyl-morpholine-3-carboxylic acid ethyl ester (comp. no. 26)

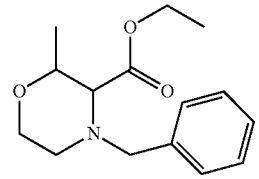 [SMILES: CCOC(=O)C1C(C)OCCN1Cc1ccccc1]

A solution of 4-benzyl-2-methyl-5-oxo-morpholine-3-carboxylic acid ethyl ester (0.24 g, 0.865 mmol; prepared according to the procedure described in Memzer A. et al., Helv. Chim. Acta 2004, 87, 90-105) in tetrahydrofuran (7 ml) was cooled to −° C. and borane-methyl sulfide complex (0.246 ml, 2.595 mmol) was added dropwise. The resulting mixture was allowed to warm to room temperature and stirred overnight. After the addition of methanol (5 ml), stirring was continued for 1 h. The solution was diluted with dichloromethane, washed with brine, and concentrated in vacuo. The resulting 4-benzyl-2methyl-morpholine-3-carboxylic acid ethyl ester was used in the next step without further purification. LC/MS (method 8); Rt=0.54 min; m/z=264.25 (M+H$^+$).

2-Methyl-morpholine-3-carboxylic acid ethyl ester (comp. no. 27)

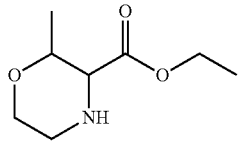

A solution of the crude 4-benzyl-2-methyl-morpholine-3-carboxylic acid ethyl ester (comp. no. 26) obtained in the preceding experiment in methanol (10 ml) was treated with a catalytic amount of palladium on charcoal (10% w/w; 25 mg). The flask was flushed with hydrogen and the hydrogen atmosphere was maintained whilst stirring at room temperature. After 5 h, the catalyst was removed by filtration, the solution was treated with a new amount of palladium on charcoal (10% w/w; 25 mg) and the hydrogen atmosphere was restored. Stirring was continued for a further 96 h. The catalyst was filtered off, washed with methanol and the combined filtrates were concentrated in vacuo to give 0.140 g of 2-methyl-morpholine-3-carboxylic acid ethyl ester, which was used in the next step without further purification. LC/MS (method 7): Rt=0.45 min; m/z=174.15 (M+H$^+$).

2-Methyl-morpholine-3-carboxylic acid (comp. no. 28)

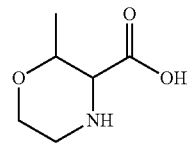

To a solution of 2-methyl-morpholine-3-carboxylic acid ethyl ester (comp. no. 27) (0.180 g, 1.039 mmol) in methanol (4 ml) was added water (2 ml) and potassium hydroxide (0.291 g, 5.195 mmol). The resulting mixture was heated to 75° C. until the color turned to red. The mixture was allowed to cool to room temperature, diluted with water and acidified to pH=1 with agueous hydrochloric acid (2 M). The solution was washed with a mixture of dichloromethane and isopropanol (3:1) and freeze-dried. The resulting white solid was used in the next step without further purification. LC/MS (method 7): Rt=0.11 min: m/z=146.20 (M+H$^+$).

The example compounds in Table 1 were obtained in analogy to the synthesis of compound no. (comp. no.) 2a.

TABLE 1

| Comp. no. | Starting compound | Formula | Rt [min] (LC/MS method) | m/z (M + H$^+$) |
|---|---|---|---|---|
| 2b | Piperidine-2-carboxylic acid | | 1.23 (4) | 194.1 |
| 2c | Thiomorpholine-3-carboxylic acid | | 1.77 (3) | 212.1 |
| 2d | Thiazolidine-2-carboxylic acid | | 1.48 (3) | 198.0 |
| 2e | Thiazolidine-4-carboxylic acid | | 1.58 (3) | 198.0 |
| 2f | 6,6-Dimethyl-morpholine-3-carboxylic acid | | 1.22 (4) | 224.14 |

TABLE 1-continued

| Comp. no. | Starting compound | Formula | Rt [min] (LC/MS method) | m/z (M + H+) |
|---|---|---|---|---|
| 2g | 2-Methyl-morpholine-3-carboxylic acid | | 1.19 (7) | 210.1 |

6-2,2,2-Trichloro-acetyl)-3,4-dihydro-1H-pyrrolo[2,1-c][1,4]oxazine-8-carboxylic acid ethyl ester (comp. no. 4a)

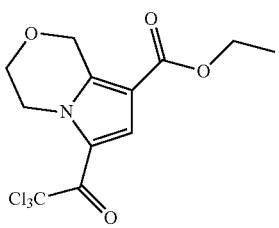

To a solution of 3,4-dihydro-1H-pyrrolo[2,1-c][1,4]oxazine-8-carboxylic acid ethyl ester (comp. no. 2a) (8.2 g, 42 mmol) in anhydrous dichloromethane (50 ml) was added trichloro-acelyl chloride (15.2 g, 84 mmol). The resulting mixture was stirred at room temperature for 3 days, and then evaporated to dryness. The crude product was purified by silica gel chromatography (eluting with 5 to 50% ethyl acetate in heptane) to give 11.3 g of 6-(2,2,2-trichloro-acetyl)-3,4-dihydro-1H-pyrrolo[2,1-c][1,4]oxazine-8-carboxylic acid ethyl ester. LC/MS (method 4): Rt=1.36 min: m/z=340.08 (M+H+).

3-(2,2,2-Trichloro-acetyl)-5,6,7,8-tetrahydro-indolizine-1-carboxylic acid ethyl ester (comp. no. 4b)

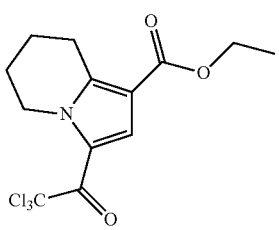

To a solution of 5,6,7,8-tetrahydro-indolizine-1-carboxylic acid ethyl ester (comp. no. 2b) (2 g, 10.3 mmol) in anhydrous dichloromethane (5 ml) was added trichloroacetyl chloride (4.7 g, 25.9 mmol). The resulting mixture was stirred at room temperature for 3 days, and then evaporated to dryness. The crude product was punned by silica gel chromatography elating with 5 to 50% ethyl acetate in heptane) to give 2.74 g of 3-(2,2,2-trichloro-acetyl)-5,6,7,8-tetrahydro-indolizine-1-carboxylic acid ethyl ester. LC/MS (method 5): Rt=5.05 min, m/z=338.02 (M+H+).

6-(2,2,2-Trichloro-acetyl)-3,4-dihydro-1H-pyrrolo[2,1-c][1,4]thiazine-8-cerboxylic acid ethyl ester (comp. no. 4c)

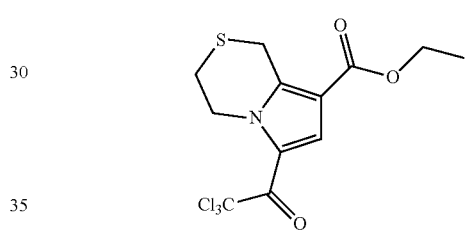

To a solution of 3,4-dihydro-1H-pyrrolo[2,1-c][1,4]thiazine-8-carboxylic acid ethyl ester (comp. no. 2c) (0.5 g, 2.37 mmol) in anhydrous dichloromethane (1.7 ml) was added trichloro-acetyl chloride (1.08 g, 5.9 mmol). The resulting mixture was stirred overnight at room temperature, after which a second portion of trichloro-acetyl chloride (0.43 g, 2.37 mmol) was added. The resulting mixture was stirred for 4 h, and then evaporated to dryness. The crude product was purified by silica gel chromatography (eluting with 5 to 50% ethyl acetate in heptane) to give 0.592 g of 6-(2,2,2-Trichloro-acetyl)-3,4 -dihydro-1H-pyrrolo[2,1-c][1,4]thiazine-8-carboxylic acid ethyl ester. LC/MS (method 4): Rt=1.41 min; m/z=356.09 (M+H+).

The example compounds in Table 2 were obtained in analogy to the synthesis of comp. no. 4a.

TABLE 2

| Comp. no. | Starting compound (comp. no.) | Formula | Rt [min] (LC/MS method) | m/z (M + H+) |
|---|---|---|---|---|
| 4d | 2,3-Dihydro-pyrrolo[2,1-b]thiazole-7-carboxylic acid ethyl ester (2d) | | 1.96 (3) | 341.94 |

TABLE 2-continued

| Comp. no. | Starting compound (comp. no.) | Formula | Rt [min] (LC/MS method) | m/z (M + H⁺) |
|---|---|---|---|---|
| 4e | 1H-Pyrrolo[1,2-c]thiazole-7-carboxylic acid ethyl ester (2e) | | 2.02 (3) | 341.92 |
| 4f | 3,3-Dimethyl-3,4-dihydro-1H-pyrrolo[2,1-c][1,4]oxazine-8-carboxylic acid ethyl ester (2f) | | | |
| 4g | 1-Methyl-3,4-dihydro-1H-pyrrolo[2,1-c][1,4]oxazine-8-carboxylic acid ethyl ester (2g) | | 1.79 (7) | 352.95 |

6(Pyrrolidine-1-carbonyl)-3,4-dihydro-1H-pyrrolo[2,1-c][1,4]oxazine-8-carboxylic acid ethyl ester (comp. no. 6a)

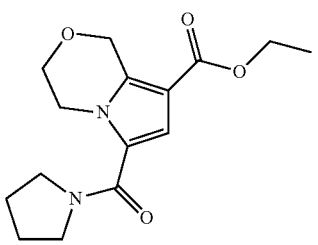 [SMILES: CCOC(=O)c1cc(C(=O)N2CCCC2)n2c1COCC2]

To a solution of 6-(2,2,2-trichloro-acetyl)-3,4-dihydro-1H-pyrrolo[2,1-c][1,4]oxazine-8-carboxylic acid ethyl ester (comp. no. 4a) (1.2 g, 3.52 mmol) in anhydrous tetrahydrofuran (7 ml) was added pyrrolidine (0.376 g, 5.28 mmol). The resulting mixture was stirred at 55°C. for 1.5 h, and then evaporated to dryness. To the residue was added 15 ml water and 30 ml ethyl acetate and the layers were separated. The aqueous layer was extracted once with 15 ml ethyl acetate. The organic layers were combined and evaporated to dryness. The product was purified by flash chromatography to give 0.95 g (92%) of 6-(pyrrolidine-1-carbonyl)-3,4-dihydro-1H-pyrrolo[2,1-c][1,4]oxazine-8-carboxylic acid ethyl ester. LC/MS (method 4): Rt=1.14 min; m/z=293.22 (M+H⁺).

6-(Pyrrolidine-1-carbonyl)-3,4-dihydro-1H-pyrrolo[2,1-c][1,4]oxazine 8 -carboxylic acid (comp. no. 7a)

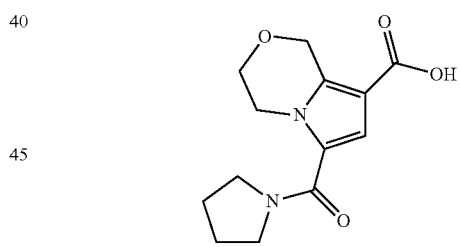

A mixture of 6-(pyrrolidine-1-carbonyl)-3,4-dihydro-1H-pyrrolo[2,1-c][1,4]oxazine-8-carboxylic acid ethyl ester (comp. no. 6a) (0.95 g, 3.25 mmol) and potassium hydroxide (0.91 g, 16.3 mmol) in water (33 ml) was stirred at 100° C. until complete conversion according to LC/MS (ca. 1 h). Approximately half of the solvents were evaporated in vacuo and the mixture was acidified with excess hydrochloric acid. The forming precipitate was filtered off, washed once with water and dried in vacuo to give 0.76 g (88%) of 6-(pyrrolidine-1-carbonyl)-3,4-dihydro-1H-pyrrolo[2,1-c][1,4]oxazine-8-carboxylic acid as white solid. LC/MS (method 4): Rt=0.92 min; m/z=265.17 (M+H⁺).

6-[(R)-1-(2,4-Difluoro-phenyl)-propylcarbamoyl]-3,4-dihydro-1H-pyrrolo[2,1-c][1,4]oxazine-8-carboxylic acid (comp. no 7b)

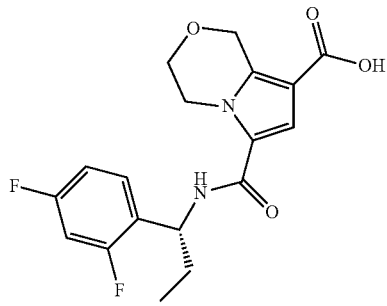 [SMILES: CC[C@@H](NC(=O)c1cc(C(=O)O)c2n1CCOC2)c1ccc(F)cc1F]

To a solution of 6-(2,2,2-trichloro-acetyl)-3,4-dihydro-1H-pyrrolo[2,1-c][1,4]oxazine-8-carboxylic acid ethyl ester (comp. no. 4a) (1 g, 2.94 mmol) in anhydrous tetrahydrofuran (9 ml) was added (R)-1-(2,4-difluoro-phenyl)-propylamine (0.5 g, 2.94 mmol) and triethylamine (1.22 ml, 8.8 mmol). The resulting mixture was stirred for 24 h, then another portion of (R)-1-(2,4-difluoro-phenyl)-propylamine (0.05 g) and triethylamine (0.8 ml) was added. The mixture was stirred for 2 days and then evaporated to dryness. To the residue was added 50 ml water, 50 ml methanol and potassium hydroxide (0.84 g, 15 mmol) and the mixture was heated to 80° C. for 15 h. A further portion of potassium hydroxide (0.84 g) was added and the mixture was heated to 80° C. for 17 h. After evaporation of methanol, dilution with 70 ml water and acidification with excess aqueous 2 N hydrochloric acid, the precipitate was filtrated and washed with 50 ml water to give 0.65 g (60% over 2 steps) of 6-[(R)-1-(2,4-difluoro-phenyl)-propylcarbamoyl]-3,4-dihydro-1H-pyrrolo[2,1-c][1,4]oxazine-8-carboxylic acid as yellowish powder. LC/MS (method 4): Rt=1.19 min; m/z=365.1 (M+H$^+$).

3,4-Dihydro-1H-pyrrolo[2,1-c][1,4]oxazine-6,8-dicarboxylic acid 8-ethyl ester (comp. no. 5a)

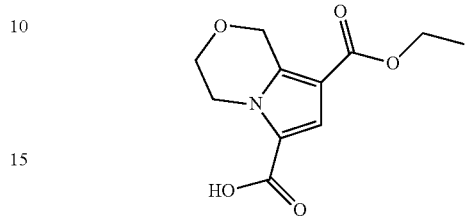

To a solution of 6-(2,2,2-trichloro-acetyl)-3,4-dihydro-1H-pyrrolo[2,1-c][1,4]oxazine-8-carboxylic acid ethyl ester (comp. no. 4a) (11 g, 32.3 mmol) in tetrahydrofuran (60 ml) was added water (110 ml) and potassium hydroxide (1.72 g, 30.7 mmol). The mixture was stirred for 5 min, then an additional portion of potassium hydroxide (250 mg) was added and the mixture was stirred for 2 h at 25° C. Tetrahydrofuran was evaporated in vacuo. After addition of 50 ml water, the mixture was acidified with 10 M aqueous hydrochloric acid. The precipitate was filtered off, washed with a small portion of water and dried in vacuo at 55° C. to give 6.56 g (85%) of 3,4-dihydro-1H-pyrrolo[2,1-c][1,4]oxazine-6,8-dicarboxylic acid 8-ethyl ester as a white solid. LC/MS (method 3): Rt=1.34 min; m/z=240.03 (M+H$^+$).

The example compounds in Table 3 were obtained in analogy to the synthesis of comp. no. 5a.

TABLE 3

| Comp. no. | Starting comp. no. | Formula | Rt [min] (LC/MS method) | m/z (M + H$^+$) |
|---|---|---|---|---|
| 5b | 4d | ![structure] | 1.41 (3) | 242.11 |
| 5d | 4c | ![structure] | 1.67 (3) | 256.17 |

TABLE 3-continued

| Comp. no. | Starting comp. no. | Formula | Rt [min] (LC/MS method) | m/z (M + H+) |
|---|---|---|---|---|
| 5e | 4f | 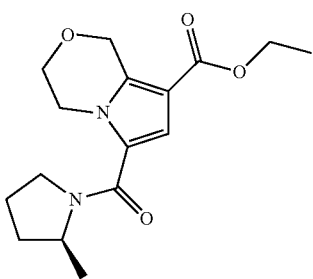 [SMILES: CCOC(=O)c1cc(C(=O)N2CCC[C@@H]2C)n2c1COCC2] | 1.13 (4) | 268.12 |
| 5f | 4b | | 1.14 (2) | 238.06 |

6-((S)-2-Methyl-pyrrolidine-1-carbonyl)-3,4-dihydro-1H-pyrrolo[2,1-c][1,4]oxazine-8-carboxylic acid ethyl ester (comp. no. 6c)

To a solution of 3,4-dihydro-1H-pyrrolo[2,1-c][1,4]oxazine-6,8-dicarboxylic acid 8-ethyl ester (comp. no. 5a) (6.09 g, 25.5 mmol) in dimethylformamide (60 ml) was added 1-hydroxybenzotriazole (3.785 g, 0.028 mol) and 1-ethyl-3-(3-dimethylaminopropyl)carbodiimide hydrochloride (5.37 g, 28 mmol). The mixture was stirred for 1 h at 50° C. then (S)-2-methylpyrrolidine (2.385 g, 28 mmol) was added and the mixture was stirred at 25° C. overnight. Solvents were evaporated, the residue was dissolved in dichloromethane and washed against saturated aqueous sodium hydrogencarbonate to give 7.8 g (100%) of 6-((S)-2-methyl-pyrrolidine-1-carbonyl)-3,4-dihydro-1H-pyrrolo[2,1-c][1,4]oxazine-8-carboxylic acid ethyl ester. LC/MS (method 2); Rt=1.06 min; m/z=307.19 (M+H+).

6-((S)-2-Methyl-pyrrolidine-1-carbonyl)-3,4dihydro-1H-pyrnolo[2,1-c][1,4]oxazine-8-carboxylic acid (comp. no. 7c)

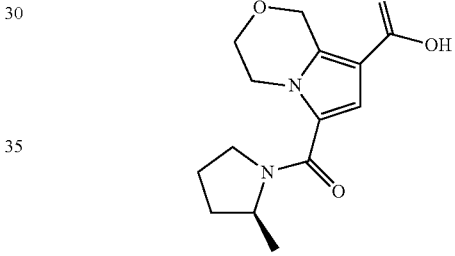

To a solution of 6-((S)-2-methyl-pyrrolidine-1-carbonyl)-3,4-dihydro-1H-pyrrolo[2,1-c][1,4]oxazine8-carboxylic acid ethyl ester (comp. no 8c) (762 mg, 2 49 mmol) in methanol (10 ml) was added water (4 ml) and 2 N aqueous potassium hydroxide (8 ml. 12 mmol). The mixture was stirred for 3 h at 80° C., then cooled down to 25° C. and acidified with excess 10 M agueous hydrochloric acid. After extraction (3 times with diohloromethane), the combined organic layers were dried over sodium sulfate and the solvents evaporated to give 595 mg (86%) 6-((S)-2-methyl-pyrrolidine-1-carbonyl)-3,4-dihydro-1H-pyrrolo[2,1-c][1,4] oxazine-8-carboxylic acid as a white solid. LC/MS (method 2): Rt=0.98 min: m/z=279.06 (M+H+).

6-[(R)-1-(4-Fluoro-phenyl)-ethylcarbamoyl]-3,4-dihydro-1H-pyrrolo[2,1-c][1,4]oxazine-8-carboxylic acid (comp. no. 7o)

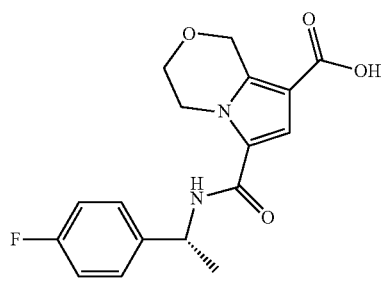 [SMILES: C[C@@H](NC(=O)c1cc(C(=O)O)c2n1CCOC2)c1ccc(F)cc1]

To a solution of 3,4-dihydro-1H-pyrrolo[2,1-c][1,4]oxazine-6,8-dicarboxylic acid 8-ethyl ester (comp. no. 5a) (6.09 g, 25.5 mmol) in dimethylformamide (60 ml) was added 1-hydroxybenzotriazole (3.785 g, 0.028 mol) and 1-ethyl-3-(3-dimethylaminopropyl)carbodiimide hydrochloride (5.37 g, 28 mmol). The mixture was stirred for 90 min at 50° C., then (R)-1-(4-fluoro-phenyl)-ethylamine (3.9 g, 28 mmol) was added and the mixture was stirred at 25° C. overnight. An excess of water was added, the solid which precipitated was filtered off, washed with a small amount of water to give 9.0 g (98%) of 6-[(R)-1-(4-fluoro-phenyl)-ethylcarbamoyl]-3,4-dihydro-1 H-pyrrolo[2,1-c][1,4]oxazine-8-carboxylic acid ethyl ester.

To a solution of 6-[(R)-1-(4-fluoro-phenyl)-ethylcarbamoyl]-3,4-dihydro-1H-pyrrolo[2,1-c][1,4]oxazine-8-carboxylic acid ethyl ester (9.0 g, 25 mmol) in methanol (38 ml) was added 2 N aqueous sodium hydroxide (38 ml, 76 mmol). The mixture was stirred for 1 h at 50° C., then cooled down to 25° C. acidified with excess 10 M aqueous hydrochloric acid. After extraction (3 times with dichloromethane), the combined organic layers were dried over sodium sulfate and the solvents evaporated to give 7.2 g (86%) 6-[(R)-1-(4-fluoro-phenyl)ethylcarbamoyl]-3,4-dihydro-1H-pyrrolo[2,1-c][1,4]oxazine-8-carboxylic acid as a white solid, LC/MS (method 4); Rt=1.11 min; m/z=333.06 (M+H$^+$).

The example compounds in Table 4 were obtained in analogy to the synthesis of comp. no. 7b (synthesis method A) or the synthesis of comp. no. 7c (synthesis method B). In some cases the products were purified by preparative reverse phase HPLC. Alternatively they were precipitated from the reaction mixture after evaporation of methanol by acidification with an excess of aqueous hydrochloric acid, filtered off, washed with a small amount of water and dried in vacuo.

TABLE 4

| Comp. no. (synthesis method) | Starting comp. no. | Formula | Rt [min] (LC/MS method) | m/z (M + H$^+$) |
|---|---|---|---|---|
| 7d (A) | 4a | | 1.16 (4) | 329.16 |
| 7e (A) | 4a | | 1.23 (4) | 381.1 |
| 7f (B) | 5d | | 1.67 (3) | 345.11 |

TABLE 4-continued

| Comp. no. (synthesis (method) | Starting comp. no. | Formula | Rt [min] (LC/MS method) | m/z (M + H⁺) |
|---|---|---|---|---|
| 7g (B) | 5a | | 1.11 (4) | 333.03 |
| 7h (B) | 5b | | 1.49 (3) | 281.15 |
| 7i (B) | 5b | | | |
| 7j (B) | 5b | | 1.74 (3) | 331.16 |
| 7k (A) | 4e | | 1.28 (9) | 335.05 |

TABLE 4-continued

| Comp. no. (synthesis (method) | Starting comp. no. | Formula | Rt [min] (LC/MS method) | m/z (M + H$^+$) |
|---|---|---|---|---|
| 7l (A) | 4e | | 1.32 (9) | 331.15 |
| 7m (B) | 5d | | 1.37 (3) | 295.09 |
| 7n (B) | 5d | | 1.62 (3) | 349.1 |
| 7p (B) | 5a | | 1.1 (2) | 397.14 |
| 7q (B) | 5a | | 1.18 (2) | 327.21 (M−H)$^-$ (a) |

TABLE 4-continued

| Comp. no. (synthesis method) | Starting comp. no. | Formula | Rt [min] (LC/MS method) | m/z (M + H+) |
|---|---|---|---|---|
| 7r (B) | 5a | | 1.12 (2) | 333.05 |
| 7s (B) | 5a | | 0.84 (2) | 265.19 |
| 7t (B) | 5a | | 0.92 (2) | 293.24 |
| 7u (A) | 4g | | 0.97 (7) | 293.1 |
| 7v (B) | 5a | | 0.98 (4) | 279.1 |

TABLE 4-continued
| Comp. no. (synthesis method) | Starting comp. no. | Formula | Rt [min] (LC/MS method) | m/z (M + H+) |
|---|---|---|---|---|
| 7w (B) | 5e | 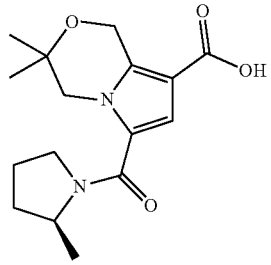 [SMILES: C[C@H]1CCCN1C(=O)c1cc(C(=O)O)c2n1CC(C)(C)OC2] | 1.06 (4) | 307.2 |
| 7x (B) | 5a | 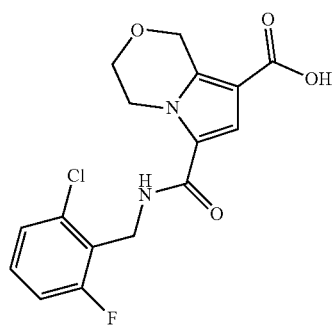 [SMILES: O=C(O)c1cc(C(=O)NCc2c(F)cccc2Cl)n2c1COCC2] | 0.98 (1) | 353.09 |
| 7z (A) | 4g | 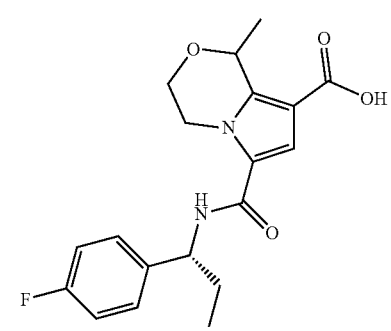 [SMILES: CC[C@@H](NC(=O)c1cc(C(=O)O)c2n1CCOC2C)c1ccc(F)cc1] | 1.31 (7) | 361.1 |
| 7aa (A) | 4g | 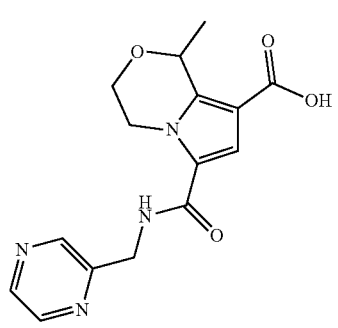 [SMILES: CC1OCCn2c(C(=O)NCc3cnccn3)cc(C(=O)O)c21] | 0.78 (7) | 317.1 |
| 7ab (A) | 4g | 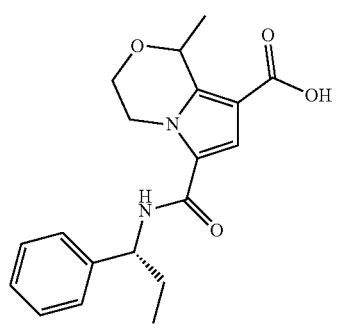 [SMILES: CC[C@@H](NC(=O)c1cc(C(=O)O)c2n1CCOC2C)c1ccccc1] | 1.26 (7) | 343.1 |

TABLE 4-continued

| Comp. no. (synthesis (method) | Starting comp. no. | Formula | Rt [min] (LC/MS method) | m/z (M + H+) |
|---|---|---|---|---|
| 7ac (B) | 5a | | 1.21 (4) | 361.22 |
| 7ad (A) | 4a | | 0.70 (7) | 292.0 |
| 7af (B) | 5f | | 1.28 (7) | 331.1 |
| 7ag (B) | 5f | | 1.02 (7) | 277.1 |
| 7ah (B) | 5f | | 1.33 (7) | 327.1 |

(a) MS ionization method ES–

3,4-Dihydro-1H-pyrrolo[2,1-c][1,4]oxazine-8-carboxylic acid (comp. no. 8a)

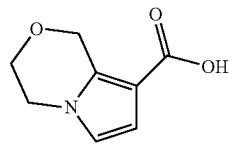 [SMILES: O=C(O)c1ccn2c1COCC2]

To a solution of 3,4-dihydro-1H-pyrrolol[2,1-c][1,4]ox-azine-8-carboxylic acid ethyl ester (comp. no. 2a) (3.2 g, 18.4 mmol) in methanol (64 ml) was added water (64 ml) and sodium hydroxide (3.3 g, 82 mmol) and the mixture was stirred at reflux until complete conversion according to LC/MC (about 4 h). Approximately half of the solvents were evaporated in vacuo and the mixture was acidified with excess hydrochloric acid. The forming precipitate was filtered off, washed once with water and dried in vacuo to give 2.7 g (100%) of 3,4-dihydro-1H-pyrrolo[2,1-c][1,4]oxazine-8-carboxylic acid as white solid. LC/MS (method 4): Rt=0.77 min, m/z=168.02 (M+H$^+$).

5,6,7,8-Tetrahydro-indolizine-1-carboxylic acid (comp. no. 8b)

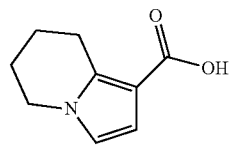 [SMILES: O=C(O)c1ccn2c1CCCC2]

To a solution of 5,6,7,8-tetrahydro-indolizine-1-carboxylic acid ethyl ester (2b) (3.0 g. 15.5 mmol) in methanol (48 ml) was added water (23 ml) and potassium hydroxide (6.4 g, 97 mmol) and the mixture was stirred at reflux until complete conversion according to LC/MS (ca. 3 h). 180 ml water was added the mixture was acidified with excess hydrochloric acid. The forming precipitate was filtered off, washed once with water and dried in vacuo to give 2.02 g (79%) of 5,6,7,8-tetrahydro-indolizine-1-carboxylic acid as white solid LC/MS (method 5; MS ionization method ES-): Rt=3.08 min; m/z 164.06 (M–H$^-$).

3,4-Dihydro-1H-pyrrolo[2,1-c][1,4]oxazine-8-carboxylic acid ((R)-1-phenyl-propyl)-amide (comp. no. 9a)

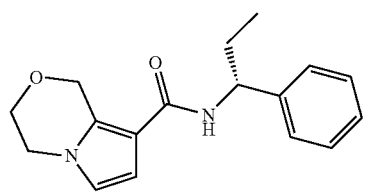 [SMILES: CC[C@@H](NC(=O)c1ccn2c1COCC2)c1ccccc1]

To a solution of 3,4-dihydro-1H-pyrrolo[2,1c][1,4]ox-azine-8-carboxylio acid (comp. no. 8a) (5 g, 29.9 mmol) in dimethylformamide (50 ml) was added 1-hydroxybenzotriazole (4.45 g, 32.9 mmol) and 1-ethyl-3-(3-dimethylaminopropyl)carbodiimide hydrochloride (6.31 g, 32.9 mmol). The mixture was stirred for 1 h at 50° C., then (R)-1-phenyl-propylamine (4.45 g, 32.9 mmol) was added and the mixture was stirred at 25° C. overnight. An excess of water was added, the precipitate was filtered off, washed with a small amount of wafer and dried in vacuo to give 5.05 g (59%) of 3,4-dihydro-1H-pyrrolo[2,1-c][1,4]oxaztne-8-carboxylic add ((R)-1-phenyl-propyl)-amide as a white solid. LC/MS (method 2); Rf=1.05 min; m/z=285.23 (M+H$^+$).

5,6,7,8-Tetrahydro-indolizine-1-carboxylic acid ((R)-1-phenyl-propyl)amide (comp. no. 9i)

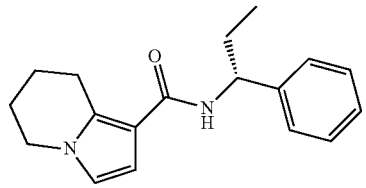 [SMILES: CC[C@@H](NC(=O)c1ccn2c1CCCC2)c1ccccc1]

To a solution of 5,6,7,8-tetrahydro-indolizine-1carboxylic acid (comp. no. 8b) (6.22 g, 37.7 mmol) in dimethylformamide (125 ml) was added 1-hydroxybenzotriazole (5.60 g, 41.4 mmol) and 1-ethyl-3-(3-dimethylaminopropyl)carbodiimide hydrochloride (7.94 g, 41.4 mmol). The mixture was stirred for 30 min at 25° C., then (R)-1-phenyl-propylamine (6.11 g, 45.2 mmol) was added and the mixture was stirred at 25° C. overnight and at 45° C. for additional 24 h. The mixture was concentrated in vacuo to 20% of its volume, 70 ml water and 30 ml ethyl acetate were added and the mixture was extracted 3 times with ethyl acetate, the combined organic layers were washed with 50 ml 1 N aqueous hydrochloric acid, then 50 ml aqueous sodium hydrogencarbonate, and evaporated to dryness. The crude product was purified by reverse phase HPLC (acetonitrile/water gradient with 0.1% trifluoroacetic acid) to give 9.33 g (88%) of 5,6,7,8-tetrahydro-indolizine-1-carboxylic acid ((R)-1-phenyl-propyl)-amide as a white solid. LC/MS (method 5): Rt=3.15 min; m/z=283.15 (M+H$^+$).

6-(2,2,2-Trichloro-acetyl)-3,4-dihydro-1H -pyrrolo[2,1-c][1,4]oxazine-8-carboxylic acid ((R)-1-phenyl-propyl)-amide (comp. no. 10a)

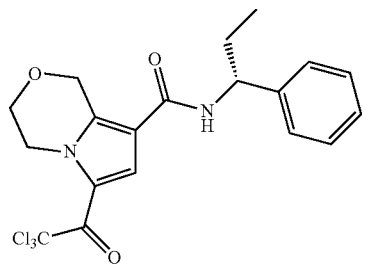

To a solution of 3,4-dihydro-1H-pyrrolo[2,1-c][1,4]ox-azine-8-carboxylic acid ((R)-1-phenyl-propyl)-amide (comp. no. 9a) (8.5 g, 29.9 mmol) in anhydrous dichloromethane (33 ml) was added trichloro-acetyl chloride (16.3 g, 89.7 mmol). The resulting mixture was stirred overnight at room temperature, after which a second portion of tnchloro-acetyl chloride (3 ml) was added. The resulting mixture was stirred for 6 h at 40° C., and then at 25° C. over 2 days, evaporated to dryness. Methyl tert-butyl ether (60 ml) was added and the mixture was stirred. The product precipitated, was filtered off, washed with a small amount of methyl tert-butyl ether and dried in vacuo to give 9.8 g (76%) of 6-(2,2,2-trichloro-acetyl)-3,4-dihydro-1H-pyrrolo[2,1-c][1,4]oxazine-8-carboxylic acid ((R)-1-phenyl-propyl)-amide. LC/MS (method 4): Rt=1.34 min; m/z=429.01 (M+H+). 3-(2,2,2-Trichloro-acetyl)-5,6,7,8-tetrahydro-indolizine-1-carboxylic acid ((R)-1-phenyl-propyl)-amide (comp. no. 10i)

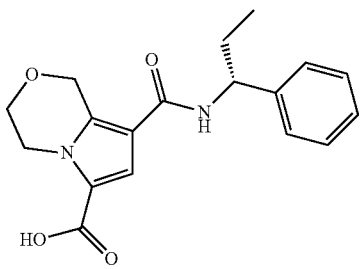

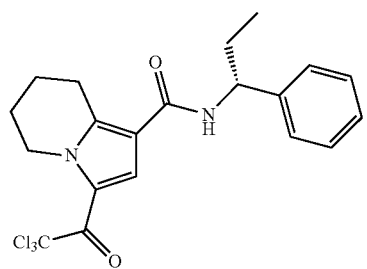

3-(2,2,2-Trichloro-acetyl)-5,6,7,8-tetrahydro-indolizine-1-carboxylic acid ((R)-1-phenyl-propyl)-amide was obtained in analogy to comp. no. 10a, starting from comp. no. 9i. LC/MS (method 5): Rt=4.95 min; m/z=427.27 (M+H+).

8-((R)-1-Phenyl-propylcarbamoyl)-3,4-dihydro-1H-pyrrolo[2,1-c][1,4]oxazine-6-carboxylic acid (comp. no. 11a)

To a solution of 6-(2,2,2-trichloro-acetyl)-3,4-dihydro-1H-pyrrolo[2,1-c][1,4]oxazine-8-carboxylic acid ((R)-1-phenyl-propyl)-amide (comp. no. 10a) (9.8 g, 22.8 mmol) in tetrahydrofuran (180 ml) was added water (160 ml) and sodium hydroxide (4.5 g, 114 mmol) and the mixture was stirred at reflux until complete conversion according to LC/MS (ca. 60 min). Approximately half of the solvents were evaporated in vacuo and the mixture was acidified with excess hydrochloric acid. The forming precipitate was filtered off, washed once with water and dried in vacuo to give 6.29 g (84%) of 8-((R)-1-phenyl-propylcarbamoyl)-3,4-dihydro-1H-pyrrolo[2,1-c][1,4]oxazine-6-carboxylic acid as white solid. LC/MS (method 4): Rt=1.14 min; m/z=329.26 (M+H+).

The example compounds in Table 5 were obtained in analogy to the synthesis of comp. no. 11a. In some cases the product was purified by preparative reverse phase HPLC.

TABLE 5

| Comp. no. | Starting compounds | Formula | Rt [min] (LC/MS method) | m/z (M + H+) |
|---|---|---|---|---|
| 11b | (8a) + (S)-2-methyl-pyrrolidine | | 1.00 (4) | 279.2 |
| 11c | (8a) + (R)-1-(2-chloro-phenyl)-propylamine | | 1.20 (4) | 363.13 |
| 11d | (8a) + (R)-1-(2-chloro-4-fluoro-phenyl)-propylamine | | 1.22 (4) | 381.1 |

TABLE 5-continued

| Comp. no. | Starting compounds | Formula | Rt [min] (LC/MS method) | m/z (M + H⁺) |
|---|---|---|---|---|
| 11f | (8a) + 2,4-difluoro benzylamine | | 0.97 (2) | 337.11 |
| 11g | (8a) + (R)-1-(4-fluoro-phenyl)-ethylamine | | 1.11 (2) | 333.08 |
| 11h | (8a) + (R)-1-(6-trifluoro-methyl-pyridin-3-yl)-propylamine | | 1.14 (2) | 398.04 |
| 11i | (8b) + (R)-1-phenyl-propylamine | | 1.30 (7) | 327.1 |

6-Bromo-3,4-dihydro-1H-pyrrolo[2,1-c][1,4]oxazine-8-carboxylic acid ((RR)-1-phenyl-propyl-amide (comp. no. 12a)

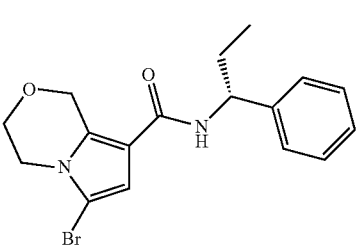 [SMILES: CC[C@@H](NC(=O)c1cc(Br)n2c1COCC2)c1ccccc1]

To a solution of 3,4-dihydro-1H-pyrrolo[2,1-c][1,4]oxazine-8-carbaxylic acid ((R)-1-phenyl-propyl)-amide (8a) (2.50 g, 8.79 mmol) in dry dichloromethane (245 ml) at −78° C. was added N-bromo-succinimide (1.565 g, 8.79 mmol) in several portions (over 2 min) and the mixture was stirred for 110 min at −78° C., then agueous 0.1 M sodium hydroxide was added, water was added, and the mixture was extracted 3 times with dichloromethane, the combined organic layers were dried over sodium sulfate, and evaporated to give 2.98 g (93%) of 6-bromo-3,4-dihydro-1H-pyrrolo[2,1-c][1,4]oxazine-8-carboxylic acid ((R)-1-phenyl-propyl)-amide. LC/MS (method 4): Rt=1.27 min; m/z=363.07 (M+H⁺).

3-Bromo-5,6,7,8-tetrahydro-indolizine-1-carboxylic acid (RR)-1-phenyl-propyl)-amide (comp. no. 12b)

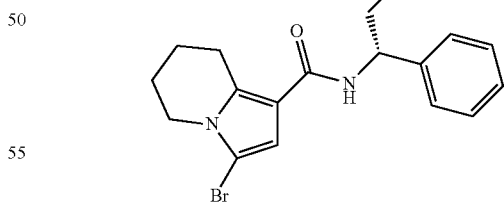

To a solution of 5,6,7,8-tetrahydro-indolizine-1-carboxylic acid ((R)-1-phenyl-propyl)-amide (9i) (9.7 g, 34.35 mmol) in dry dichloromethane (200 ml) at −78° C. was added N-bromo-succinimide (6.11 g, 34.35 mmol) in several portions (over 2 min) and the mixture was stirred for 1 h min at −78° C., 1 h at 0° C. and 30 min at 25° C. Then 500 ml aqueous 2% sodium hydroxide was added, and the mixture was extracted 3 times with dichloromethane, the combined organic layers were dried over sodium sulfate, evaporated and the crude product was purified by reverse phase HPLC (acetonitrile/water gradient with 0.1% trifluoroacetic acid) to give 5.24 g (42%) of 3-bromo-5,6,7,8-tetrahydro-indolizine-1-carboxylic acid ((R)-1-phenyl-propyl)-amide. LC/MS (method 4): Rt=1.33 min; m/z=361.21 (M+H⁺).

(S)-2-Methyl-propane-2-sulfinic acid 1-pyrimidin-2-yl-methylideneamide (comp. no. 13a)

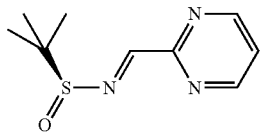

A mixture of 2-pyrimidine-carboxaldehyde (11.5 g, 107 mmol). (S)-(−)-2-methyl-2-propanesulfanimide (12.9 g, 107 mmol) and potassium hydrogensulfate (14.5 g, 107 mmol) in toluene (57 ml) was heated at 50° C. overnight. After decanting the solution, the solid residue is washed 3 times with dichloromethane, the washings combined with the decanted solution and solvents are evaporated in vacuo to give 18.2 g (81%) of (S)-2-methyl-propane-2-sulfinic acid 1-pyrimidin-2-yl-methylideneamide. LC/MS (method 3): Rt=1.29 min; m/z=212.09 (M+H⁺).

(S)-2-Methyl-propane-2-sulfinic acid propylideneamide (comp. no. 13b)

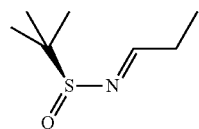

(S)-2-Methyl-propane-2-sulfinic acid propylideneamide was synthesized in analogy to comp. no. 13a. LC/MS (method 5): Rt=3.36 min; m/z=162.14 (M+H⁺).

(S)-2-Methyl-propane-2-sulfinic acid ((S)-1-pyrimidin-2-yl-propyl)-amide (comp. no. 14a)

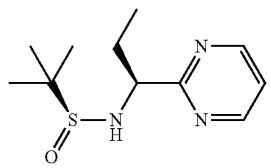 [SMILES: CC[C@H](N[S@@](=O)C(C)(C)C)c1ncccn1]

and (S)2-methyl-propane-2-sulfinic acid ((R)-1-pyrimidin-2-yl-propyl)-amide (comp. no. 14b)

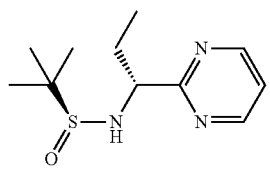 [SMILES: CC[C@@H](N[S@@](=O)C(C)(C)C)c1ncccn1]

To a solution of (S)-2-methyl-propane-2-sulfinic acid 1-pyrimidin-2-yl-methylideneamide (18.2 g, 86.1 mmol) in dry tetrahydrofuran at −78° C. was added a 1.0 M solution of ethylmagnesium bromide in tetrahydrofuran (85 ml, 95 mmol) and the mixture was stirred at −78° C. for 45 min, 120 ml of aqueous sodium hydrogencarbonate was added, the mixture was extracted 3 times with dichloromethane (200 ml) and after evaporation of all solvents the crude product was purified by reverse phase HPLC (acetonitrile/water gradient with 0.1% trifluoroacetic acid) to give 1.47 g of (S)-2-methyl-propane-2-sulfinic acid ((S)-1-pyrimidin-2-yl-propyl)amide (LC/MS (method 5): Rt=2.99 min: m/z=242.21 (M+H⁺)) and 2.6 g of (S)-2-methyl-propane-2-sulfinic acid ((R)-1-pyrimidin-2-yl-propyl)-amide (LC/MS (method 2): Rt=0.97 min; m/z=242.07 (M+H⁺)).

(S)-1-Pyrimidin-2-yl-propylamine hydrochloride (comp. no. 15a)

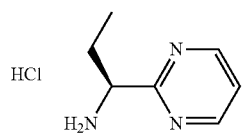

To a solution of (S)-2-methyl-propane-2-sulfinic acid ((S)1-pyrimidin-2-yl-propyl)-amide (comp. no. 14a) (1.4 g, 5.8 mmol) in methanol was added 4 M hydrogen chloride in dioxane (4.35 ml) and the mixture was stirred for 1 h at 25° C. Water (100 ml) was added and the aqueous phase was washed with methyl tert-butyl ether. The aqueous layer was freeze-dried to give 0.919 g (75%) of (S)-1-pyrimidin-2-yl propylamine hydrochloride. LC/MS (method 5): Rt=0.69 min; m/z=138.15 (M+H⁺).

(R)-1-Pyrimidin-2-yl-propylamine hydrochloride (comp. no. 15b)

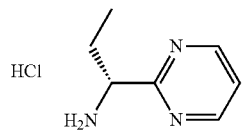

To a solution of (S)-2-methyl-propane-2-sulfinic acid ((R)-1-pyrimidin-2-yl-propyl)-amide (comp. no. 14b) (2.6 g, 10.8 mmol) in methanol was added 4 M hydrogen chloride in dioxane (4.35 ml) and the mixture was stirred for 1 h at 25° C. Water (100 ml) was added and the aqueous phase was washed with methyl tert-butyl ether. The aqueous layer was freeze-dried to give 1.7 g (75%) of (R)-1-pyrimidin-2-yl-propylamine hydrochloride. LC/MS (method 5): Rt=0.68 min; m/z=138.15 (M+H⁺).

(S)-2-Methyl-propane-2-sulfinic acid ((S)-1-(2-trifluoromethyl-pyrimidin-5-yl)-propyl)-amide (comp. no. 14k)

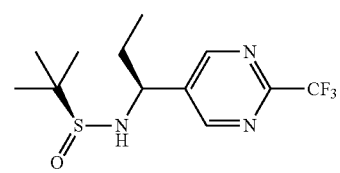 [SMILES: CC[C@H](N[S@@](=O)C(C)(C)C)c1cnc(C(F)(F)F)nc1]

and (S)-2-Methyl-propane-2-sulfinic acid ((R)-1-(2-trifluoromethyl-pyrimidin-5-yl)-propyl)-amide (comp. no. 14l)

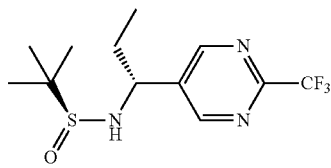 [SMILES: CC[C@@H](N[S@@](=O)C(C)(C)C)c1cnc(C(F)(F)F)nc1]

To a solution of 5-bromo-2-trifluoromethyl-pyrimidine (200 mg, 0.879 mmol) in dry diethyl ether (1.5 ml) at −78° C. was added a 2.5 M solution of n-butyl lithium hexane (0.32 ml, 0.811 mmol) and the mixture was stirred at −78° C. for 15 min. A solution of (S)-2-methyl-propane-2-sulfinic acid propylideneamide (comp. no. 13b) (110 mg, 0.676 mmol) in dry toluene (1 ml) was added at −78° C., the mixture was stirred for 5 min at −78° C. and then poured into a saturated aqueous ammonium chloride solution. The mixture was extracted 3 times with dichloromethane, dried over sodium sulfate, and after evaporation of all solvents tie crude product was purified by flash chromatography (silica gel, elution with heptane/ethyl acetate) to give 15 mg of (S)-2-methyl-propane-2-sulfinic acid ((R)-1-(2-trifluoromethyl-pyrimidin-5-yl)-propyl)-amide (LC/MS (method 7): Rt=1.37 min; m/z=310.1 (M+H⁺)) and 20 mg of (S)-2-methyl-propane-2-sulfinic acid ((R)-1-(2-trifluoromethyl-pyrimidin-5-yl)-propyl)-amide (LC/MS (method 7): Rt=1.37 min; m/z=310.1 (M+H⁺)).

(S)-1-(2-Trifluoromethyl-pyrimidin-5-yl)-propylamide hydrochloride (comp. no. 15k)

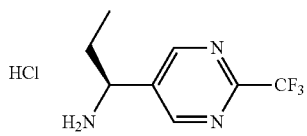

(S)-1-(2-Trifluoromethyl-pyrimidin-5-yl)-propylamine amine hydrochloride was obtained in analogy to comp. no. 15a from (S)-2-methyl-propane-2-sulfinic acid ((S)-1-(2-trifluoromethyl-pyrimidin-5-yl)propyl)-amide (comp. no. 14k).

(R)-1-(2-Trifluoromethyl-pyrimidin-5-yl)-propylamine hydrochloride (comp. no. 15l)

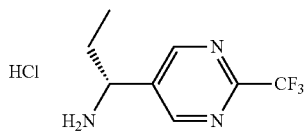

(R)-1-(2-Trifluoromethylpyrimidin-5-yl)-propylamine hydrochloride was obtained in analogy to comp. no. 15a from (S)-2-methyl-propane-2-sulfinic acid ((R)-1-(2-trifluoromethyl-pyrimidin-5-yl)-propyl)-amide (comp. no. 14l).

(S)-2-Methyl-propane-2-sulfinic acid [(S)-1-(4,6-bis-trifluoromethyl-pyridin-3-yl)-propyl]-amide (comp. no. 14m)

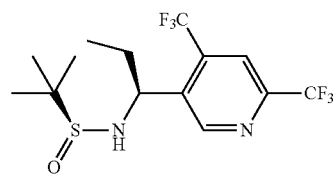 [SMILES: CC[C@H](N[S@@](=O)C(C)(C)C)c1cnc(C(F)(F)F)cc1C(F)(F)F]

and (S)-2-Methyl-propane-2-sulfinic acid [(R)-1-(4,6-bis-trifluoromethyl-pyridin-3-yl)-propyl]-amide (comp. no. 14n)

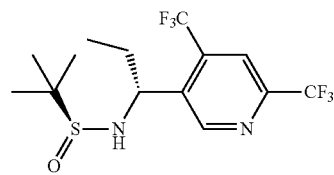 [SMILES: CC[C@@H](N[S@@](=O)C(C)(C)C)c1cnc(C(F)(F)F)cc1C(F)(F)F]

To a solution of 5-bromo-2,4-bis-trifluoromethyl-pyridine (200 mg, 0.885 mmol) in dry diethyl ether (1.5 ml) at −78° C. was added a 2.5 M solution of n-butyllithium in hexane (0.25 ml, 0.685 mmol) and the mixture was stirred at −78° C. for 15 min. A solution of (S)-2 -methyl-propane-2-sulfinic acid propylideneamide (comp. no. 13b) (85 mg, 0.527 mmol) in dry toluene (1 ml) was added at −78° C., the mixture was stirred for 5 min at −78° C. and then poured into a saturated aqueous ammonium chloride solution. The mixture was extracted 3 times with dichloromethane, dried over sodium sulfate, and after evaporation of all solvents the crude product was purified by flash chromatography (silica gel, elution with heptane/ethyl acetate) to give 27 mg (14%) of (S)-2-methyl-propane-2-sulfinic acid [(S)-1-(4,6-bis-trifluoromethyl-pyridin-3-yl)-propyl]-amide (LC/MS (method 2; MS ionization method ES−); Rt=1.3 min; m/z=375.1 (M−H⁻)) and 29 mg (15%) of (S)-2-methyl-propane-2-sulfinic acid [(R)-1-(4,6-bis-trifluoromethyl-pyridin-3-yl)-propyl]-amide (LC/MS (method 2; MS ionization method ES−): Rt=1.3 min; m/z=375.12 (M−H⁻)).

(S)-1-(4,6-Bis-trifluoromethyl-pyridin-3-yl)-propylamide hydrochloride (comp. no. 15m)

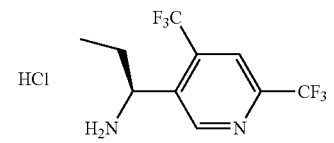

(S)-1-(4,6-Bis-trifluoromethyl-pyridin-3-yl)-propylamine hydrochloride was obtained in analogy to comp. no. 15a from (S)-2-methyl-propane-2-sulfinic acid [(S)-1-(4,6-bis-trifluoromethyl-pyridin-3-yl)-propyl]-amide (comp. no. 14m). LC/MS (method 7): Rt=0.93 min; m/z=273.1 (M+H⁺).

(R)-1-(4,6-Bis-trifluoromethyl-pyridin-3-yl)-propylamine hydrochloride (comp. no. 15n)

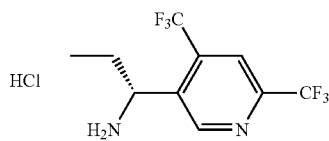

(R)-1-(4,6-Bis-trifluoromethyl-pyridin-3-yl)-propylamine hydrochloride was obtained in analogy to comp. no. 15a from (S)-2-methyl-propane-2-sulfinic acid [(R)-1-(4,6-bis-trifluoromethyl-pyridin-3-yl)-propyl]-amide (comp. no. 14n). LC/MS (method 7): Rt=0.93 min; m/z=273.1 (M+H⁺).

1-(5-Methoxy-pyrazin-2-yl)-ethylamine (comp. no. 15ac)

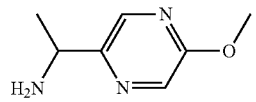

To a solution of 5-methoxy-pyrazine-2-carbonitrile (1.0 g, 7.4 mmol) in tetrahydrofuran at −78° C. was added drop wise 1 M methylmagnesium bromide (8.14 ml, 8.14 mmol) and the mixture was stirred for 1 h at 25° C. Sodium borohydride (250 mg, 6.62 mmol) was added at 78° C. and the mixture was allowed to warm to 25° C. Aqueous ammonium chloride was added and after addition of excess potassium carbonate the mixture was extracted 3 times with dichloromethane, solvents were evaporated to give 0.05 g (4%) of crude 1-(5-methoxy-pyrazin-2-yl)-ethylamine. LC/MS (method 5): Rt=1.26 min; m/z=154.15 (M+H⁺).

The example compounds in Table 6 were obtained in analogy to the synthesis of comp. no. 15a and comp. no. 15b.

TABLE 6

| Comp. no. | Starting comp. | Formula | Rt [min] (LC/MS method) | m/z (M + H⁺) |
|---|---|---|---|---|
| 15c | 5-Trifluoromethyl-pyrimidine-2-carbaldehyde | *(structure)* | 1.8 (5) | 206.17 |
| 15d | 5-Trifluoromethyl-pyrimidine-2-carbaldehyde | *(structure)* | 1.8 (5) | 206.17 |
| 15e | 3-Fluoro-4-trifluoromethyl-benzaldehyde | *(structure)* | 0.97 (7) | 222.1 |
| 15f | 3-Fluoro-4-trifluoromethyl-benzaldehyde | *(structure)* | 0.98 (7) | 222.1 |
| 15g | 4-Fluoro-3-trifluoromethyl-benzaldehyde | *(structure)* | 0.94 (7) | 222.1 |
| 15h | 4-Fluoro-3-trifluoromethyl-benzaldehyde | *(structure)* | 0.94 (7) | 222.1 |

TABLE 6-continued

| Comp. no. | Starting comp. | Formula | Rt [min] (LC/MS method) | m/z (M + H⁺) |
|---|---|---|---|---|
| 15i | 4-Chloro-6-trfluoromethyl-pyridine-3-carbaldehyde | 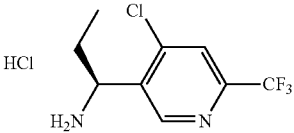 | 0.86 (2) | 238.99 |
| 15j | 4-Chloro-6-trifluoromethyl-pyridine-3-carbaldehyde | 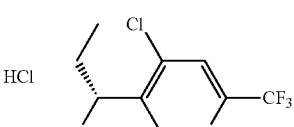 | 0.85 (2) | 238.98 |
| 15q | 2,6-Difluoro-4-trifluoromethyl-benzaldehyde | 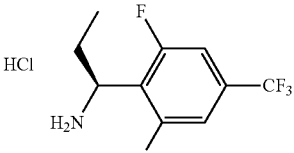 | 1.1 (3) | 240.2 |
| 15r | 2,6-Difluoro-4-trifluoromethyl-benzaldehyde | 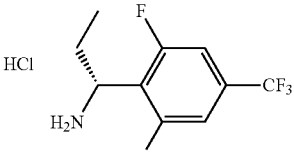 | 1.1 (3) | 240.2 |
| 15u | 5-Methoxy-6-trifluoromethyl-pyridine-3-carbaldehyde | 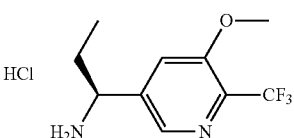 | 1.06 (3) | 235.03 |
| 15v | 5-Methoxy-6-trifluoromethyl-pyridine-3-carbaldehyde | 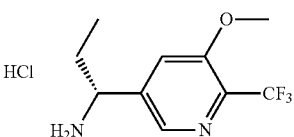 | 1.06 (3) | 235.04 |
| 15w | 5-Methoxy-pyrazine-2-carbaldehyde | 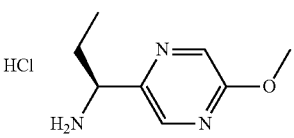 | 0.49 (2) | 168.19 |
| 15x | 5-Methoxy-pyrazine-2-carbaldehyde | 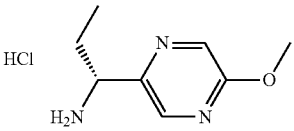 | 0.46 (4) | 168.15 |
| 15y | 2-Methoxy-pyrimidine-5-carbaldehyde | 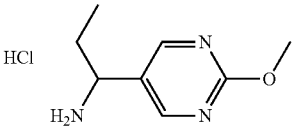 (enantiomer 1) | 1.28 (5) | 168.16 |

TABLE 6-continued

| Comp. no. | Starting comp. | Formula | Rt [min] (LC/MS method) | m/z (M + H+) |
|---|---|---|---|---|
| 15z | 2-Methoxy-pyrimidine-5-carbaldehyde | HCl 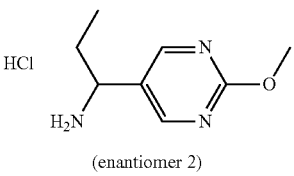 (enantiomer 2) | 0.99-1.3 (broad) (5) | 168.16 |
| 15aa | Pyrazine-2-carbaldehyde | HCl 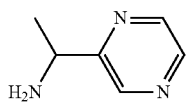 (enantiomer 1) | 0.48 (5) | 124.13 |
| 15ab | Pyrazine-2-carbaldehyde | HCl 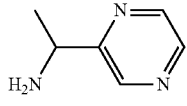 (enantiomer 2) | 0.48 (5) | 124.13 |

The example compounds in Table 7 were obtained in analogy to the synthesis of comp. no. 15k and comp. no. 15l.

TABLE 7

| Comp. no. | Starting comp. | Formula | Rt [min] (LC/MS method) | m/z (M + H+) |
|---|---|---|---|---|
| 15o | 2-Bromo-5-trifluoromethyl-thiazole | HCl 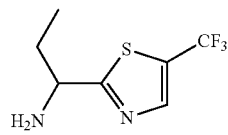 (enantiomer 1) | 0.38 | 211.15 |
| 15p | 2-Bromo-5-trifluoromethyl-thiazole | HCl 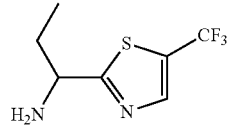 (enantiomer 2) | 0.38 | 211.15 |
| 15s | 5-Bromo-2-methoxy-3-trifluoromethyl-pyridine | HCl 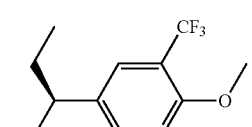 | 2.55 | 235.09 |
| 15t | 5-Bromo-2-methoxy-3-trifluoromethyl-pyridine | HCl 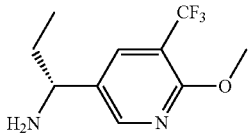 | 2.55 | 235.16 |

(R)-Pyrrolidin-2-yl-acetic acid ethyl ester hydrochloride (comp. no. 19a)

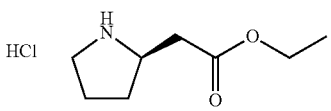

A solution of (R)-2-carboxymethyl-pyrrolidine-1-carboxylic acid tert-butyl ester in 2 N hydrogen chloride in dioxane (250 mg, 1.1 mmol) in 4 N hydrogen chloride in dioxane (2 ml, 8 mmol) was stirred for 2 h at 25° C. and evaporated to dryness and redissolved in ethanol. After addition of a few drops of 12 M aqueous hydrochloric acid the mixture was stirred at 25° C. overnight. Solvents were evaporated to give 200 mg (95%) of (R)-pyrrolidin-2-yl-acetic acid ethyl ester hydrochloride (25 mg, 55%).

The example compounds in Table 8 were obtained in analogy to the synthesis of comp. no. 19a. Ethanol was replaced by isopropanol in the final esterification step.

Cyclopropyl-(R)-pyrrolidin-2-yl-methanol (comp. no. 21a)

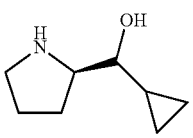

To a solution of (R)-2-formyl-pyrrolidine-1-carboxylic acid tert-butyl ester (200 mg, 1 mmol) in tetrahydrofuran at −78° C. was added a 1 M solution of cyclopropylmagnesium chloride (1.3 ml, 1.3 mmol). After stirring for 1 h at room temperature and addition of aqueous sodium hydrogencarbonate, extraction (3 times with dichloromethane), drying of the combined organic layers over sodium sulfate and evaporation of the solvents the crude product was heated with aqueous sodium hydroxide at 100° C. for 3 days to give 20 mg of crude cyclopropyl-(R)-pyrroildin-2-yl-methanol which was used in the next step without further purification.

TABLE 8

| Comp. no. | Starting compound | Formula | Rt [min] (LC/MS method) | m/z (M + H+) |
|---|---|---|---|---|
| 19b | (R)-2-carboxymethyl-pyrrolidine-1-carboxylic acid tert-butyl ester | | 0.63 (4) | 172.19 |
| 19c | Methylamino-acetic acid | | 0.83 (5) | 132.18 |
| 19d | (S)-2-Methylamino-propionic acid | | 0.37 (7) | 146.2 |

Cyclopropylmethyl-(1-pyrimidin-2-yl-ethyl)-amine (comp. no. 20a)

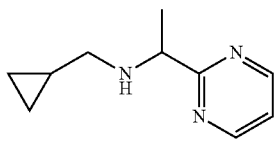

A mixture of 1-pyrimidin-2-yl-ethylamine hydrochloride (50 mg, 0.313 mmol), triethylamine (95 mg, 1 mmol) and cyclopropylmethyl bromide (0.034 ml, 0.344 mmol) in acetonitrile was stirred at 80° C. overnight. After evaporation of the solvents, addition of aqueous sodium hydrogencarbonate, extraction (3 times with dichloromethane), drying of the combined organic layers over sodium sulfate and evaporation of the solvents, crude cyclopropylmethyl-(1-pyrimidin-2-yl-ethyl)-amine was obtained which was used immediately in the next step without further purification.

(R)-1-Pyrrolidin-2-yl-ethanol hydrochloride (comp. no. 21b)

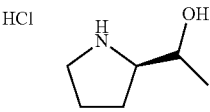

and (R)-2-(1-methoxy-ethyl)-pyrrolidine-hydrochloride (comp. no. 21c)

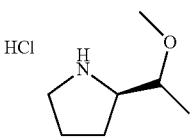

To a solution of (R)-2-formyl-pyrrolidine-1-carboxylic acid tert-butyl ester (300 mg, 1.5 mmol) in tetrahydrofuran at −78° C. was added a 3 M solution of methylmagnesium chloride (0.753 ml, 2.1 mmol). After stirring for 1 h at room temperature and addition of aqueous sodium hydrogencarbonate, extraction (3 times with dichloromethane), drying of the combined organic layers over sodium sulfate and evaporation of the solvents sodium hexamethyldisilazide (194 mg, 1.06 mmol) was added and after 5 min iodomethane (150 mg, 1.08 mmol) was added. The mixture was stirred overnight. After standard aqueous work-up, the resulting mixture was dissolved sn dichloromethane and treated with 4 N hydrogen chloride in dioxane. After 2 h the solvents were evaporated to give a mixture of (R)-1-pyrrolidin-2-yl-ethanol hydrochloride and (R)-2-(1-methoxy-ethyl)-pyrrolidine hydrochloride which was used in the next step without further purification.

(S)-3-Cyclopropylmethoxy-pyrrolidine hydrochloride (comp. no. 22a)

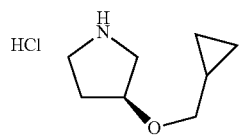

To a solution of (S)-3-hydroxy-pyrrolidine-1-carboxylic acid tert-butyl ester (3.0 g, 16 mmol) in dry dimethylformamide at 0° C. was added sodium hexamethyldisilazide (3.5 g, 19 mmol) and after stirring for 5 min cyclopropylmethyl bromide (2.38 g, 17.6 mmol) was added and the mixture was stirred for 40 min at 0° C., then at room temperature for 3 h. After further addition of 1.5 g sodium hexamethyldisilazide and 1.4 g cyclopropylmethyl bromide the mixture was heated at 100° C. for 1 h. After addition of aqueous sodium hydrogencarbonate, the mixture was extracted 3 times with dichloromethane, the solvents were evaporated and the crude mixture was dissolved in dichlorometbane (20 ml) and 4 M hydrogen chloride in dioxane (42 ml, 168 mmol). After addition of aqueous hydrochloric acid the organic layer was discarded and the aqueous layer was freeze-dried to give 2.89 g of crude (S)-3-cyclopropylmethoxy-pyrrolidine hydrochloride which was used in the next step without further purification. LC/MS (method 7): Rt=0.34 min; m/z=142.1 (M+H+)

(S)-3-Isobutoxy-pyrrolidine (comp. no. 22b)

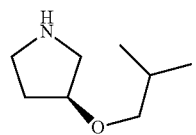

The compound as its trifluoroacetic acid salt was obtained from (S)-3-hydroxy-pyrrolidine-1-carboxylic acid tert-butyl ester following a reaction sequence according to the synthesis of comp. no. 22a. Trifluoroacetic acid was used instead of hydrogen chloride in the final deprotection. LC/MS (method 5): Rt=0.78 min; m/z=144.2 (M+H+).

N-(R)-1-Pyrrolidin-2-ylmethyl-acetamide hydrochloride (comp. no 23a)

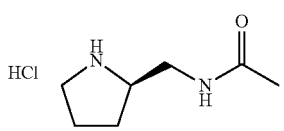

To a solution of (R)-2-aminomethyl-pyrrolidine-1-carboxylic acid tert-butyl ester (125 mg, 0.624 mmol) in dry dichloromethane at 0° C. was added triethylamine (190 mg, 1.872 mmol) and acetyl chloride (54 mg, 0.686 mmol) and the mixture was stirred for 1 h at room temperature. After addition of aqueous sodium hydrogencarbonate, the mixture was extracted 3 times with dichloromethane, and the solvents were evaporated. The crude mixture was stirred for 2 h at room temperature on an excess of 4 N hydrogen chloride in dioxane, the solvents were evaporated to give 100 mg of crude N-(R)-1-pyrrolidin-2ylmethyl-acetamide hydrochloride which was used in the next step without further purification. LC/MS (method 5): Rt=0.48 min, m/z=143.13 (M+H+)., (R)-2Pyrrolidin-2-yl-pyrazine hydrochloride (comp. no. 24a)

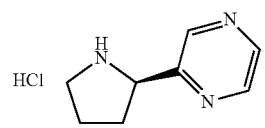 [SMILES: Cl ; c1cnc([C@H]2CCCN2)cn1]

According to WO 2008/053319, to a solution of (−)-sparteine (2.7 g, 11.7 mmol) and pyrrolidine-1-carboxylic acid tert-butyl ester (2 g, 11.7 mmol) in dry methyl tert-butyl ether was added at 78° C. 1.4 M sec-butyllithium in cyclohexane (8.3 ml, 11.7 mmol) over 30 min and the mixture was stirred at −78° C. for 3 h. 0.5 M zinc chloride solution in tetrahydrofuran (14 ml, 7 mmol) was added at −78° C. and the mixture was stirred for 30 min at −78° C. and 30 min at 25° C. This mixture was added via a syringe to a solution of 2-bromopyrazine (1.48 g, 9.34 mmol), palladium(II) acetate (105 mg, 0.467 mmol) and tetrafluoroboric acid tri-tert-butylphosphine adduct (169 mg, 0.584 mmol) at −78° C. The mixture was stirred and allowed to slowly warm to 25° C. overnight. The solid was filtered off, to the solution was added aqueous sodium hydrogencarbonate, and the mixture was extracted 3 times with dichloromethane, solvents were evaporated and the residue was purified by reverse phase HPLC (acetonitrile/water gradient with 0.1% trifluoroacetic acid) to give 750 mg of crude product which was dissolved in dichloromethane (5 ml) and treated with 4 N hydrogen chloride in dioxane (0.8 ml, 3.2 mmol) tor 2 days, and alter addition of water was lyophilized to give 200 mg (17%) of crude (R)-2-pyrrolidin-2-yl-pyrazine hydrochloride which was used without purification in the next step. LC/MS (method 7): Rt=0.14 mm; m/z=150.1 (M+H+).

(S)-3-Methyl-1-pyridin-yl-piperazine (comp. no. 25a)

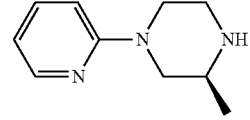

A solution of (S)-2-methyl-piperazine-1-carboxylic acid tert-butyl ester (100 mg, 0.5 mmol), 2-bromopyridine (156 mg, 1 mmol) and 1,8-diazabicyclo[5.4.0]undec-7-ene (228 mg, 1.5 mmol) in Nmethylpyrroildinone (10 ml) was stirred at 130° C. for 2 h. (S)-2-methyl-4-pyridin-2-yl-piperazine-1-carboxylic acid tert-butyl ester was isolated by reverse phase HPLC (acetonitrile/water gradient with 0.1% trifluoroacetic acid), then deprotected with trirluoroacetic acid/ dichloromefhane (1 h) to give, after evaporation of all solvents, (S)-3-methy-1-pyridin-2-yl-piperazine as its trifluoroacetic acid salt which was used without purification in the next step.

(S)-3-Methyl-1-(3,3,3-trifluoro-propyl)-piperazine (comp. no. 25b)

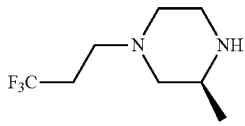

A solution of (S)-2-methyl-piperazine-1-carboxylic acid tert-butyl ester (200 mg, 1 mmol), 1,1,1-trifluoro-3-iodo-propane (268 mg, 1.2 mmol) and triethylamine (200 mg, 2 mmol) in acetonitrile (10 ml) was stirred at 80° C. for 3 days. After standard work-up (aqueous sodium hydrogencarbonate, dichloromethane), (S)-2-methyl-4-(3,3,3-trifluoro-propyl)-piperazine-1-carboxylic acid tert-butyl ester was deprotected under standard conditions with trifluoroacetic acid (1 h) to give (S)-3-methyl-1-(3,3,3-trifluoro-propyl)-piperazine trifluoroacetic acid salt which was used without purification in the next step. LC/MS (method 7): Rt=0.07 min; m/z=197.2 (M+H+).

6-((S)-2-methyl-pyrrolidine-1-carbonyl)-3,4-dihydro-1H-pyrrolo[2,1-c][1,4]oxazine-8-carboxyic acid ((R)-1-phenyl-propyl)-amide (comp. no 16a)

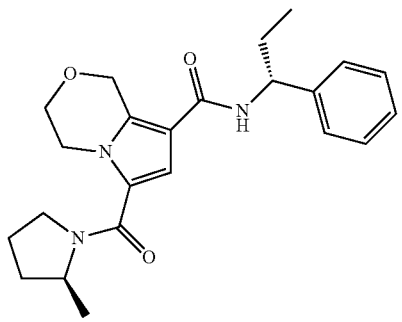 [SMILES: CC[C@@H](NC(=O)c1cc(C(=O)N2CCC[C@@H]2C)n2c1COCC2)c1ccccc1]

To a solution of 6-((S)-2-methyl-pyrrolidine-1-carbonyl)-3,4-dihydro-1H-pyrrolo[2,1-c][1,4]oxazine-8-carboxylic acid (comp. no. 7c) (300 mg, 0.914 mmol) in dimethylformamide (4 ml) was added 1-hydroxybenzotriazole (130 mg, 1 mmol) and 1-ethyl-3-(30dimethylaminopropyl)carbodiimide hydrochloride (193 mg, 1 mmol). The mixture was stirred for 90 min at 50° C., then (R)-1-phenyl-propylamine (85 mg, 1 mmol) was added and the mixture was stirred at 25° C. overnight. An excess of water was added, the solid which precipitated was filtered off, washed with a small amount of water and purified by reverse phase HPLC (acetonitrile/water gradient with 0.1% trifluoroacetic acid) to give 243 mg (67%) of 6-((S)-2-methyl-pyrrolidine-1-carbonyl)-3,4-dihydro-1H-pyrrolo[2,1-c][1,4]oxazine-8-carboxylic acid ((R)-1-phenyl-propyl)-amide (comp. no. 16a; compounds with a compound number starting with "16" are compounds of the formula I) as white solid LC/MS (method 4): Rt=1.12 min; m/z=396.22 (M+H+). 1H-NMR: δ(ppm)=8.07 (1H, d), 7.26-7.35 (5H, m), 7.19-7.22 (1H, m), 4.98 (1H, d), 4.81-4.89 (2H, m), 4.17-4.30 (2H, m), 3.92-3.99 (2H, m), 3.80-3.85 (1H, m). 3.68 (2H, bs), 2.03-2.09 (1H, m), 1.92-1.99 (1H, m), 1.74-1.84 (3H, m), 1.53-1.59 (1H, m), 1.18 (3H, d), 0.88 (3H, t).

6-((S)-2-Methyl-pyrrolidine-1-carbonyl)-3,4-dihydro-1H-pyrrolo[2,1-c][1,4]oxazine-8-carboxylic acid [(R)-1-(5-chloro-6-methoxy-pyridin-3-yl)-propyl]-amide (comp. no. 16b)

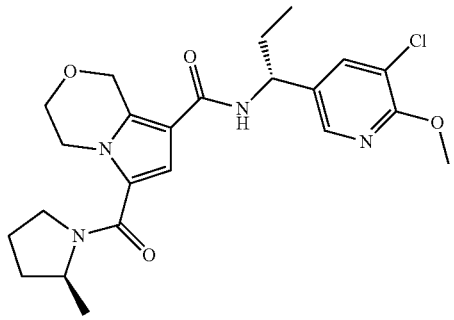 [SMILES: CC[C@@H](NC(=O)c1cc(C(=O)N2CCC[C@@H]2C)n2c1COCC2)c1cnc(OC)c(Cl)c1]

To a solution of 6-((S)-2-methyl-pyrrolidine-1-carbonyl)-3,4-dihydro-1H-pyrrolo[2,1-c][1,4]oxazine-8-carboxylic acid (comp. no. 7c) (75 mg, 0.270 mmol) in dimethylformamide (2 ml) was added 1-hydroxybenzotriazole (41 mg, 0.30 mmol) and 1-ethyl-3-(3-dimethylaminopropyl)carbodiimide hydrochloride (58 mg, 0.30 mmol). The mixture was stirred for 2 h at 50° C., then (R)-1-(5-chloro-6-methoxy-pyridin-3-yl)-propylamine hydrochloride (70 mg, 0.3 mmol) and triethylamine (82 mg, 0.81 mmol) were added and the mixture was stirred at 25° C. overnight. The mixture was filtered through a small filter cartridge and the solution was purified by reverse phase HPLC (acetonitrile/water gradient with 0.1% trifluoroacetic acid) to give 103 mg (83%) of 6-((S)-2-methyl-pyrrolidine-1-carbonyl)-3,4-dihydro-1H-pyrrolo[2,1-c][1,4]oxazine-8-carboxylic acid [(R)-1-(5-chloro-6-methoxy-pyridin-3-yl)-propyl]-amide as white solid. LC/MS (method 2): Rt=1.24 min; m/z=461.12 (M+H+). 1H-NMR: δ(ppm)=8.08 (2H, m), 7.86 (1H, s), 7.19 (1H, s), 4.97 (1H, d): 4/83-4.89 (2H, m), 3.80-4.30 (8H, m), 3.68 (2H, bs), 2.03-2.10 (1H, m): 1.99-1.92 (1H, m), 1.72-1.84 (3H, m), 1.52-1.59 (1H, m). 1.18-1.19 (3H, d), 0.87 (3H, t).

6-((S)-2-Methyl-pyrrolidine-1-carbonyl)-3,4-dihydro-1H-pyrrolo[2,1-c][1,4]oxazine-8-carboxylic acid [(R)-1-(3-chloro-4-trifluoromethyl-phenyl)-propyl]-amide (comp. no. 16c)

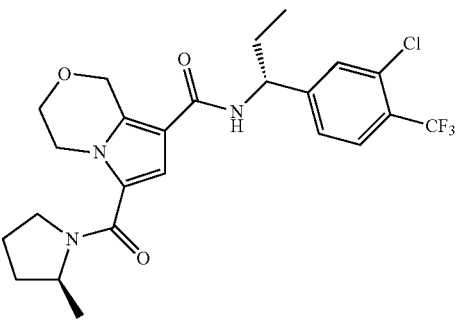 [SMILES: CC[C@@H](NC(=O)c1cc(C(=O)N2CCC[C@@H]2C)n2c1COCC2)c1ccc(C(F)(F)F)c(Cl)c1]

To a solution of 6-((S)-2-methyl-pyrrolidine-1-carbonyl)-3,4-dihydro-1H-pyrrolo[2,1-c][1,4]oxazine-8-carboxylic acid (comp. no 7c) (75 mg, 0.270 mmol) in dimethylformamide (2 ml) was added 1-hydroxybenzotriazole (41 mg, 0.30 mmol) and 1-ethyl-3-(3-dimethylaminopropyl)carbodiimide hydrochloride (58 mg, 0.30 mmol). The mixture was stirred for 2 h at 50° C., then (R)-1-(3-chloro-4-trifluoromethyl-phenyl)-propylamine hydrochloride (81 mg, 0.3 mmol) and triethylamine (82 mg, 0.81 mmol) were added and the mixture was stirred at 25° C. overnight. The mixture was filtered through a small filter cartridge and the solution was purified by reverse phase HPLC (acetonitrile/water gradient with 0.1% trifluoroacetic acid) to give 98 mg (73%) of 6-((S)-2-methyl-pyrrolidine-1-carbonyl)-3,4-dihydro-1H-pyrrolo[2,1-c][1,4]oxazine-8-carboxylic acid [(R)-1-(3-chloro-4-trifluoromethyl-phenyl)-propyl]-amide as white solid. LC/MS (method 3): Rt=2.03 min; m/z=498.22 (M+H$^+$). $^1$H-NMR; δ(ppm)=8.20 (1H, d), 7.83 (1H, d), 7.67 (1H, s), 7.50 (1H, d), 7.25 (1H, s), 4.96 (1H, d), 4.83-4.91 (m, 2H), 4.18-4.30 (2H, m), 3.92-4.01 (2H, m), 3.79-3.85 (1H, m), 3.69 (2H, bs), 2.07 (1H, m), 1.96 (1H, m), 1.76-1.85 (3H, m), 1.54-1.60 (1H, m), 1.19 (3H, d), 0.90 (3H, t).

6-((S)-2-Methyl-pyrrolidine-1-carbonyl)-3,4-dihydro-1H-pyrrolo[2,1-c][1,4]oxazine-8-carboxylic acid [(R)-1-(3-chloro-4-cyano-phenyl)-propyl]-amide (comp. no. 16d)

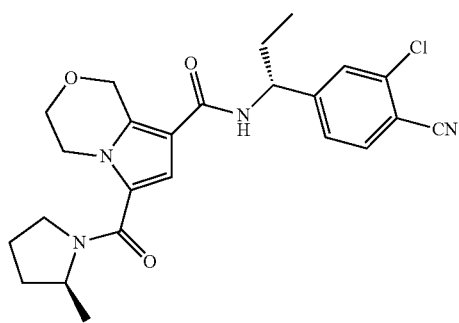 [SMILES: CC[C@@H](NC(=O)c1cc(C(=O)N2CCC[C@@H]2C)n2c1COCC2)c1ccc(C#N)c(Cl)c1]

To a solution of 6-((S)-2-methyl-pyrrolidine-1-carbonyl)-3,4-dihydro-1H-pyrrolo[2,1-c][1,4]oxazine-8-carboxylic acid (comp. no. 7c) (75 mg, 0.270 mmol) in dimethylformamide (2 ml) was added 1-hydroxybenzothazole (41 mg, 0.30 mmol) and 1-ethyl-3-(3-dimethylaminopropyl)carbodiimide hydrochloride (58 mg, 0.30 mmol). The mixture was stirred for 2 h at 50° C., then 4-((R)-1-amino-propyl)-2-chloro-benzonitrile hydrochloride (68 mg, 0.3 mmol) and triethylamine (60 mg, 0.6 mmol) were added and the mixture was stirred at 25° C. overnight. The mixture was filtered through a small filter cartridge and the solution was purified by reverse phase HPLC (acetonitrile/water gradient with 0.1% trifluoroacetic acid) to give 82 mg (67%) of 6-((S)-2-methyl-pyrrolidine-1-carbonyl)-3,4-dihydro-1H- pyrrolo[2,1-c][1,4]oxazine-8-carboxylic acid [(R)-1-(3-chloro-4-cyano-phenyl)-propyl]-amide as white solid. LC/MS (method 2): Rt=1.24 min; m/zp32 455.08 (M+H$^+$). $^1$H-NMR: δ(ppm)=8.20 (1H, d), 7.94 (1H, d), 7.70 (1H, s), 7.50 (1H, d), 7.24 (1H, s), 4.95 (1H, d), 4.82-4.92 (2H, m), 4.20-4.29 (2H, m), 3.70-4.00 (5H, m), 2.07 (1H, m), 1.97 (1H, m), 1.74-1.85 (3H, m), 1.57 (1H, m), 1.19 (3H, d), 0.89 (3H, t).

6-((S)-2- Methyl-pyrrolidine-1-carbonyl)-3,4-dihydro-1H-pyrrolo[2,1-c][1,4]oxazine-8-carboxylic acid [(R)-1-(6-trifluoromethyl-pyridin-3-yl)-propyl]-amide (comp. no. 16e)

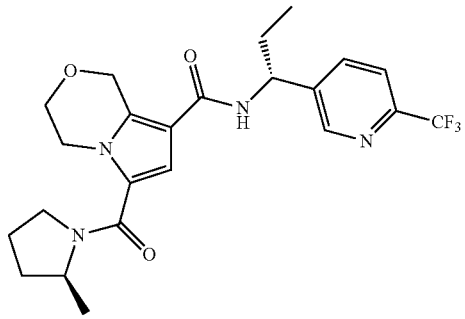 [SMILES: CC[C@@H](NC(=O)c1cc(C(=O)N2CCC[C@@H]2C)n2c1COCC2)c1ccc(C(F)(F)F)nc1]

To a solution of 6-((S)-2-methyl-pyrrolidine-1-carbonyl)-3,4-dihydro-1H-pyrrolo[2,1-c][1,4]oxazine-8-carboxylic acid (comp. no. 7c) (50 mg, 0.188 mmol) in dimethylformamide (2 ml) was added 1-hydroxybenzotriazole (27 mg, 0.197 mmol) and 1-ethyl-3-(3-dimethylaminopropyl)carbodiimide hydrochloride (38 mg, 0.197 mmol). The mixture was stirred for 90 min at 50° C., then (R)-1-(6-trifluoromethyl-pyridin-3-yl)-propylamine hydrochloride (48 mg, 0.20 mmol) and triethylamine (55 mg, 0.54 mmol) were added and the mixture was stirred at 25° C. overnight. The mixture was filtered through a small filter cartridge and the solution was punned by reverse phase HPLC (acetonitrile/water gradient with 0.1% trifluoroacetic acid) to gsve 45 mg (54%) of 6-((S)-2-methyl-pyrrolidine-1-carbonyl)-3,4-dihydro-1H-pyrrolo[2,1-c][1,4]oxazine-8-carboxylic acid [(R)-1-(6-trifluoromethyl-pyridin-3-yl)-propyl]-amide as white solid. LC/MS (method 5): Rt=4.12 min; m/z=485.35 (M+H$^+$). $^1$H-NMR (400 MHz); δ(ppm) 8.76 (1H, s), 8.26 (1H, d), 8.01 (1H, d), 7.89 (1H, d), 7.24 (1H, s), 4.93-4.98 (2H, m). 4.84 (1H, d), 4.20-4.29 (2H, m), 3.92-3.99 (2H, m), 3.78-3.84 (1H, m), 3.69 (2H, bs), 2.07 (1H, m), 1.96 (1H, m), 1.77-1.89 (3H, m), 1.56 (1H, m), 1.19 (3H, d), 0.92 (3H, t).

6-((S)-2-Methyl-pyrrdidine-1-carbonyl)-3,4-dihydro-1H-pyrrolo[2,1-c][1,4]oxazine-8-carboxylic acid [(R)-1-(4-trifluoromethyl-phenyl)-propyl]-amide (comp. no. 16f)

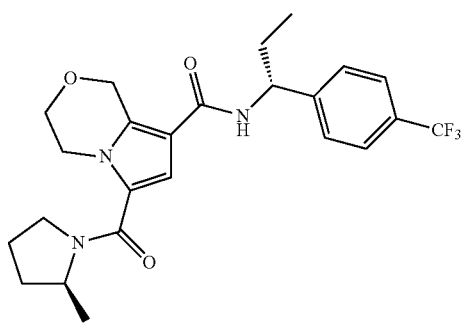

To a solution of 6-((S)-2-methyl-pyrrolidine-1-carbonyl)-3,4-dihydro-1H-pyrrolo[2,1-c][1,4]oxazine-8-carboxylic acid (comp. no. 7c) (150 mg, 0.593 mmol) in dimethylformamide (4 ml) was added 1-hydroxybenzothazole (80 mg, 0.593 mmol) and 1-ethyl-3-(3-dimethylaminopropyl)carbodiimide hydrochloride (114 mg, 0.593 mmol). The mixture was stirred for 90 min at 50° C., then (R)-1-(4-trifluoromethyl-phenyl)-propylamine (120 mg, 0.593 mmol) was added and the mixture was stirred at 25° C. overnight. The mixture was purified by reverse phase HPLC (acetonitrile/water gradient with 0.1% trifluoroacetic acid) to give 163 mg (65%) of 6-((S)-2-methyl-pyrrolidine-1-carbonyl)-3,4-dihydro-1H-pyrrolo[2,1-c][1,4]oxazine-8-carboxylic acid [(R)-1-(4-trifluoromethyl-phenyl)-propyl]-amide as white solid. LC/MS (method 4:): Rt=1.29 min; m/z=464.22 (M+H$^+$). $^1$H-NMR: δ(ppm)=8.18 (1H, d), 7.69 (2H, d), 7.55 (2H, d), 7.26 (1H, s), 4.96 (1H, d), 4.83-4.92 (2H, m), 4.20-4.30 (2H, m), 3.92-3.99 (2H, m), 3.80-3.85 (1H, m), 3.69, (2H, m), 1.96 (1H, m), 1.76-1.85 (3H, m, 1.54-1.59 (1H, m), 1.19 (3H, d), 0.90 (3H, t).

3,4-Dihydro-1H-pyrrolo[2,1-c][1,4]oxazine-6,8-dicarboxylica cid 6-{[(R)-1-(4-fluoro-phenyl)-ethyl]-amide} 8-{[(R)-1-(6-trifluoromethyl-pyridin-3-yl)-propyl]-amide} (comp. no. 16g)

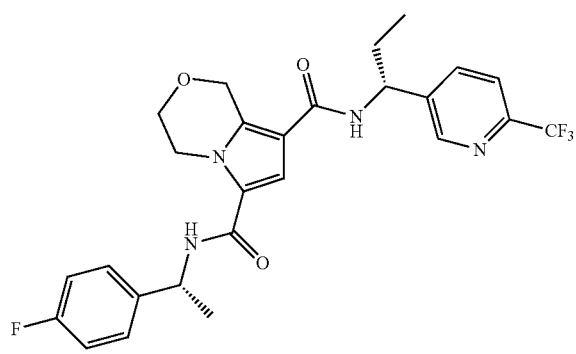 [SMILES: CC[C@@H](NC(=O)c1cc(C(=O)N[C@H](C)c2ccc(F)cc2)n2c1COCC2)c1ccc(C(F)(F)F)nc1]

To a solution of 6-[(R)-1-(4-fluoro-phenyl)ethylcarbamoyl]-3,4-dihydro-1H-pyrrolo[2,1-c][1,4]oxazine-8-carboxylic acid (comp. no. 7o) (100 mg, 0.301 mmol) in dimethylformamide (2 ml) was added 1-hydroxybenzotriazole (45 mg, 0.331 mmol) and 1-ethyl-3-(3-dimethylaminopropyl) carbodiimide hydrochloride (64 mg, 0.331 mmol). The mixture was stirred for 90 min at 50° C., then another portion of 1-hydroxybenzotriazole (5 mg, 0.033 mmol) and 1-ethyl-3-(3-dimethylaminopropyl)carbodiimide hydrochloride (5 mg, 0.033 mmol) was added. The mixture was stirred for 45 mm at 50° C., then (R)-1-(6-trifluoromethyl-pyridin-3-yl)-propylamine hydrochloride (80 mg, 0.331 mmol) and triethylamine (67 mg, 0.66 mmol) were added and the mixture was stirred at 25° C. overnight. Water and dichloromethane were added, the organic layer was washed with water and aqueous sodium hydrogencartionate and after evaporation of solvents the crude product was purified by reverse phase HPLC (acetonitrile/water gradient with 0.1% trifluoroacetic acid) to give 89 mg (57%) of 3,4-dihydro-1H-pyrrolo[2,1-c][1,4]oxazine-6,8-dicarboxylic acid 6-{[(R)-1-(4-fluoro-phenyl)-ethyl]-amide} 8-{[(R)-1-(6-trifluoromethyl-pyridin-3-yl)-propyl]-amide} as white solid. LC/MS (method 2): Rt=1.28 min: m/z=519.11 (M+H$^+$). $^1$H-NMR: δ(ppm)=8.77 (1H, s), 8.52 (1H, d), 8.37 (1H, d), 8.04 (1H, d), 7.88 (1H, d), 7.41-7.44 (2H, m), 7.31 (1H, s), 7.14 (2H, t), 5.07-5.12 (1H, m), 4.85-4.98 (3H, m), 4.12-4.21 (2H, m), 3.86-3.89 (2H, m), 179-1.94 (2H, m), 1.43 (3H, d), 0.91 (3H, t).

3,4-Dihydro-1H-pyrrolo[2,1-c][1,4]oxazine-6,8-dicarboxylic acid 6-{[(R)-1-(4-fluoro-phenyl)-ethyl]-amide} 8-[((S)-1-pyrimidin-2-yl-propyl)-amide] (comp. no. 16h)

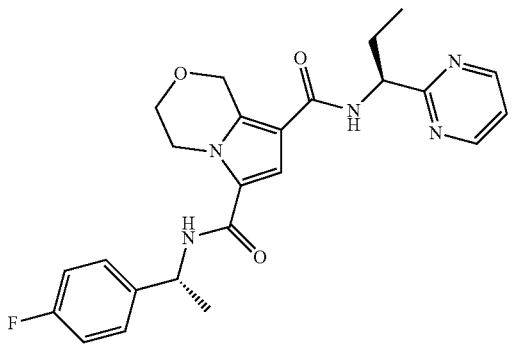 [SMILES: CC[C@H](NC(=O)c1cc(C(=O)N[C@H](C)c2ccc(F)cc2)n2c1COCC2)c1ncccn1]

To a solution of 6-[(R)-1-(4-fluoro-phenyl)-ethylcarbamoyl]-3,4-dihydro-1H-pyrrolo[2,1-c][1,4]oxazine-8-carboxylic acid (comp. no. 7o) (230 mg, 0.692 mmol) in dimethylformamide (4 ml) was added 1-hydroxybenzotriazole (103 mg, 0.761 mmol) and 1-ethyl-3-(3-dimethylaminopropyl) carbodiimide hydrochloride (146 mg, 0.761 mmol). The mixture was stirred for 90 min at 50° C., then (S)-1-pyrimidin-2-yl-propylamine hydrochloride (comp. no. 15a) (120 mg, 0.331 mmol) and triethylamine (210 mg, 2.06 mmol) were added and the mixture was stirred at 25° C. overnight. Water and dichloromethane were added, the organic layer was washed with water and aqueous sodium hydrogencarbonate and after evaporation of solvents the crude product was purified by reverse phase HPLC (acetonitrile/water gradient with 0.1% trifluoroacetic acid). After evaporation of acetonitrile and addition of aqueous sodium hydrogencarbonate, extraction (3 times with dichloromethane), drying over sodium sulfate and evaporation of solvents, the residue was dissolved in methyl tert-butyl ether, heptane was added and the mixture was evaporated to dryness to give 125 mg (40%) of 3,4-dihydro-1H-pyrrolo [2,1-c][1,4]oxazine-6,8-dicarboxylic acid 6-{[(R)-1-(4-fluoro-phenyl)-ethyl]-amide} 8-[((S)-1-pyrimidin-2-yl-propyl)-amide] as white solid. LC/MS (method 4): Rt=1.15 min; m/z=452.1 (M+H$^+$). $^1$H-NMR (400 MHz): δ(ppm) =8.77 (1H, d), 8.48 (1H, d), 7.93 (1H, d), 7.38-7.44 (4 H, m), 7.14 (2H, t), 5.06-5.13 (1H, m), 4.99-5.04 (1H, m), 4.91 (2H, q), 4.19 (2H, m), 3.89 (2H, t), 1.76-1.99 (2H, m), 1.44 (3H, d), 0.88 (3H, t).

3,4-Dihydro-1H-pyrrolo[2,1-c][1,4]oxazine-6,8-dicarboxylic acid bis-[((R)-1-phenyl-propyl)-amide] (comp. no. 16i)

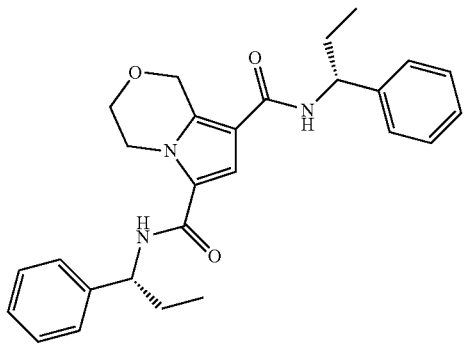 [SMILES: CC[C@@H](NC(=O)c1cc(C(=O)N[C@H](CC)c2ccccc2)n2c1COCC2)c1ccccc1]

A solution of 6-bromo-3,4-dihydro-1H-pyrrolo[2,1-c][1,4]oxazine-8-carboxylic acid ((R)-1-phenyl-propyl)amide (comp. no. 12a) (200 mg, 0.551 mmol), molybdenum(0) hexacarbonyl (44 mg, 0.165 mmol), trans-di-(μ-acetato)bis[2-(di-o-tolylphosphino)benzyl]dipalladium (II) (52 mg, 0.055 mmol), 1,8-diazabicyclo[5.4.0]undec-7-ene (500 mg, 3.31 mmol) and (R)-1-phenyl-propylamine (745 mg, 5.51 mmol) in dry tetrahydrofuran (5 ml) was heated for 30 min at 130° C. in a microwave reactor, then aqueous sodium hydrogencarbonate was added and the mixture was extracted 3 times with dichloromethane. The combined organic layers were dried over sodium sulfate, evaporated to dryness and the crude product was purified by reverse phase HPLC (acetonitrile/water gradient with 0.1% trifluoroacetic acid) to give 86 mg (35%) of 3,4-dihydro-1H-pyrrolo[2,1-c][1,4]oxazine-6,8-dicarboxylic acid bis-[((R)-1-phenyl-propyl)-amide] as white solid. LC/MS (method 4): Rt=1.28 min; m/z=446.38 (M+H$^+$). $^1$H-NMR: δ(ppm)=8.44 (1H, d), 8.15 (1H, d), 7.25-7.40 (9H, m), 7.22 (2H, q), 4.80-5.00 (4 H, m), 4.15 (2H, m), 3.87 (2H, m), 1.73-1.80 (4 H, m), 0.85-0.90 (6H, m).

3,4-Dihydro-1H-pyrrolo[2,1-c][1,4]oxazine-6,8-dicarboxylic acid 6-{[(R)-1-(6-methoxy-pyridin-3-yl)-propyl]-amide} 8-[((R)-1-phenyl-propyl)-amide] (comp. no. 16j)

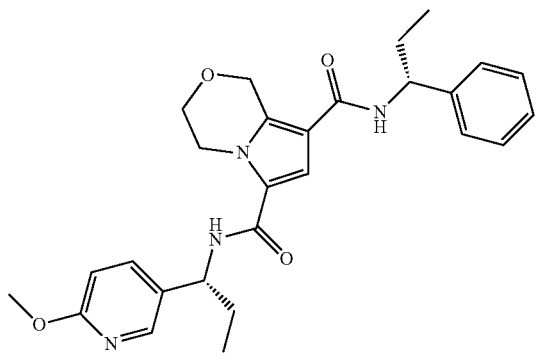 [SMILES: CC[C@@H](NC(=O)c1cc(C(=O)N[C@H](CC)c2ccc(OC)nc2)n2c1COCC2)c1ccccc1]

To a solution of 8-((R)-1-phenyl-propylcarbamoyl)-3,4-dihydro-1H-pyrrolo[2,1-c][1,4]oxazine-6-carboxylic acid (comp. no. 11a) (750 mg, 2.28 mmol) in dimethylformamide (25 ml) was added 1-hydroxybenzotriazole (339 mg, 2.51 mmol) and 1-ethyl-3-(3-dimethylaminopropyl)carbodiimide hydrochloride (482 mg, 2.51 mmol). The mixture was stirred for 2 h at 25° C., then another portion of 1-hydroxybenzotriazole (34 mg, 0.25 mmol) and 1-ethyl-3-(3-dimethylaminopropyl)carbodiimide hydrochloride (48 mg, 0.25 mmol) was added and the mixture was stirred for additional 20 min. (R)-1-(6-methoxy-pyridin-3-yl)-propylamine (418 mg, 2.52 mmol) was added and the mixture was stirred at 25° C. overnight. Another 3 portions of (R)-1-(6-methoxy-pyridin-3-yl)-propylamine (total of 160 mg, 0.963 mmol) were added and the mixture was stirred for 6 h. Approximately half of the solvents were evaporated, excess dichloromethane was added and the mixture was washed consecutively with water, aqueous sodium hydrogencarbonate and brine. The organic layer was evaporated to dryness. The residue was stirred in 20 ml diethyl ether for 1 h, the solid formed was filtered to give 0.85 g (78%) of 3,4-dihydro-1H-pyrrolo[2,1-c][1,4]oxazine-6,8-dicarboxylic acid 6-{[(R)-1-(6-methoxy-pyridin-3-yl)-propyl]-amide} 8-[((R)-1-phenyl-propyl)-amide] as white solid. LC/MS (method 4): Rt=1.26 min; m/z=477.4 (M+H$^+$). $^1$H-NMR: δ(ppm)=8.46 (1H, d), 8.15-8.17 (2H, m), 7.74 (1H, d), 7.28-7.37 (5H, m), 7.20 (1H, t), 8.80 (1H, d), 4.80-4.92 (4 H, m), 4.15 (2H, m), 3.86-3.89 (2H, m), 3.83 (3H, s), 1.73-1.88 (4 H, m), 0.80-0.92 (6H, m).

{[8-((R)-1-Phenyl-propylcarbamoyl)-3,4-dihydro-1H-pyrrolo[2,1-c][1,4]oxazine-6-carbonyl]-amino}-acetic acid ethyl ester (comp. no. 16k)

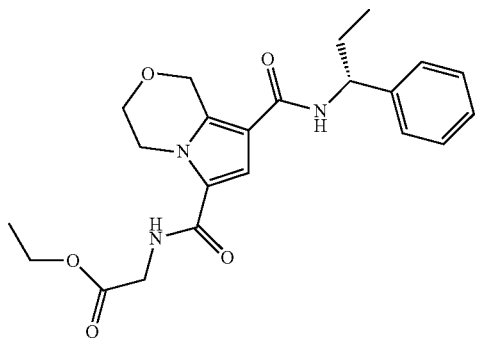 [SMILES: CCOC(=O)CNC(=O)c1cc(C(=O)N[C@H](CC)c2ccccc2)c2n1CCOC2]

To a solution of 8-((R)-1-phenyl-propylcarbamoyl)-3,4-dihydro-1H -pyrrolo[2,1-c][1,4]oxazine-6 -carboxylic acid (comp. no. 11a) (50 mg, 0.168 mmol) in dimethylformamide (1.7 ml) was added 1-hydroxybenzotriazole (23 mg, 0.168 mmol) and 1ethyl-3-(3-dimethylaminopropyl)carbodiimide hydrochloride (32 mg, 0.168 mmol). The mixture was stirred for 1 h at 40° C., then amino-acetic acid ethyl ester (17 mg, 0.168 mmol) was added and the mixture was stirred at 25° C. overnight. Excess dichloromethane was added and the mixture was washed consecutively with water, aqueous sodium hydrogencarbonate and brine. The organic layer was evaporated to dryness. The residue was dissolved in a small amount of acetonitrile, excess water was added and the solution was freeze-dried to give 52 mg (82%) of {[8-((R)-1-phenyl-propylcarbamoyl)-3,4-dihydro-1H-pyrrolo[2,1-c][1,4]oxazine-6-crbonyl]-amino}-acetic acid ethyl ester. LC/MS (method 4): Rt=1.19 min; m/z=414.2 (M+H$^+$). $^1$H-NMR: δ(ppm)=8.48 (1H, t), 8.21 (1H, d), 7.35-7.36 (3H, m), 7.30 (2 H, t), 7.21 (1H, t), 4.91 (2H, dd), 4.82 (1H, q), 4.19 (2H, t), 4.11 (2H, q), 3.90-3.92 (4 H, m), 1.71-1.83 (2H, m), 1.21 (3H, t), 0.88 (3H, t).

(S)-2-{Methyl-[8-((R)-1-phenyl-propylcarbamoyl)-3,4-dihydro-1H-pyrrolo[2,1-c][14]oxazine-6-carbonyl]-amino}-propionic acid ethyl ester (comp. no. 16l)

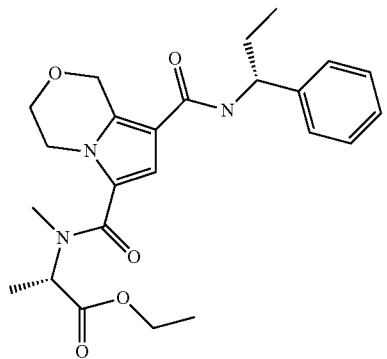 [SMILES: CCOC(=O)[C@H](C)N(C)C(=O)c1cc(C(=O)N[C@H](CC)c2ccccc2)c2n1CCOC2]

To a solution of 8-((R)-1-phenyl-propylcarbamoyl)-3,4-dihydro-1H-pyrrolo[2,1-c][1,4]oxazine-6-carboxylic acid (comp. no. 11a) (100 mg, 0.335 mmol) in dimethylformamide (2.2 ml) was added 1-hydroxybenzotriazole (45 mg, 0.335 mmol) and 1-ethyl-3-(3-dimethylaminopropyl)carbodiimide hydrochloride (64 mg, 0.335 mmol). The mixture was stirred for 1 h at 25° C., then (S)-2-methylaminopropionic add ethyl ester hydrochloride (56 mg, 0.335 mmol) (prepared from (S)-2-methylamino-propionic acid by heating in ethanol and 4 M hydrogen chloride in dioxane for 18 h and evaporation of the solvents) and triethylamine (62 mg, 0.61 mmol) were added and the mixture was stirred at 25° C. overnight. Another portion of 1-ethyl-3-(3-dimethylaminopropyl)carbodiimide hydrochloride (13 mg, 0.067 mmol) and (S)-2-methylamino-propionic acid ethyl ester hydrochloride (12 mg, 0.067 mmol) were added and the mixture was stirred for 1 h. After filtration of the mixture through a short filter cartridge the solution was purified by reverse phase HPLC (acetonitrile/water gradient with 0.1% trifluoroacetic acid) to give 68 mg (51%) (S)-2-{Methyl-[8-((R)-1-phenyl-propylcarbamoyl)-3,4-dihydro-1H-pyrrolo[2,1-c][1,4]oxazine-6-carbonyl]-amino}-propionic acid ethyl ester. LC/MS (method 2): Rt=1.11 min: m/z=442.3 (M+H$^+$). $^1$H-NMR: δ(ppm)=8.46 (1H, t), 8.21 (1H, d), 7.35-7.36 (3H, m), 7.30 (2H, t), 7.21 (1H, t), 4.91 (2H, dd), 4.82 (1H, q), 4.19 (2Hm t), 4.11 (2H, q), 3.90-3.92 (4 H, m), 1.71-1.83 (2H, m), 1.21 (3H, t), 0.88 (3H, t).

(R)-1-[8-((R)-1-Phenyl-propylcarbamoyl)-1H-pyrrolo[2,1-c][1,4]oxazine-6-carbonyl]-pyrrolidine-2-carboxylic acid methyl ester (comp. no. 16m)

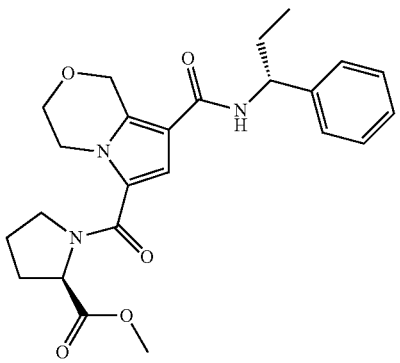 [SMILES: CC[C@@H](NC(=O)c1cc(C(=O)N2CCC[C@@H]2C(=O)OC)n2c1COCC2)c1ccccc1]

To a solution of 8-((R)-1-phenyl-propylcarbamoyl)-3,4-dihydro-1H-pyrrolo[2,1-c][1,4]oxazine-6-carboxylic acid (comp. no. 11a) (200 mg, 0.61 mmol) in dimethylformamide (2 ml) was added 1-hydroxybenxothazole (91 mg, 0.670 mmol) and 1-ethyl-3-(3-dimethylaminopropyl)carbodiimide hydrochloride (128 mg, 0.670 mmol). The mixture was stirred for 45 min at 25° C., then (R)-pyrrolidine-2-carboxylic acid methyl ester hydrochloride (111 mg; 0.670 mmol) and triethylamine (123 mg, 1.218 mmol) were added and the mixture was stirred at 25° C. overnight. Excess dichloromethane was added and the mixture was washed consecutively with water aqueous sodium hydrogencarbonate and brine. The organic layer was evaporated to dryness. The crude product was purified by flash chromatography (silica gel, elution with heptane/ethyl acetate) to give 55 mg (21%) of (R)-1-[8-((R)-1-phenyl-propylcarbamoyl)-3,4-dihydro-1H-pyrrolo[2,1-c][1,4]oxazine-6-carbonyl]-pyrrolidine-2-carboxylic acid methyl ester). LC/MS (method 4): Rt=1.21 min; m/z=440.29 (M+H$^+$).

(R)-1-[8-((R)-1-Phenyl-propylcarbamoyl)-3,4-dihydro-1H-pyrrolo[2,1-c][1,4]oxazine-6-carbonyl]-pyrroliidine-2-carboxylic acid isopropyl ester (comp. no. 16n)

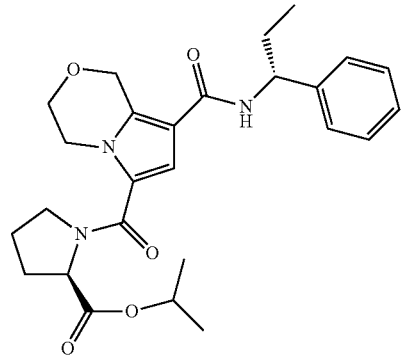 [SMILES: CC[C@@H](NC(=O)c1cc(C(=O)N2CCC[C@@H]2C(=O)OC(C)C)n2c1COCC2)c1ccccc1]

A mixture of (R)-1-[8-((R)-1-phenyl-propylcarbamoyl)-3,4-dihydro-1H-pyrrolo[2,1-c][1,4]oxazine-6carbonyl]-pyrrolidine-2-carboxylic acid methyl ester (comp. no. 16m) (171 mg, 0.389 mmol) in tetrahydrofuran (5 ml) and water (4 ml), and 2 aqueous sodium hydroxide (1 ml, 2 mmol) was refluxed for 3 h, cooled to room temperature, acidified with excess aqueous hydrochloric acid, and extracted with dichloromethane. Solvents were evaporated to gsve 140 mg of (R)-1-[8-((R)-1-phenyl-propylcarbamoyl)-3,4-dihydro-1H-pyrrolo[2,1-c][1,4]oxazine-6-carbonyl]-pyrrolidine-2-carboxylic acid.

A solution of (R)-1-[8-((R)-1-phenyl-propylcarbamoyl)-3,4-dihydro-1H-pyrrolo[2,1-c][1,4]oxazine-6-carbonyl]-pyrrolidine-2-carboxylic acid in isopropanol and 2 drops of concentrated aqueous hydrochloric acid was heated to reflux overnight. Solvents were evaporated. The residue was dissolved in a small amount of acetonitrile, excess water was added and the solution was freeze-dried to give 27 mg (49%) of (R)-1-[8-((R)-1-phenyl-propylcarbamoyl)-3,4-dihydro-1H-pyrrolo[2,1-c][1,4]oxazine-6-carbonyl]-pyrrolidine-2-carboxylic acid isopropyl ester. LC/MS (method 4): Rt=1.27 min; m/z=468.35 (M+H$^+$).

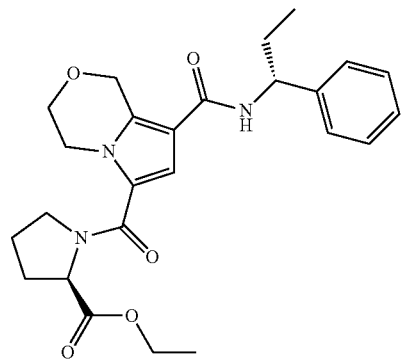 [SMILES: CCOC(=O)[C@H]1CCCN1C(=O)c1cc(C(=O)N[C@H](CC)c2ccccc2)c2n1CCOC2]

The compound was obtained from comp. no. 16m as starting compound in analogy to the synthesis of comp. no. 16n. Isopropanol was replaced by ethanol to form the ester. LC/MS (method 4): Rt=1.24 min; m/z=454.27 (M+H$^+$)

6-((R)-2-Trifluoromethyl-pyrrolidine-1-carbonyl)-3,4-di-hydro-1H-pyrrolo[2,1-c][1,4]oxazine-8-carboxylic acid [(R)-1-(6-trifluoromethyl-pyridin-3-yl)-propyl]-amide (comp. no. 16o)

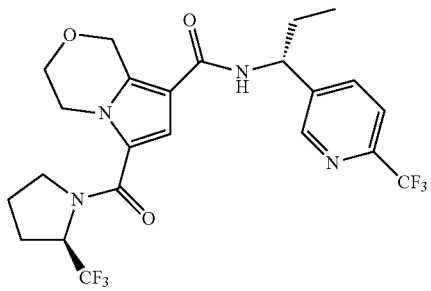 [SMILES: CC[C@@H](NC(=O)c1cc(C(=O)N2CCC[C@@H]2C(F)(F)F)n2c1COCC2)c1ccc(C(F)(F)F)nc1]

To a solution of 8-[(R)-1-(6-trifluoromethyl-pyridin-3-yl)-propylcarbamoyl]-3,4-dihydro-1H-pyrrolo[2,1-c][1,4]oxazine-6-carboxylic acid (comp. no. 11h) (62 mg, 0.187 mmol) in dimethylformamide (0.6 ml) was added 1-hydroxybenzotriazole (28 mg, 0.206 mmol) and 1-ethyl-3-(3-dimethylaminopropyl)carbodiimide hydrochloride (40 mg, 0.206 mmol). The mixture was stirred for 3 h at 50° C., then (R)-2-trifluoromethyl-pyrrolidine (42 mg, 0.206 mmol) and triethylamine (38 mg, 0.37 mmol) were added and the mixture was stirred at 25° C. for 24 h. An excess of water was added, the solid which precipitated was filtered off, washed with a small amount of water and dried in vacuo to give 66 mg (68%) of 6-((R)-2-trifluoromethyl-pyrrolidine-1-carbonyl)-3,4-dihydro-1H-pyrrolo[2,1-c][1,4]oxazine-8-carboxylic acid [(R)-1-(6-trifluoromethyl-pyridin-3-yl)propyl]-amide. LC/MS (method 5:): Rt=4.55 min; m/z=5.19.13 (M+H+).

3,4-Dihydro-1H-pyrrolo[2,1-c][1,4]oxazine-6,8-dicarboxylic acid 6-[(3,5-dimethyl-isoxazol-4-ylmethyl)-amide] 8-[((R)-1-phenyl-propyl)-amide] (comp. no. 16pq)

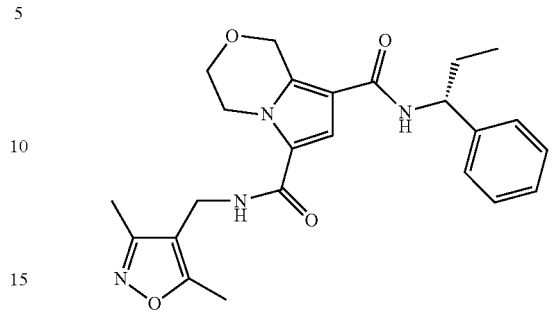

A solution of 6-(2,2,2-trichloro-acetyl)-3,4-dihydro-1H-pyrrolo[2,1-c][1,4]oxazine-8-carboxylic acid ((R)-1-phenyl-propyl)-amide (comp. no. 10a) (60 mg, 0.140 mmol) and C-(3,5-dimethyl-isoxazol-4-yl)-methylamine (21 mg, 0.167 mmol) in tetrahydrofuran was refluxed for 2 h. Another portion of C-(3,5-dimethyl-isoxazol-4-yl)-methylamine (21 mg, 0.167 mmol) was added and the mixture was stirred at 25° C. overnight. After addition of aqueous sodium m/drogencarbonate, the mixture was extracted 3 times with dichloromethane, solvents were evaporate and the residue was purified flash chromatography (silica gel, elution with heptane/ethyl acetate) to give 20 mg (33%) of 3,4-dihydro-1H-pyrrolo[2,1-c][1,4]oxazine-6,8-dicarboxylic acid 6-[(3,5-dimethyl-isoxazol-4-ylmethyl)-amide] 8-[((R)-1-phenyl-propyl)-amide]. LC/MS (method 4). Rt=1.18 min; m/z=437.16 (M+H+).

The example compounds of the formula I in Table 9 were obtained in analogy to the synthesis of comp. no. 16pq. In case the hydrochloride salt of the amine was used, an excess of 3 equivalents triethylamine was additionally added to the reaction mixture.

TABLE 9

| Comp no. (starting comp. no.) | Formula | Rt [min] (LC/MS method) | m/z (M + H+) |
|---|---|---|---|
| 16gr (10a) | | 1.16 (4) | 447.41 |
| 16gs (10a) | | 1.22 (4) | 443.37 |

TABLE 9-continued

| | | | |
|---|---|---|---|
| 16hs (10a) | | 1.31 (4) | 446.26 |
| 16ht (10a) | | 1.29 (4) | 450.24 |
| 16nb (10i) | | 1.22 (4) | 435.31 |
| 16nf (10i) | | 1.31 (4) | 416.29 |

TABLE 9-continued

| Comp. no. | Chemical name |
|---|---|
| 16gr | 3,4-Dihydro-1H-pyrrolo[2,1-c][1,4]oxazine-6,8-dicarboxylic acid 8-[((R)-1-phenyl-propyl)-amide] 6-[((R)-1-pyridin-2-yl-propyl)-amide] |
| 16gs | 3,4-Dihydro-1H-pyrrolo[2,1-c][1,4]oxazine-6,8-dicarboxylic acid 6-(3-cyano-benzylamide) 8-[((R)-1-phenyl-propyl)-amide] |
| 16hs | 3,4-Dihydro-1H-pyrrolo[2,1-c][1,4]oxazine-6,8-dicarboxylic acid 6-[((S)-1-phenyl-propyl)-amide] 8-[((R)-1-phenyl-propyl)-amide] |
| 16ht | 3,4-Dihydro-1H-pyrrolo[2,1-c][1,4]oxazine-6,8-dicarboxylic acid 6-{[(S)-1-(4-fluoro-phenyl)-ethyl]-amide} 8-[((R)-1-phenyl-propyl)-amide] |
| 16nb | 5,6,7,8-Tetrahydro-indolizine-1,3-dicarboxylic acid 3-[(5-fluoro-pyridin-3-ylmethyl)-amide] 1-[((R)-1-phenyl-propyl)-amide] |
| 16nf | 5,6,7,8-Tetrahydro-indolizine-1,3-dicarboxylic acid 3-benzylamide 1-[((R)-1-phenyl-propyl)-amide] |
| 16ng | 5,6,7,8-Tetrahydro-indolizine-1,3-dicarboxylic acid 3-[(1-phenyl-cyclopentylmethyl)-amide] 1-[((R)-1-phenyl-propyl)-amide] |

The example compounds or the formula I in Table 10 were obtained in analogy to the synthesis of comp. no. 16e. Where mentioned in the Table, the racemic amine was used in the reaction, and the diastereomeric products were separated by chromatography on a chiral phase.

TABLE 10

| Comp. no. (starting comp. no.) | Formula | Rt [min] (LC/MS method) | m/z (M + H⁺) |
|---|---|---|---|
| 16p (7c) | | 1.28 (4) | 428.31 |
| 16q (7c) | | 1.28 (4) | 430.18 |

TABLE 10-continued
| | | | |
|---|---|---|---|
| 16r (7c) | 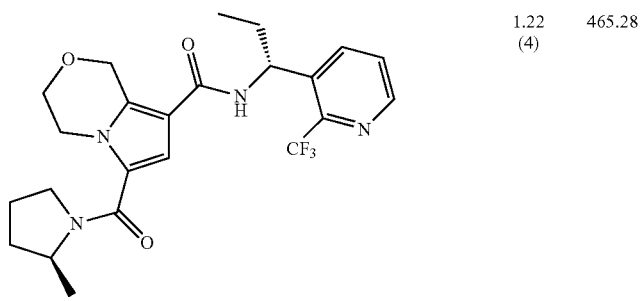 | 1.22 (4) | 465.28 |
| 16s (7c) | 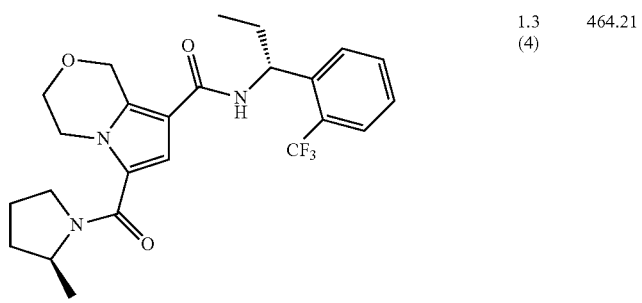 | 1.3 (4) | 464.21 |
| 16t (7c) | 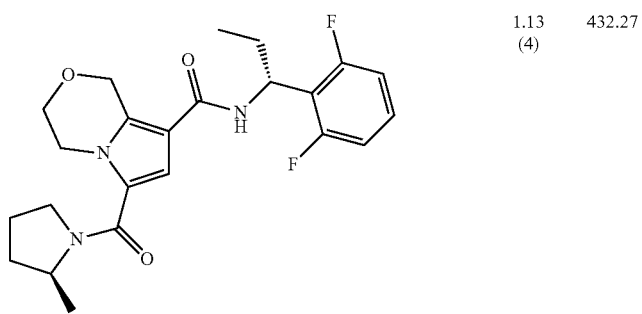 | 1.13 (4) | 432.27 |
| 16u (7c) | 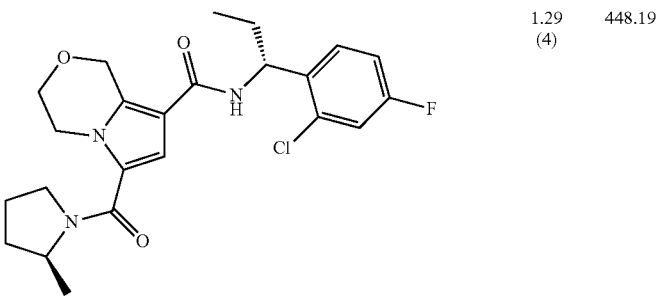 | 1.29 (4) | 448.19 |
| 16v (7c) | 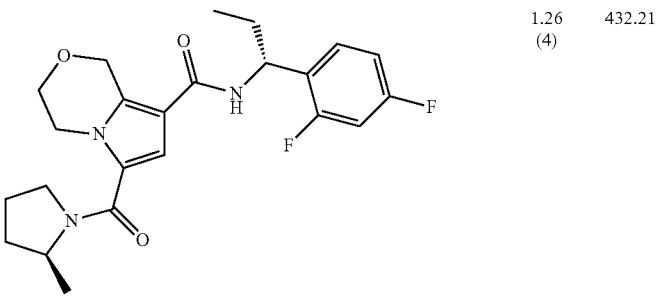 | 1.26 (4) | 432.21 |

TABLE 10-continued
| | | | |
|---|---|---|---|
| 16w (7c) | 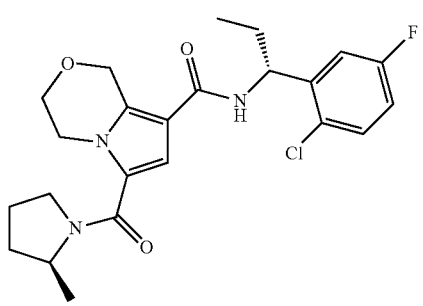 [SMILES: CC[C@@H](NC(=O)c1cc(C(=O)N2CCC[C@@H]2C)n2c1COCC2)c1cc(F)ccc1Cl] | 1.3 (4) | 448.18 |
| 16x (7c) | 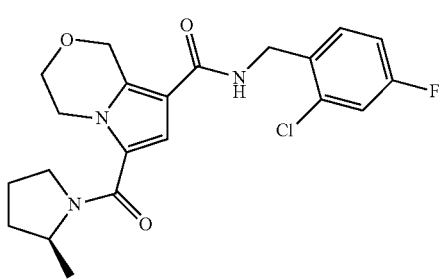 [SMILES: C[C@H]1CCCN1C(=O)c1cc(C(=O)NCc2ccc(F)cc2Cl)c2n1CCOC2] | 4.18 (5) | 420.15 |
| 16y (7c) | 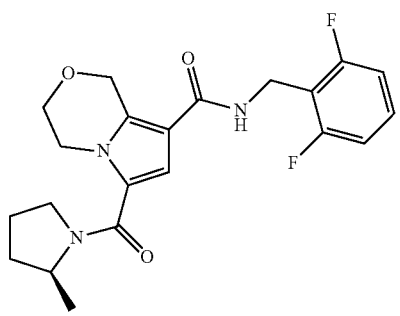 [SMILES: C[C@H]1CCCN1C(=O)c1cc(C(=O)NCc2c(F)cccc2F)c2n1CCOC2] | 1.18 (4) | 404.16 |
| 16z (7c) | 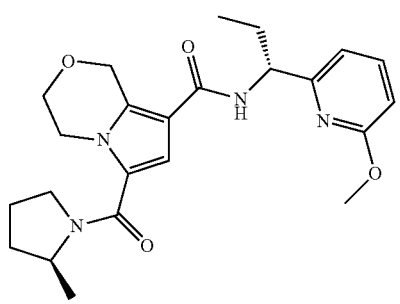 [SMILES: CC[C@@H](NC(=O)c1cc(C(=O)N2CCC[C@@H]2C)n2c1COCC2)c1cccc(OC)n1] | 4.12 (5) | 427.34 |
| 16aa (7c) | 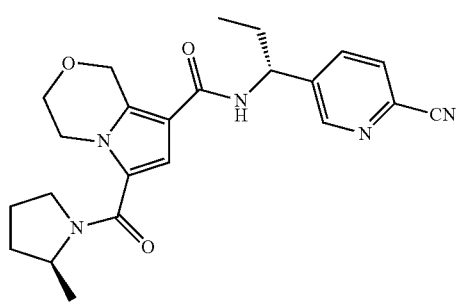 [SMILES: CC[C@@H](NC(=O)c1cc(C(=O)N2CCC[C@@H]2C)n2c1COCC2)c1ccc(C#N)nc1] | 1.02 (2) | 422.3 |

TABLE 10-continued
| | | | | |
|---|---|---|---|---|
| 16ab (7c) | 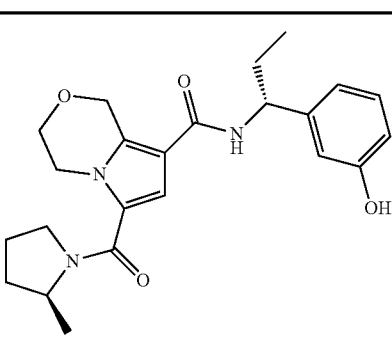 | 1.14 (4) | 412.29 | |
| 16ae (7c) | 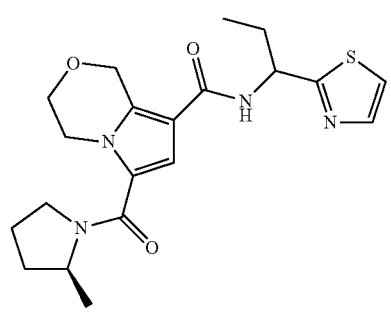 [SMILES: CCC(NC(=O)c1cc(C(=O)N2CCC[C@@H]2C)n2c1COCC2)c1nccs1] | 3.43 (5) | 403.26 | |
| 16af (7c) | 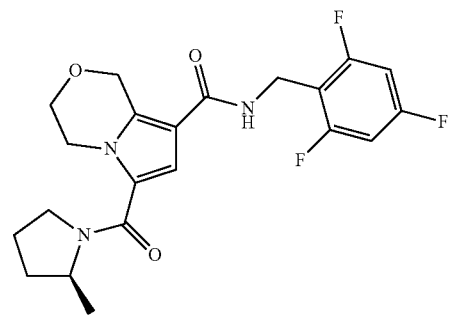 [SMILES: C[C@H]1CCCN1C(=O)c1cc(C(=O)NCc2c(F)cc(F)cc2F)c2n1CCOC2] | 1.07 (2) | 422.23 | |
| 16ag (7c) | 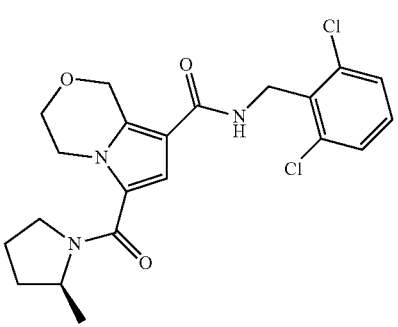 [SMILES: C[C@H]1CCCN1C(=O)c1cc(C(=O)NCc2c(Cl)cccc2Cl)c2n1CCOC2] | 1.11 (2) | 436.2 | |
| 16ah (7c) | 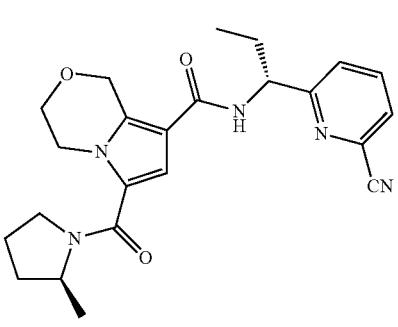 [SMILES: CC[C@@H](NC(=O)c1cc(C(=O)N2CCC[C@@H]2C)n2c1COCC2)c1cccc(C#N)n1] | 3.79 (5) | 422.26 | |

TABLE 10-continued
| 16ai (7c) | 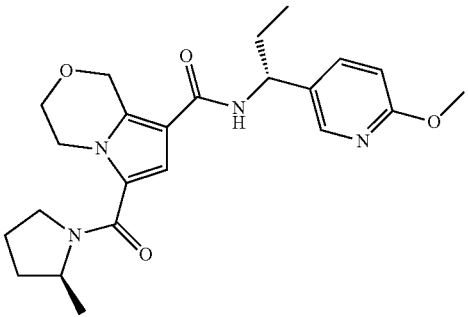 [SMILES: CC[C@@H](NC(=O)c1cc(C(=O)N2CCC[C@@H]2C)n2c1COCC2)c1ccc(OC)nc1] | 1.04 (2) | 427.01 |
| 16aj (7c) | 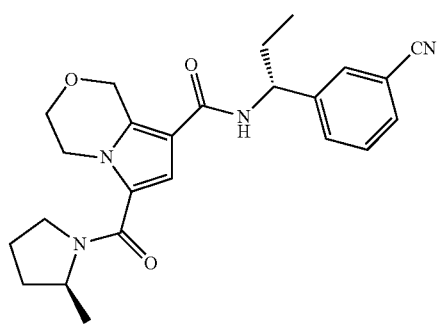 [SMILES: CC[C@@H](NC(=O)c1cc(C(=O)N2CCC[C@@H]2C)n2c1COCC2)c1cccc(C#N)c1] | 4.02 (5) | 421.42 |
| 16ak (7c) | 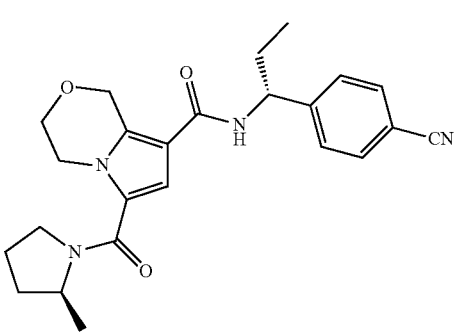 [SMILES: CC[C@@H](NC(=O)c1cc(C(=O)N2CCC[C@@H]2C)n2c1COCC2)c1ccc(C#N)cc1] | 1.08 (2) | 421.28 |
| 16al (7c) | 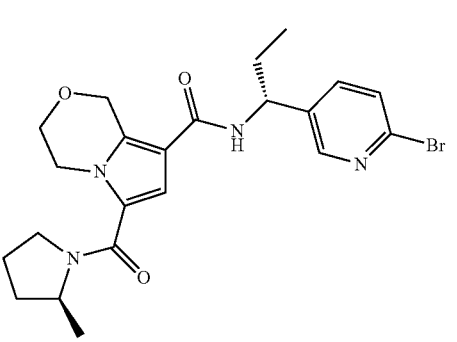 [SMILES: CC[C@@H](NC(=O)c1cc(C(=O)N2CCC[C@@H]2C)n2c1COCC2)c1ccc(Br)nc1] | 1.07 (2) | 475.18 |
| 16am (7c) | 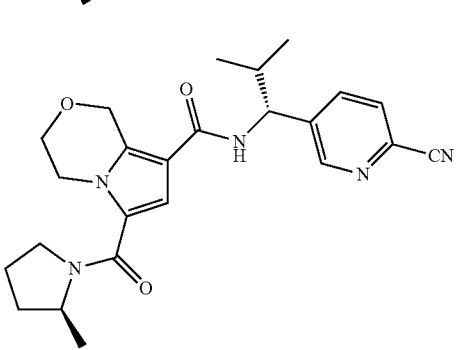 | 1.18 (4) | 436.25 |

TABLE 10-continued
| 16an (7c) | 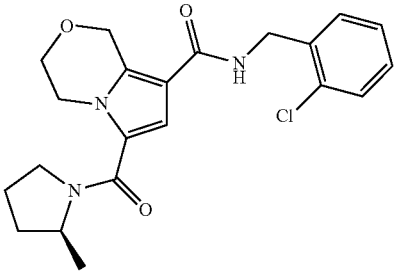 [SMILES: C[C@H]1CCCN1C(=O)c1cc(C(=O)NCc2ccccc2Cl)c2n1CCOC2] | 1.21 (4) | 402.17 |
| 16ao (7c) | 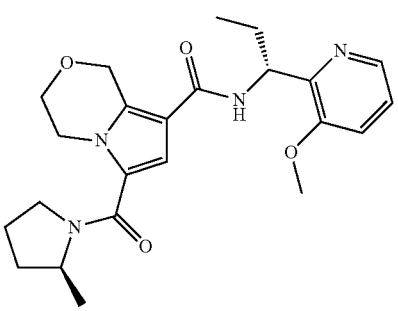 [SMILES: CC[C@@H](NC(=O)c1cc(C(=O)N2CCC[C@@H]2C)n2c1COCC2)c1ncccc1OC] | 1.1 (4) | 427.26 |
| 16ap (7c) | 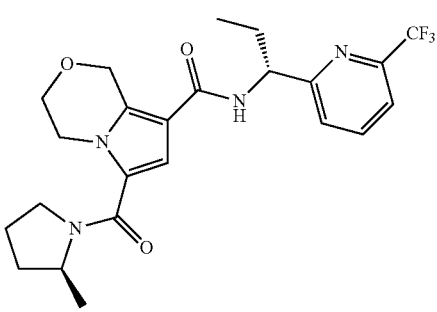 [SMILES: CC[C@@H](NC(=O)c1cc(C(=O)N2CCC[C@@H]2C)n2c1COCC2)c1cccc(C(F)(F)F)n1] | 1.26 (4) | 465.21 |
| 16aq (7c) | 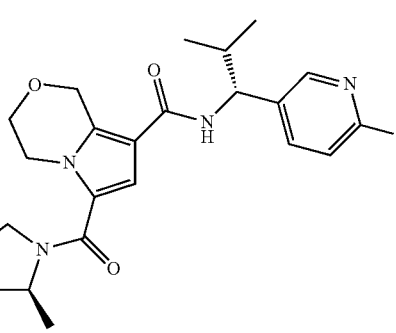 | 1.13 (2) | 479.25 |
| 16ar (7c) | 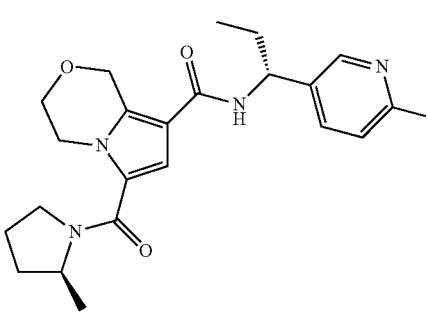 | 1.07 (2) | 431.2 |

TABLE 10-continued
| 16as (7c) | 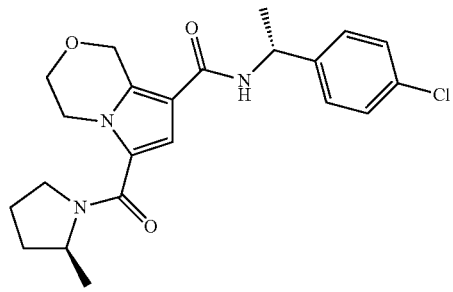 [SMILES: C[C@@H](NC(=O)c1cc(C(=O)N2CCC[C@@H]2C)n2c1COCC2)c1ccc(Cl)cc1] | 1.24 (4) | 416.13 |
| 16at (7c) | 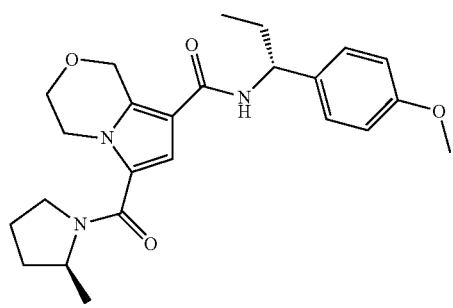 [SMILES: CC[C@@H](NC(=O)c1cc(C(=O)N2CCC[C@@H]2C)n2c1COCC2)c1ccc(OC)cc1] | 1.21 (4) | 426.2 |
| 16au (7c) | 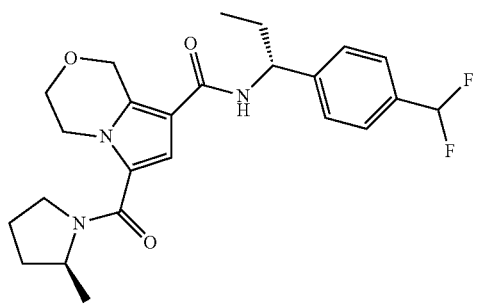 [SMILES: CC[C@@H](NC(=O)c1cc(C(=O)N2CCC[C@@H]2C)n2c1COCC2)c1ccc(C(F)F)cc1] | 1.23 (4) | 446.19 |
| 16av (7c) | 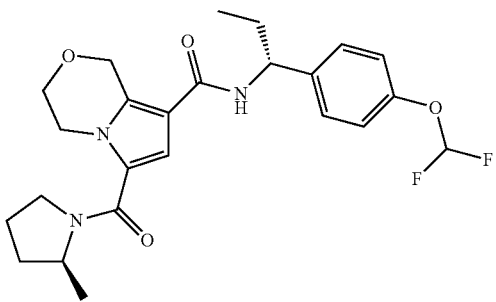 [SMILES: CC[C@@H](NC(=O)c1cc(C(=O)N2CCC[C@@H]2C)n2c1COCC2)c1ccc(OC(F)F)cc1] | 1.25 (4) | 462.18 |
| 16aw (7c) | 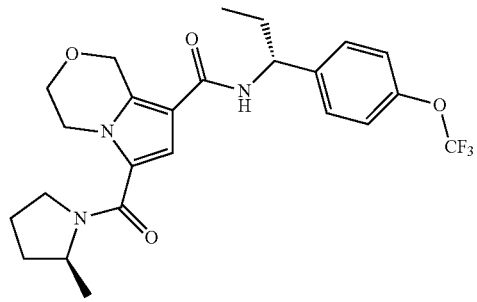 [SMILES: CC[C@@H](NC(=O)c1cc(C(=O)N2CCC[C@@H]2C)n2c1COCC2)c1ccc(SC(F)(F)F)cc1] | 1.3 (4) | 480.19 |

TABLE 10-continued

| | | | |
|---|---|---|---|
| 16ax (7c) | | 1.33 (4) | 496.16 |
| 16ay (7c) | | 1.21 (4) | 429.21 |
| 16az (7c) | | 1.23 (4) | 414.19 |
| 16ba (7c) | | 1.22 (4) | 457.15 |
| 16bb (7c) | | 1.24 (4) | 455.14 |

TABLE 10-continued
| | | | | |
|---|---|---|---|---|
| 16bc (7c) | 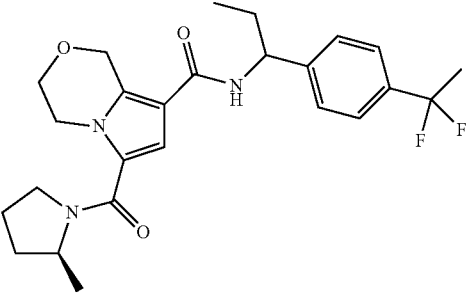 [SMILES: CCC(NC(=O)c1cc(C(=O)N2CCC[C@@H]2C)n2c1COCC2)c1ccc(C(C)(F)F)cc1] | 1.26 (4) | 460.19 | |
| 16bd (7c) | 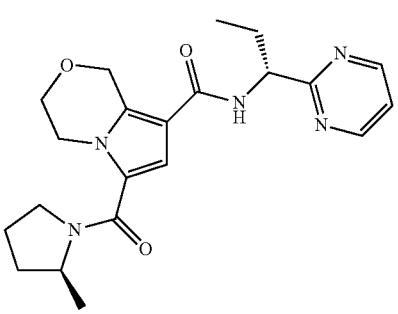 [SMILES: CC[C@@H](NC(=O)c1cc(C(=O)N2CCC[C@@H]2C)n2c1COCC2)c1ncccn1] | 3.09 (5) | 398.27 | |
| 16be (7c) | 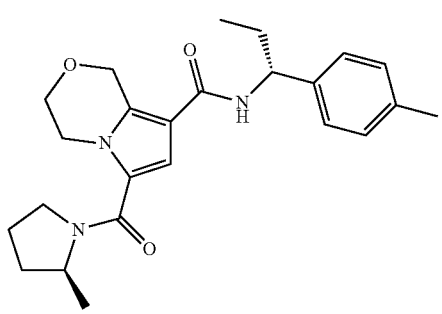 [SMILES: CC[C@@H](NC(=O)c1cc(C(=O)N2CCC[C@@H]2C)n2c1COCC2)c1ccc(C)cc1] | 1.14 (2) | 410.36 | |
| 16bf (7c) | 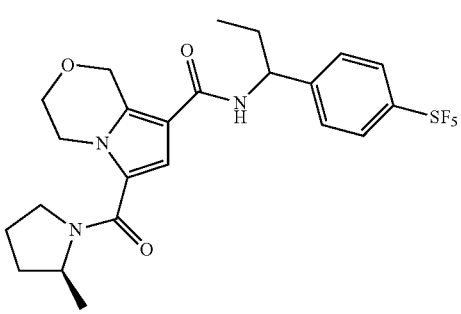 | 1.33 (2) | 522.05 | |
| 16bg (7c) | 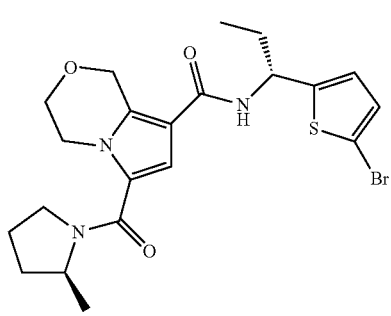 [SMILES: CC[C@@H](NC(=O)c1cc(C(=O)N2CCC[C@@H]2C)n2c1COCC2)c1ccc(Br)s1] | 1.31 (2) | 480.09 | |

TABLE 10-continued

| Compound (Method) | Structure | RT (min) | MS (M+H) |
|---|---|---|---|
| 16bh (7c) | 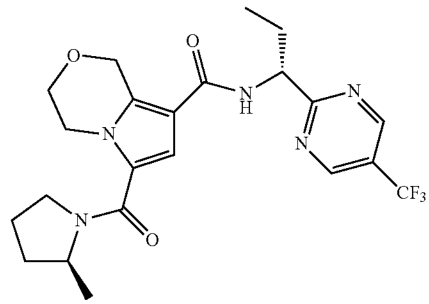 | 1.21 (2) | 466.16 |
| 16bi (7c + 15d) | 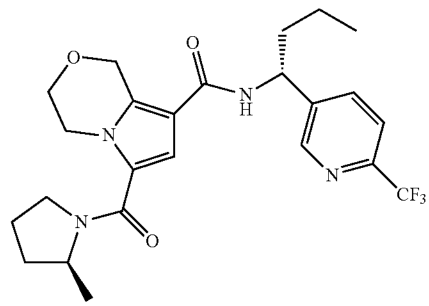 [SMILES: CCC[C@@H](NC(=O)c1cc(C(=O)N2CCC[C@@H]2C)n2c1COCC2)c1ccc(C(F)(F)F)nc1] | 1.26 (2) | 479.15 |
| 16bj (7c) | 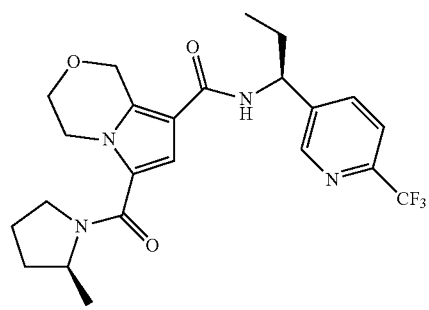 [SMILES: CC[C@H](NC(=O)c1cc(C(=O)N2CCC[C@@H]2C)n2c1COCC2)c1ccc(C(F)(F)F)nc1] | 1.24 (2) | 465.1 |
| 16bk (7c) | 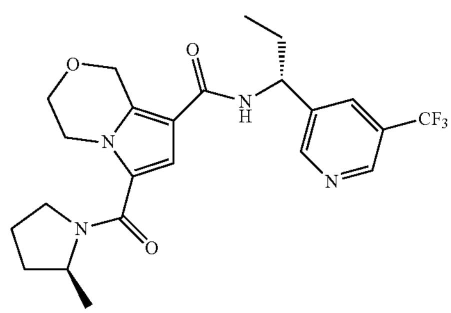 [SMILES: CC[C@@H](NC(=O)c1cc(C(=O)N2CCC[C@@H]2C)n2c1COCC2)c1cncc(C(F)(F)F)c1] | 1.2 (2) | 465.20 |
| 16bl (7c) | 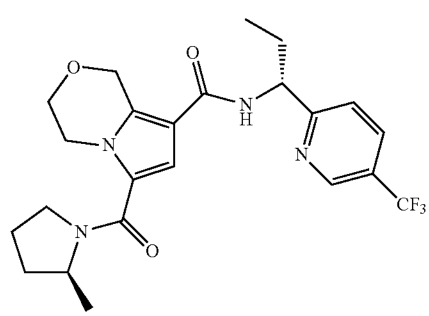 [SMILES: CC[C@@H](NC(=O)c1cc(C(=O)N2CCC[C@@H]2C)n2c1COCC2)c1ccc(C(F)(F)F)cn1] | 1.24 (2) | 465.12 |

TABLE 10-continued
| | | | | |
|---|---|---|---|---|
| 16bm (7c + 15f) | 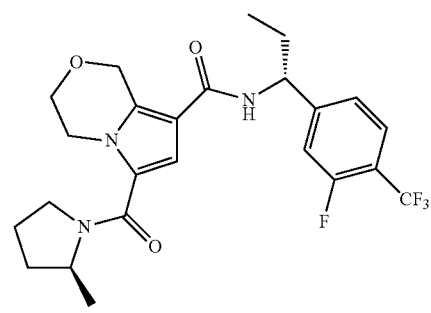 [SMILES: CC[C@@H](NC(=O)c1cc(C(=O)N2CCC[C@@H]2C)n2c1COCC2)c1ccc(C(F)(F)F)c(F)c1] | 1.30 (2) | 462.10 | |
| 16bn (7c + 15e) | 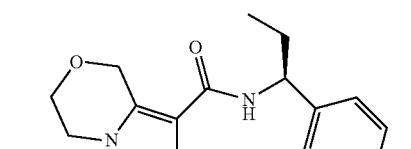 | 1.3 (2) | 482.1 | |
| 16bo (7c + 15h) | 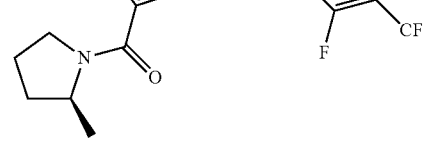 | 1.3 (2) | 482.1 | |
| 16bp (7c + 15g) | 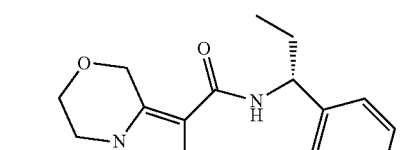 | 1.29 (2) | 482.07 | |
| 16br (7c + 15j) | 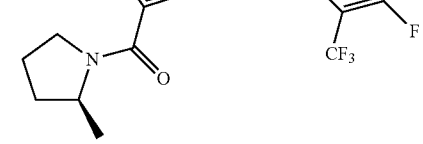 | 1.28 (2) | 499.09 | |

TABLE 10-continued

| | | | |
|---|---|---|---|
| 16bs (7c + 15i) | [structure] | 1.28 (2) | 499.06 |
| 16bt (7c + 15l) | [structure] | 1.2 (2) | 466.11 |
| 16bu (7c) | [structure] | 1.25 (2) | 463.08 |
| 16bv (7c) | [structure] | 1.22 (2) | 465.04 |
| 16bw (7c) | [structure] | 1.15 (2) | 431.09 |

TABLE 10-continued

| | | | |
|---|---|---|---|
| 16bx (7c + 15n) | | 1.31 (2) | 533.08 |
| 16by (7c + 15m) | | 1.31 (2) | 533.08 |
| 16bz (7c) | | 1.3 (2) | 476.14 |
| 16ca (7c) | | 1.24 (2) | 457.12 |
| 16cb (7c) | | 1.25 (2) | 479.16 |

TABLE 10-continued
| | | | |
|---|---|---|---|
| 16cc (7c) | 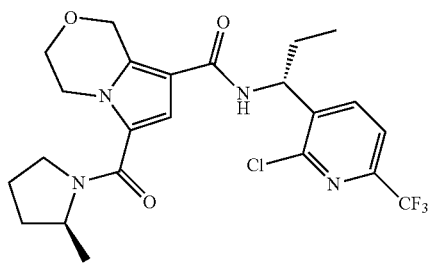 [SMILES: CC[C@@H](NC(=O)c1cc(C(=O)N2CCC[C@@H]2C)n2c1COCC2)c1ccc(C(F)(F)F)nc1C] | 1.28 (2) | 499.07 |
| 16cd (7c + 15o) | 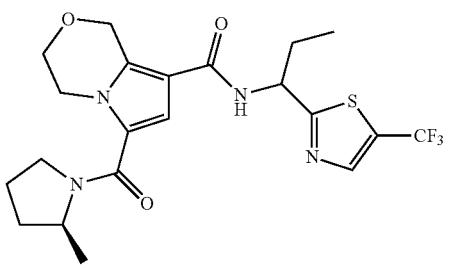 (diastereomer 1) | 1.25 (2) | 471.05 |
| 16ce (7c + 15p) | 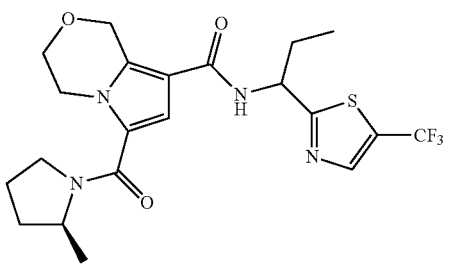 (diastereomer 2) | 1.25 (2) | 471.06 |
| 16cf (7c) | 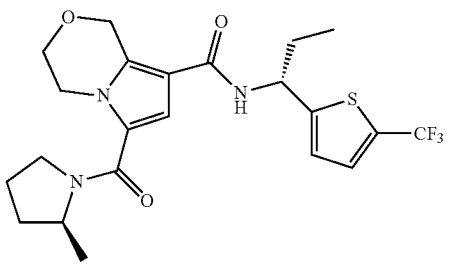 [SMILES: CC[C@@H](NC(=O)c1cc(C(=O)N2CCC[C@@H]2C)n2c1COCC2)c1ccc(C(F)(F)F)s1] | 1.3 (2) | 470.23 |
| 16cg (7c) | 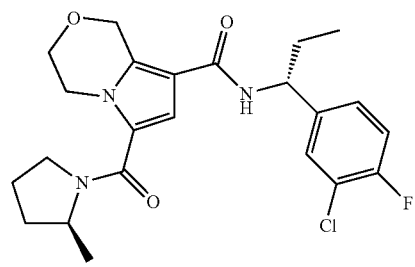 [SMILES: CC[C@@H](NC(=O)c1cc(C(=O)N2CCC[C@@H]2C)n2c1COCC2)c1ccc(F)c(Cl)c1] | 1.83 (3) | 448.32 |

TABLE 10-continued
| | | | |
|---|---|---|---|
| 16ch (7c) | 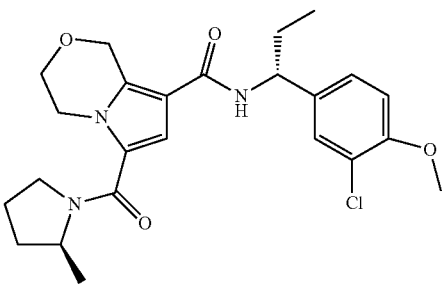 [SMILES: CC[C@@H](NC(=O)c1cc(C(=O)N2CCC[C@@H]2C)n2c1COCC2)c1ccc(OC)c(Cl)c1] | 1.78 (3) | 460.35 |
| 16ci (7c) | 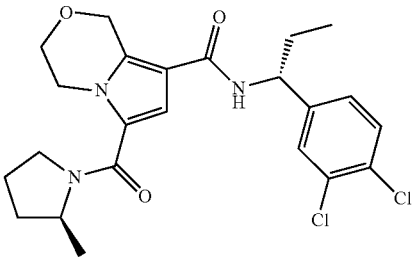 [SMILES: CC[C@@H](NC(=O)c1cc(C(=O)N2CCC[C@@H]2C)n2c1COCC2)c1ccc(Cl)c(Cl)c1] | 1.89 (3) | 464.3 |
| 16cj (7c) | 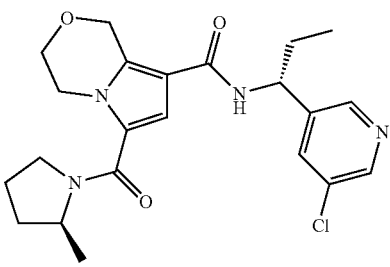 [SMILES: CC[C@@H](NC(=O)c1cc(C(=O)N2CCC[C@@H]2C)n2c1COCC2)c1cncc(Cl)c1] | 1.76 (3) | 431.23 |
| 16ck (7c) | 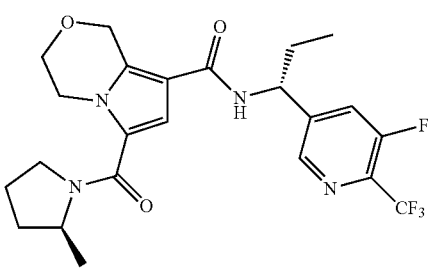 [SMILES: CC[C@@H](NC(=O)c1cc(C(=O)N2CCC[C@@H]2C)n2c1COCC2)c1cnc(C(F)(F)F)c(F)c1] | 1.78 (3) | 483.41 |
| 16cl (7c + 15r) | 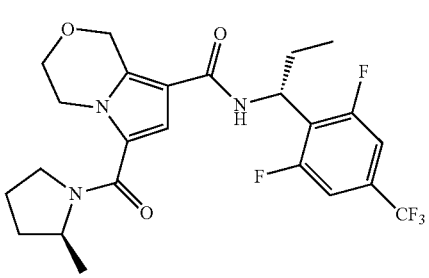 [SMILES: CC[C@@H](NC(=O)c1cc(C(=O)N2CCC[C@@H]2C)n2c1COCC2)c1c(F)cc(C(F)(F)F)cc1F] | 1.9 (3) | 500.24 |
| 16cm (7c + 15q) | 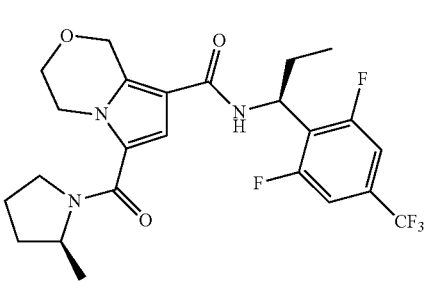 [SMILES: CC[C@H](NC(=O)c1cc(C(=O)N2CCC[C@@H]2C)n2c1COCC2)c1c(F)cc(C(F)(F)F)cc1F] | 1.9 (3) | 500.28 |

TABLE 10-continued

| | | | |
|---|---|---|---|
| 16cn (7c + 15t) | *[structure]* | 1.82 (3) | 495.37 |
| 16co (7c) | *[structure]* | 1.77 (3) | 465.24 |
| 16cp (7c) | *[structure]* | 2.08 (3) | 532.3 |
| 16cq (7c) | *[structure]* | 2.06 (3) | 498.27 |
| 16cs (7c) | *[structure]* | 2.03 (3) | 498.33 |

TABLE 10-continued
| ID | Structure | RT (method) | MS |
|---|---|---|---|
| 16ct (7c) | 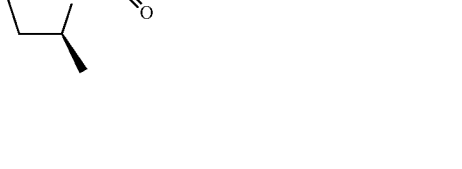 | 1.88 (3) | 482.39 |
| 16cu (7c) (racemic amine + chiral chromatography) | 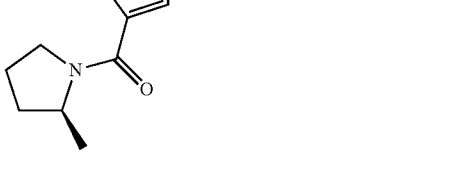 | 1.67 (3) | 463.2 |
| 16cv (7c) (racemic amine + chiral chromatography) |  | 1.67 (3) | 463.24 |
| 16cw (7c) | 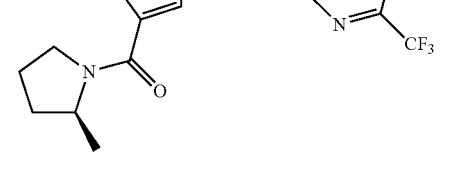 | 1.73 (3) | 495.23 |
| 16cy (7a) | 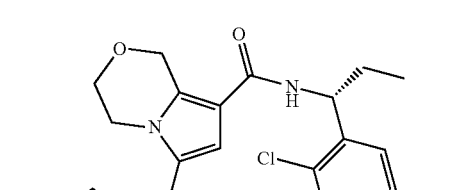 | 1.25 (4) | 416.18 |

TABLE 10-continued
| | | | |
|---|---|---|---|
| 16cz (7a) | 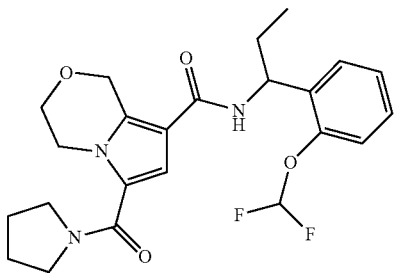 [SMILES: CCC(NC(=O)c1cc(C(=O)N2CCCC2)n2c1COCC2)c1ccccc1OC(F)F] | 1.24 (4) | 448.22 |
| 16da (7a) | 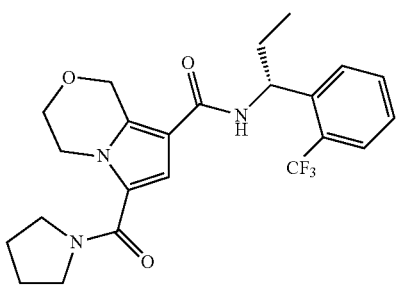 [SMILES: CC[C@@H](NC(=O)c1cc(C(=O)N2CCCC2)n2c1COCC2)c1ccccc1C(F)(F)F] | 1.26 (4) | 450.21 |
| 16db (7a) | 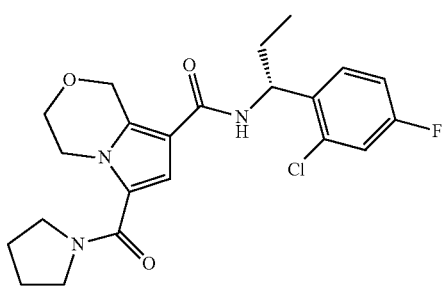 [SMILES: CC[C@@H](NC(=O)c1cc(C(=O)N2CCCC2)n2c1COCC2)c1ccc(F)cc1Cl] | 1.26 (4) | 434.16 |
| 16de (7a) | 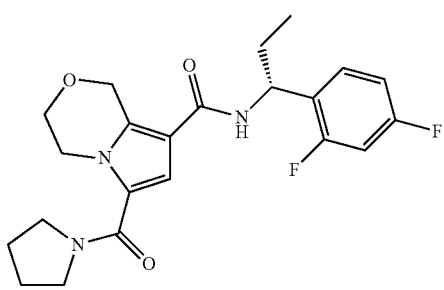 [SMILES: CC[C@@H](NC(=O)c1cc(C(=O)N2CCCC2)n2c1COCC2)c1ccc(F)cc1F] | 1.23 (4) | 418.18 |
| 16df (7a) | 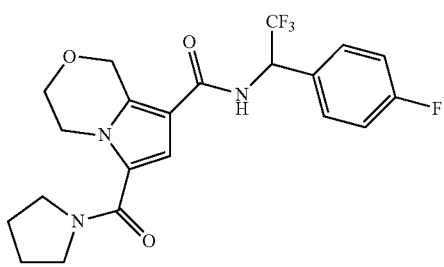 [SMILES: O=C(NC(c1ccc(F)cc1)C(F)(F)F)c1cc(C(=O)N2CCCC2)n2c1COCC2] | 1.25 (4) | 440.17 |

TABLE 10-continued
| | | | |
|---|---|---|---|
| 16dg (7a) | 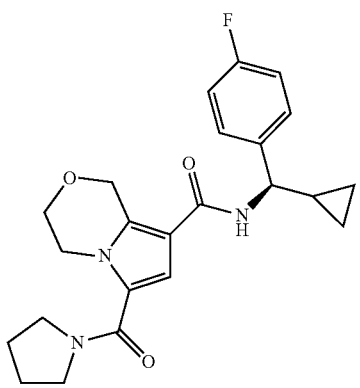 [SMILES: O=C(N[C@@H](c1ccc(F)cc1)C1CC1)c1cc(C(=O)N2CCCC2)n2c1COCC2] | 1.22 (4) | 412.22 |
| 16dh (7a) | 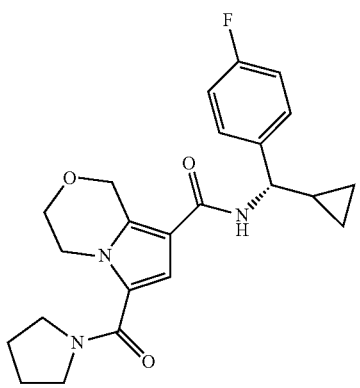 [SMILES: O=C(N[C@H](c1ccc(F)cc1)C1CC1)c1cc(C(=O)N2CCCC2)n2c1COCC2] | 1.22 (4) | 412.25 |
| 16di (7a) | 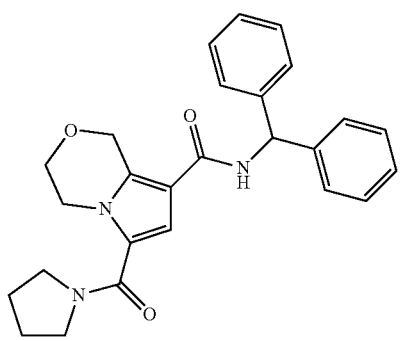 [SMILES: O=C(NC(c1ccccc1)c1ccccc1)c1cc(C(=O)N2CCCC2)n2c1COCC2] | 1.12 (2) | 430.25 |
| 16dj (7a) | 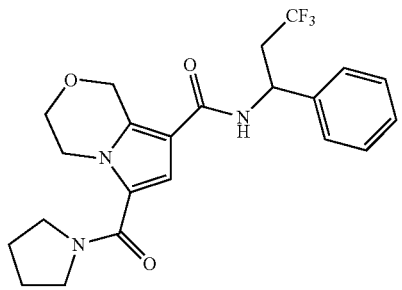 [SMILES: O=C(NC(CC(F)(F)F)c1ccccc1)c1cc(C(=O)N2CCCC2)n2c1COCC2] | 1.21 (4) | 436.21 |

TABLE 10-continued
| 16dk (7o) | 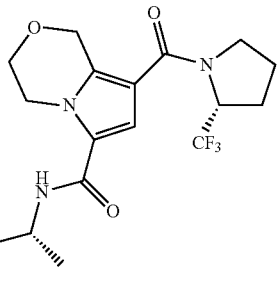 | 1.27 (4) | 454.19 |
| 16dl (7o +19a) | 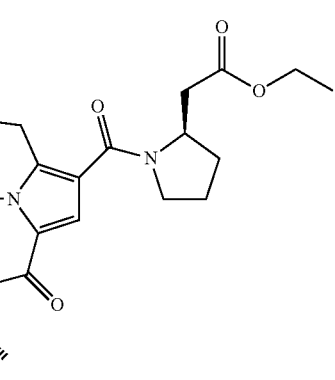 | 1.25 (4) | 472.22 |
| 16dm (7o) | 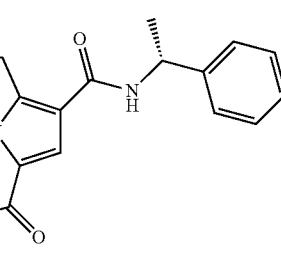 | 1.27 (4) | 454.29 |
| 16dn (7o) | 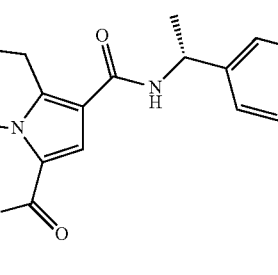 | 1.27 (4) | 436.25 |
| 16do (7o) | 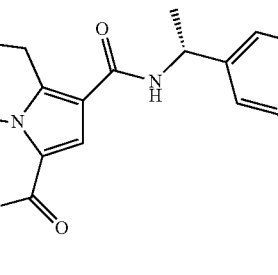 | 1.28 (4) | 454.24 |

TABLE 10-continued

| | | | |
|---|---|---|---|
| 16dq (7o) | [structure] | 1.28 (4) | 454.24 |
| 16dr (7o) | [structure] | 1.2 (4) | 414.14 |
| 16ds (7o) | [structure] | 1.19 (4) | 386.19 |
| 16dt (7o) | [structure] | 1.26 (4) | 519.22 |
| 16du (7o) | [structure] | 1.24 (4) | 481.25 |

TABLE 10-continued
| 16dv (7o + 15w) | 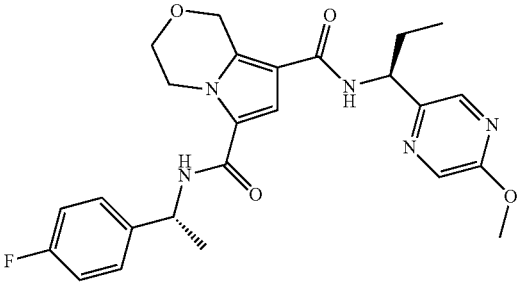 [SMILES: CC[C@H](NC(=O)c1cc(C(=O)N[C@H](C)c2ccc(F)cc2)n2c1COCC2)c1cnc(OC)cn1] | 1.23 (2) | 482.23 |
| 16dw (7o + 15x) | 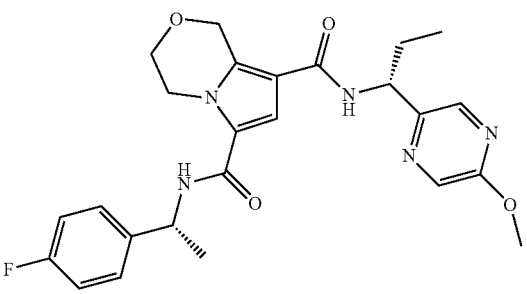 [SMILES: CC[C@@H](NC(=O)c1cc(C(=O)N[C@H](C)c2ccc(F)cc2)n2c1COCC2)c1cnc(OC)cn1] | 1.25 (4) | 482.13 |
| 16dx (7o) (racemic amine + chiral chromatography) | 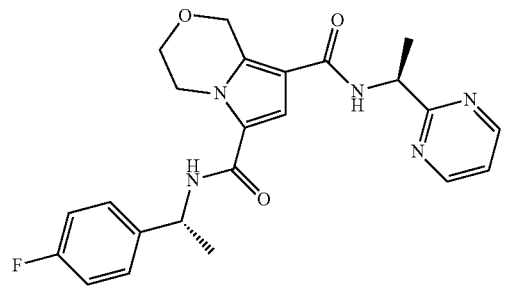 [SMILES: C[C@H](NC(=O)c1cc(C(=O)N[C@H](C)c2ccc(F)cc2)n2c1COCC2)c1ncccn1] | 1.0 (4) | 438.25 |
| 16dy (7o) (racemic amine + chiral chromatography) | 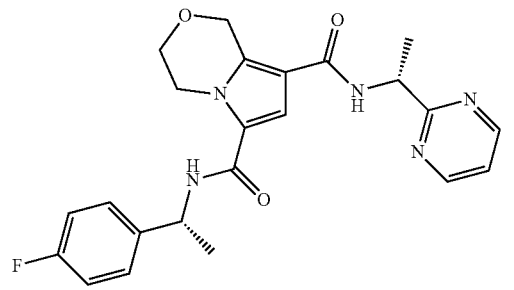 [SMILES: C[C@@H](NC(=O)c1cc(C(=O)N[C@H](C)c2ncccn2)c2n1CCOC2)c1ccc(F)cc1] | 1.0 (4) | 438.25 |
| 16dz (7o + 15b) | 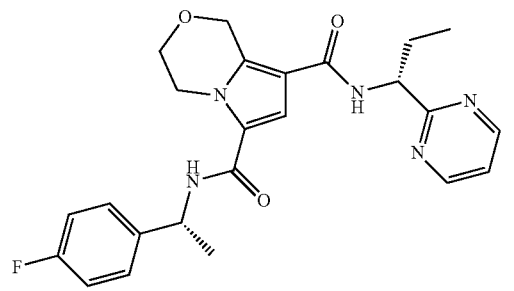 [SMILES: CC[C@@H](NC(=O)c1cc(C(=O)N[C@H](C)c2ccc(F)cc2)n2c1COCC2)c1ncccn1] | 1.05 (1) | 452.21 |

TABLE 10-continued
| | | | |
|---|---|---|---|
| 16ea (7o + 20a) | 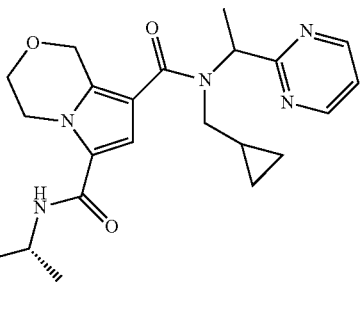 | 1.23 (4) | 492.28 |
| 16eb (7o) | 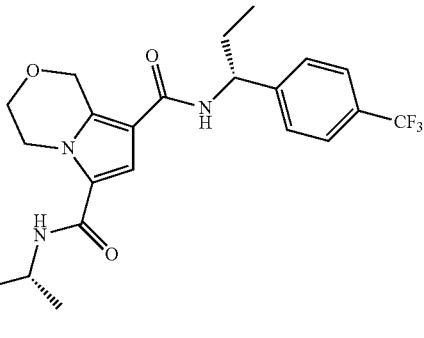 | 1.34 (2) | 518.12 |
| 16ec (7o) | 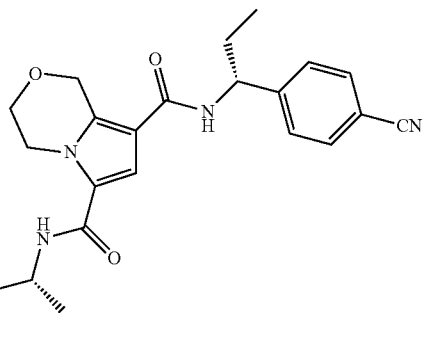 | 1.26 (2) | 475.1 |
| 16ed (7o + 15d) | 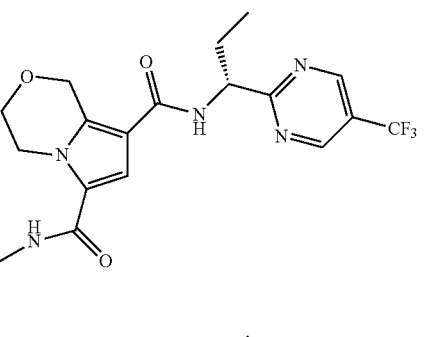 | 1.26 (2) | 520.28 |
| 16ee (7o + 15c) | 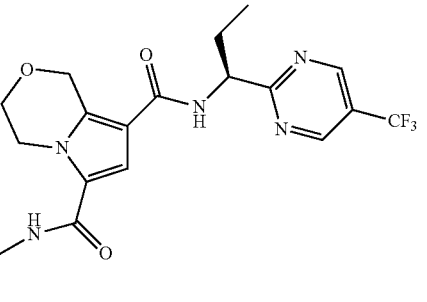 | 4.5 (5) | 520.25 |

TABLE 10-continued
| | | | |
|---|---|---|---|
| 16ef (7r + 15c) | 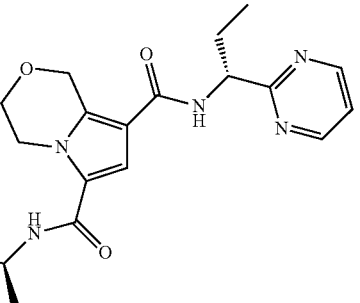 | 3.75 (5) | 452.22 |
| 16eg (7o) | 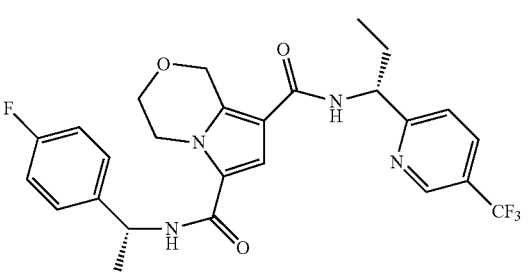 [SMILES: CC[C@@H](NC(=O)c1cc(C(=O)N[C@H](C)c2ccc(F)cc2)n2c1COCC2)c1ccc(C(F)(F)F)cn1] | 1.29 (2) | 519.11 |
| 16ei (11a) | 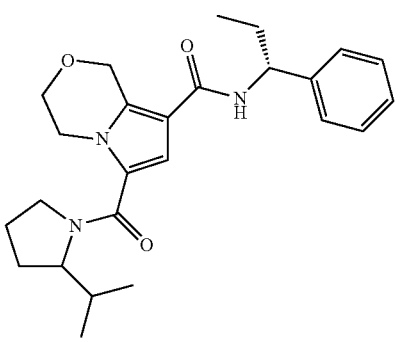 [SMILES: CC[C@@H](NC(=O)c1cc(C(=O)N2CCCC2C(C)C)n2c1COCC2)c1ccccc1] | 1.19 (4) | 424.2 |
| 16em (11a) | 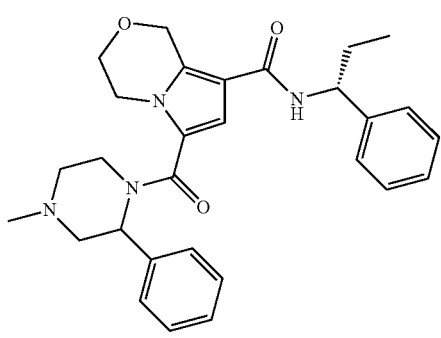 [SMILES: CC[C@@H](NC(=O)c1cc(C(=O)N2CCN(C)CC2c2ccccc2)n2c1COCC2)c1ccccc1] | 3.37 (6) | 487.33 |
| 16en (11a) | 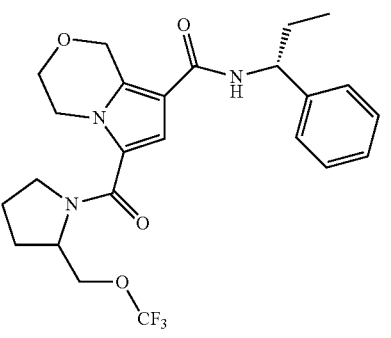 [SMILES: CC[C@@H](NC(=O)c1cc(C(=O)N2CCCC2COC(F)(F)F)n2c1COCC2)c1ccccc1] | 1.31 (4) | 480.29 |

TABLE 10-continued

| | | | |
|---|---|---|---|
| 16eo (11a) | | 3.93 (6) | 426.28 |
| 16ep (11a) | | 3.9 (6) | 470.32 |
| 16eq (11a) | | 1.12 (4) | 463.13 |
| 16er (11a) | | 1.23 (4) | 477.34 |
| 16es (11a) | | 1.1 (4) | 426.28 |

TABLE 10-continued

| 16et (11a + 21a) | [structure] | 1.30 (9) | 452.10 |
| 16eu (11a) | [structure] | 1.29 (4) | 450.31 |
| 16ev (11a + 22a) | [structure] | 1.26 (4) | 452.34 |
| 16ew (11a) | [structure] | 1.22 (4) | 440.33 |
| 16ex (11a) | [structure] | 1.34 (4) | 438.4 |

TABLE 10-continued
| 16ey (11a + 21b) | 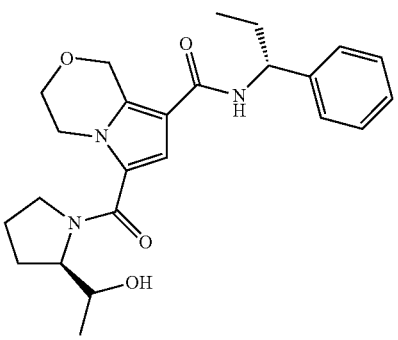 [SMILES: CC[C@@H](NC(=O)c1cc(C(=O)N2CCC[C@@H]2C(C)O)n2c1COCC2)c1ccccc1] | 1.18 (4) | 426.31 |
| --- | --- | --- | --- |
| 16ez (11a + 21c) | 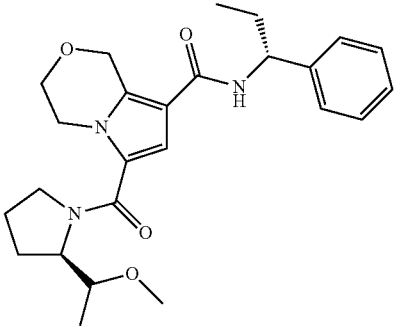 [SMILES: CC[C@@H](NC(=O)c1cc(C(=O)N2CCC[C@@H]2C(C)OC)n2c1COCC2)c1ccccc1] | 1.26 (4) | 440.34 |
| 16fb (11a) | 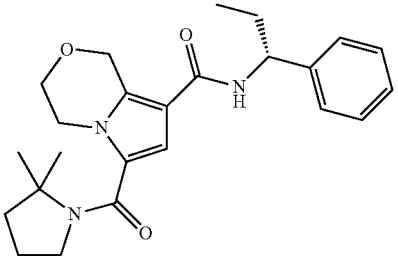 [SMILES: CC[C@@H](NC(=O)c1cc(C(=O)N2CCCC2(C)C)n2c1COCC2)c1ccccc1] | 1.29 (4) | 410.32 |
| 16fc (11a) (racemic amine + chiral chromatography) | 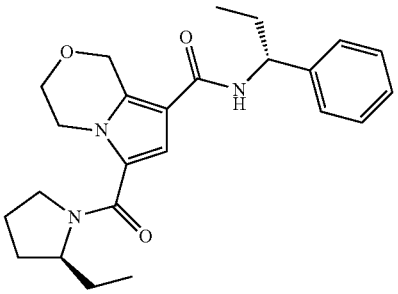 [SMILES: CC[C@H]1CCCN1C(=O)c1cc(C(=O)N[C@H](CC)c2ccccc2)c2n1CCOC2] | 1.27 (4) | 410.28 |
| 16fd (11a) (racemic amine + chiral chromatography) | 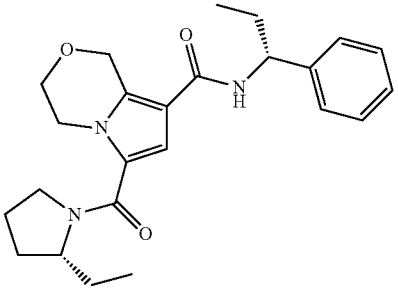 [SMILES: CC[C@@H]1CCCN1C(=O)c1cc(C(=O)N[C@H](CC)c2ccccc2)c2n1CCOC2] | 1.28 (4) | 410.29 |

TABLE 10-continued
| | | | |
|---|---|---|---|
| 16fe (11a) | 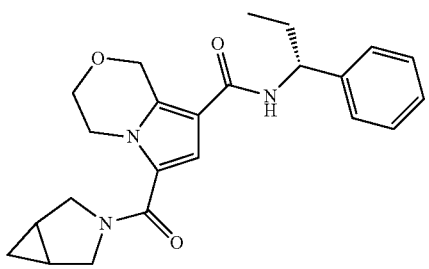 [SMILES: CC[C@@H](NC(=O)c1cc(C(=O)N2CC3CC3C2)n2c1COCC2)c1ccccc1] | 1.34 (g) | 394.15 |
| 16fg (11a + 22b) | 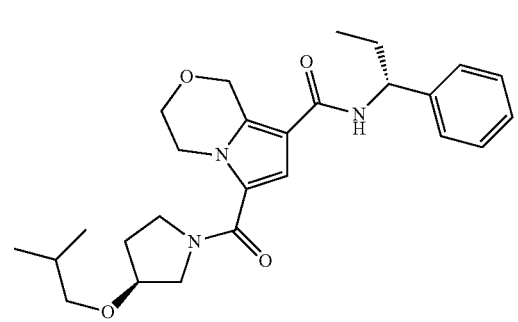 [SMILES: CC[C@@H](NC(=O)c1cc(C(=O)N2CC[C@H](OCC(C)C)C2)n2c1COCC2)c1ccccc1] | 1.31 (4) | 454.33 |
| 16fh (11a + 23a) | 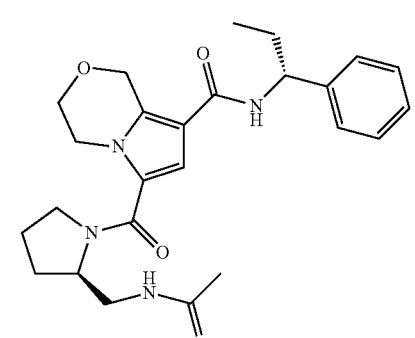 | 1.14 (4) | 453.25 |
| 16fi (11a + 19a) | 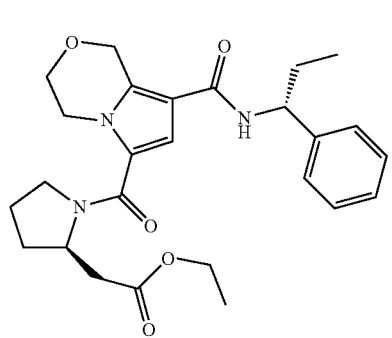 [SMILES: CCOC(=O)C[C@H]1CCCN1C(=O)c1cc(C(=O)N[C@H](CC)c2ccccc2)c2n1CCOC2] | 1.26 (4) | 468.24 |
| 16fj (11a) | 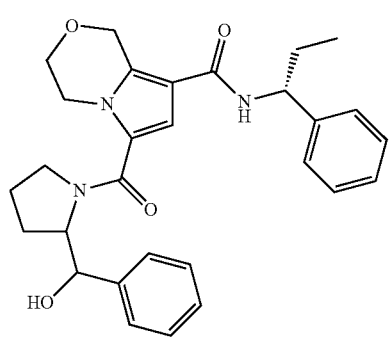 [SMILES: CC[C@@H](NC(=O)c1cc(C(=O)N2CCCC2C(O)c2ccccc2)n2c1COCC2)c1ccccc1] | 1.27 (4) | 488.26 |

TABLE 10-continued
| | | | |
|---|---|---|---|
| 16fk (11a) | 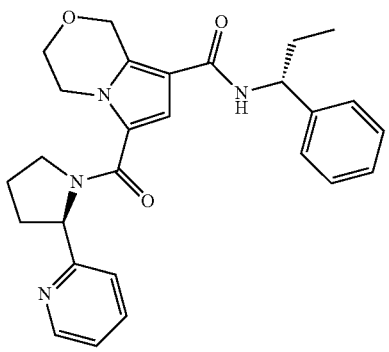 [SMILES: CC[C@@H](NC(=O)c1cc(C(=O)N2CCC[C@@H]2c2ccccn2)n2c1COCC2)c1ccccc1] | 1.02 (4) | 459.3 |
| 16fl (11a) | 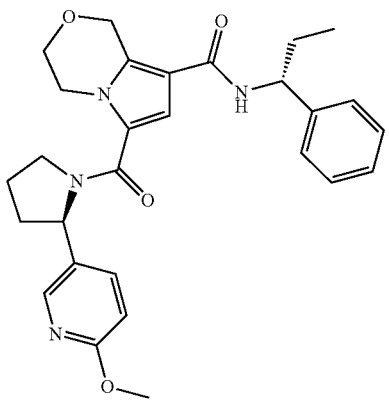 [SMILES: CC[C@@H](NC(=O)c1cc(C(=O)N2CCC[C@@H]2c2ccc(OC)nc2)n2c1COCC2)c1ccccc1] | 1.25 (4) | 489.24 |
| 16fm (11a) | 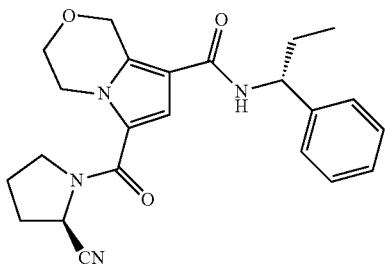 [SMILES: CC[C@@H](NC(=O)c1cc(C(=O)N2CCC[C@@H]2C#N)n2c1COCC2)c1ccccc1] | 1.07 (4) | 407.23 |
| 16fn (11a) | 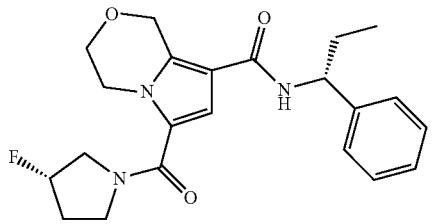 [SMILES: CC[C@@H](NC(=O)c1cc(C(=O)N2CC[C@H](F)C2)n2c1COCC2)c1ccccc1] | 1.18 (4) | 400.2 |
| 16fo (11a) | 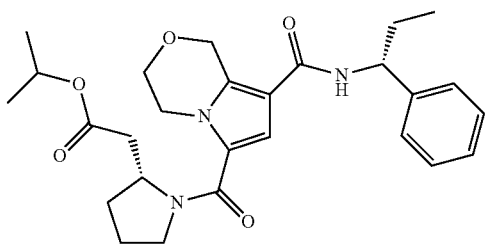 [SMILES: CC[C@@H](NC(=O)c1cc(C(=O)N2CCC[C@@H]2CC(=O)OC(C)C)n2c1COCC2)c1ccccc1] | 1.29 (4) | 482.26 |

TABLE 10-continued

| | | | |
|---|---|---|---|
| 16fp (11a + 24a) | [structure] | 1.17 (4) | 460.23 |
| 16fq (11a) | [structure] | 2.99 (5) | 474.32 |
| 16fr (11a) | [structure] | 0.89 (2) | 481.63 |
| 16fs (11a + 25a) | [structure] | 0.95 (2) | 487.94 |
| 16ft (11a + 25b) | [structure] | 3.45 (5) | 507.31 |

TABLE 10-continued

| | | | |
|---|---|---|---|
| 16fu (11a) | | 1.29 (4) | 492.25 |
| 16fv (11a) | | 1.06 (1) | 462.27 |
| 16fw (11a) | | 1.1 (1) | 476.29 |
| 16fx (11a) | | 4.16 (5) | 406.41 |
| 16fy (11a) | | 1.16 (4) | 407.24 |

TABLE 10-continued
| | | | |
|---|---|---|---|
| 16fz (11a) | 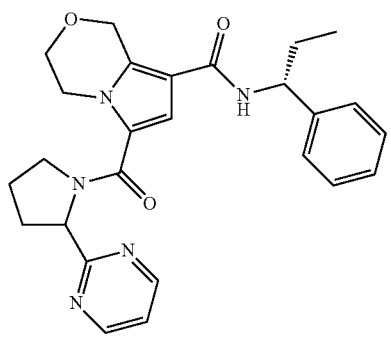 [SMILES: CC[C@@H](NC(=O)c1cc(C(=O)N2CCCC2c2ncccn2)n2c1COCC2)c1ccccc1] | 1.18 (2) | 460.13 |
| 16ga (11a) | 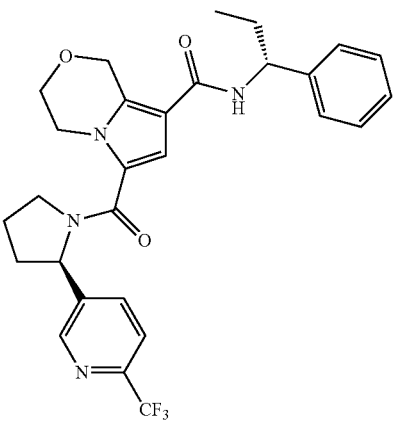 [SMILES: CC[C@@H](NC(=O)c1cc(C(=O)N2CCC[C@@H]2c2ccc(C(F)(F)F)nc2)n2c1COCC2)c1ccccc1] | 1.28 (2) | 527.11 |
| 16gb (11a) | 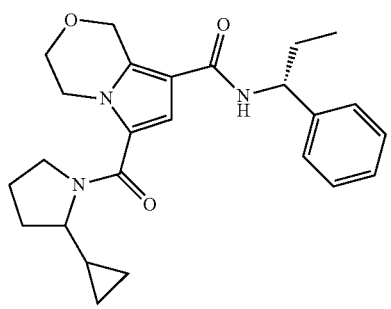 [SMILES: CC[C@@H](NC(=O)c1cc(C(=O)N2CCCC2C2CC2)n2c1COCC2)c1ccccc1] | 1.26 (2) | 422.18 |
| 16gc (11a) | 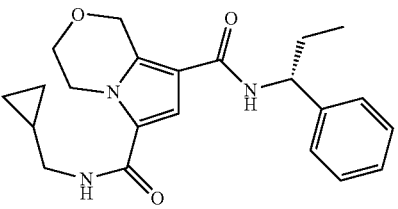 [SMILES: CC[C@@H](NC(=O)c1cc(C(=O)NCC2CC2)n2c1COCC2)c1ccccc1] | 1.1 (4) | 382.17 |
| 16gl (11a) | 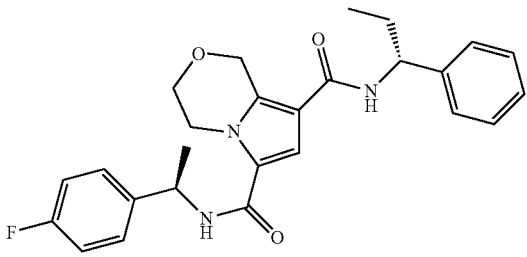 [SMILES: CC[C@@H](NC(=O)c1cc(C(=O)N[C@H](C)c2ccc(F)cc2)n2c1COCC2)c1ccccc1] | 1.3 (4) | 450.28 |

TABLE 10-continued

| 16go (11a) | | 1.15 (4) | 398.3 |
| 16gq (7c) | | 1.21 (2) | 439.13 |
| 16gt (11a) | | 1.12 (4) | 420.27 |
| 16gu (11a) | | 1.16 (4) | 437.24 |
| 16gv (11a) | | 1.17 (4) | 496.25 |
| 16gw (11a) | | 1.13 (4) | 433.33 |

TABLE 10-continued
| | | | |
|---|---|---|---|
| 16gx (11a) | 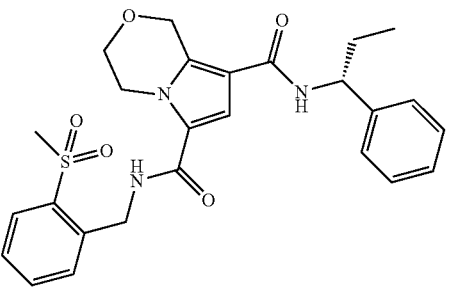 [SMILES: CC[C@@H](NC(=O)c1cc(C(=O)NCc2ccccc2S(C)(=O)=O)n2c1COCC2)c1ccccc1] | 1.09 (4) | 496.09 |
| 16gy (11a) | 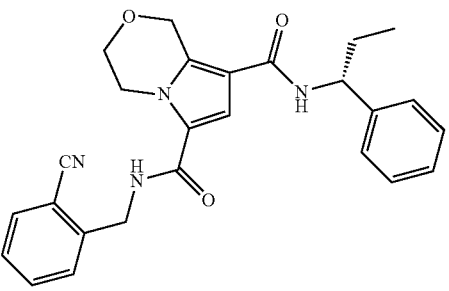 [SMILES: CC[C@@H](NC(=O)c1cc(C(=O)NCc2ccccc2C#N)n2c1COCC2)c1ccccc1] | 1.12 (4) | 443.12 |
| 16gz (11a) | 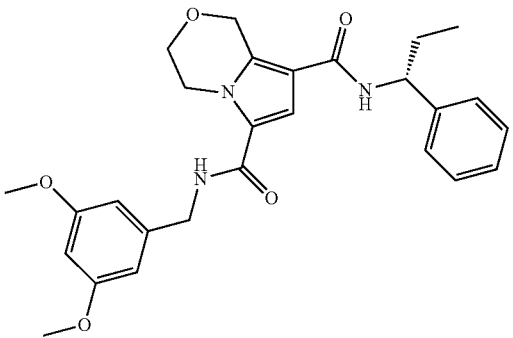 [SMILES: CC[C@@H](NC(=O)c1cc(C(=O)NCc2cc(OC)cc(OC)c2)n2c1COCC2)c1ccccc1] | 1.47 (g) | 478.20 |
| 16ha (7ad) | 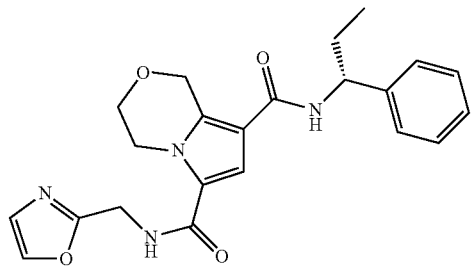 [SMILES: CC[C@@H](NC(=O)c1cc(C(=O)NCc2ncco2)n2c1COCC2)c1ccccc1] | 1.12 (4) | 409.25 |
| 16hb (11a) | 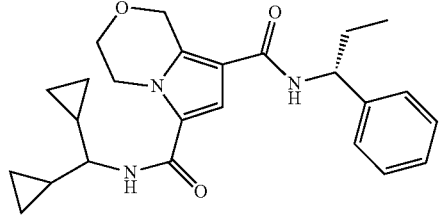 [SMILES: CC[C@@H](NC(=O)c1cc(C(=O)NC(C2CC2)C2CC2)n2c1COCC2)c1ccccc1] | 1.28 (4) | 422.31 |
| 16hc (11a) | 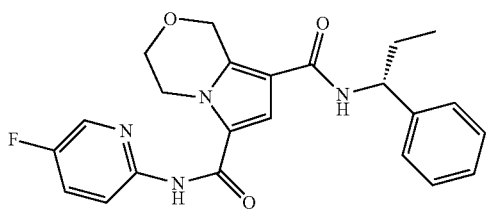 [SMILES: CC[C@@H](NC(=O)c1cc(C(=O)Nc2ccc(F)cn2)n2c1COCC2)c1ccccc1] | 1.26 (4) | 423.25 |

TABLE 10-continued
| | | | |
|---|---|---|---|
| 16hd (11a) | 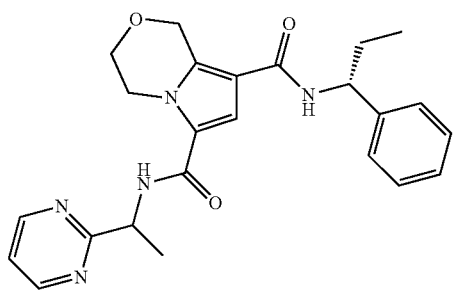 [SMILES: CC[C@@H](NC(=O)c1cc(C(=O)NC(C)c2ncccn2)n2c1COCC2)c1ccccc1] | 1.16 (4) | 434.29 |
| 16he (11a) | 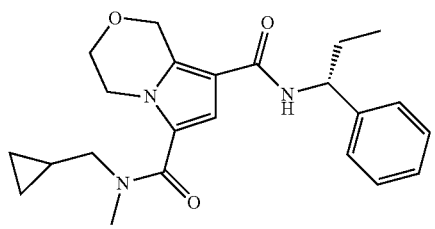 [SMILES: CC[C@@H](NC(=O)c1cc(C(=O)N(C)CC2CC2)n2c1COCC2)c1ccccc1] | 1.24 (4) | 396.28 |
| 16hf (11a) | 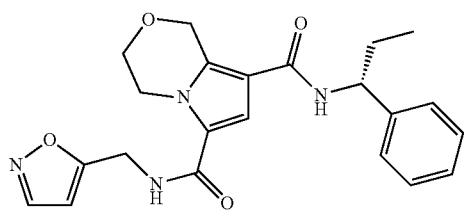 [SMILES: CC[C@@H](NC(=O)c1cc(C(=O)NCc2ccno2)n2c1COCC2)c1ccccc1] | 3.49 (6) | 409.23 |
| 16hg (11a) | 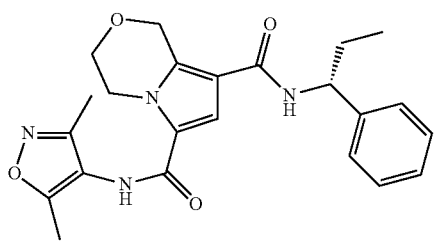 [SMILES: CC[C@@H](NC(=O)c1cc(C(=O)Nc2c(C)noc2C)n2c1COCC2)c1ccccc1] | 1.19 (4) | 423.28 |
| 16hh (11a) | 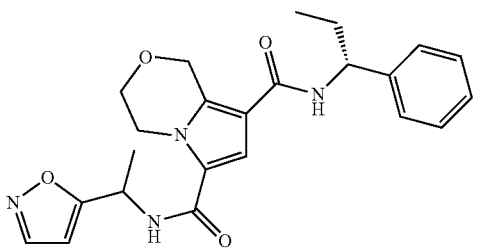 [SMILES: CC[C@@H](NC(=O)c1cc(C(=O)NC(C)c2ccno2)n2c1COCC2)c1ccccc1] | 1.2 (4) | 423.27 |
| 16hi (11a) | 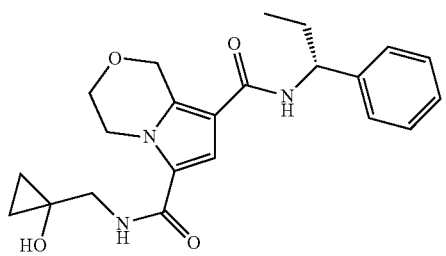 [SMILES: CC[C@@H](NC(=O)c1cc(C(=O)NCC2(O)CC2)n2c1COCC2)c1ccccc1] | 1.13 (4) | 398.27 |

TABLE 10-continued
| | | | |
|---|---|---|---|
| 16hj (11a) | 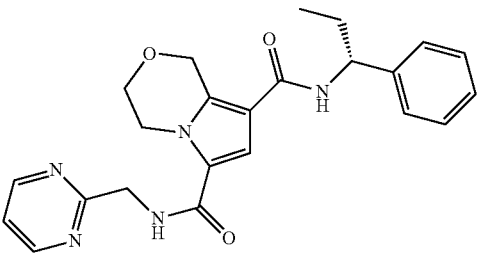 [SMILES: CC[C@@H](NC(=O)c1cc(C(=O)NCc2ncccn2)n2c1COCC2)c1ccccc1] | 1.12 (4) | 420.25 |
| 16hk (11a) | 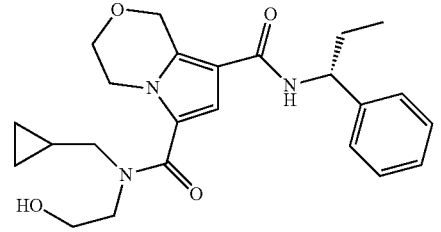 [SMILES: CC[C@@H](NC(=O)c1cc(C(=O)N(CCO)CC2CC2)n2c1COCC2)c1ccccc1] | 1.17 (4) | 426.23 |
| 16hi (11a) | 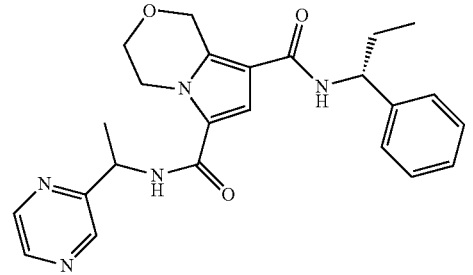 [SMILES: CC[C@@H](NC(=O)c1cc(C(=O)NC(C)c2cnccn2)n2c1COCC2)c1ccccc1] | 1.16 (4) | 434.19 |
| 16hm (11a) | 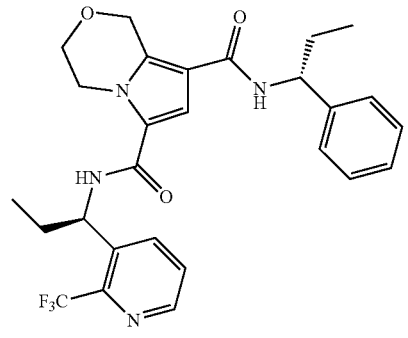 [SMILES: CC[C@@H](NC(=O)c1cc(C(=O)N[C@H](CC)c2cccnc2C(F)(F)F)n2c1COCC2)c1ccccc1] | 1.29 (4) | 515.23 |
| 16hn (11a) | 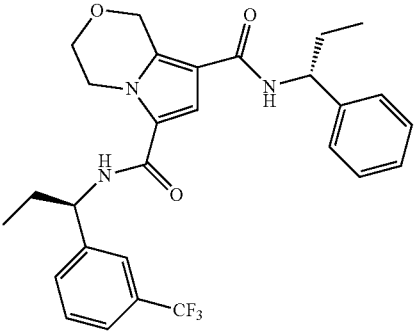 [SMILES: CC[C@@H](NC(=O)c1cc(C(=O)N[C@H](CC)c2cccc(C(F)(F)F)c2)n2c1COCC2)c1ccccc1] | 1.29 (4) | 515.23 |

TABLE 10-continued
| | | | |
|---|---|---|---|
| 16ho (11a) | 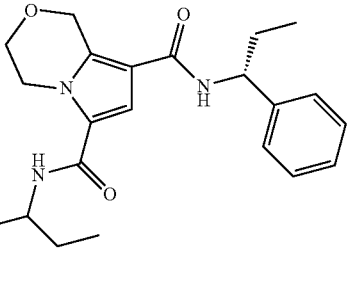 | 3.07 (5) | 461.33 |
| 16hp (11a) | 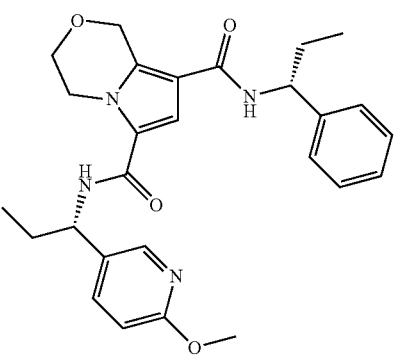 [SMILES: CC[C@H](NC(=O)c1cc(C(=O)N[C@H](CC)c2ccccc2)c2n1CCOC2)c1ccc(OC)nc1] | 1.26 (4) | 477.29 |
| 16hq (11a) | 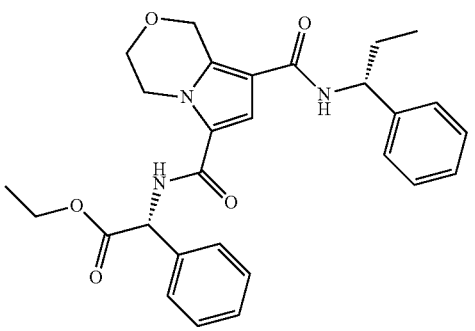 [SMILES: CCOC(=O)[C@H](NC(=O)c1cc(C(=O)N[C@H](CC)c2ccccc2)c2n1CCOC2)c1ccccc1] | 1.18 (4) | 490.3 |
| 16hr (11a) | 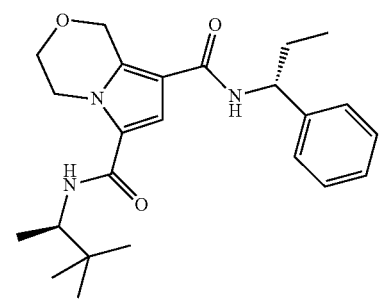 [SMILES: CC[C@@H](NC(=O)c1cc(C(=O)N[C@H](C)C(C)(C)C)n2c1COCC2)c1ccccc1] | 1.18 (4) | 412.31 |
| 16hu (11a + 15y) | 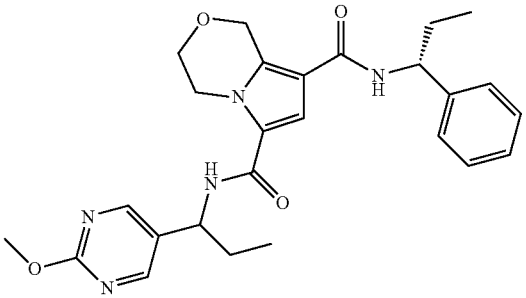<br>(diastereomer 1) | 1.21 (4) | 478.26 |

TABLE 10-continued

| | | | |
|---|---|---|---|
| 16hv (11a + 15z) | [structure] (diastereomer 2) | 1.21 (4) | 478.25 |
| 16hw (11a + 15b) | [structure] | 1.2 (4) | 448.23 |
| 16hx (11a + 15a) | [structure] | 1.2 (4) | 448.23 |
| 16hy (11a + 15x) | [structure] | 1.27 (4) | 478.3 |
| 16hz (11a + 15w) | [structure] | 1.27 (4) | 478.24 |

TABLE 10-continued
| | | | |
|---|---|---|---|
| 16ia (11a) | 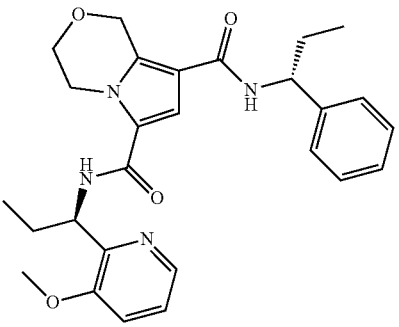 [SMILES: CC[C@@H](NC(=O)c1cc(C(=O)N[C@H](CC)c2ncccc2OC)n2c1COCC2)c1ccccc1] | 1.29 (4) | 477.25 |
| 16ib (11a) | 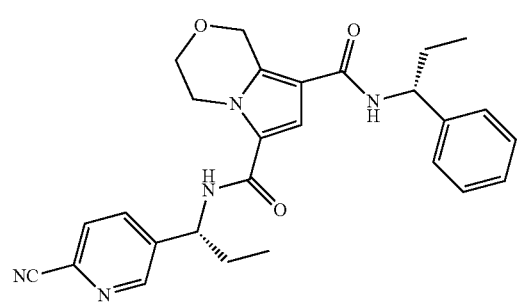 [SMILES: CC[C@@H](NC(=O)c1cc(C(=O)N[C@H](CC)c2ccc(C#N)nc2)n2c1COCC2)c1ccccc1] | 1.24 (4) | 472.21 |
| 16ic (11a) | 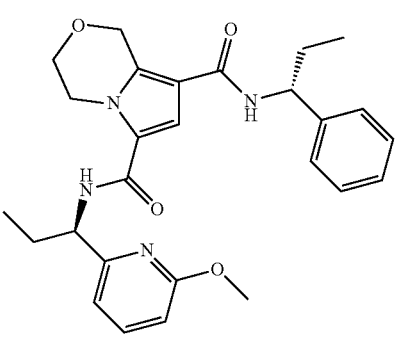 [SMILES: CC[C@@H](NC(=O)c1cc(C(=O)N[C@H](CC)c2cccc(OC)n2)n2c1COCC2)c1ccccc1] | 1.32 (4) | 477.25 |
| 16id (11a) | 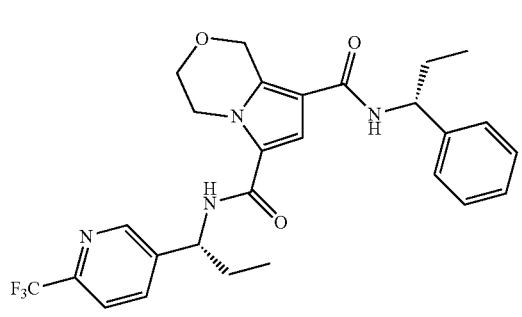 [SMILES: CC[C@@H](NC(=O)c1cc(C(=O)N[C@H](CC)c2ccc(C(F)(F)F)nc2)n2c1COCC2)c1ccccc1] | 1.3 (4) | 515.23 |
| 16ie (11a + 15ab) | 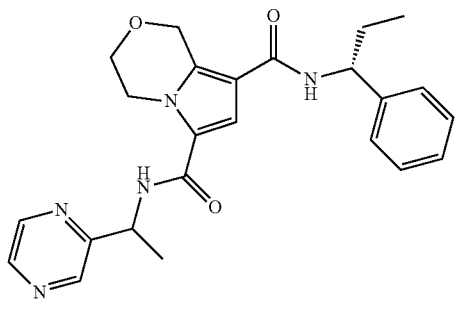
(diastereomer 2) | 1.16 (4) | 434.24 |

TABLE 10-continued

| | | | |
|---|---|---|---|
| 16if (11a + 15aa) | (diastereomer 1) | 1.16 (4) | 434.24 |
| 16ig (11a) | | 1.29 (4) | 477.27 |
| 16ih (11a) | | 1.28 (4) | 430.22 |
| 16ii (11a) | | 1.06 (4) | 409.16 |
| 16ij (11a) | | 1.23 (4) | 453.18 |

TABLE 10-continued
| | | | | |
|---|---|---|---|---|
| 16ik (11a) | 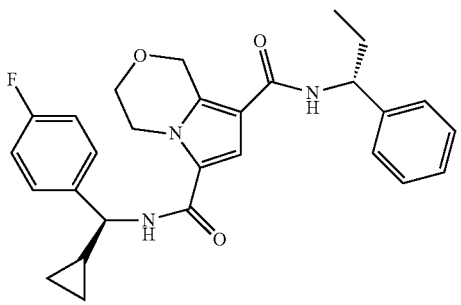 [SMILES: CC[C@@H](NC(=O)c1cc(C(=O)N[C@H](c2ccc(F)cc2)C2CC2)n2c1COCC2)c1ccccc1] | | 1.32 (4) | 476.25 |
| 16il (11a) | 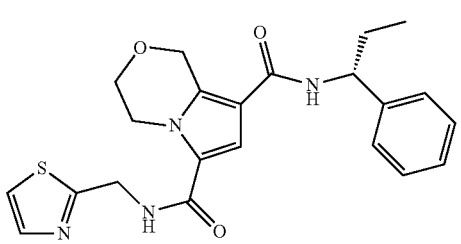 [SMILES: CC[C@@H](NC(=O)c1cc(C(=O)NCc2nccs2)n2c1COCC2)c1ccccc1] | | 1.16 (4) | 425.15 |
| 16im (11a) (racemic amine + chiral chromatography) | 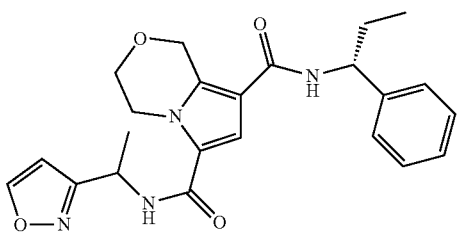 (diastereomer 1) | | 1.06 (4) | 423.25 |
| 16in (11a) (racemic amine + chiral chromatography) | 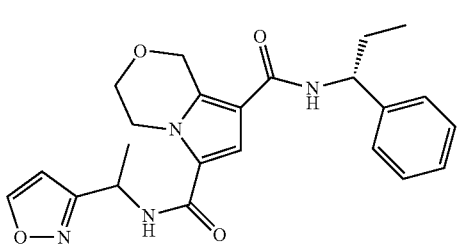 (diastereomer 2) | | 1.06 (4) | 423.29 |
| 16io (11a) | 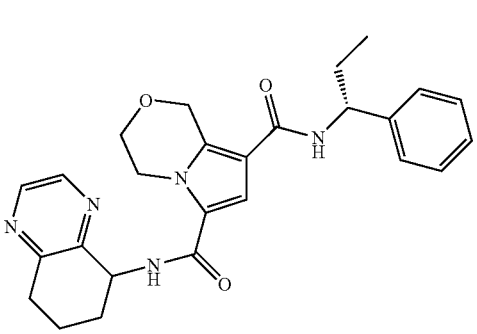 [SMILES: CC[C@@H](NC(=O)c1cc(C(=O)NC2CCCc3nccnc32)n2c1COCC2)c1ccccc1] | | 1.17 (4) | 460.26 |

TABLE 10-continued
| | | | |
|---|---|---|---|
| 16ip (11a) | 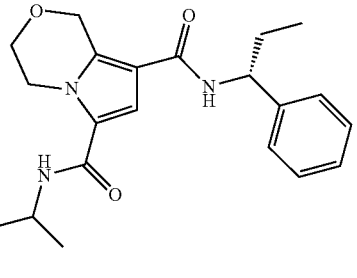 | 1.18 (4) | 511.25 |
| 16iq (11a) | 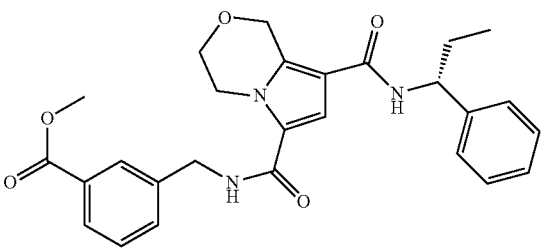 [SMILES: CC[C@@H](NC(=O)c1cc(C(=O)NCc2cccc(C(=O)OC)c2)n2c1COCC2)c1ccccc1] | 1.25 (4) | 476.28 |
| 16ir (11a) | 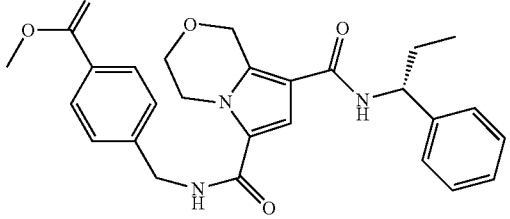 | 1.25 (4) | 476.29 |
| 16is (11a) | 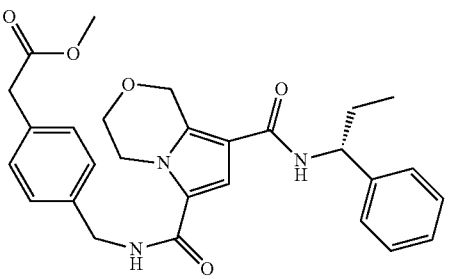 [SMILES: CC[C@@H](NC(=O)c1cc(C(=O)NCc2ccc(CC(=O)OC)cc2)n2c1COCC2)c1ccccc1] | 1.25 (4) | 490.29 |
| 16it (11a) | 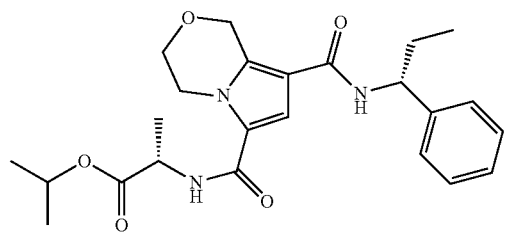 [SMILES: CC[C@@H](NC(=O)c1cc(C(=O)N[C@@H](C)C(=O)OC(C)C)n2c1COCC2)c1ccccc1] | 1.26 (4) | 442.3 |
| 16iu (11a + 19c) | 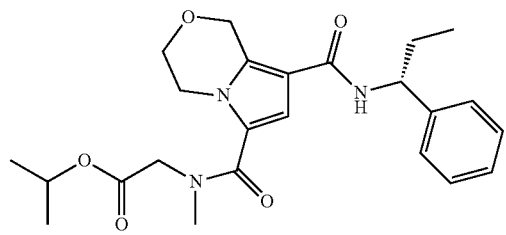 | 1.25 (4) | 442.3 |

TABLE 10-continued
| | | | |
|---|---|---|---|
| 16iv (11a + 15ac) | 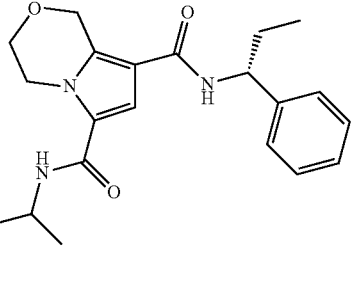 | 1.23 (4) | 464.28 |
| 16iw (11a) | 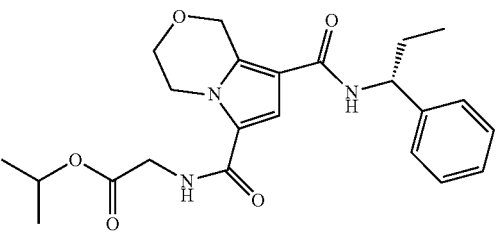 [SMILES: CC[C@@H](NC(=O)c1cc(C(=O)N(C)CC(=O)OC(C)C)n2c1COCC2)c1ccccc1] | 1.09 (2) | 428.27 |
| 16ix (11a) | 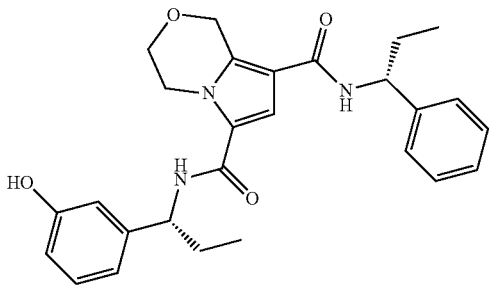 [SMILES: CC[C@@H](NC(=O)c1cc(C(=O)N[C@H](CC)c2cccc(O)c2)n2c1COCC2)c1ccccc1] | 1.23 (4) | 462.31 |
| 16iy (11a) | 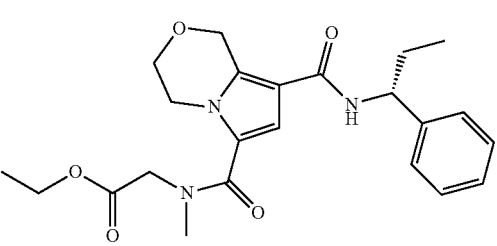 [SMILES: CCOC(=O)CN(C)C(=O)c1cc(C(=O)N[C@H](CC)c2ccccc2)c2n1CCOC2] | 1.22 (4) | 428.31 |
| 16iz (11a) | 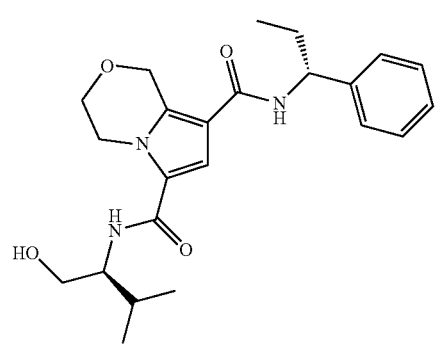 [SMILES: CC[C@@H](NC(=O)c1cc(C(=O)N[C@H](CO)C(C)C)n2c1COCC2)c1ccccc1] | 1.16 (4) | 414.17 |
| 16ja (11a + 19d) | 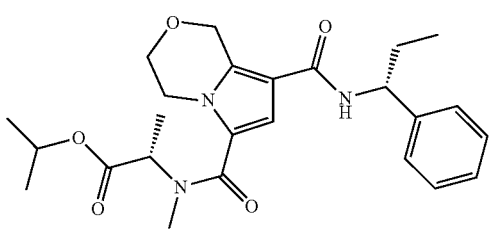 [SMILES: CC[C@@H](NC(=O)c1cc(C(=O)N(C)[C@@H](C)C(=O)OC(C)C)n2c1COCC2)c1ccccc1] | 1.15 (2) | 456.32 |

TABLE 10-continued
| | | | |
|---|---|---|---|
| 16jc (11a) | 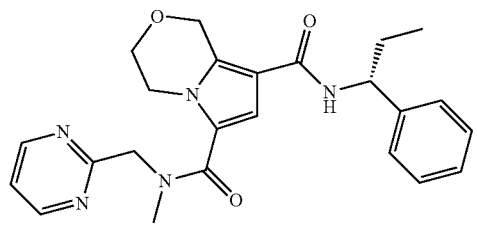 [SMILES: CC[C@@H](NC(=O)c1cc(C(=O)N(C)Cc2ncccn2)n2c1COCC2)c1ccccc1] | 1.13 (4) | 434.37 |
| 16jd (11a) | 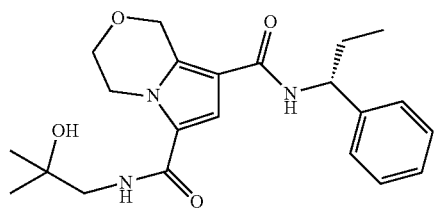 [SMILES: CC[C@@H](NC(=O)c1cc(C(=O)NCC(C)(C)O)n2c1COCC2)c1ccccc1] | 1.13 (4) | 400.35 |
| 16je (11a) | 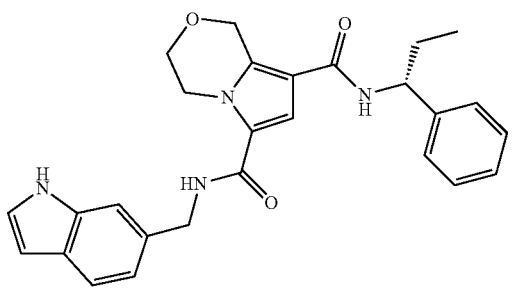 [SMILES: CC[C@@H](NC(=O)c1cc(C(=O)NCc2ccc3cc[nH]c3c2)n2c1COCC2)c1ccccc1] | 1.25 (4) | 457.38 |
| 16jf (11a) | 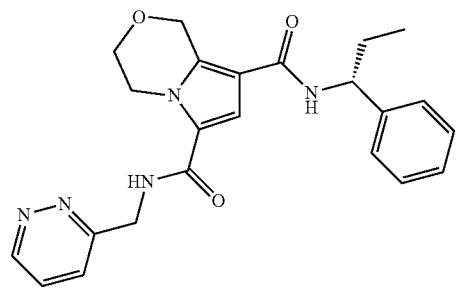 [SMILES: CC[C@@H](NC(=O)c1cc(C(=O)NCc2cccnn2)n2c1COCC2)c1ccccc1] | 3.32 (5) | 420.38 |
| 16jg (11a) | 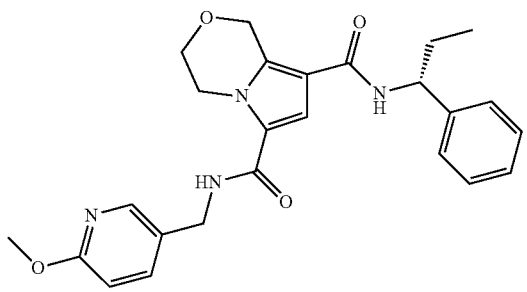 [SMILES: CC[C@@H](NC(=O)c1cc(C(=O)NCc2ccc(OC)nc2)n2c1COCC2)c1ccccc1] | 1.2 (4) | 449.25 |
| 16jh (11a) | 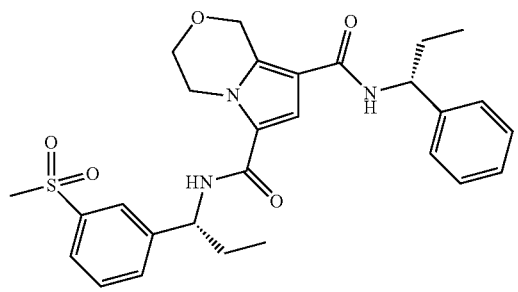 [SMILES: CC[C@@H](NC(=O)c1cc(C(=O)N[C@H](CC)c2cccc(S(C)(=O)=O)c2)n2c1COCC2)c1ccccc1] | 4.26 (5) | 524.35 |

TABLE 10-continued
| | | | |
|---|---|---|---|
| 16ji (11a) | 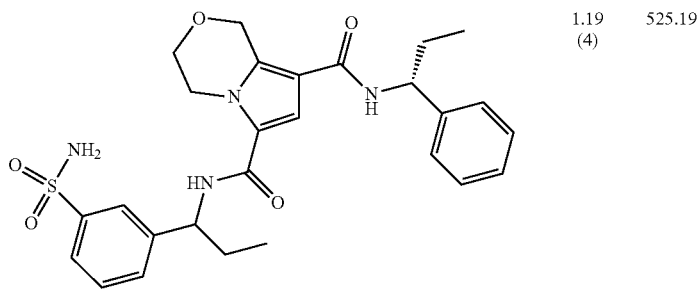 | 1.19 (4) | 525.19 |
| 16jj (11a) | 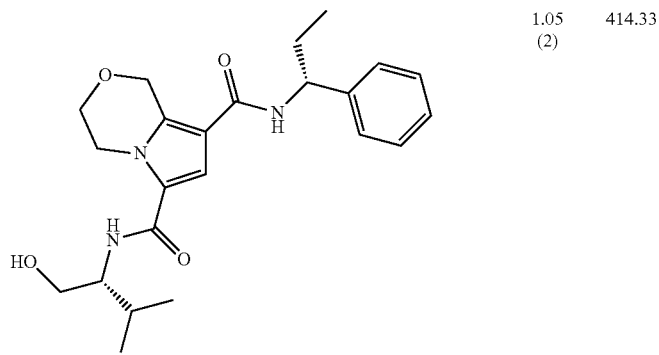 | 1.05 (2) | 414.33 |
| 16jk (7d) | 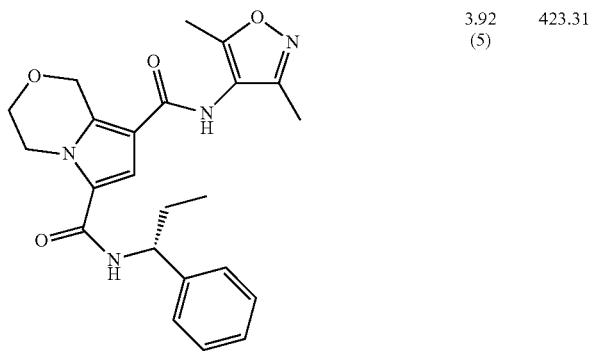 | 3.92 (5) | 423.31 |
| 16jl (7d) | 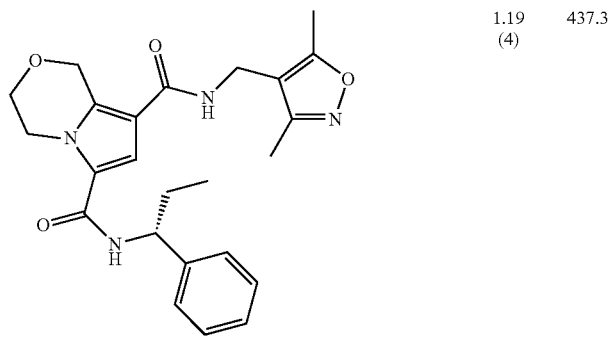 | 1.19 (4) | 437.3 |

| | | | |
|---|---|---|---|
| 16jm (7d) | [structure] | 1.12 (4) | 420.24 |
| 16jn (7d) | [structure] | 1.14 (4) | 409.25 |
| 16jo (7d) | [structure] | 1.26 (4) | 477.27 |
| 16jp (7q) | [structure] | 1.29 (4) | 450.21 |

TABLE 10-continued
| | | | |
|---|---|---|---|
| 16jq (7q) | 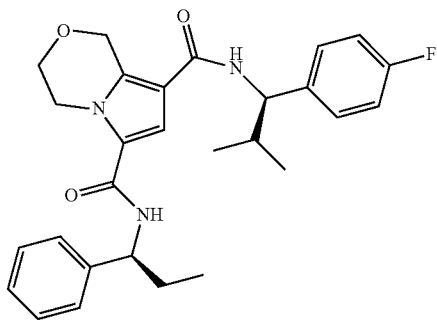 [SMILES: CC[C@H](NC(=O)c1cc(C(=O)N[C@@H](c2ccc(F)cc2)C(C)C)c2n1CCOC2)c1ccccc1] | 1.34 (4) | 478.24 |
| 16jr (7q) | 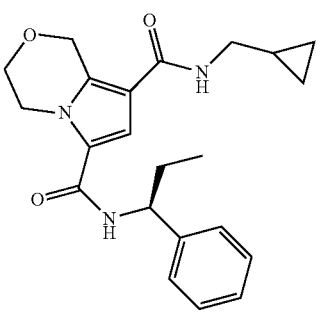 [SMILES: CC[C@H](NC(=O)c1cc(C(=O)NCC2CC2)c2n1CCOC2)c1ccccc1] | 1.22 (4) | 382.21 |
| 16js (7d) | 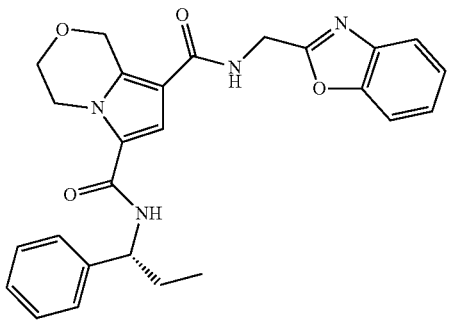 [SMILES: CC[C@@H](NC(=O)c1cc(C(=O)NCc2nc3ccccc3o2)c2n1CCOC2)c1ccccc1] | 1.24 (4) | 459.19 |
| 16jt (7d) | 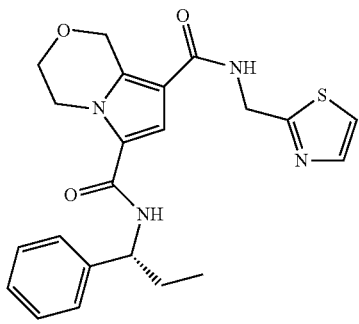 [SMILES: CC[C@@H](NC(=O)c1cc(C(=O)NCc2nccs2)c2n1CCOC2)c1ccccc1] | 1.17 (4) | 425.15 |

TABLE 10-continued
| | | | |
|---|---|---|---|
| 16ju (7d) | 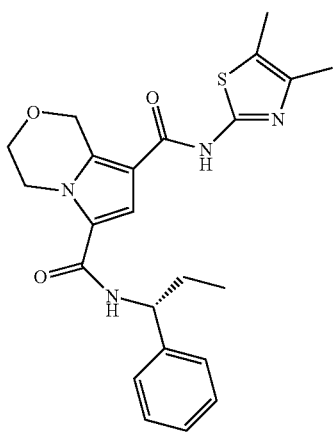 [SMILES: CC[C@@H](NC(=O)c1cc(C(=O)Nc2nc(C)c(C)s2)c2n1CCOC2)c1ccccc1] | 1.29 (4) | 439.17 |
| 16jv (7d) | 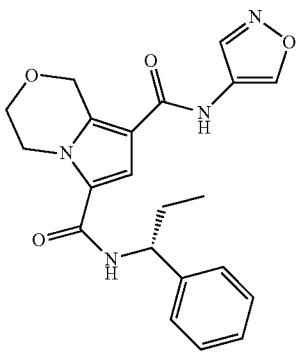 [SMILES: CC[C@@H](NC(=O)c1cc(C(=O)Nc2cnoc2)c2n1CCOC2)c1ccccc1] | 1.19 (4) | 395.16 |
| 16jw (7d + 15aa) | 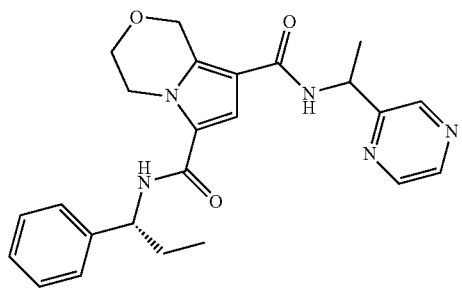<br>(diastereomer 1) | 1.04 (4) | 434.28 |
| 16jx (7d) | 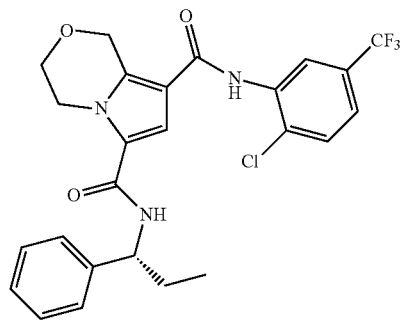 [SMILES: CC[C@@H](NC(=O)c1cc(C(=O)Nc2cc(C(F)(F)F)ccc2Cl)c2n1CCOC2)c1ccccc1] | 1.4 (4) | 506.22 |

TABLE 10-continued
| | | | |
|---|---|---|---|
| 16jy (7d) | 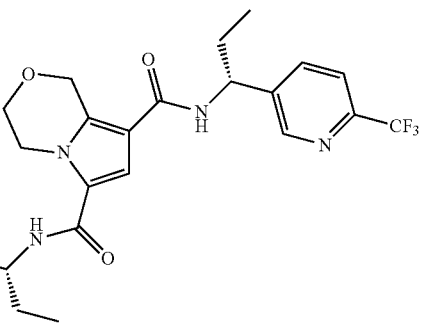 | 1.17 (2) | 515.33 |
| 16jz (7d) (racemic amine + chiral chromatography) | 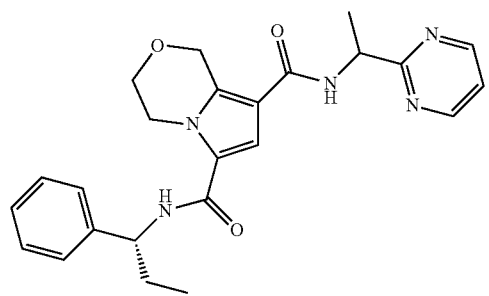 (diastereomer 1) | 1.16 (2) | 434.13 |
| 16ka (7d) (racemic amine + chiral chromatography) | 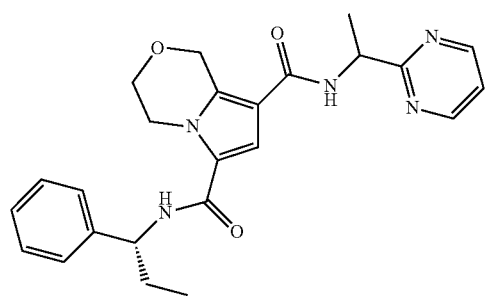 (diastereomer 2) | 1.16 (2) | 434.12 |
| 16kb (7q + 15b) | 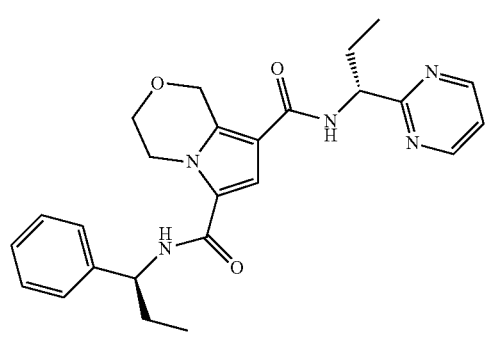 [SMILES: CC[C@H](NC(=O)c1cc(C(=O)N[C@H](CC)c2ncccn2)c2n1CCOC2)c1ccccc1] | 3.9 (5) | 448.26 |
| 16kc (7q + 15a) | 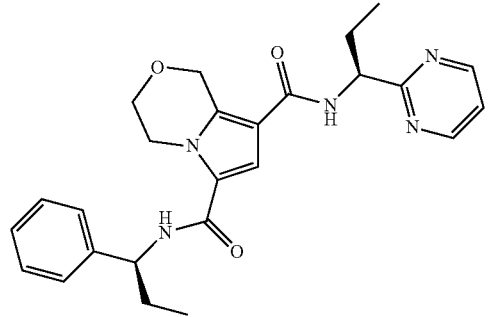 [SMILES: CC[C@H](NC(=O)c1cc(C(=O)N[C@@H](CC)c2ncccn2)c2n1CCOC2)c1ccccc1] | 3.89 (5) | 448.26 |

TABLE 10-continued

| | | | |
|---|---|---|---|
| 16kd (7d + 15b) | [structure] | 3.89 (5) | 448.26 |
| 16ke (7d + 15a) | [structure] | 3.89 (5) | 448.19 |
| 16kf (7q) | [structure] | 1.32 (2) | 515.09 |
| 16kg (7q + 15b) | [structure] | 1.14 (2) | 434.12 |
| 16kh (7d) | [structure] | 1.19 (4) | 412.28 |

TABLE 10-continued
| | | | |
|---|---|---|---|
| 16ki (7d) | 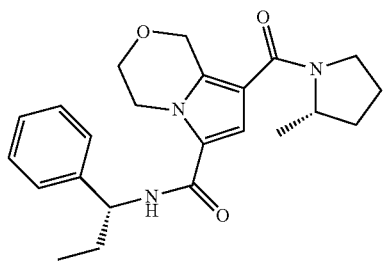 [SMILES: CC[C@@H](NC(=O)c1cc(C(=O)N2CCC[C@@H]2C)c2n1CCOC2)c1ccccc1] | 1.25 (4) | 396.29 |
| 16kj (7d) | 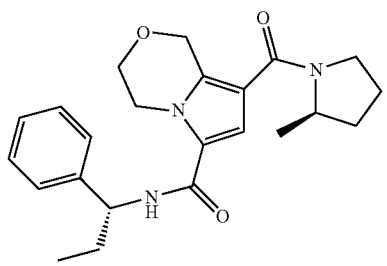 [SMILES: CC[C@@H](NC(=O)c1cc(C(=O)N2CCC[C@H]2C)c2n1CCOC2)c1ccccc1] | 1.25 (4) | 396.29 |
| 16kk (7d) | 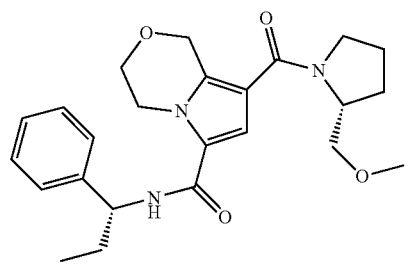 [SMILES: CC[C@@H](NC(=O)c1cc(C(=O)N2CCC[C@@H]2COC)c2n1CCOC2)c1ccccc1] | 1.24 (4) | 426.31 |
| 16kl (7d) | 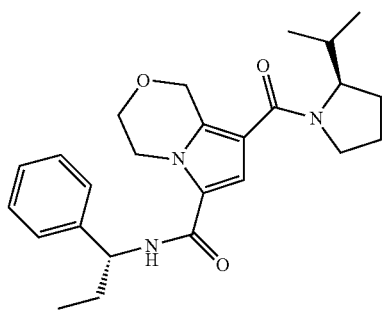 [SMILES: CC[C@@H](NC(=O)c1cc(C(=O)N2CCC[C@@H]2C(C)C)c2n1CCOC2)c1ccccc1] | 1.32 (4) | 424.31 |
| 16km (7d) | 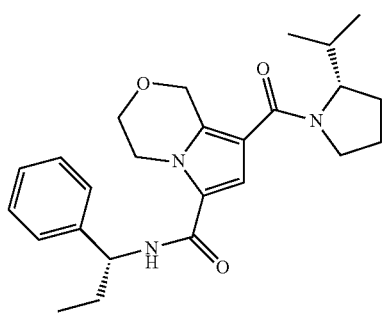 [SMILES: CC[C@@H](NC(=O)c1cc(C(=O)N2CCC[C@H]2C(C)C)c2n1CCOC2)c1ccccc1] | 1.32 (4) | 424.31 |

TABLE 10-continued

| | | | |
|---|---|---|---|
| 16kn (7e + 15ab) | | 1.23 (4) | 486.16 |
| 16ko (7e) | | 1.19 (4) | 472.16 |
| 16kp (7e) | | 1.23 (4) | 486.18 |
| 16kq (7f) | | 1.34 (4) | 466.23 |
| 16kr (7f) | | 1.28 (4) | 412.22 |

TABLE 10-continued
| | | | |
|---|---|---|---|
| 16ks (7h) | 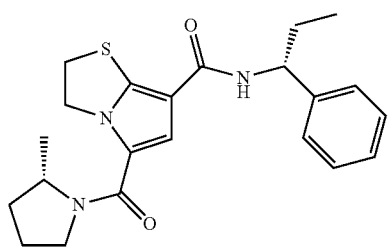 [SMILES: CC[C@@H](NC(=O)c1cc(C(=O)N2CCC[C@@H]2C)n2c1SCC2)c1ccccc1] | 1.26 (4) | 398.19 |
| 16kt (7i) | 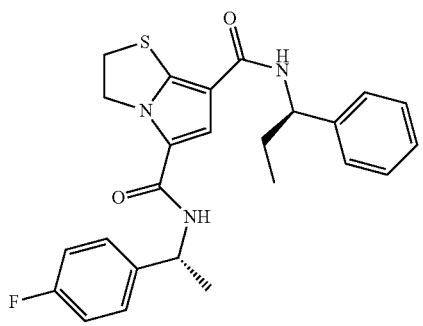 [SMILES: CC[C@@H](NC(=O)c1cc(C(=O)N[C@H](C)c2ccc(F)cc2)n2c1SCC2)c1ccccc1] | 1.3 (4) | 452.18 |
| 16ku (7j) | 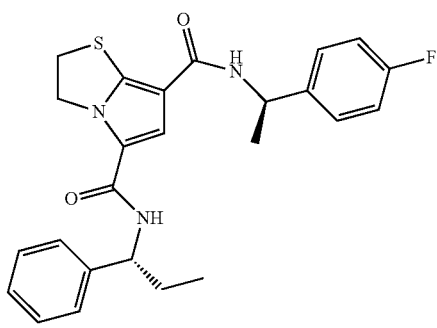 [SMILES: CC[C@@H](NC(=O)c1cc(C(=O)N[C@H](C)c2ccc(F)cc2)c2n1CCS2)c1ccccc1] | 1.3 (4) | 452.18 |
| 16kv (7j) | 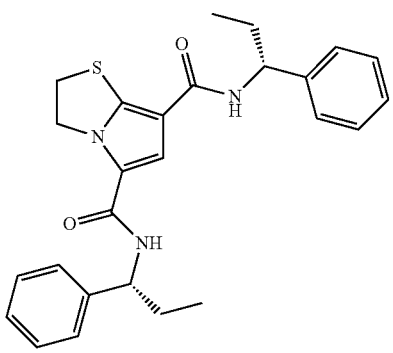 [SMILES: CC[C@@H](NC(=O)c1cc(C(=O)N[C@H](CC)c2ccccc2)n2c1SCC2)c1ccccc1] | 1.32 (4) | 448.2 |
| 16kw (7l) | 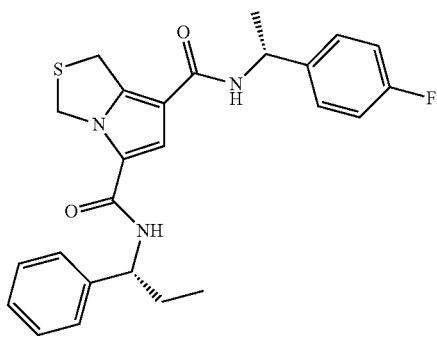 [SMILES: CC[C@@H](NC(=O)c1cc(C(=O)N[C@H](C)c2ccc(F)cc2)c2n1CSC2)c1ccccc1] | 1.32 (4) | 452.16 |

TABLE 10-continued
| | | | |
|---|---|---|---|
| 16kx (7l) | 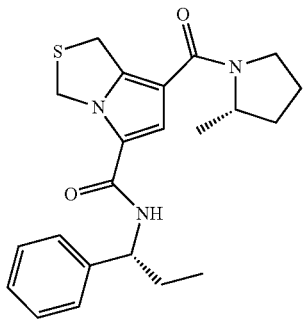 [SMILES: CC[C@@H](NC(=O)c1cc(C(=O)N2CCC[C@@H]2C)c2n1CSC2)c1ccccc1] | 1.29 (4) | 398.19 |
| 16ky (7k) | 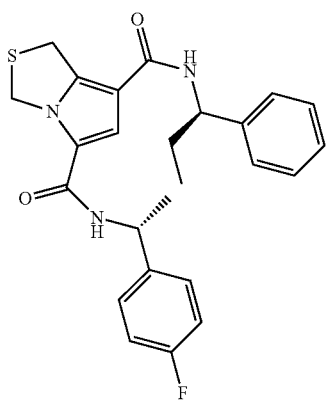 [SMILES: CC[C@@H](NC(=O)c1cc(C(=O)N[C@H](C)c2ccc(F)cc2)n2c1CSC2)c1ccccc1] | 1.32 (4) | 452.21 |
| 16kz (7m) | 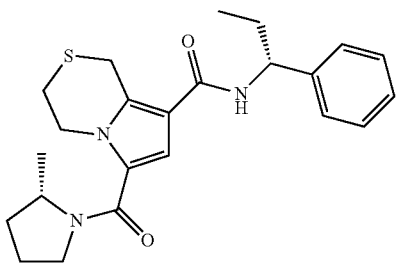 [SMILES: CC[C@@H](NC(=O)c1cc(C(=O)N2CCC[C@@H]2C)n2c1CSCC2)c1ccccc1] | 1.28 (4) | 412.19 |
| 16la (7n) | 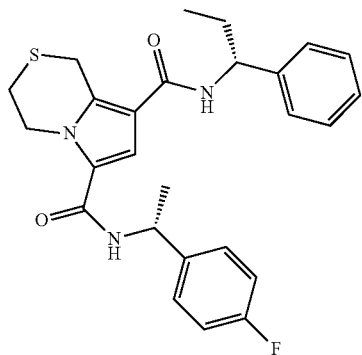 [SMILES: CC[C@@H](NC(=O)c1cc(C(=O)N[C@H](C)c2ccc(F)cc2)n2c1CSCC2)c1ccccc1] | 1.33 (4) | 466.21 |

TABLE 10-continued
| | | | |
|---|---|---|---|
| 16lb (7p + 15b) | 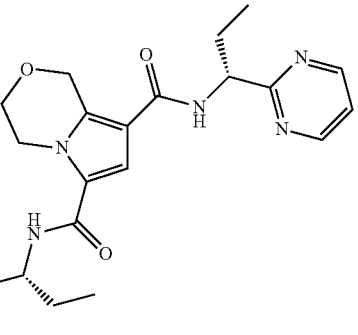 | 1.26 (2) | 516.1 |
| 16ld (7s) | 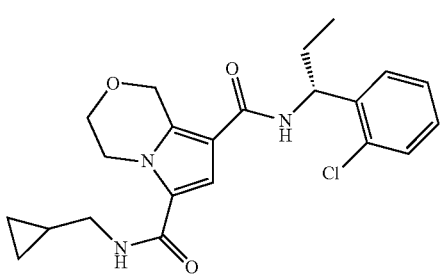 [SMILES: CC[C@@H](NC(=O)c1cc(C(=O)NCC2CC2)n2c1COCC2)c1ccccc1Cl] | 1.26 (4) | 416.17 |
| 16le (7t) (chiral chromatography) | 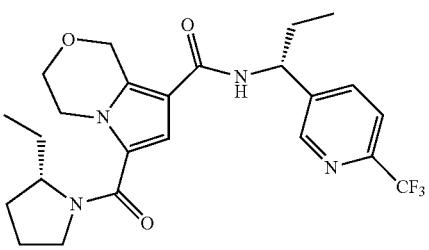 [SMILES: CC[C@H]1CCCN1C(=O)c1cc(C(=O)N[C@H](CC)c2ccc(C(F)(F)F)nc2)c2n1CCOC2] | 4.38 (5) | 479.24 |
| 16lf (7u) | 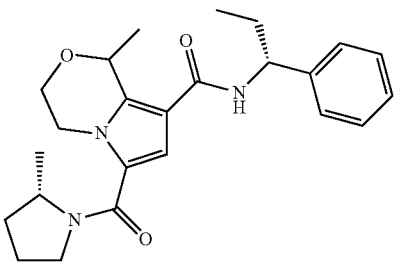 [SMILES: CC[C@@H](NC(=O)c1cc(C(=O)N2CCC[C@@H]2C)n2c1C(C)OCC2)c1ccccc1] | 1.26 (4) | 410.25 |
| 16lg (7ab) | 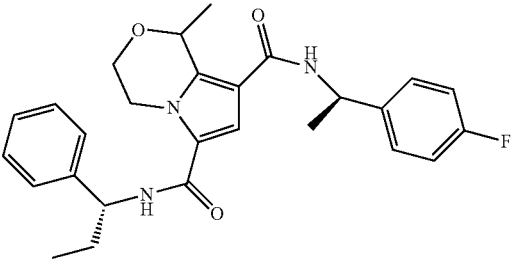 [SMILES: CC[C@@H](NC(=O)c1cc(C(=O)N[C@H](C)c2ccc(F)cc2)c2n1CCOC2C)c1ccccc1] | 1.31 (4) | 464.24 |

TABLE 10-continued

| | | | |
|---|---|---|---|
| 16lh (7z) | [structure] | 1.33 (4) | 478.24 |
| 16li (7aa) | [structure] | 1.15 (4) | 434.2 |
| 16lj (7ac) | [structure] | 1.29 (4) | 428.3 |
| 16lk (7ac) | [structure] | 1.24 (4) | 455.26 |
| 16ll (7ac) | [structure] | 1.2 (4) | 441.25 |

TABLE 10-continued
| | | | |
|---|---|---|---|
| 16lm (7ac) | 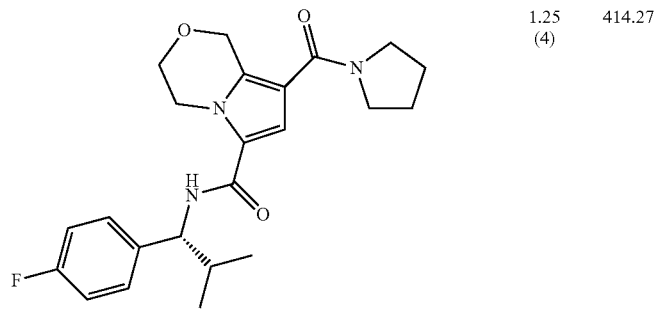 | 1.25 (4) | 414.27 |
| 16ln (7ac) | 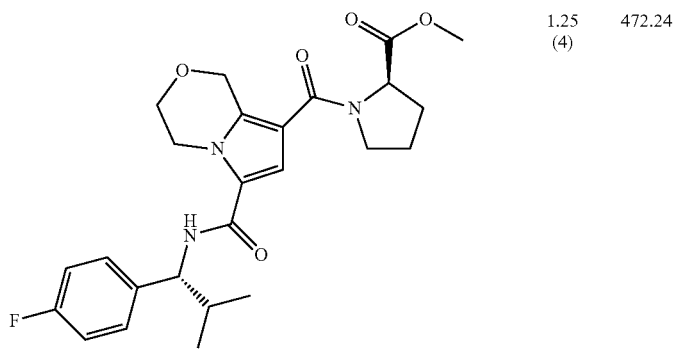 | 1.25 (4) | 472.24 |
| 16lo (7ac) | 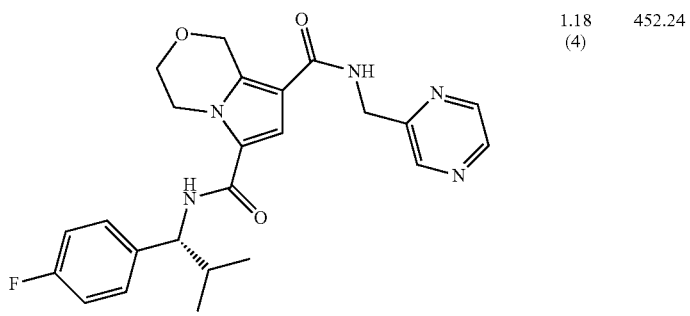 | 1.18 (4) | 452.24 |
| 16lp (7ac + 15ab) | 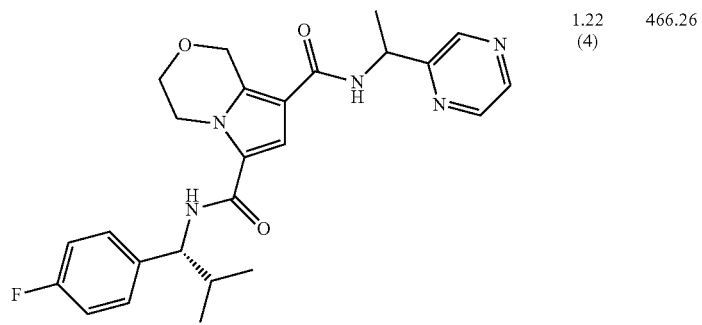<br>(diastereomer 2) | 1.22 (4) | 466.26 |

TABLE 10-continued

| | | | |
|---|---|---|---|
| 16lq (7ac + 15aa) | (diastereomer 1) | 1.22 (4) | 466.3 |
| 16lr (7ac) (racemic amine + chiral chromatography) | | 1.08 (4) | 466.28 |
| 16ls (7ac) (racemic amine + chiral chromatography) | | 1.08 (4) | 466.28 |
| 16lu (7af) | | 1.17 (2) | 436.12 |
| 16lv (7ag) | | 1.19 (4) | 420.36 |

| | | | |
|---|---|---|---|
| 16lw (7ag) | 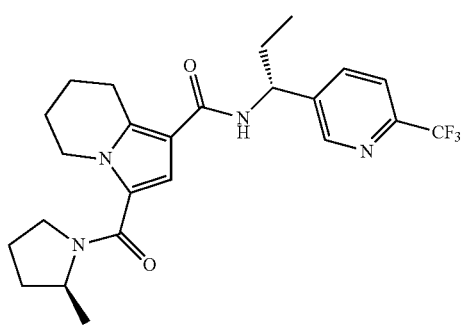 [SMILES: CC[C@@H](NC(=O)c1cc(C(=O)N2CCC[C@@H]2C)n2c1CCCC2)c1ccc(C(F)(F)F)nc1] | 1.25 (4) | 463.32 |
| 16lx (7ag) | 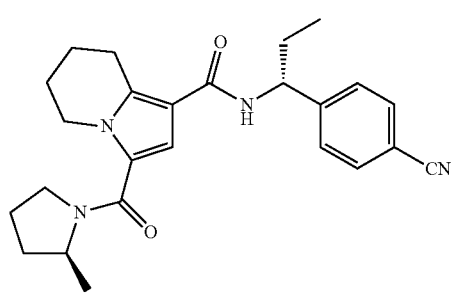 [SMILES: CC[C@@H](NC(=O)c1cc(C(=O)N2CCC[C@@H]2C)n2c1CCCC2)c1ccc(C#N)cc1] | 1.22 (4) | 419.29 |
| 16ly (7ag) | 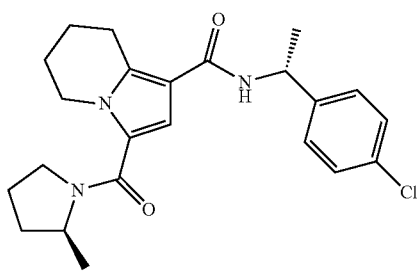 [SMILES: C[C@@H](NC(=O)c1cc(C(=O)N2CCC[C@@H]2C)n2c1CCCC2)c1ccc(Cl)cc1] | 1.28 (4) | 414.15 |
| 16lz (7ag) | 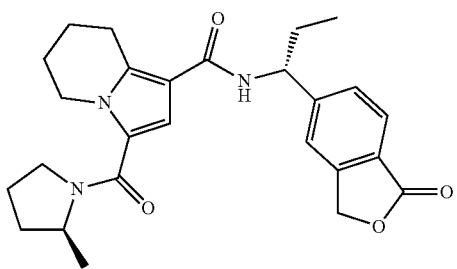 [SMILES: CC[C@@H](NC(=O)c1cc(C(=O)N2CCC[C@@H]2C)n2c1CCCC2)c1ccc2c(c1)COC2=O] | 1.65 3 | 450.43 |
| 16ma (7ah) | 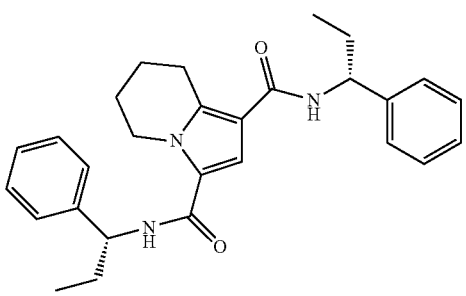 [SMILES: CC[C@@H](NC(=O)c1cc(C(=O)N[C@H](CC)c2ccccc2)n2c1CCCC2)c1ccccc1] | 1.35 (4) | 444.36 |

TABLE 10-continued
| | | | |
|---|---|---|---|
| 16mc (7ah) | 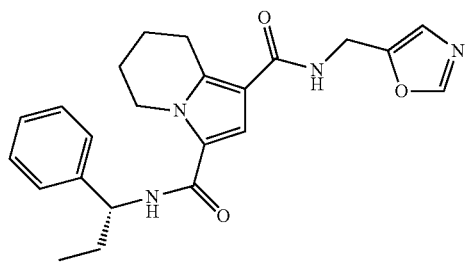 [SMILES: CC[C@@H](NC(=O)c1cc(C(=O)NCc2cnco2)c2n1CCCC2)c1ccccc1] | 1.19 (4) | 407.25 |
| 16md (7ah) | 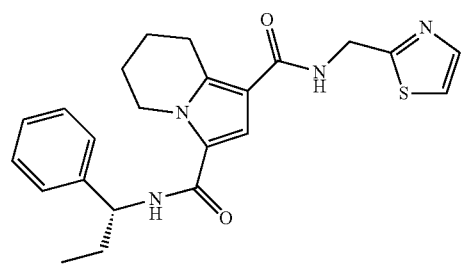 [SMILES: CC[C@@H](NC(=O)c1cc(C(=O)NCc2nccs2)c2n1CCCC2)c1ccccc1] | 1.22 (4) | 423.24 |
| 16me (7ah) | 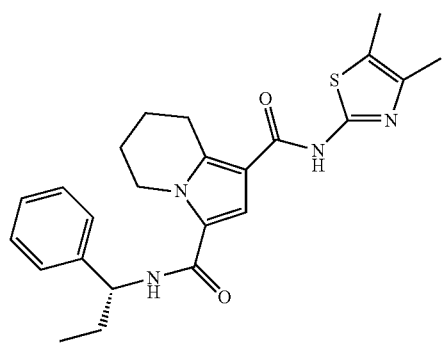 [SMILES: CC[C@@H](NC(=O)c1cc(C(=O)Nc2nc(C)c(C)s2)c2n1CCCC2)c1ccccc1] | 1.35 (4) | 437.24 |
| 16nd (11i) | 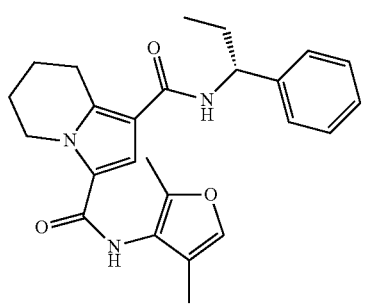 [SMILES: CC[C@@H](NC(=O)c1cc(C(=O)Nc2c(C)coc2C)n2c1CCCC2)c1ccccc1] | 1.24 (4) | 421.28 |
| 16nc (11i) | 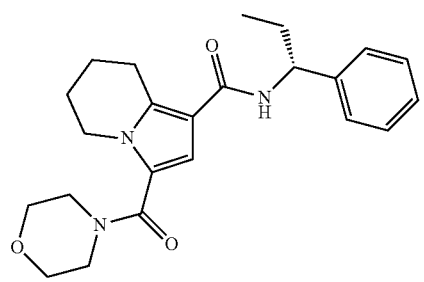 [SMILES: CC[C@@H](NC(=O)c1cc(C(=O)N2CCOCC2)n2c1CCCC2)c1ccccc1] | 3.75 (6) | 396.27 |

TABLE 10-continued
| | | | |
|---|---|---|---|
| 16ne (11i) | 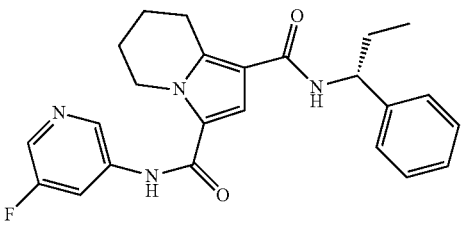 [SMILES: CC[C@@H](NC(=O)c1cc(C(=O)Nc2cncc(F)c2)n2c1CCCC2)c1ccccc1] | 1.28 (4) | 421.27 |
| 16nh (11b) | 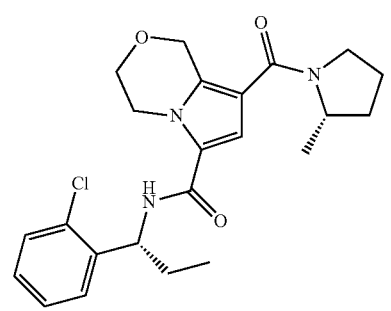 [SMILES: CC[C@@H](NC(=O)c1cc(C(=O)N2CCC[C@@H]2C)c2n1CCOC2)c1ccccc1Cl] | 1.29 (4) | 430.18 |
| 16ni (11b) | 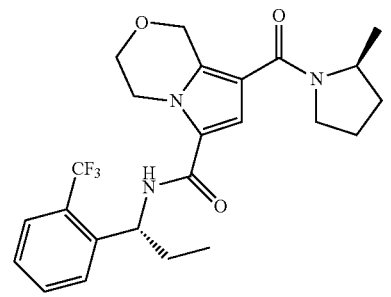 [SMILES: CC[C@@H](NC(=O)c1cc(C(=O)N2CCC[C@@H]2C)c2n1CCOC2)c1ccccc1C(F)(F)F] | 1.31 (4) | 464.2 |
| 16nj (11b) | 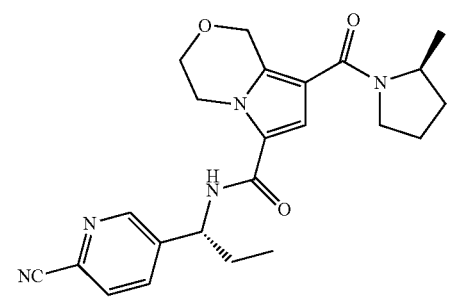 [SMILES: CC[C@@H](NC(=O)c1cc(C(=O)N2CCC[C@@H]2C)c2n1CCOC2)c1ccc(C#N)nc1] | 1.03 (4) | 422.28 |
| 16nk (11b) | 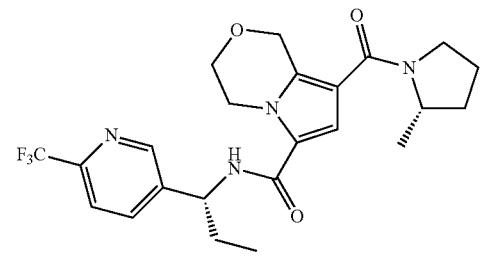 | 1.11 (2) | 465.25 |
| 16nl (11b) | 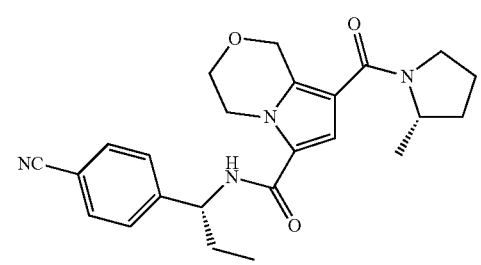 [SMILES: CC[C@@H](NC(=O)c1cc(C(=O)N2CCC[C@@H]2C)c2n1CCOC2)c1ccc(C#N)cc1] | 1.09 (2) | 421.26 |

TABLE 10-continued
| | | | |
|---|---|---|---|
| 16nm (11b) | 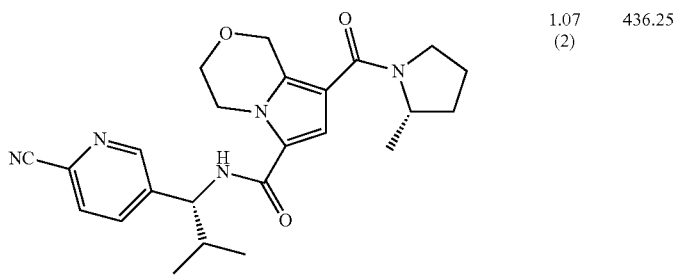 | 1.07 (2) | 436.25 |
| 16nn (11d) | 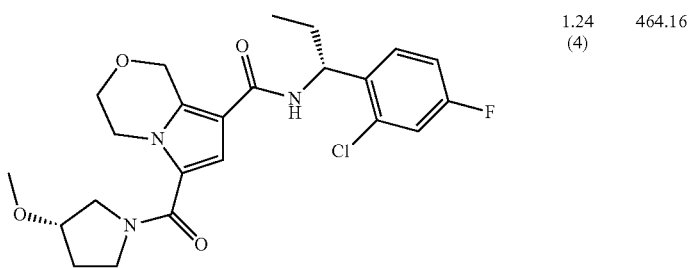 | 1.24 (4) | 464.16 |
| 16no (11d) | 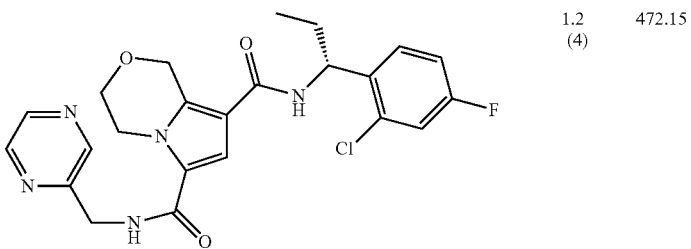 | 1.2 (4) | 472.15 |
| 16np (11d) | 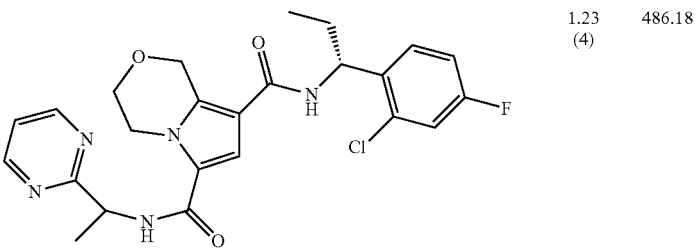 | 1.23 (4) | 486.18 |
| 16nq (11c) | 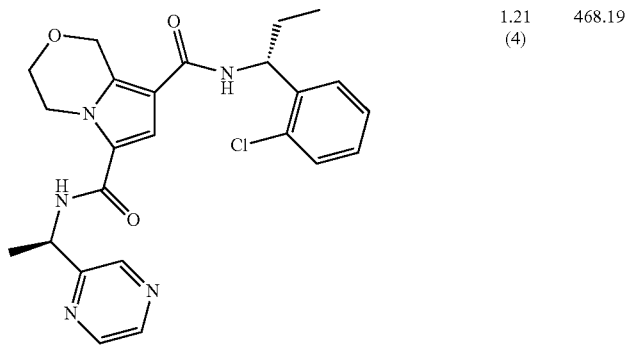 | 1.21 (4) | 468.19 |

TABLE 10-continued

| | | | |
|---|---|---|---|
| 16nr (11c) | | 1.21 (4) | 468.2 |
| 16ns (11f) | | 1.16 (4) | 456.21 |
| 16nt (11f) | | 1.28 (4) | 485.27 |
| 16nu (7c) | | 1.08 (2) | 420.21 |
| 16nv (11g + 15b) | | 1.16 (2) | 452.12 |

TABLE 10-continued
| | | | |
|---|---|---|---|
| 16nw (11g + 15a) | 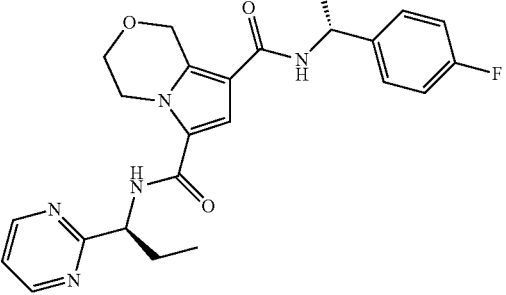 [SMILES: CC[C@@H](NC(=O)c1cc(C(=O)NCc2ccc(F)cc2F)c2n1CCOC2)c1cnccn1] | 1.16 (2) | 452.1 |
| 16nx (7w) | 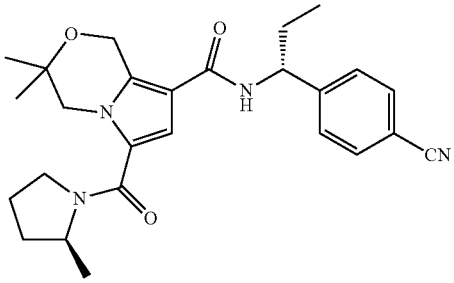 [SMILES: CC[C@@H](NC(=O)c1cc(C(=O)N2CCC[C@@H]2C)n2c1COC(C)(C)C2)c1ccc(C#N)cc1] | 1.24 (4) | 449.2 |
| 16ny (7v) | 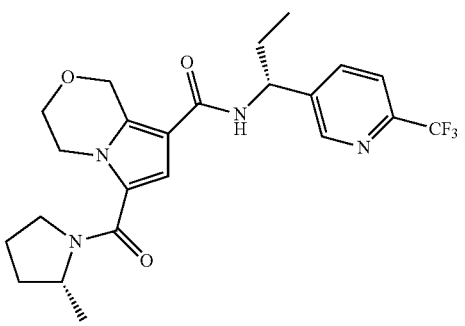 [SMILES: CC[C@@H](NC(=O)c1cc(C(=O)N2CCC[C@H]2C)n2c1COCC2)c1ccc(C(F)(F)F)nc1] | 1.1 (2) | 465.22 |
| 16nz (11h) | 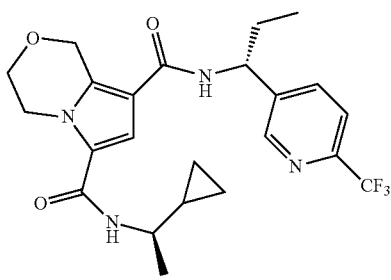 [SMILES: CC[C@@H](NC(=O)c1cc(C(=O)N[C@H](C)C2CC2)n2c1COCC2)c1ccc(C(F)(F)F)nc1] | 1.23 (2) | 465.16 |
| 16pa (11h) | 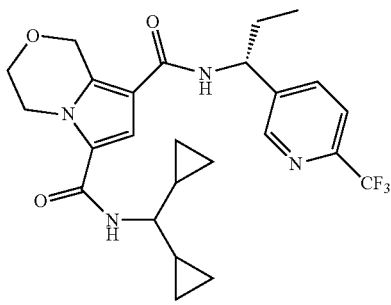 [SMILES: CC[C@@H](NC(=O)c1cc(C(=O)NC(C2CC2)C2CC2)n2c1COCC2)c1ccc(C(F)(F)F)nc1] | 1.27 (2) | 491.18 |

TABLE 10-continued
| | | | |
|---|---|---|---|
| 16pb (11h) | 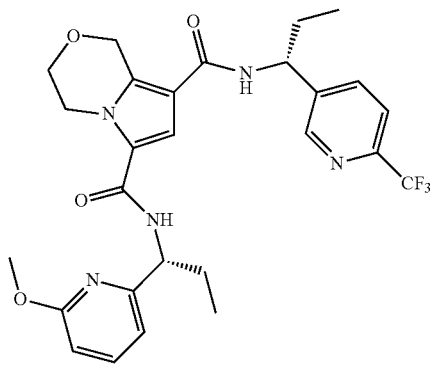 [SMILES: CC[C@@H](NC(=O)c1cc(C(=O)N[C@H](CC)c2cccc(OC)n2)n2c1COCC2)c1ccc(C(F)(F)F)nc1] | 1.3 (2) | 546.17 |
| 16pc (11h) | 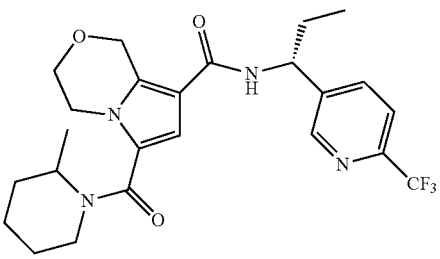 [SMILES: CC[C@@H](NC(=O)c1cc(C(=O)N2CCCCC2C)n2c1COCC2)c1ccc(C(F)(F)F)nc1] | 1.25 (2) | 479.17 |
| 16pd (11h) (racemic amine + chiral chromatography) | 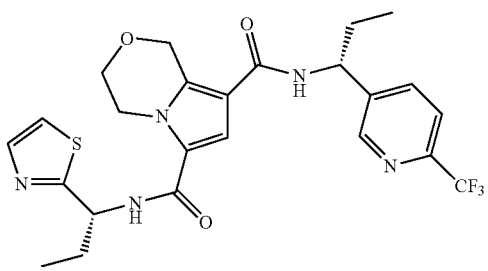 [SMILES: CC[C@@H](NC(=O)c1cc(C(=O)N[C@H](CC)c2nccs2)n2c1COCC2)c1ccc(C(F)(F)F)nc1] | 1.21 (2) | 522.27 |
| 16pe (11h) | 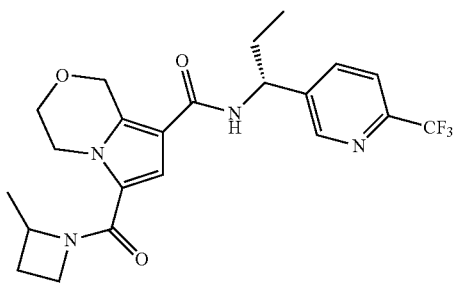 [SMILES: CC[C@@H](NC(=O)c1cc(C(=O)N2CCC2C)n2c1COCC2)c1ccc(C(F)(F)F)nc1] | 1.19 (2) | 451.24 |
| 16pf (7c) | 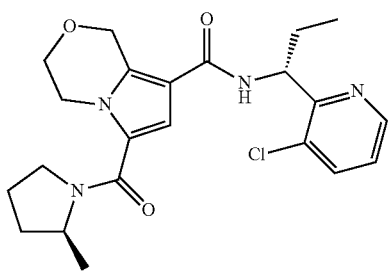 [SMILES: CC[C@@H](NC(=O)c1cc(C(=O)N2CCC[C@@H]2C)n2c1COCC2)c1ncccc1Cl] | 1.09 (2) | 431.24 |

TABLE 10-continued
| | | | |
|---|---|---|---|
| 16pg (7c) | 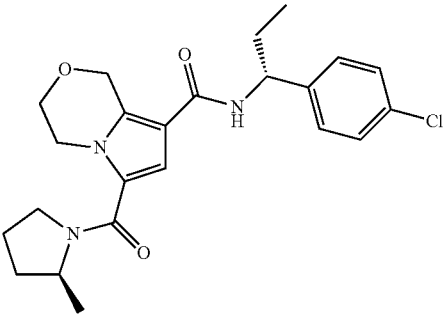 [SMILES: CC[C@@H](NC(=O)c1cc(C(=O)N2CCC[C@@H]2C)n2c1COCC2)c1ccc(Cl)cc1] | 1.27 (4) | 430.19 |
| 16ph (7c) | 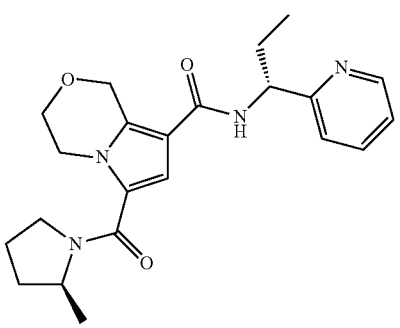 [SMILES: CC[C@@H](NC(=O)c1cc(C(=O)N2CCC[C@@H]2C)n2c1COCC2)c1ccccn1] | 2.64 (5) | 397.32 |
| 16pi (7w) | 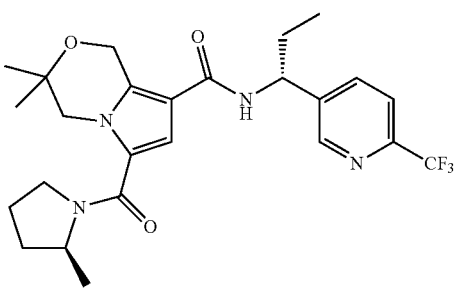 [SMILES: CC[C@@H](NC(=O)c1cc(C(=O)N2CCC[C@@H]2C)n2c1COC(C)(C)C2)c1ccc(C(F)(F)F)nc1] | 1.26 (4) | 493.2 |
| 16pj (7b) | 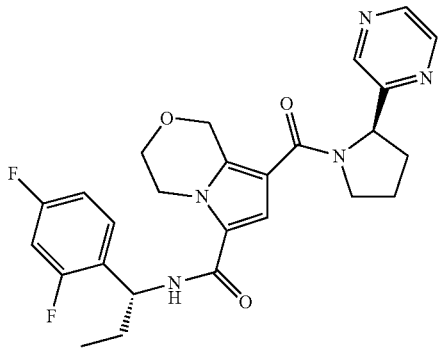 [SMILES: CC[C@@H](NC(=O)c1cc(C(=O)N2CCC[C@@H]2c2cnccn2)c2n1CCOC2)c1ccc(F)cc1F] | 1.21 (4) | 496.22 |
| 16pk (7b + 15ab) | 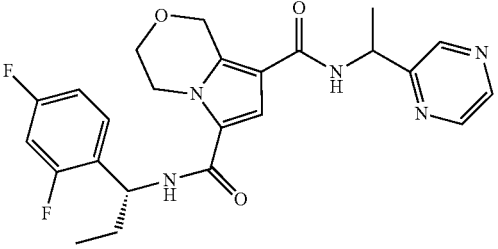<br>(diastereomer 2) | 1.2 (4) | 470.19 |

TABLE 10-continued

| Comp. no. | Structure | | MW |
|---|---|---|---|
| 16pl (7b + 15aa) | (diastereomer 1) | 1.2 (4) | 470.25 |
| 16po (11b) | 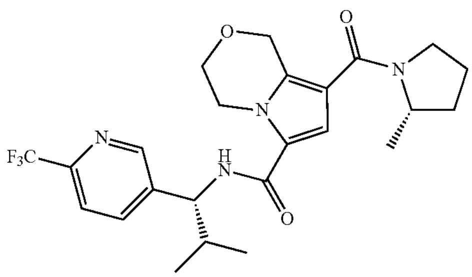 [SMILES: CC(C)[C@@H](NC(=O)c1cc(C(=O)N2CCC[C@@H]2C)c2n1CCOC2)c1ccc(C(F)(F)F)nc1] | 1.14 (2) | 479.27 |
| 16pp (7c) | 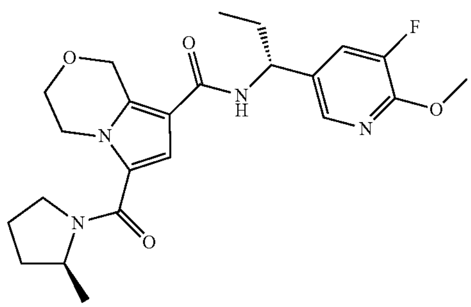 [SMILES: CC[C@@H](NC(=O)c1cc(C(=O)N2CCC[C@@H]2C)n2c1COCC2)c1cnc(OC)c(F)c1] | 1.69 (3) | 445.32 |

| Comp. no. | Chemical name |
|---|---|
| 16p | 6-((S)-2-Methyl-pyrrolidine-1-carbonyl)-3,4-dihydro-1H-pyrrolo[2,1-c][1,4]oxazine-8-carboxylic acid [(R)-1-(4-fluoro-phenyl)-2-methyl-propyl]-amide |
| 16q | 6-((S)-2-Methyl-pyrrolidine-1-carbonyl)-3,4-dihydro-1H-pyrrolo[2,1-c][1,4]oxazine-8-carboxylic acid [(R)-1-(2-chloro-phenyl)-propyl]-amide |
| 16r | 6-((S)-2-Methyl-pyrrolidine-1-carbonyl)-3,4-dihydro-1H-pyrrolo[2,1-c](1,4]oxazine-8-carboxylic acid [(R)-1-(2-trifluoromethyl-pyridin-3-yl)-propyl]-amide |
| 16s | 6-((S)-2-Methyl-pyrrolidine-1-carbonyl)-3,4-dihydro-1H-pyrrolo[2,1-c][1,4]oxazine-8-carboxylic acid [(R)-1-(2-trifluoromethyl-phenyl)-propyl]-amide |
| 16t | 6-((S)-2-Methyl-pyrrolidine-1-carbonyl)-3,4-dihydro-1H-pyrrolo[2,1-c][1,4]oxazine-8-carboxylic acid [(R)-1-(2,6-difluoro-phenyl)-propyl]-amide |
| 16u | 6-((S)-2-Methyl-pyrrolidine-1-carbonyl)-3,4-dihydro-1H-pyrrolo[2,1-c][1,4]oxazine-8-carboxylic acid [(R)-1-(2-chloro-4-fluoro-phenyl)-propyl]-amide |
| 16v | 6-((S)-2-Methyl-pyrrolidine-1-carbonyl)-3,4-dihydro-1H-pyrrolo[2,1-c][1,4]oxazine-8-carboxylic acid [(R)-1-(2,4-difluoro-phenyl)-propyl]-amide |
| 16w | 6-((S)-2-Methyl-pyrrolidine-1-carbonyl)-3,4-dihydro-1H-pyrrolo[2,1-c][1,4]oxazine-8-carboxylic acid [(R)-1-(2-chloro-5-fluoro-phenyl)-propyl]-amide |
| 16x | 6-((S)-2-Methyl-pyrrolidine-1-carbonyl)-3,4-dihydro-1H-pyrrolo[2,1-c][1,4]oxazine-8-carboxylic acid 2-chloro-4-fluoro-benzylamide |
| 16y | 6-((S)-2-Methyl-pyrrolidine-1-carbonyl)-3,4-dihydro-1H-pyrrolo[2,1-c][1,4]oxazine-8-carboxylic acid 2,6-difluoro-benzylamide |
| 16z | 6-((S)-2-Methyl-pyrrolidine-1-carbonyl)-3,4-dihydro-1H-pyrrolo[2,1-c][1,4]oxazine-8-carboxylic acid [(R)-1-(6-methoxy-pyridin-2-yl)-propyl]-amide |
| 16aa | 6-((S)-2-Methyl-pyrrolidine-1-carbonyl)-3,4-dihydro-1H-pyrrolo[2,1-c][1,4]oxazine-8-carboxylic acid ((R)-1-(6-cyano-pyridin-3-yl)-propyl]-amide |
| 16ab | 6-((S)-2-Methyl-pyrrolidine-1-carbonyl)-3,4-dihydro-1H-pyrrolo[2,1-c][1,4]oxazine-8-carboxylic acid [(R)-1-(3-hydroxy-phenyl)-propyl]-amide |

TABLE 10-continued

| | |
|---|---|
| 16ae | 6-((S)-2-Methyl-pyrrolidine-1-carbonyl)-3,4-dihydro-1H-pyrrolo[2,1-c][1,4]oxazine-8-carboxylic acid (1-thiazol-2-yl-propyl)-amide |
| 16af | 6-((S)-2-Methyl-pyrrolidine-1-carbonyl)-3,4-dihydro-1H-pyrrolo[2,1-c][1,4]oxazine-8-carboxylic acid 2,4,6-trifluoro-benzylamide |
| 16ag | 6-((S)-2-Methyl-pyrrolidine-1-carbonyl)-3,4-dihydro-1H-pyrrolo[2,1-c)[1,4]oxazine-8-carboxylic acid 2,6-dichloro-benzylamide |
| 16ah | 6-((S)-2-Methyl-pyrrolidine-1-carbonyl)-3,4-dihydro-1H-pyrrolo[2,1-c][1,4]oxazine-8-carboxylic acid [(R)-1-(6-cyano-pyridin-2-yl)-propyl]-amide |
| 16ai | 6-((S)-2-Methyl-pyrrolidine-1-carbonyl)-3,4-dihydro-1H-pyrrolo[2,1-c][1,4]oxazine-8-carboxylic acid [(R)-1-(6-methoxy-pyridin-3-yl)-propyl]-amide |
| 16aj | 6-((S)-2-Methyl-pyrrolidine-1-carbonyl)-3,4-dihydro-1H-pyrrolo[2,1-c][1,4]oxazine-8-carboxylic acid [(R)-1-(3-cyano-phenyl)-propyl]-amide |
| 16ak | 6-((S)-2-Methyl-pyrrolidine-1-carbonyl)-3,4-dihydro-1H-pyrrolo[2,1-c][1,4]oxazine-8-carboxylic acid [(R)-1-(4-cyano-phenyl)-propyl]-amide |
| 16al | 6-((S)-2-Methyl-pyrrolidine-1-carbonyl)-3,4-dihydro-1H-pyrrolo[2,1-c][1,4]oxazine-8-carboxylic acid [(R)-1-(6-bromo-pyridin-3-yl)-propyl]-amide |
| 16am | 6-((S)-2-Methyl-pyrrolidine-1-carbonyl)-3,4-dihydro-1H-pyrrolo[2,1-c][1,4]oxazine-8-carboxylic acid [(R)-1-(6-cyano-pyridin-3-yl)-2-methyl-propyl]-amide |
| 16an | 6-((S)-2-Methyl-pyrrolidine-1-carbonyl)-3,4-dihydro-1H-pyrrolo[2,1-c][1,4]oxazine-8-carboxylic acid 2-chloro-benzylamide |
| 16ao | 6-((S)-2-Methyl-pyrrolidine-1-carbonyl)-3,4-dihydro-1H-pyrrolo[2,1-c][1,4]oxazine-8-carboxylic acid [(R)-1-(3-methoxy-pyridin-2-yl)-propyl]-amide |
| 16ap | 6-((S)-2-Methyl-pyrrolidine-1-carbonyl)-3,4-dihydro-1H-pyrrolo[2,1-c][1,4]oxazine-8-carboxylic acid [(R)-1-(6-trifluromethyl-pyridin-2-yl)-propyl]-amide |
| 16aq | 6-((S)-2-Methyl-pyrrolidine-1-carbonyl)-3,4-dihydro-1H-pyrrolo[2,1-c][1,4]oxazine-8-carboxylic acid [(R)-2-methyl-1-(6-trifluromethyl-pyridin-3-yl)-propyl]-amide |
| 16ar | 6-((S)-2-Methyl-pyrrolidine-1-carbonyl)-3,4-dihydro-1H-pyrrolo[2,1-c][1,4]oxazine-8-carboxylic acid [(R)-1-(6-chloro-pyridin-3-yl)-propyl]-amide |
| 16as | 6-((S)-2-Methyl-pyrrolidine-1-carbonyl)-3,4-dihydro-1H-pyrrolo[2,1-c][1,4]oxazine-8-carboxylic acid [(R)-1-(4-chloro-phenyl)-ethyl]-amide |
| 16at | 6-((S)-2-Methyl-pyrrolidine-1-carbonyl)-3,4-dihydro-1H-pyrrolo[2,1-c][1,4]oxazine-8-carboxylic acid [(R)-1-(4-methoxy-phenyl)-propyl]-amide |
| 16au | 6-((S)-2-Methyl-pyrrolidine-1-carbonyl)-3,4-dihydro-1H-pyrrolo[2,1-c][1,4]oxazine-8-carboxylic acid [(R)-1-(4-difluromethyl-phenyl)-propyl]-amide |
| 16av | 6-((S)-2-Methyl-pyrrolidine-1-carbonyl)-3,4-dihydro-1H-pyrrolo[2,1-c][1,4]oxazine-8-carboxylic acid [(R)-1-(4-difluoromethoxy-phenyl)-propyl]-amide |
| 16aw | 6-((S)-2-Methyl-pyrrolidine-1-carbonyl)-3,4-dihydro-1H-pyrrolo[2,1-c][1,4]oxazine-8-carboxylic acid [(R)-1-(4-trifluoromethoxy-phenyl)-propyl]-amide |
| 16ax | 6-((S)-2-Methyl-pyrrolidine-1-carbonyl)-3,4-dihydro-1H-pyrrolo[2,1-c][1,4]oxazine-8-carboxylic acid [(R)-1-(4-trifluromethylsulfanyl-phenyl)-propyl]-amide |
| 16ay | 6-((S)-2-Methyl-pyrrolidine-1-carbonyl)-3,4-dihydro-1H-pyrrolo[2,1-c][1,4]oxazine-8-carboxylic acid [(R)-1-(4-cyano-2-fluoro-phenyl)-propyl]-amide |
| 16az | 6-((S)-2-Methyl-pyrrolidine-1-carbonyl)-3,4-dihydro-1H-pyrrolo[2,1-c][1,4]oxazine-8-carboxylic acid [(R)-1-(4-fluoro-phenyl)-propyl]-amide |
| 16ba | 6-((S)-2-Methyl-pyrrolidine-1-carbonyl)-3,4-dihydro-1H-pyrrolo[2,1-c][1,4]oxazine-8-carboxylic acid [(R)-1-(4-cyano-2,6-difluoro-phenyl)-propyl]-amide |
| 16bb | 6-((S)-2-Methyl-pyrrolidine-1-carbonyl)-3,4-dihydro-1H-pyrrolo[2,1-c][1,4]oxazine-8-carboxylic acid [(R)-1-(2-chloro-4-cyano-phenyl)-propyl]-amide |
| 16bc | 6-((S)-2-Methyl-pyrrolidine-1-carbonyl)-3,4-dihydro-1H-pyrrolo[2,1-c][1,4]oxazine-8-carboxylic acid {1-[4-(1,1-difluro-ethyl)-phenyl]-propyl}-amide |
| 16bd | 6-((S)-2-Methyl-pyrrolidine-1-carbonyl)-3,4-dihydro-1H-pyrrolo[2,1-c][1,4]oxazine-8-carboxylic acid ((R)-1-pyrimidin-2-yl-propyl)-amide |
| 16be | 6-((S)-2-Methyl-pyrrolidine-1-carbonyl)-3,4-dihydro-1H-pyrrolo[2,1-c][1,4]oxazine-8-carboxylic acid [(R)-1-(6-cyano-pyridin-2-yl)-propyl]-amide |
| 16bf | 6-((S)-2-Methyl-pyrrolidine-1-carbonyl)-3,4-dihydro-1H-pyrrolo[2,1-c][1,4]oxazine-8-carboxylic acid [1-(4-pentafluorosulfanyl)-phenyl)-propyl]-amide |
| 16bg | 6-((S)-2-Methyl-pyrrolidine-1-carbonyl)-3,4-dihydro-1H-pyrrolo[2,1-c][1,4]oxazine-8-carboxylic acid [(R)-1-(5-bromo-thiophen-2-yl)-propyl]-amide |
| 16bh | 6-((S)-2-Methyl-pyrrolidine-1-carbonyl)-3,4-dihydro-1H-pyrrolo[2,1-c][1,4]oxazine-8-carboxylic acid [(R)-1-(5-trifluoromethyl-pyrimidin-2-yl)-propyl]-amide |
| 16bi | 6-((S)-2-Methyl-pyrrolidine-1-carbonyl)-3,4-dihydro-1H-pyrrolo[2,1-c][1,4]oxazine-8-carboxylic acid [(R)-1-(6-trifluoromethyl-pyridin-3-yl)-propyl]-amide |

TABLE 10-continued

| | |
|---|---|
| 16bj | 6-((S)-2-Methyl-pyrrolidine-1-carbonyl)-3,4-dihydro-1H-pyrrolo[2,1-c][1,4]oxazine-8-carboxylic acid [(S)-1-(6-trifluoromethyl-pyridin-3-yl)-propyl]-amide |
| 16bk | 6-((S)-2-Methyl-pyrrolidine-1-carbonyl)-3,4-dihydro-1H-pyrrolo[2,1-c][1,4]oxazine-8-carboxylic acid [(R)-1-(5-trifluoromethyl-pyridin-3-yl)-propyl]-amide |
| 16bl | 6-((S)-2-Methyl-pyrrolidine-1-carbonyl)-3,4-dihydro-1H-pyrrolo[2,1-c][1,4]oxazine-8-carboxylic acid [(R)-1-(5-trifluoromethyl-pyridin-2-yl)-propyl]-amide |
| 16bm | 6-((S)-2-Methyl-pyrrolidine-1-carbonyl)-3,4-dihydro-1H-pyrrolo[2,1-c][1,4]oxazine-8-carboxylic acid [(R)-1-(3-fluoro-4-trifluoromethyl-phenyl)-propyl]-amide |
| 16bn | 6-((S)-2-Methyl-pyrrolidine-1-carbonyl)-3,4-dihydro-1H-pyrrolo[2,1-c][1,4]oxazine-8-carboxylic acid [(S)-1-(3-fluoro-4-trifluoromethyl-phenyl)-propyl]-amide |
| 16bo | 6-((S)-2-Methyl-pyrrolidine-1-carbonyl)-3,4-dihydro-1H-pyrrolo[2,1-c][1,4]oxazine-8-carboxylic acid [(R)-1-(4-fluoro-3-trifluoromethyl-phenyl)-propyl]-amide |
| 16bp | 6-((S)-2-Methyl-pyrrolidine-1-carbonyl)-3,4-dihydro-1H-pyrrolo[2,1-c][1,4]oxazine-8-carboxylic acid [(S)-1-(4-fluoro-3-trifluoromethyl-phenyl)-propyl]-amide |
| 16br | 6-((S)-2-Methyl-pyrrolidine-1-carbonyl)-3,4-dihydro-1H-pyrrolo[2,1-c][1,4]oxazine-8-carboxylic acid [(R)-1-(4-chloro-6-trifluoromethyl-pyridin-3-yl)-propyl]-amide |
| 16bs | 6-((S)-2-Methyl-pyrrolidine-1-carbonyl)-3,4-dihydro-1H-pyrrolo[2,1-c][1,4]oxazine-8-carboxylic acid [(S)-1-(4-chloro-6-trifluoromethyl-pyridin-3-yl)-propyl]-amide |
| 16bt | 6-((S)-2-Methyl-pyrrolidine-1-carbonyl)-3,4-dihydro-1H-pyrrolo[2,1-c][1,4]oxazine-8-carboxylic acid [(R)-1-(2-trifluoromethyl-pyridin-5-yl)-propyl]-amide |
| 16bu | 6-((S)-2-Methyl-pyrrolidine-1-carbonyl)-3,4-dihydro-1H-pyrrolo[2,1-c][1,4]oxazine-8-carboxylic acid [(R)-1-(3-fluoro-2-trifluoromethyl-pyridin-4-yl)-propyl]-amide |
| 16bv | 6-((S)-2-Methyl-pyrrolidine-1-carbonyl)-3,4-dihydro-1H-pyrrolo[2,1-c][1,4]oxazine-8-carboxylic acid [(R)-1-(3,5-dichloro-pyridin-4-yl)-propyl]-amide |
| 16bw | 6-((S)-2-Methyl-pyrrolidine-1-carbonyl)-3,4-dihydro-1H-pyrrolo[2,1-c][1,4]oxazine-8-carboxylic acid [(R)-1-(3-chloro-pyridin-4-yl)-propyl]-amide |
| 16bx | 6-((S)-2-Methyl-pyrrolidine-1-carbonyl)-3,4-dihydro-1H-pyrrolo[2,1-c][1,4]oxazine-8-carboxylic acid [(S)-1-(4,6-bis-trifluoromethyl-pyridin-3-yl)-propyl]-amide |
| 16by | 6-((S)-2-Methyl-pyrrolidine-1-carbonyl)-3,4-dihydro-1H-pyrrolo[2,1-c][1,4]oxazine-8-carboxylic acid [(R)-1-(4,6-bis-trifluoromethyl-pyridin-3-yl)-propyl]-amide |
| 16bz | 6-((S)-2-Methyl-pyrrolidine-1-carbonyl)-3,4-dihydro-1H-pyrrolo[2,1-c][1,4]oxazine-8-carboxylic acid [(R)-1-(2,2-difluoro-benzo[1,3]dioxol-5-yl)-propyl]-amide |
| 16ca | 6-((S)-2-Methyl-pyrrolidine-1-carbonyl)-3,4-dihydro-1H-pyrrolo[2,1-c][1,4]oxazine-8-carboxylic acid [(R)-1-(4-cyano-3,5-difluoro-phenyl)-propyl]-amide |
| 16cb | 6-((S)-2-Methyl-pyrrolidine-1-carbonyl)-3,4-dihydro-1H-pyrrolo[2,1-c][1,4]oxazine-8-carboxylic acid [(R)-1-(2-methyl-6-trifluoromethyl-pyridin-3-yl)-propyl]-amide |
| 16cc | 6-((S)-2-Methyl-pyrrolidine-1-carbonyl)-3,4-dihydro-1H-pyrrolo[2,1-c][1,4]oxazine-8-carboxylic acid [(R)-1-(2-chloro-6-trifluoromethyl-pyridin-3-yl)-propyl]-amide |
| 16cd | 6-((S)-2-Methyl-pyrrolidine-1-carbonyl)-3,4-dihydro-1H-pyrrolo[2,1-c][1,4]oxazine-8-carboxylic acid [1-(5-trifluoromethyl-thiazol-2-yl)-propyl]-amide (diastereomer 1) |
| 16ce | 6-((S)-2-Methyl-pyrrolidine-1-carbonyl)-3,4-dihydro-1H-pyrrolo[2,1-c][1,4]oxazine-8-carboxylic acid [1-(5-trifluoromethyl-thiazol-2-yl)-propyl]-amide (diastereomer 2) |
| 16cf | 6-((S)-2-Methyl-pyrrolidine-1-carbonyl)-3,4-dihydro-1H-pyrrolo[2,1-c][1,4]oxazine-8-carboxylic acid [(R)-1-(5-trifluoromethyl-thiopen-2-yl)-propyl]-amide |
| 16cg | 6-((S)-2-Methyl-pyrrolidine-1-carbonyl)-3,4-dihydro-1H-pyrrolo[2,1-c][1,4]oxazine-8-carboxylic acid [(R)-1-(3-chloro-4-fluoro-phenyl)-propyl]-amide |
| 16ch | 6-((S)-2-Methyl-pyrrolidine-1-carbonyl)-3,4-dihydro-1H-pyrrolo[2,1-c][1,4]oxazine-8-carboxylic acid [(R)-1-(3-chloro-4-methoxy-phenyl)-propyl]-amide |
| 16ci | 6-((S)-2-Methyl-pyrrolidine-1-carbonyl)-3,4-dihydro-1H-pyrrolo[2,1-c][1,4]oxazine-8-carboxylic acid [(R)-1-(3,4-dichloro-phenyl)-propyl]-amide |
| 16cj | 6-((S)-2-Methyl-pyrrolidine-1-carbonyl)-3,4-dihydro-1H-pyrrolo[2,1-c][1,4]oxazine-8-carboxylic acid [(R)-1-(5-chloro-pyridin-3-yl)-propyl]-amide |
| 16ck | 6-((S)-2-Methyl-pyrrolidine-1-carbonyl)-3,4-dihydro-1H-pyrrolo[2,1-c][1,4]oxazine-8-carboxylic acid [(R)-1-(5-fluoro-6-trifluoromethyl-pyridin-3-yl)-propyl]-amide |
| 16cl | 6-((S)-2-Methyl-pyrrolidine-1-carbonyl)-3,4-dihydro-1H-pyrrolo[2,1-c][1,4]oxazine-8-carboxylic acid [(R)-1-(2,6-difluoro-4-trifluoromethyl-phenyl)-propyl]-amide |

TABLE 10-continued

| | |
|---|---|
| 16cm | 6-((S)-2-Methyl-pyrrolidine-1-carbonyl)-3,4-dihydro-1H-pyrrolo[2,1-c][1,4]oxazine-8-carboxylic acid [(S)-1-(2,6-difluoro-4-trifluoromethyl-phenyl)-propyl]-amide |
| 16cn | 6-((S)-2-Methyl-pyrrolidine-1-carbonyl)-3,4-dihydro-1H-pyrrolo[2,1-c][1,4]oxazine-8-carboxylic acid [(R)-1-(6-methoxy-5-trifluoromethyl-pyridin-3-yl)-propyl]-amide |
| 16co | 6-((S)-2-Methyl-pyrrolidine-1-carbonyl)-3,4-dihydro-1H-pyrrolo[2,1-c][1,4]oxazine-8-carboxylic acid [(R)-1-(5,6-dichloro-pyridin-3-yl)-propyl]-amide |
| 16cp | 6-((S)-2-Methyl-pyrrolidine-1-carbonyl)-3,4-dihydro-1H-pyrrolo[2,1-c][1,4]oxazine-8-carboxylic acid [(R)-1-(2,4-bis-trifluoromethyl-phenyl)-propyl]-amide |
| 16cq | 6-((S)-2-Methyl-pyrrolidine-1-carbonyl)-3,4-dihydro-1H-pyrrolo[2,1-c][1,4]oxazine-8-carboxylic acid [(R)-1-(2-chloro-4-trifluoromethyl-phenyl)-propyl]-amide |
| 16cs | 6-((S)-2-Methyl-pyrrolidine-1-carbonyl)-3,4-dihydro-1H-pyrrolo[2,1-c][1,4]oxazine-8-carboxylic acid [(R)-1-(4-chloro-3-trifluoromethyl-phenyl)-propyl]-amide |
| 16ct | 6-((S)-2-Methyl-pyrrolidine-1-carbonyl)-3,4-dihydro-1H-pyrrolo[2,1-c][1,4]oxazine-8-carboxylic acid [(R)-1-(2-fluoro-4-trifluoromethyl-phenyl)-propyl]-amide |
| 16cu | 6-((S)-2-Methyl-pyrrolidine-1-carbonyl)-3,4-dihydro-1H-pyrrolo[2,1-c][1,4]oxazine-8-carboxylic acid [(S)-2-trifluoromethyl-6,7-dihydro-5H-[1]pyridin-5-yl)-amide |
| 16cv | 6-((S)-2-Methyl-pyrrolidine-1-carbonyl)-3,4-dihydro-1H-pyrrolo[2,1-c][1,4]oxazine-8-carboxylic acid [(R)-2-trifluoromethyl-6,7-dihydro-5H-[1]pyridin-5-yl)-amide |
| 16cw | 6-((S)-2-Methyl-pyrrolidine-1-carbonyl)-3,4-dihydro-1H-pyrrolo[2,1-c][1,4]oxazine-8-carboxylic acid [(R)-1-(5-methoxy-6-trifluoromethyl-pyridin-3-yl)-propyl]-amide |
| 16cy | 6-(Pyrrolidine-1-carbonyl)-3,4-dihydro-1H-pyrrolo[2,1-c][1,4]oxazine-8-carboxylic acid [(R)-1-(2-chloro-phenyl)-propyl]-amide |
| 16cz | 6-(Pyrrolidine-1-carbonyl)-3,4-dihydro-1H-pyrrolo[2,1-c][1,4]oxazine-8-carboxylic acid [1-(2-difluromethoxy-phenyl)-propyl]-amide |
| 16da | 6-(Pyrrolidine-1-carbonyl)-3,4-dihydro-1H-pyrrolo[2,1-c][1,4]oxazine-8-carboxylic acid [(R)-1-(2-trifluromethyl-phenyl)-propyl]-amide |
| 16db | 6-(Pyrrolidine-1-carbonyl)-3,4-dihydro-1H-pyrrolo[2,1-c][1,4]oxazine-8-carboxylic acid [(R)-1-(2-chloro-4-fluoro-phenyl)-propyl]-amide |
| 16de | 6-(Pyrrolidine-1-carbonyl)-3,4-dihydro-1H-pyrrolo[2,1-c][1,4]oxazine-8-carboxylic acid [(R)-1-(2,4-difluoro-phenyl)-propyl]-amide |
| 16df | 6-(Pyrrolidine-1-carbonyl)-3,4-dihydro-1H-pyrrolo[2,1-c][1,4]oxazine-8-carboxylic acid [2,2,2-trifluoro-1-(4-fluoro-phenyl)-ethyl]-amide |
| 16dg | 6-(Pyrrolidine-1-carbonyl)-3,4-dihydro-1H-pyrrolo[2,1-c][1,4]oxazine-8-carboxylic acid [(R)-cyclopropyl-(4-fluoro-phenyl)-methyl]-amide |
| 16dh | 6-(Pyrrolidine-1-carbonyl)-3,4-dihydro-1H-pyrrolo[2,1-c][1,4]oxazine-8-carboxylic acid [(S)-cyclopropyl-(4-fluoro-phenyl)-methy]-amide |
| 16di | 6-(Pyrrolidine-1-carbonyl)-3,4-dihydro-1H-pyrrolo[2,1-c][1,4]oxazine-8-carboxylic acid benzhydryl-amide |
| 16dj | 6-(Pyrrolidine-1-carbonyl)-3,4-dihydro-1H-pyrrolo[2,1-c][1,4]oxazine-8-carboxylic acid [3,3,3-trifluoro-1-phenyl-propyl]-amide |
| 16dk | 8-((R)-2-Trifluoromethyl-pyrrolidine-1-carbonyl)-3,4-dihydro-1H-pyrrolo[2,1-c][1,4]oxazine-6-carboxylic acid [(R)-1-(4-fluoro-phenyl)-ethyl]-amide |
| 16dl | ((R)-1-{6-[(R)-1-(4-Fluoro-phenyl)-ethylcarbamoyl]-3,4-dihydro-1H-pyrrolo-[2,1-c][1,4]oxazine-8-carbonyl}-pyrrolidin-2-yl)-acetic acid ethyl ester |
| 16dm | 3,4-Dihydro-1H-pyrrolo[2,1-c][1,4]oxazine-6,8-dicarboxylic acid bis-{[(R)-1-(4-fluoro-phenyl)-ethyl]-amide} |
| 16dn | 3,4-Dihydro-1H-pyrrolo[2,1-c][1,4]oxazine-6,8-dicarboxylic acid 6-{[(R)-1-(4-fluoro-phenyl)-ethyl]-amide} 8-[((R)-1-phenyl-ethyl)-amide] |
| 16do | 3,4-Dihydro-1H-pyrrolo[2,1-c][1,4]oxazine-6,8-dicarboxylic acid 6-{[(R)-1-(4-fluoro-phenyl)-ethyl]-amide} 8-{[(R)-1-(2-fluoro-phenyl)-ethyl]-amide} |
| 16dq | 3,4-Dihydro-1H-pyrrolo[2,1-c][1,4]oxazine-6,8-dicarboxylic acid 6-{[(R)-1-(4-fluoro-phenyl)-ethyl]-amide} 8-{(R)-1-(2-fluoro-phenyl)-ethyl]-amide} |
| 16dr | 3,4-Dihydro-1H-pyrrolo[2,1-c][1,4]oxazine-6,8-dicarboxylic acid 6-{[(R)-1-(4-fluoro-phenyl)-ethyl]-amide} 8-[(2,2,2-trifluoro-ethyl)-amide] |
| 16ds | 3,4-Dihydro-1H-pyrrolo[2,1-c][1,4]oxazine-6,8-dicarboxylic acid 8-cyclopropylmethyl-amide 6-{[(R)1-(4-fluoro-phenyl)-ethyl]-amide} |
| 16dt | 3,4-Dihydro-1H-pyrrolo[2,1-c][1,4]oxazine-6,8-dicarboxylic acid 6-{[(R)-1-(4-fluoro-phenyl)-ethyl]-amide} 8-{[(R)-1-(2-trifluromethyl-pyridin-3-yl)-propyl]-amide} |
| 16du | 3,4-Dihydro-1H-pyrrolo[2,1-c][1,4]oxazine-6,8-dicarboxylic acid 6-{[(R)-1-(4-fluoro-phenyl)-ethyl]-amide} 8-{[(R)-1-(6-methoxy-pyridin-3-yl)-propyl]-amide} |
| 16dv | 3,4-Dihydro-1H-pyrrolo[2,1-c][1,4]oxazine-6,8-dicarboxylic acid 6-{[(R)-1-(4-fluoro-phenyl)-ethyl]-amide} 8-{[(S)-1-(5-methoxy-pyrazin-2-yl)-propyl]-amide} |
| 16dw | 3,4-Dihydro-1H-pyrrolo[2,1-c][1,4]oxazine-6,8-dicarboxylic acid 6-{[(R)-1-(4-fluoro-phenyl)-ethyl]-amide} 8-{[(R)-1-(5-methoxy-pyrazin-2-yl)-propyl]-amide} |
| 16dx | 3,4-Dihydro-1H-pyrrolo[2,1-c][1,4]oxazine-6,8-dicarboxylic acid 6-{[(R)-1-(4-fluoro-phenyl)-ethyl]-amide} 8-[((S)-1-pyrimidin-2-yl-ethyl)-amide] |

TABLE 10-continued

| | |
|---|---|
| 16dy | 3,4-Dihydro-1H-pyrrolo[2,1-c][1,4]oxazine-6,8-dicarboxylic acid 6-{[(R)-1-(4-fluoro-phenyl)-ethyl]-amide} 8-[((R)-1-pyrimidin-2-yl-ethyl)-amide] |
| 16dz | 3,4-Dihydro-1H-pyrrolo[2,1-c][1,4]oxazine-6,8-dicarboxylic acid 6-{[(R)-1-(4-fluoro-phenyl)-ethyl]-amide} 8-[((R)-1-pyrimidin-2-yl-propyl)-amide] |
| 16ea | 3,4-Dihydro-1H-pyrrolo[2,1-c][1,4]oxazine-6,8-dicarboxylic acid 8-[cyclopropylmethyl-(1-pyrimidin-2-yl-ethyl)-amide] 6-{[(R)-1-(4-fluoro-phenyl)-ethyl]-amide} |
| 16eb | 3,4-Dihydro-1H-pyrrolo[2,1-c][1,4]oxazine-6,8-dicarboxylic acid 6-{[(R)-1-(4-fluoro-phenyl)-ethyl]-amide} 8-[[(R)-1-(4-trifluoromethyl-phenyl)-propyl]-amide} |
| 16ec | 3,4-Dihydro-1H-pyrrolo[2,1-c][1,4]oxazine-6,8-dicarboxylic acid 8-{[(R)-1-(4-cyano-phenyl)-propyl]-amide} 6-{[(R)-1-(4-fluoro-phenyl)-ethyl]-amide} |
| 16ed | 3,4-Dihydro-1H-pyrrolo[2,1-c][1,4]oxazine-6,8-dicarboxylic acid 6-{[(R)-1-(4-fluoro-phenyl)-ethyl]-amide} 8-{[(R)-1-(5-trifluoromethyl-pyrimidin-2-yl-propyl]-amide} |
| 16ee | 3,4-Dihydro-1H-pyrrolo[2,1-c][1,4]oxazine-6,8-dicarboxylic acid 6-{[(R)-1-(4-fluoro-phenyl)-ethyl]-amide} 8-{[(S)-1-(5-trifluoromethyl-pyrimidin-2-yl-propyl]-amide} |
| 16ef | 3,4-Dihydro-1H-pyrrolo[2,1-c][1,4]oxazine-6,8-dicarboxylic acid 6-{[(S)-1-(4-fluoro-phenyl)-ethyl]-amide} 8-[((R)-1-pyrimidin-2-yl-propyl)-amide] |
| 16eg | 3,4-Dihydro-1H-pyrrolo[2,1-c][1,4]oxazine-6,8-dicarboxylic acid 6-{[(R)-1-(4-fluoro-phenyl)-ethyl]-amide} 8-{[(R)-1-(5-trifluromethyl-pyridin-2-yl)-propyl]-amide} |
| 16ei | 6-(2-isopropyl-pyrrolidine-1-carbonyl)-3,4-dihydro-1H-pyrrolo[2,1-c][1,4]oxazine-8-carboxylic acid ((R)-1-phenyl-propyl)-amide |
| 16em | 6-(4-Methyl-2-phenyl-piperazine-1-carbonyl)-3,4-dihydro-1H-pyrrolo[2,1-c][1,4]oxazine-8-carboxylic acid ((R)-1-phenyl-propyl)-amide |
| 16en | 6-(2-Trifluoromethoxymethyl-pyrroiidine-1-carbonyl)-3,4-dihydro-1H-pyrrolo[2,1-c][1,4]oxazine-8-carboxylic acid ((R)-1-phenyl-propyl)-amide |
| 16eo | 6-((R)-2-Methoxymethyl-pyrrolidine-1-carbonyl)-3,4-dihydro-1H-pyrrolo[2,1-c][1,4]oxazine-8-carboxylic acid ((R)-1-phenyl-propyl)-amide |
| 16ep | 6-((2R,5R)-2,5-Bis-methoxymethyl-pyrrolidine-1-carbonyl)-3,4-dihydro-1H-pyrrolo[2,1-c][1,4]oxazine-8-carboxylic acid ((R)-1-phenyl-propyl)-amide |
| 16eq | 6-[2-(3-Methyl-isoxazol-5-yl)-pyrrolidine-1-carbonyl]-3,4-dihydro-1H-pyrrolo[2,1-c][1,4]oxazine-8-carboxylic acid ((R)-1-phenyl-propyl)-amide |
| 16er | 6-[2-(3,5-Dimethyl-isoxazol-4-yl)-pyrrolidine-1-carbonyl]-3,4-dihydro-1H-pyrrolo[2,1-c][1,4]oxazine-8-carboxylic acid ((R)-1-phenyl-propyl)-amide |
| 16es | 6-((S)-3-Ethoxy-pyrrolidine-1-carbonyl)-3,4-dihydro-1H-pyrrolo[2,1-c][1,4]oxazine-8-carboxylic acid ((R)-1-phenyl-propyl)-amide |
| 16et | 6-[(R)-2-(Cyclopropyl-hydroxy-methyl)-pyrrolidine-1-carbonyl]-3,4-dihydro-1H-pyrrolo[2,1-c][1,4]oxazine-8-carboxyiic acid ((R)-1-phenyl-propyl)-amide |
| 16eu | 6-((R)-2-Trifluoromethyl-pyrrolidine-1-carbonyl)-3,4-dihydro-1H-pyrrolo[2,1-c][1,4]oxazine-8-carboxylic acid ((R)-1-phenyl-propyl)-amide |
| 16ev | 6-((S)-3-Cyclopropylmethoxy-pyrrolidine-1-carbonyl)-3,4-dihydro-1H-pyrrolo[2,1-c][1,4]oxazine-8-carboxylic acid ((R)-1-phenyl-propyl)-amide |
| 16ew | 6-[2-(l-Hydroxy-1-methyl-ethyl)-pyrrolidine-1-carbonyl]-3,4-dihydro-1H-pyrrolo(2,1-c][1,4]oxazine-8-carboxylic acid ((R)-phenyl-propyl)-amide |
| 16ex | 6-(2-tert-Butyl-pyrrolidine-1-carbonyl)-3,4-dihydro-1H-pyrrolo[2,1-c][l,4]oxazine-8-carboxylic acid ((R)-1-phenyl-propyl)-amide |
| 16ey | 6-[(R)-2-(1-Hydroxy-ethyl)-pyrrolidine-1-carbonyl]-3,4-dihydro-1H-pyrrolo[2,1-c][1,4]oxazine-8-carboxylic acid ((R)-1-phenyl-propyl)-amide |
| 16ez | |6-[(R)-2-(1-Methoxy-ethyl)-pyrrolidine-1-carbonyl]-3,4-dihydro-1H-pyrrolo[2,1-c][1,4]oxazine-8-carboxylic acid ((R)-1-phenyl-propy)-amide |
| 16fb | 6-(2,2-Dimethyl-pyrrolidine-1-carbonyl)-3,4-dihydro-1H-pyrrolo[2,1-c][1,4]oxazine-8-carboxylic acid ((R)-1-phenyl-propyl)-amide |
| 16fc | 6-((S)-2-Ethyl-pyrrolidine-1-carbonyl)-3,4-dihydro-1H-pyrrolo[2,1-c][1,4]oxazine-8-carboxylic acid ((R)-1-phenyl-propyl)-amide |
| 16fd | 6-((R)-2-Ethyl-pyrrolidine-1-carbonyl)-3,4-dihydro-1H-pyrrolo[2,1-c][1,4]oxazine-8-carboxylic acid ((R)-1-phenyl-propyl)-amide |
| 16fe | 6-(3-Aza-bicyclo[3.1.0]hexane-3-carbonyl)-3,4-dihydro-1H-pyrrolo|2,1-c][1,4]oxazine-8-carboxylic acid ((R)-1-phenyl-propyl)-amide |
| 16fg | 6-((S)-3-Isobutoxy-pyrrolidine-1-carbonyl)-3,4-dihydro-1H-pyrrolo[2,1-c][1,4]oxazine-8-carboxylic acid ((R)-1-phenyl-propyl)-amide |
| 16fh | 6-[(R)-2-(Acetylamino-methyl)-pyrrolidine-1-carbonyl]-3,4-dihydro-1H-pyrrolo[2,1-c][1,4]oxazine-8-carboxylic acid ((R)-1-phenyl-propyl)-amide |
| 16fi | ((R)-1-[8-((R)-1-Phenyl-propylcarbamoyl)-3,4-dihydro-1H-pyrrolo[2,1-c][1,4]oxazine-6-carbonyl]-pyrrolidin-2-yl}-acetic acid ethyl ester |
| 16fj | 6-[2-(Hydroxy-phenyl-methyl)-pyrrolidine-1-carbonyl]-3,4-dihydro-1H-pyrrolo[2,1-c][1,4]oxazine-8-carboxylic acid ((R)-1-phenyl-propyl)-amide |

TABLE 10-continued

| | |
|---|---|
| 16fk | 6-((R)-2-Pyridin-2-yl-pyrrolidine-1-carbonyl)-3,4-dihydro-1H-pyrrolo[2,1-c][1,4]oxazine-8-carboxylic acid ((R)-1-phenyl-propyl)-amide |
| 16fl | 6-[(R)-2-(6-Methoxy-pyridin-3-yl)-pyrrolidine-1-carbonyl]-3,4-dihydro-1H-pyrrolo|2,1-c][1,4]oxazine-8-carboxylic acid ((R)-1-phenyl-propyl)-amide |
| 16fm | 6-((R)-2-Cyano-pyrrolidine-1-carbonyl)-3,4-dihydro-1H-pyrrolo[2,1-c)[1,4]oxazine-8-carboxylic acid ((R)-1-phenyl-propyl)-amide |
| 16fn | 6-((S)-3-Fluoro-pyrrolidine-1-carbonyl)-3,4-dihydro-1H-pyrrolo[2,1-c][1,4]oxazine-8-carboylic acid ((R)-1-phenyl-propyl)-amide |
| 16fo | {(R)-1-[8-((R)-1-Phenyl-propylcarbamoyl)-3,4-dihydro-1H-pyrrolo[2,1-c][1,4]oxazine-6-carbonyl]-pyrrolidin-2-yl}-acetic acid isopropyl ester |
| 16fp | 6-((R)-2-Pyrazin-2-yl-pyrrolidine-1-carbonyl)-3,4-dihydro-1H-pyrrolo[2,1-c][1,4]oxazine-8-carboxylic acid ((R)-1-phenyl-propyl)-amide |
| 16fq | 6-(4-Pyridin-2-yl-piperazine-1-carbonyl)-3,4-dihydro-1H-pyrrolo[2,1-c][1,4]oxazine-8-carboxylic acid (R)-1-phenyl-propyl)-amide |
| 16fr | 6-(2-Morpholin-4-ylmethyl-pyrrolidin-1-carbonyl)-3,4-dihydro-1H-pyrrolo[2,1-c][1,4]oxazine-8-carboxylic acid ((R}-1-phenyl-propyl)-amide |
| 16fs | 6-((S)-2-Methyl-4-pyridin-2-yl-piperazine-1-carbonyl)-3,4-dihydro-1H-pyrrolo[2,1-c][1,4]oxazine-8-carboxylic acid ((R)-1-phenyl-propyl)-amide |
| 16ft | 6-[(S)-2-Methyl-4-(3,3,3-trifluoro-propyl)-piperazine-1-carbonyl]-3,4-dihydro-1H-pyrrolo[2,1-c][1,4]oxazine-8-carboxylic acid ((R)-1-phenyl-propyl)-amide |
| 16fu | 6-[(S)-3-(4-Fluoro-phenoxy)-pyrrolidine-1-carbony]-3,4-dihydro-1H-pyrrolo[2,1-c][1,4]oxazine-8-carboxylic acid ((R)-1-phenyl-propyl)-amid |
| 16fv | 6-[2-(1-Methyl-1H-pyrazol-3-yl)-pyrrolidine-1-carbonyl]-3,4-dihydro-1H-pyrrolo[2,1-c][1,4]oxazine-8-carboxylic acid ((R)-1-phenyl-propyl)-amide |
| 16fw | 6-[2-(1-Pyrazol-1-yl-ethyl)-pyrrolidine-1-carbonyl]-3,4-dihydro-1H-pyrrolo[2,1-c][1,4]oxazine-8-carboxylic acid ((R)-1-phenyl-propyl)-amide |
| 16fx | 6-(2-Ethynyl-pyrrolidine-1-carbonyl)-3,4-dihydro-1H-pyrrolo[2,1 c][1,4]oxazine-8-carboxylic acid ((R)-1-phenyl-propyl)-amide |
| 16fy | 6-((R)-3-Cyano-pyrrolidine-1-carbonyl)-3,4-dihydro-1H-pyrrolo[2,1-c][1,4]oxazine-8-carboxylic acid ((R)-1-phenyl-propyl)-amide |
| 16fz | 6-(2-Pyrimidin-2-yl-pyrrolidine-1-carbonyl)-3,4-dihydro-1H-pyrrolo[2,1-c][1,4]oxazine-8-carboxylic acid ((R)-1-phenyl-propyl)-amide |
| 16ga | 6-[(R)-2-(6-Trifluoromethyl-pyridin-3-yl)-pyrrolidine-1-carbonyl]-3,4-dihydro-1H-pyrrolo[2,1-c][1,4]oxazine-8-carboxylic acid ((R)-1-phenyl-propyl)-amide |
| 16gb | 6-(2-Cyclopropyl-pyrrolidine-1-carbonyl)-3,4-dihydro-1H-pyrrolo[2,1-c][1,4]oxazine-8-carboxylic acid ((R)-1-phenyl-propyl)-amide |
| 16gc | 3,4-Dihydro-1H-pyrrolo[2,1-c][1,4]oxazine-6,8-dicarboxylic acid 6-cyclopropylmethyl-amide 8-[((R)-1-phenyl-propyl)-amide] |
| 16gl | 3,4-Dihydro-1H-pyrrolo[2,1-c][1,4]oxazine-6,8-dicarboxylic acid 6-{[(R)-1-(4-fluoro-phenyl)-ethyl]-amide} 8-[((R)-1-phenyl-propyl)-amide] |
| 16go | 3,4-Dihydro-1H-pyrrolo[2,1-c][1,4]oxazine-6,8-dicarboxylic acid 6-[(2,2-dimethyl-propyl)amide] 8-[((R)-1-phenyl-propyl)-amide] |
| 16gq | 6-((S)-2-Methyl-pyrrolidine-1-carbonyl)-3,4-dihydro-1H-pyrrolo(2,1-c][1,4]oxazine-8-carboxylic acid [(R)-1-(3-cyano-4-fluoro-phenyl)-propyl]-amide |
| 16gt | 3,4-Dihydro-1H-pyrrolo[2,1-c][1,4]oxazine-6,8-dicarboxylic acid 8-[((R)-1-phenyl-propyl)-amide] 6-[(pyrazin-2-ylmethyl)-amide] |
| 16gu | 3,4-Dihydro-1H-pyrrolo[2,1-c][1,4]oxazine-6,8-dicarboxylicacid 6-[(5-fluoro-pyridin-3-ylmethyl)-amide] 8-[((R)-1-phenyl-propyl)-amide] |
| 16gv | 3,4-Dihydro-1H-pyrrolo[2,1-c][1,4]oxazine-6,8-dicarboxylic acid 6-(3-methanesulfonyl-benzylamide) 8-[((R)-1-phenyl-propyl)-amide] |
| 16gw | 3,4-Dihydro-1H-pyrrolo[2,1-c][1,4]oxaline--6,8-diccaboxylic acid 6-(methyl-pyridin-2-ylmethyl-amide) 8-[((R)-1-phenyl-propyl)-amide] |
| 16gx | 3,4-Dihydro-1H-pyrrolo[2,1-c][1,4]oxazine-6,8-dicarboxylic acid 6-(2-methanesulfonyl-benzylamide) 8-[((R)-1-pheny)-propyl)-amide] |
| 16gy | 3,4-Dihydro-1H-pyrrolo[2,1-c][1,4]oxazine-6,8-dicarboxylic acid 6-(2-cyano-benzylamide) 8-[((R)-1-phenyl-propyl)-amide] |
| 16gz | 3,4-Dihydro-1H-pyrrolo[2,1-c][1,4]oxazine-6,8-dicarboxylic acid 6-(3,5-dimethoxy-benzylamide) 8-[((R)-1-phenyl-propyl)-amide] |
| 16ha | 3,4-Dihydro-1H-pyrrolo[2,1-c][1,4]oxazine-6,8-dicarboxylic acid 6-[(oxazol-2-ylmethyl)-amide] 8-[((R)-1-phenyl-propyl)-amide] |
| 16hb | 3,4-Dihydro-1H-pyrrolo[2,1-c][1,4]oxazine-6,8-dicarboxylic acid 6-dicyclopropylmethyl-amide 8-[((R)-1-phenyl-propyl)-amide] |
| 16hc | 3,4-Dihydro-1H-pyrrolo[2,1-c][1,4]oxazine-6,8-dicarboxylic acid 6-[(5-fluoro-pyridin-2-yl)-amide] 8-[((R)-1-phenyl-propyl )-amide] |
| 16hd | 3(4-Dihydro-1H-pyrrolo[2,1-c][1,4]oxazine-6,8-dicarboxylic acid 8-[((R)-1-phenyl-propyl)-amide] 6-[(1-pyrimidin-2-yl-ethyl)-amide] |
| 16he | 3,4-Dihydro-1H-pyrrolo[2,1-c][1,4]oxazine-6,8-dicarboxylic acid 6-(cyclopropylmethyl-methyl-amide) 8-[((R)-1-phenyl-propyl)-amide] |
| 16hf | 3,4-Dihydro-1H-pyrrolo[2,1-c][1,4]oxazine-6,8-dicarboxylic acid 6-[(isoxazol-5-ylmethyl)-amide] 8-[((R)-1-phenyl-propyl)-amide] |
| 16hg | 3,4-Dihydro-1H-pyrrolo[2,1-c][1,4]oxazine-6,8-dicarboxylic acid 6-[(3,5-dimethyl-isoxazol-4yl)-amide] 8-[{(R)-1-phenyl-propyl)-amide] |
| 16hh | 3,4-Dihydro-1H-pyrrolo[2,1-c][1,4]oxazine-6,8-dicarboxylic acid 6-[(1-isoxazol-5-yl-ethyl)-amide] 8-[((R)-1-phenyl-propyl)-amide] |
| 16hi | 3,4-Dihydro-1H-pyrrolo[2,1-c][1,4]oxazine-6,8-dicaboxylic acid 6-[(1-hydroxy-cyclopropylmethyl)-amide] 8-[((R)-1-phenyl-propyl)-amide] |

TABLE 10-continued

| | |
|---|---|
| 16hj | 3,4-Dihydro-1H-pyrrolo[2,1-c][1,4]oxazine-6,8-dicarboxylic acid 8-[((R)-1-phenyl-propyl)-amide] 6-[(pyrimidin-2-ylmethyl)-amide] |
| 16hk | 3,4-Dihydro-1H-pyrrolo[2,1-c][1,4]oxazine-6,8-dicarboxylic acid 6-[cyclopropylmethyl-(2-hydroxy-ethyl)-amide] 8-[((R)-1-phenyl-propyl)-amide] |
| 16hl | 3,4-Dihydro-1H-pyrrolo[2,1-c][1,4]oxazine-6,8-dicarboxylic acid 8-[[(R)-1-phenyl-propyl)-amide] 6-[(1-pyrazin-2-yl-ethyl)-amide] |
| 16hm | 3,4-Dihydro-1H-pyrrolo[2,1-c][1,4]oxazine-6,8-dicarboxylic acid 8-[((R)-I 1-phenyl-propyl)-amide] 6-{[(R)-1-(2-trifluoromethyl-pyridin-3-yl)-propyl]-amide} |
| 16hn | 3,4-Dihydro-1H-pyrrolo[2,1-c][1,4]oxazine-6,8-dicarboxylic acid 8-[((R)-1-phenyl-propyl)-amide] 6-{[(R)-1-(5-trifluoromethyl-pyridin-3-yl)-propyl]-amide} |
| 16ho | 3,4-Dihydro-1H-pyrrolo[2,1-c][1,4]oxazine-6,8-dicarboxylic acid 6-{[1-(6-methyl-pyridin-3-yl)-propyl]-amide} 8-[((R)-1-phenyl-propyl)-amide] |
| 16hp | 3,4-Dihydro-1H-pyrrolo[2,1-c][1,4]oxazine-6,8-dicarboxylic acid 6-{[(S)-1-(6-methoxy-pyridin-3-yl)-propyl]-amide} 8-[((R)-1-phenyl-propyl)-amide] |
| 16hq | (R)-Phenyl-{[8-((R)-1-phenyl-propylcarbamol)-3,4-dihydro-1H-pyrrolo[2,1-c](1,4)oxazine-6-carbonyl]-amino}-acetic acid ethyl ester |
| 16hr | 3,4-Dihydro-1H-pyrrolo[2,1-c][1,4]oxazine-6,8-dicarboxylic acid 8-[((R)-1-phenyl-propyl)-amide) 6-[((R)-1,2,2-trimethyl-propyl)-amide] |
| 16hu | 3,4-Dihydro-1H-pyrrolo[2,1-c][1,4]oxazine-6,8-dicarboxylic acid 6-{[1-{2-methoxy-pyrimidin-5-yl)-propyl]-amide} 8-[((R)-1-phenyl-propyl)-amide] (diastereomer 1) |
| 16hv | 3,4-Dihydro-1H-pyrrolo[2,1-c][1,4]oxazine-6,8-dicarboxylic acid 6-{[1-(2-methoxy-pyrimidin-5-yl)-propyl]-amide} 8-[((R)-1-phenyl-propyl)-amide] (diastereomer 2) |
| 16hw | 3,4-Dihydro-1H-pyrrolo[2,1-c][1,4]oxazine-6,8-dicarboxylic acid 8-[((R)-1-phenyl-propyl)-amide] 6-[((R)-1-pyrazin-2-yl-propyl)-amide] |
| 16hx | 3,4-Dihydro-1H-pyrrolo[2,1-c][1,4]oxazine-6,8-dicarboxylic acid 8-[((R)-1-phenyl-propyl)-amide] 6-[((S)-1-pyrazin-2-yl-propyl)-amide] |
| 16hy | 3,4-Dihydro-1H-pyrrolo[2,1-c][1,4]oxazine-6,8-dicarboxylic acid 6-{[(R)-1-(5methoxy-pyrazin-2-yl)-propyl]-amide} 8-[((R)-1-phenyl-propyl)-amide] |
| 16hz | 3,4-Dihydro-1H-pyrrolo[2,1-c][1,4]oxazine-6(8-dicarboxylic acid 6-{[(S)-1-(5-methoxy-pyrazin-2-yl)-propyl]-amide} 8-[((R)-1-phenyl-propyl)-amide] |
| 16ia | 3,4-Dihydro-1H-pyrrolo[2,1-c][1,4]oxazine-6,8~dicarboxylic acid 6-{[(R)-1-(3-methoxy-pyridin-2-yl)-propyl]-amide} 8-[((R)-1-phenyl-propyl)-amide] |
| 16ib | 3,4-Dihydro-1H-pyrrolo[2,1-c][1,4]oxazine-6,8-dicarboxylic acid 6-{[(R)-1-(6-cyano-pyridin-3-yl)-propyl]-amide} 8-[((R)-1-phenyl-propyl)-amide] |
| 16ic | 3,4-Dihydro-1H-pyrrolo[2,1-c][1,4]oxazine-6,8-dicarboxylic acid 6-{[(R)-1-(6-rnethoxy-pyridin-2-yl)-propyl]-amide} 8-[((R)-1-phenyl-propyl)-amide] |
| 16id | 3,4-Dihydro-1H-pyrrolo[2,1-c][1,4]oxazine-6,8-dicarboxylic acid 8-[((R)-1-phenyl-propyl)amide] 6-{[(R)-1-(6-trifluoromethyl-pyridin-3-yl)-propyl]-amide} |
| 16ie | 3,4-Dihydro-1H-pyrrolo[2,1-c][1,4]oxazine-6,8-dicarboxylic acid 8-[((R)-1-phenyl-propyl)-amide] 6-[(-1-pyrazin-2-yl-ethyl)-amide] (diastereomer 2) |
| 16if | 3,4-Dihydro-1H-pyrrolo[2,1-c][1,4]oxazine-6,8-dicarboxylic acid 8-[((R)-1-phenyl-propyl)-amide] 6-[(-1-pyrazin-2-yl-ethyl)-amide] (diastereomer 1) |
| 16ig | [3,4-Dihydro-1H-pyrrolo[2,1-c][1,4]oxazine-6,8-dicarboxylic acid 6-{[(R)-1-(2-methoxy-pyridin-3-yl)-propyl]-amide} 8-[((R)-1-phenyl-propyl)-amide] |
| 16ih | 6-(1,3-Dihydro-isoindole-2-carbonyl)-3,4-dihydro-1H-pyrrolo[2,1-c][1,4]oxazine-8-carboxylic acid ((R)-1-phenyl-propyl)-amide |
| 16ii | 3,4-Dihydro-1H-pyrrolo[2,1-c][1,4]oxazine-6,8-dicarboxylic acid 8-[((R)-1-phenyl-propyl)-amide] 6-[(2H-[1,2,4]triazol-3-ylmethyl)-amide] |
| 16ij | 3,4-Dihydro-1H-pyrrolo[2,1-c][1,4]oxazine-6,8-dicarboxylic acid 8-[((R)-1-phenyl-propyl)-amide] 6-[(1-thiazol-2-yl-propyl)-amide] |
| 16ik | 3,4-Dihydro-1H-pyrrolo[2,1-c][1,4]oxazine-6,8-dicarboxylic acid 6-{[(S)-cyclopropyl-(4-fluoro-phenyl)-methyl]-amide} 8-[((R)-1-phenyl-propyl)-amide] |
| 16il | 3,4-Dihydro-1H-pyrrolo[2,1-c][1,4]oxazine-6,8-dicarboxylic acid 8-[((R)-1-phenyl-propyl)-amide] 6-[(thiazole-2-ylmethyl)-amide] |
| 16im | 3,4-Dihydro-1H-pyrrolo[2,1-c][1,4]oxazine-6,8-dicarboxylic acid 6-[(-1-isoxazol-3-yl-ethyl)-amide] 8-[((R)-1-phenyl-propyl)-amide] (diastereomer 1) |
| 16in | 3,4-Dihydro-1H-pyrrolo[2,1-][1,4]oxazine-6,8-dicarboxylic acid 6-[(-1-isoxazol-3-yl-ethyl)-amide] 8-[((R)-1-phenyl-propyl)-amide] (diastereorner 2) |
| 16io | 3,4-Dihydro-1H-pyrrolo[2,1-c][1,4]oxazine-6,8-dicarboxylic acid 8-[((R)-1-phenyl-propyl)-amide] 6-[(5,6,7,8-tetrahydro-quinoxalin-5yl)-amide] |
| 16ip | 3,4-Dihydro-1H-pyrrolo[2,1-c][1,4]oxazine-6,8-dicarboxylic acid 8-[((R)-1-phenyl-propyl)-arnide] 6-{[1-(3-sulfamoyl-phenyl)-ethyl]-amide} |
| 16iq | 3-({[8-((R)-1-Phenyl-propylcarbamoyl)-3,4-dihydro-1H-pyrrolo[2,1-c][1,4]oxazine-6-carbonyl]-amino}-methyl)-benzoic acid methyl ester |
| 16ir | 4-({[8-((R)-1-Phenyl-propylcarbamoyl)-3,4-dihydro-1H-pyrrolo[2,1-c][1,4]oxazine-6-carbonyl-amino]-methyl)-benzoic acid methyl ester |
| 16is | 4-({[8-((R)-1-Phenyl-propylcarbamoyl)-3,4-dihydro-1H-pyrrolo[2,1-c][1,4]oxazine-6-carbonyl]-amino}-methyl)-phenyl)-acetic acid methyl ester |

TABLE 10-continued

| | |
|---|---|
| 16it | (S)-2-{[8-((R)-1-Phenyl-propylcarbamoyl)-3,4-dihydro-1H-pyrrolo[2,1-c][1,4]oxazine-6-carbonyl-amino}-propionic acid isopropyl ester |
| 16iu | {Methyl-[8-((R)-1-phenyl-propylcarbamoyl)-3,4-dihydro-1H-pyrrolo[2,1-c][1,4]oxazine-6-carbonyl]-amino}-acetic acid isopropyl ester |
| 16iv | 3,4-Dihydro-1H-pyrrolo[2,1-c][1,4]oxazine-6,8-diicarboxylic acid 6-{[1-(5-methoxy-pyrazin-2-yl)-ethyl]-amide} 8-[((R)-1-phenyl-propyl)-amide] |
| 16iw | {(8-((R)-1-Phenyl-propylcarbamoyl)-3,4-dihydro-1H-pyrrolo[2,1-c][1,4]oxazine-6-carbonyl]-amino}-acetic acid isopropyl ester |
| 16ix | 3,4-Dihydro-1H-pyrrolo[2,1-c][1,4]oxazine-6,8-dicarboxylic acid 6-{[(R)-1-(3-hydroxy-phenyl)-propyl]-amide} 8-[((R)-1-phenyl-propyl)-amide] |
| 16iy | {Methyl-[8-((R)-1-phenyl-propylcarbamoyl)-3,4-dihydro-1H-pyrrolo[2,1-c][1,4]oxazine-6-carbonyl]-amino}-acetic acid ethyl ester |
| 16iz | 3,4-Dihydro-1H-pyrrolo[2,1-c][1,4]oxazine-6,8-diicarboxylic acid 6-[((S)-1-hydroxymethyl-2-methyl-propyl)-amide] 8-[({R)-1-phenyl-propyl)-amide] |
| 16ja | (S)-2-[Methyl-[8-((R)-1-phenyl-propylcarbamoyl)-3,4-dihydro-1H-ester pyrrolo[2,1-c][1,4]oxazine-6-carbonyl]-amino}-propionic acid isopropyl |
| 16jc | 3,4-Dihydro-1H-pyrrolo[2,1-c][1,4]oxazine-6,8-dicarboxylic acid 6-(methyl-pyrimidin-2-ylmethyl-amide) 8-[((R)-1-phenyl-propyl)-amide] |
| 16jd | 3,4-Dihydro-1H-pyrrolo[2,1-c][1,4]oxazine-6,8-dicarboxylic acid 6-[(2-hydroxy-2-methyl-propyl)-amide] 8-[((R)-1-phenyl-propyl)-amide] |
| 16je | 3,4-Dihydro-1H-pyrrolo[2,1-c][1,4]oxazine-6,8-dicarboxylic acid 6-[(1H-indol-6-ylmethyl)-amide] 8-[((R)-1-phenyl-propyl)-amide] |
| 16jf | 3,4-Dihydro-1H-pyrrolo[2,1-c][1,4]oxazine-6,8-dicarboxylic acid 8-[((R)-1-phenyl-propyl)-amide] 6-[(pyridazin-3-ylmethyl)-amide] |
| 16jg | 3,4-Dihydro-1H-pyrrolo[2,1-c][1,4]oxazine-6,8-dicarboxylic acid 6-[(6-methoxy-pyridin-3-ylmethyl)-amide] 8-[((R)-1-phenyl-propyl)-amide] |
| 16jh | 3,4-Dihydro-1H-pyrrolo[2,1-c][1,4]oxazine-6,8-dicarboxylic acid 6-{[(R)-1-(3-methanesulfonyl-phenyl)-propyl]-amide}-8-[((R)-1-phenyl-propyl)-amide] |
| 16ji | 3,4-Dihydro-1H-pyrrolo[2,1-c][1,4]oxazine-6,8-dicarboxylic acid 8-[((R)-1-phenyl-propyl)-amide] 6-{[1-(3-sulfamoyl-phenyl)-propyl]-amide} |
| 16jj | 3,4-Dihydro-1H-pyrrolo[2,1-c][1,4]oxazine-6,8-dicarboxylic acid 6-[((R)-1-hydroxymethyl-2-methyl-propyl-amide] 8-[((R)-1-phenyl-propyl)-amide] |
| 16jk | 3,4-Dihydro-1H-pyrrolo[2,1-c][1,4]oxazine-6,8-dicarboxylic acid 8-[(3,5-dimethyl-isoxazol-4-yl)-amide] 6-[((R)-1-phenyl-propyl)-amide] |
| 16jl | 3,4-Dihydro-1H-pyrrolo[2,1-c][1,4]oxazine-6,8-dicarboxylic acid 8-[(3,5-dimethyl-isoxazol-4-ylmethyl)-amide] 6-[((R)-1-phenyl-propyl)-amide] |
| 16jm | 3,4-Dihydro-1H-pyrrolo[2,1-c][1,4]oxazine-6,8-dicarboxylic acid 6-[((R)-1-phenyl-propyl)-amide] 8-[(pyrimidin-2-ylmethyl)-amide] |
| 16jn | 3,4-Dihydro-1H-pyrrolo[2,1-c][1,4]oxazine-6,8-dicarboxylic acid 8-[(oxazol-2-ylmethyl)-amide] 6-[((R)-1-phenyl-propyl)-amide] |
| 16jo | 3,4-Dihydro-1H-pyrrolo[2,1-c][1,4]oxazine-6,8-dicarboxylic acid 8-{[(R)-1-(6-methoxy-pyridin-3-yl)-propyl]-amide} 6-[((R)-1-phenyl-propyl)-amide] |
| 16jp | 3,4-Dihydro-1H-pyrrolo[2,1-c][1,4]oxazine-6,8-dicarboxylic acid 8-{[(R)-1-(4-fluoro-phenyl)-ethyl]-amide} 6-[((S)-1-phenyl-propyl)-amide] |
| 16jq | 3,4-Dihydro-1H-pyrrolo[2,1-c][1,4]oxazine-6,8-dicarboxylic acid 8-{[(R)-1-(4-fluoro-phenyl)-2-methyl-propyl]-amide} 6-[((S)-1-phenyl-propyl)-amide] |
| 16jr | 3,4-Dihydro-1H-pyrrolo[2,1-c][1,4]oxazine-6,8-dicarboxylic acid 8-cyclopropylmethyl-amide 6-[((S)-1-phenyl-propyl)-amide] |
| 16js | 3,4-Dihydro-1H-pyrrolo[2,1-c][1,4]oxazine-6,8-dicarboxylic acid 8-[(benzooxazol-2-ylmethyl)-amide] 6-[((R)-1-phenyl-propyl)-amide] |
| 16jt | 3,4-Dihydro-1H-pyrrolo[2,1-c][1,4]oxazine-6,8-dicarboxylic acid 6-[((R)-1-phenyl-propyl)-amide] 8-[(thiazol-2-ylmethyl)-amide] |
| 16ju | 3,4-Dihydro-1H-pyrrolo[2,1-c][1,4]oxazine-6,8-dicarboxylic acid 8-[(4,5-dimethyl-thiazol-2-yl)-amide] 6-[((R)-1-phenyl-propyl)-amide] |
| 16jv | 3,4-Dihydro-1H-pyrrolo[2,1-c][1,4]oxazine-6,8-dicarboxylic acid 8-isoxazol-4-ylamide 6-[((R)-1-phenyl-propyl)-amide] |
| 16jw | 3,4-Dihydro-1H-pyrrolo[2,1-c][1,4]oxazine-6,8-dicarboxylic acid 6-[((R)-1-phenyl-propyl)-amide] 8-[(1-pyrazin-2-yl-ethyl)-amide] (diastereomer 1) |
| 16jx | 3,4-Dihydro-1H-pyrrolo[2,1-c][1,4]oxazine-6,8-dicarboxylic acid 8-[(2-chloro-5-trifluoromethyl-phenyl)-amide] 6-[((R)-phenyl-propyl)-amide] |
| 16jy | 3,4-Dihydro-1H-pyrrolo[2,1-c][1,4]oxazine-6,8-dicarboxylic acid 6-[((R)-1-phenyl-propyl)-amide] 8-{[(R)-1-(6-trifluoromethyl-pyridin-3-yl)-propyl]-amide} |
| 16jz | 3,4-Dihydro-1H-pyrrolo[2,1-c][1,4]oxazine-6,8-dicarboxylic acid 6-[((R)-1-phenyl-propyl)-amide] 8-[(1-pyrimidin-2-yl-ethyl)-amide] (diastereomer 1) |
| 16ka | 3,4-Dihydro-1H-pyrrolo[2,1-c][1,4]oxazine-6,8-dicarboxylic acid 6-[((R)-1-phenyl-propyl)-amide] 8-[(1-pyrimidin-2-yl-ethyl)-amide] (diastereomer 2) |
| 16kb | 3,4-Dihydro-1H-pyrrolo[2,1-c][1,4]oxazine-6,8-dicarboxylic acid 6-[((S)-1-phenyl-propyl)-amide] 8-[((R)-1-pyrimidin-2-yl-propyl)-amide] |
| 16kc | 3,4-Dihydro-1H-pyrrolo[2,1-c][1,4]oxazine-6,8-dicarboxylic acid 6-[((S)-1-phenyl-propyl)-amide] 8-[((S)-1-pyrimidin-2-yl-propyl)-amide] |
| 16kd | 3,4-Dihydro-1H-pyrrolo[2,1-c][1,4]oxazine-6,8-dicarboxylic acid 6-[((R)-1-phenyl-propyl)-amide] 8-[((R)-1-pyrimidin-2-yl-propyl)-amide] |
| 16ke | 3,4-Dihydro-1H-pyrrolo[2,1-c][1,4]oxazine-6,8-dicarboxylic acid 6-[((R)-1-phenyl-propyl)-amide] 8-[((S)-1-pyrimidin-2-yl-propyl)-amide] |
| 16kf | 3,4-Dihydro-1H-pyrrolo[2,1-c][1,4]oxazine-6,8-dicarboxylic acid 6-[((S)-1-phenyl-propyl)-amide] 8-{[(R)-1-(6-trifluoromethyl-pyridin-3-yl)-propyl]-amide} |

TABLE 10-continued

| | |
|---|---|
| 16kg | 3,4-Dihydro-1H-pyrrolo[2,1-c][1,4]oxazine-6,8-dicarboxylic acid 6-[((S)-1-phenyl-propyl)-amide] 8-[((R)-1-pyrimidin-2-yl-ethyl)-amide] |
| 16kh | 8-((S)-3-Methyl-morpholine-4-carbonyl)-3,4-dihydro-1H-pyrrolo[2,1-c][1,4]oxazine-6-carboxylic acid ((R)-1-phenyl-propyl)-amide |
| 16ki | 8-((S)-2-Methyl-pyrrolodine-1-carbonyl)-3,4-dihydro-1H-pyrrolo[2,1-c][1,4]oxazine-6-carboxylic acid ((R)-1-phenyl-propyl)-amide |
| 16kj | 8-((R)-2-Methyl-pyrrolidine1-carbonyl)-3,4-dihydro-1H-pyrrolo[2,1-c][1,4]oxazine-6-carboxylic acid ((R)-1-phenyl-propyl)-amide |
| 16kk | 8-((R)-2-Methoxymethyl-pyrrolidine-1-carbonyl)-3,4-dihydro-1H-pyrrolo[2,l-c][1,4]oxazine-6-carboxylic acid ((R)-1-phenyl-propyl)-amide |
| 16kl | 8-((R)-2-Isopropyl-pyrrolidine-1-carbonyl)-3,4-dihydro-1H-pyrrolo[2,1-c][1,4]oxazine-6-carboxylic acid ((R)-1-phenyl-propyl)-amide |
| 16km | 8-((S)-2-Isopropyl-pyrrolidine-1-carbonyl)-3,4-dihydro-1H-pyrrolo[2,1-c][1,4]oxazine-6-carboxylic acid ((R)-1-phenyl-propyl)-amide |
| 16kn | 3,4-Dihydro-1H-pyrrolo[2,1-c][1,4]oxazine-6,8-dicaboxylic acid 6-{[(R)-1-(2-chloro-4-fluoro-phenyl)-propyl]-amide} 8-[((R)-1-pyrazin-2-yl-ethyl)-amide] |
| 16ko | 3,4-Dihydro-1H-pyrrolo[2,1-c][1,4]oxazine-6,8-dicarboxylic acid 6-{[(R)-1-2-chloro-4-fluoro-phenyl)-propyl]-amide} 8-[(pyrazin-2-ylmethyl)-amide] |
| 16kp | 3,4-Dihydro-1H-pyrrolo[2,1-c][1,4]oxazine-6,8-dicarboxylic acid 6-{[(R)-1-(2-chloro-4-fluoro-phenyl)-propyl]-amide} 8-[(1-pyrimidin-2-yl-ethyl)-amide] |
| 16kq | 3,4-Dihydro-1H-pyrrolo[2,1-c][1,4]thiazine-6,8-dicarboxylic acid 8-{[(R)-1-(4-fluoro-phenyl)-ethyl]-amide} 6-[((R)-1-phenyl-propyl)-amide] |
| 16kr | 8-((S)-2-Methyl-pyrrolidine-1-carbonyl)-3,4-dihydro-1H-pyrrolo[2,1-c][1,4]thiazine-6-carboxylic acid ((R)-1-phenyl-propyl)-amide |
| 16ks | 5-((S)-2-Methyl-pyrrolidine-1-carbonyl)-2,3-dihydro-pyrrolo[2,1-b]thiazole-7-carboxylic acid ((R)-1-phenyl-propyl)-amide |
| 16kt | 2,3-Dihydro-pyrrolo[2,1-b]thiazole-5,7-dicarboxylic acid 5-{[(R)-1-(4-fluoro-phenyl)-ethyl]-amide} 7-[((R)-1-phenyl-propyl)-amide] |
| 16ku | 2,3-Dihydro-pyrrolo[2,1-b]thiazole-5,7-dicarboxylic acid 7-{[(R)-1-(4-fluoro-phenyl)-ethyl-amide} 5-[((R)-1-phenyl-propyl)-amide] |
| 16kv | 2,3-Dihydro-pyrrolo[2,1-b]thiazole-5,7-dicarboxylic acid bis-[((R)-1-phenyl-propyl)-amide] |
| 16kw | 1H-Pyrrolo[1,2-c]thiazole-5,7-dicarboxylic acid 7-{[(R)-1-(4-fluoro-phenyl)-ethyl]-amide} 5-[((R)-1-phenyl-propyl)-amide] |
| 16kx | 7-((S)-2-Methyl-pyrrolidine-1-carbonyl)-1H-pyrrolo[1,2-c]thiazole-5-carboxylic acid ((R)-1-phenyl-propyl)-amide |
| 16ky | 1H-Pyrrolo[1,2-c]thiazole-5,7-dicarboxylic acid 5-{[(R)-1-(4-fluoro-phenyl)-ethyl]-amide} 7-[((R)-1-phenyl-propyl)-amide] |
| 16kz | 6((S)-2-Methyl-pyrrolidine-1-carbonyl)-3,4-dihydro-1H-pyrrolo[2,1-c][1,4]thiazine-8-carboxylic acid ((R)-1-phenyl-propyl)-amide |
| 16la | 3,4-Dihydro-1H-pyrrolo[2,1-c][1,4]thiazine-6,8-dicarboxylic acid 6-{[(R)-1-(4-fluoro-phenyl)-ethyl]-amide} 8-[((R)-1-phenyl-propyl)-amide] |
| 16lb | 3,4-Dihydro-1H-pyrrolo[2,1-c][1,4]oxazine-6,8-dicarboxylic acid 8[((R)-1-pyrimidin-2-yl-propyl)-amide] 6-{[(R)-1-(4-trifluoromethyl-phenyl)-propyl]-amide} |
| 16ld | 3,4-Dihydro-1H-pyrrolo[2,1-c][1,4]oxazine-6,8-dicarboxylic acid 8[((R)-1-(2-chloro-phenyl)-propyl]-amide} 6-cyclopropylmethyl-amide |
| 16le | 6-((S)-2-Ethyl-pyrrolidine-1-carbonyl)-3,4-dihydro-1H-pyrrolo[2,1-c][1,4]oxazine-8-carboxylic acid [(R)-1-(6-trifluoromethyl-pyridin-3-yl)-propyl]-amide |
| 16lf | 1-Methyl-6-((S)-2-methyl-pyrrolidine-1-carbonyl)-3,4-dihydro-1H-pyrrolo[2,1-c][1,4]oxazine-8-carboxylic acid ((R)-1-phenyl-propyl)-amide |
| 16lg | 1-Methyl-3,4-dihydro-1H-pyrrolo[2,1-c][1,4]oxazine-6,8-dicarboxylic acid 8-{[(R)-1-(4-fluoro-phenyl)-ethyl]-amide} 6-[((R)-1-phenyl-propyl)-amide] |
| 16lh | 1-Methyl-3,4-dihydro-1H-pyrrolo[2,1-c][1,4]oxazine-6,8-dicarboxylic acid 6-{[(R)-1-(4-fluoro-phenyl)-propyl]-amide} 8-[((R)-phenyl-propyl)-amide] |
| 16li | 1-Methyl-3,4-dihydro-1H-pyrrolo[2,1-c][1,4]oxazine-6,8-dicarboxylic acid 8-[((R)-1-phenyl-propyl)-amide] 6-[(pyrazin-2-ylmethyl)-amide] |
| 16lj | 8-((S)-2-Methyl-pyrrolidine-1-carbonyl)-3,4-dihydro-1H-pyrrolo[2,1-c](1,4]oxazine-6-carboxylic acid [(R)-1-(4-fluoro-phenyl)-2-methyl-propyl]-amide |
| 16lk | 3,4-Dihydro-1H-pyrrolo[2,1-c][1,4]oxazine-6,8-dicarboxylic acid 6-{[(R)-1-(4-fluoro-phenyl)-2-methyl-propyl]-amide} 8-((1-isoxazol-5-yl-ethyl)-amide] |
| 16ll | 3,4-Dihydro-1H-pyrrolo[2,1-c][1,4]oxazine-6,8-dicarboxylic acid 6-{[(R)-1-(4-fluoro-phenyl)-2-methyl-propyl]-amide} 8-[(oxazol-2-ylmethyl)-amide] |
| 16lm | 8-(Pyrrolidine-1-carbonyl)-3,4-dihydro-1H-pyrrolo[2,1-c][1,4]oxazine-6-carboxylic acid [(R)-1-(4-fluoro-phenyl)-2-methyl-propyl]-amide |
| 16ln | (R)-1-{6-[(R)-1-(4-Fluoro-phenyl)-2-methyl-propylcarbamoyl]-3,4-dihydro-1H-pyrrolo[2,1-c][1,4]oxazine-8-carbonyl}-pyrrolidine-2-carboxylic acid methyl ester |
| 16lo | 3,4-Dihydro-1H-pyrrolo[2,1-c][1,4]oxazine-6,8-dicarboxylic acid 6-{[(R)-1-(4-fluoro-phenyl)-2-methyl-propyl]-amide} 8-[(pyrazin-2-ylmethy])-amide] |
| 16lp | 3,4-Dihydro-1H-pyrrolo[2,1-c][1,4]oxazine-6,8-dicarboxylic acid 6-{[(R)-1-(4-fluoro-phenyl)-2-methyl-propyl]-amide} 8-[(1-pyrazin-2-yl-ethyl)-amide} {diastereorner 2) |

TABLE 10-continued

| | |
|---|---|
| 16lq | 3,4-Dihydro-1H-pyrrolo[2,1-c][1,4]oxazine-6,8-dicarboxylic acid 6-{[(R)-1-(4-fluoro-phenyl)-2-methyl-propyl]-amide} 8-[(1-pyrazin-2-yl-ethyl)-amide] (diastereomer 1) |
| 16lr | 3,4-Dihydro-1H-pyrrolo[2,1-c][1,4]oxazine-6,8-dicarboxylic acid 6-{[(R)-1-(4-fluoro-phenyl)-2-rnethyl-propyl]-amide} 8-[((S)-1-pyrimidin-2-yl-ethyl)-amide) |
| 16ls | 3,4-Dihydro-1H-pyrrolo[2,1-c][1,4]oxazine-6,8-dicarboxylic acid 6-{[(R)-1-(4-fluoro-phenyl)-2-rnethyl-propyl]-amide} 8-[((R)-1-pyrimidin-2-yl-ethyl)-amide] |
| 16lu | 5,6,7,8-Tetrahydro-indotizine-1,3-dicarboxylic acid 3~{[(R)-1-(4-fluoro-phenyl)-ethyl]amide} 1-[(1-pyrimidin-2-yl-ethyl)-amide] |
| 16lv | 3-((S)-2-Methyl-pyrrolidine-1-carbonyl)-5,6,7,8-tetrahydro-indolizine-1-carboxylic acid [(R)-1-(6-cyano-pyridin-3-yl)-propyl]-amide |
| 16lw | 3-((S)-2-Methyl-pyrrolidine-1-carbonyl)-5,6,7,8-tetrahydro-indolizine-1-carboxylic acid [(R)-1-(6-trifluoromethyl-pyridin-3-yl)-propyl]-amide |
| 16lx | 3-((S)-2-Methyl-pyrrolidine-1-carbonyl)-5,6,7,8-tetrahydro-indolizine-1-carboxylic acid [(R)-1-(4-cyano-phenyl)-propyl]-amide |
| 16ly | 3-((S)-2-Methyl-pyrrolidine-1-carbonyl)-5,6,7,8-tetrahydro-indolizine-1-carboxylic acid [(R)-1-(4-chloro-phenyl)-ethyl-amide |
| 16lz | 3-((S)-2-Methyl-pyrrolidine-1-carbonyl)-5,6,7,8-tetrahydro-indolizine-1-carboxylic acid [(R)-1-(1-oxo-1,3-dihydro-isobenzofuran-5-yl)-propyl]-amide |
| 16ma | 5,6,7,8-Tetrahydro-indolizine-1,3-dicarboxylic acid bis-[(R)-1-phenyl-propyl]-amide] |
| 16mc | 5,6,7,8-Tetrahydro-indolizine-1,3-dicarboxylic acid 1-[(oxazol-5-ylmethyl)-amide] 3-[((R)-1-phenyl-propyl)-amide] |
| 16md | 5,6,7,8-Tetrahydro-indolizine-1,3-dicarboxylic acid 3-[((R)-1-phenyl-propyl)-amide] 1-(thiazol-2-ylmethyl)-amide] |
| 16me | 5,6,7,8-Tetrahydro-indolizine-1,3-dicarboxylic acid 3-[((R)-1-phenyl-propyl)-amide] 1-[(4,5-dimethyl-thiazol-2-yl)-amide] |
| 16nd | 5,6,7,8-Tetrahydro-indolizine-1,3-dicarboxylic acid 3-[(3,5-dimethyl-isoxazol-4-yl)-amide] 1-[((R)-1-phenyl-propyl)-amide] |
| 16nc | 3-(Morpholine-4-carbonyl)-5,6,7,8-tetrahydro-indolizine-1-carboxylic acid ((R)-1-phenyl-propyl)-amide |
| 16ne | 5,6,7,8-Tetrahydro-indolizine-1,3-dicarboxylic acid 3-[(5-fluoro-pyridin-3-yl)-amide] 1-[((R)-1-phenyl-propyl)-amide] |
| 16nh | 8-((S)-2-Methyl-pyrrolidine-1-carbonyl)-3,4-dihydro-1H-pyrrolo[2,1-c][1,4]oxazine-6-carboxylic acid [(R)-1-(2-chloro-phenyl)-propyl]-amide |
| 16ni | 8-((S)-2-Methyl-pyrrolidine-1-carbonyl)-3,4-dihydro-1H-pyrrolo[2,1-c][1,4]oxazine-6-carboxylic acid [(R)-1-(2-trifluoromethyl-phenyl)-propyl]-amide |
| 16nj | 8-((S)-2-Methyl-pyrrolidine-1-carbonyl)-3,4-dihydro-1H-pyrrolo[2,1-c][1,4]oxazine-6-carboxylic acid [(R)-1-(6-cyano-pyridin-3-yl)-propyl]-amide |
| 16nk | 8-((S)-2-Methyl-pyrrolidine-1-carbonyl)-3,4-dihydro-1H-pyrrolo[2,1-c][1,4]oxazine-6-carboxylic acid [(R)-1-(6-trifluoromethyh-pyridin-3-yl)-propyl]-amide |
| 16nl | 8-((S)-2-Methyl-pyrrolidine-1-carbonyl)-3,4-dihydro-1H-pyrrolo[2,1-c][1,4]oxazine-6-carboxylic acid [(R)-1-(4-cyano-phenyl)-propyl]-amide |
| 16nm | 8-((S)-2-Methyl-pyrrolidine-1-carbonyl)-3,4-dihydro-1H-pyrrolo[2,1-c][1,4]oxazine-6-carboxylic acid [(R)-1 (6-cyano-pyridin-3-yl)-2-methyl-propyl]-amide |
| 16nn | 6-((S)-3-Methoxy-pyrrolidine-1-carbonyl)-3,4-dihydro-1H-pyrrolo[2,1-c][1,4]oxazine-8-carboxylic acid [(R)-1-(2-chloro-4-fluoro-phenyl)-propyl]-amide |
| 16no | 3,4-Dihydro-1H-pyrrolo[2,1-c][1,4]oxazine-6,8-dicarboxylic acid 8-{[(R)-1-(2-chloro-4-fluoro-phenyl)-propyl]-amide} 6-[(pyrazin-2-ylmethyl)-amide] |
| 16np | 3,4-Dihydro-1H-pyrrolo[2,1-c][1,4]oxazine-6,8-dicarboxylic acid 8-{[(R)-1-(2-chloro-4-fluoro-phenyl)-propyl]-amide} 6-[(1-pyrimidin-2-yl-ethyl)-amide] |
| 16nq | 3,4-Dihydro-1H-pyrrolo[2,1-c][1,4]oxazine-6,8-dicarboxylic acid 8-{[(R)-1-(2-chloro-phenyl)-propyl]-amide} 6-[((R)-1-pyrazin-2-yl-ethyl)-amide] |
| 16nr | 3,4-Dihydro-1H-pyrrolo[2,1-c][1,4]oxazine-6,8-dicarboxylic acid 8-{[(R)-1-(2-chloro-phenyl)-propyl-amide} 6-[(1-pyrimidin-2-yl-ethyl)-amide] |
| 16ns | 3,4-Dihydro-1H-pyrrolo[2,1-c][1,4]oxazine-6,8-dicarboxylic acid 8-(2,4-difluoro-benzylamide) 6-[((R)-1-pyrazin-2-yl-propyl)-amide] |
| 16nt | 3,4-Dihydro-1H-pyrrolo[2,1-c][1,4]oxazine-6,8-dicarboxylic acid 8-(2,4-difluoro-benzylamide) 6-[((R)-1-(6-methoxy-pyridin-2-yl)propyl)-amide} |
| 16nu | 6-((S)-2-Methyl-pyrrolidine-1-carbonyl)-3,4-dihydro-1H-pyrrolo[2,1-c][1,4]oxazine-8-carboxylic acid 2-chloro-6-fluoro-benzylamide |
| 16nv | 3,4-Dihydro-1H-pyrrolo[2,1-c][1,4]oxazine-6,8-dicarboxylic acid 8-{[(R)-1-(4-fluoro-phenyl)-ethyl-amide} 6-[((R)-1-pyrimidin-2-yl-propyl)-amide] |
| 16nw | 3,4-Dihydro-1H-pyrrolo[2,1-c][1,4]oxazine-6,8-dicarboxylic acid 8-{[(R)-1-(4-fluoro-phenyl)-ethyl-amide} 6-[((S)-1-pyrimidin-2-yl-propyl)-amide] |
| 16nx | 3,3-Dimethyl-6-((S)-2-methyl-pyrrolidine-1-carbonyl)-3,4-dihydro-1H-pyrrolo[2,1-c][1,4]oxazine-8-carboxylic acid [(R)-1-(4-cyano-phenyl)-propyl]-amide |
| 16ny | 6-((R)-2-Methyl-pyrrolidine-1-carbonyl)-3,4-dihydro-1H-pyrrolo[2,1-c][1,4]oxazine-8-carboxylic acid [(R)-1-(6-trifiuoromethyl-pyridin-3-yl)-propyl]-amide |
| 16nz | 3,4-Dihydro-1H-pyrrolo[2,1-c][1,4]oxazine-6,8-dicarboxylic acid 6-[((R)-1-cyclopropyl-ethyl)-amide] 8-{[(R)-1-(6-trifluoromethyl-pyridin-3-yl)-propyl]-amide} |

TABLE 10-continued

| | |
|---|---|
| 16pa | 3,4-Dihydro-1H-pyrrolo[2,1-c][1,4]oxazine-6,8-dicarboxylic acid 6-dicyclopropylmethyl-amide 8-{[(R)-1-(6-trifluoromethyl-pyridin-3-yl)-propyl]-amide} |
| 16pb | 3,4-Dihydro-1H-pyrrolo[2,1-c][1,4]oxazine-6,8-dicarboxylic acid 6-{[(R)-1-(6-methoxy-pyridin-2-yl)-propyl]-amide} 8-{[(R)-1-(6-trifluoromethyl-pyridin-3-yl)-propyl]-amide} |
| 16pc | 6-(2-Methyl-piperidine-1-carbonyl)-3,4-dihydro-1H-pyrrolo[2,1-c][1,4]oxazine-8-carboxylic acid [(R)-1-(6-trifluoromethyl-pyridin-3-yl)-propyl]-amide |
| 16pd | 3,4-Dihydro-1H-pyrrolo[2,1-c][1,4]oxazine-6,8-dicarboxylic acid 6[((R)-1-thiazol-2-yl-propyl)-amide] 8-{[(R)-1-(6-trifluoromethyl-pyridin-3-yl)-propyl]-amide} |
| 16pe | 6-(2-Methyl-azetidine-1-carbonyl)-3,4-dihydro-1H-pyrrolo[2,1-c][1,4]oxazine-8-carboxylic acid [(R)-1-(6-trifluoromethyl-pyridin-3-yl)-propyl]-amide |
| 16pf | 6-((S)-2-Methyl-pyrrolidine-1-carbonyl)-3,4-dihydro-1H-pyrrolo[2,1-c][1,4]oxazine-8-carboxylic acid [(R)-1-(3-chloro-pyridin-2-yl)-propyl]-amide |
| 16pg | 6-((S)-2-Methyl-pyrrolidine-1-carbonyl)-3,4-dihydro-1H-pyrrolo[2,1-c][1,4]oxazine-8-carboxylic acid [(R)-1(4-chloro-phenyl)-propyl]-amide |
| 16ph | 6-((S)-2-Methyl-pyrrolidine-1-carbonyl)-3,4-dihydro-1H-pyrrolo[2,1-c][1,4]oxazine-8-carboxylic acid ((R)-1-pyridin-2-yl-propyl)-amide |
| 16pi | 3,3-Dimethyl-6-((S)-2-methyl-pyrrolidine-1-carbonyl)-3,4-dihydro-1H-pyrrolo[2,1-c][1,4]oxazine-8-carboxylic acid [(R)-1-(6-trifluoromethyl-pyridin-3-yl)-propyl]-amide |
| 16pj | 8-((R)-2-Pyrazin-2-yl-pyrrolidine-1-carbonyl)-3,4-dihydro-1H-pyrrolo[2,1-c][1,4]oxazine-6-carboxylic acid [(R)-1-(2,4-difluoro-phenyl)-propyl]-amide |
| 16pk | 3,4-Dihydro-1H-pyrrolo[2,1-c][1,4]oxazine-6,8-dicarboxylic acid 6-{[(R)-1-(2,4-difluoro-phenyl)-propyl]-amide} 8-[(1-pyrazin-2-yl-ethyl)-amide] (diastereomer 2) |
| 16pl | 3,4-Dihydro-1H-pyrrolo[2,1-c][1,4]oxazine-6,8-dicarboxylic acid 6-{[(R)-1-(2,4-difluoro-phenyl)-propyl-amide} 8-[(1-pyrazin-2-yl-ethyl)-amide] (diastereomer 1) |
| 16po | 8-((S)-2-Methyl-pyrrolidine-1-carbonyl)-3,4-dihydro-1H-pyrrolo[2,1-c][1,4]oxazine-6-carboxylic acid [(R)-2-methyl-1-(6-trifluoromethyl-pyridin-3-yl)-propyl]-amide |
| 16pp | 6-((S)-2-Methyl-pyrrolidine-1-carbonyl)-3,4-dihydro-1H-pyrrolo[2,1-c][1,4]oxazine-8-carboxylic acid [(R)-1-(5-fluoro-6-methoxy-pyridin-3-yl)-propyl]-amide |

The example compounds of the formula I in Table 11 were obtained in analogy to the syntheses of comp. no. 16i.

TABLE 11

| Comp. no. | Starting comp. no. | Formula | Rt [min] (LC/MS method) | m/z (M + H⁺) |
|---|---|---|---|---|
| 16cx | 12a | | 1.17 (4) | 382.3 |
| 16eh | 12a | | 1.14 (4) | 398.31 |

TABLE 11-continued
| | | | | |
|---|---|---|---|---|
| 16ei | 12a | 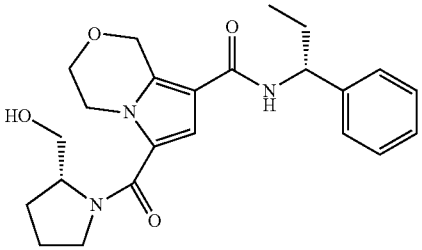 [SMILES: CC[C@@H](NC(=O)c1cc(C(=O)N2CCC[C@@H]2CO)n2c1COCC2)c1ccccc1] | 1.14 (4) | 412.36 |
| 16ej | 12a | 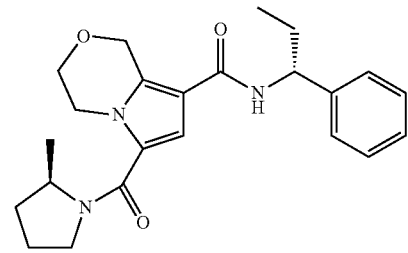 [SMILES: CC[C@@H](NC(=O)c1cc(C(=O)N2CCC[C@H]2C)n2c1COCC2)c1ccccc1] | 1.12 (4) | 396.19 |
| 16ek | 12a | 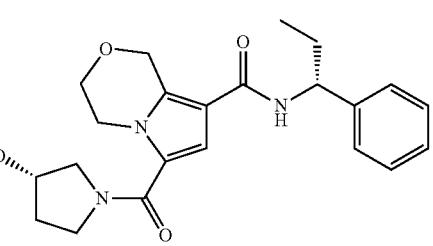 | 1.06 (4) | 412.19 |
| 16gd | 12a | 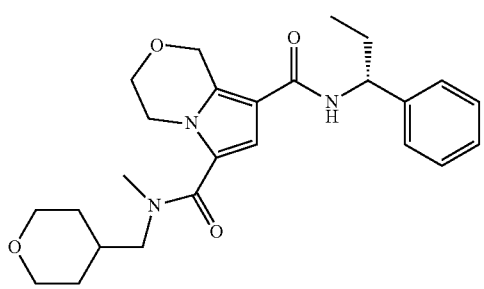 [SMILES: CC[C@@H](NC(=O)c1cc(C(=O)N(C)CC2CCOCC2)n2c1COCC2)c1ccccc1] | 1.18 (4) | 440.38 |
| 16ge | 12a | 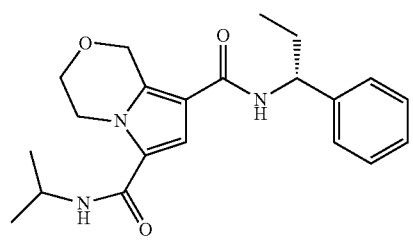 [SMILES: CC[C@@H](NC(=O)c1cc(C(=O)NC(C)C)n2c1COCC2)c1ccccc1] | 1.21 (4) | 370.24 |
| 16gf | 12a | 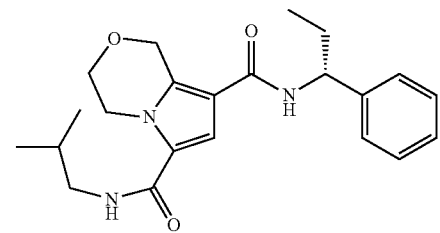 [SMILES: CC[C@@H](NC(=O)c1cc(C(=O)NCC(C)C)n2c1COCC2)c1ccccc1] | 1.13 (4) | 384.14 |

TABLE 11-continued
| | | | | |
|---|---|---|---|---|
| 16gg | 12a | 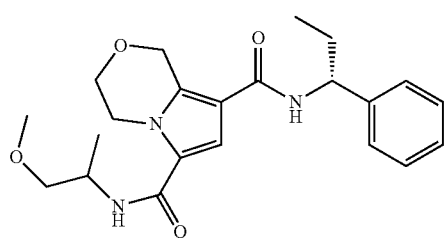 [SMILES: CC[C@@H](NC(=O)c1cc(C(=O)NC(C)COC)n2c1COCC2)c1ccccc1] | 1.07 (4) | 400.16 |
| 16gh | 12a | 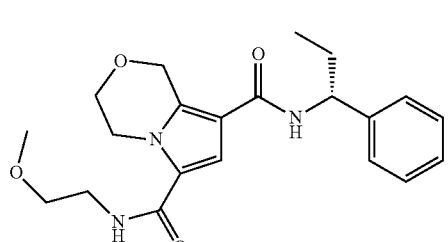 | 1.03 (4) | 386.11 |
| 16gi | 12a | 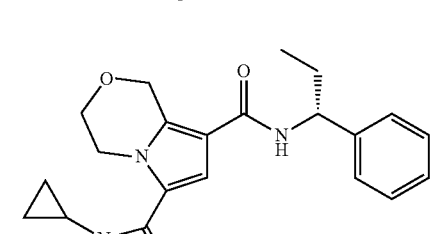 | 1.06 (4) | 368.12 |
| 16gj | 12a | 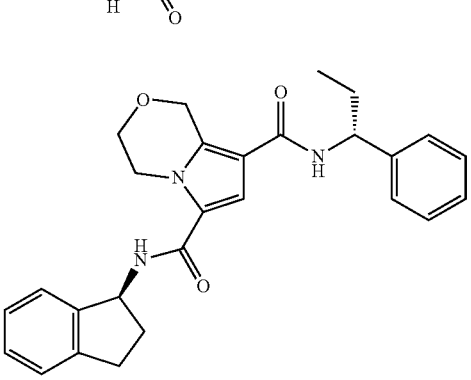 | 1.31 (4) | 444.34 |
| 16gk | 12a | 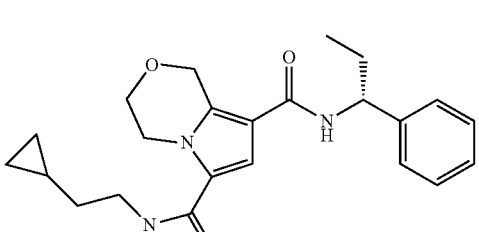 | 1.24 (4) | 396.33 |
| 16gm | 12a | 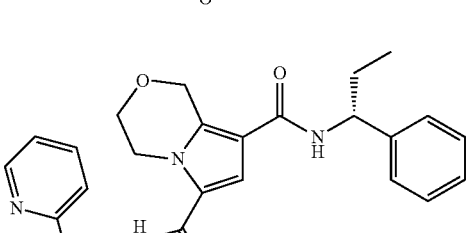 | 0.9 (4) | 433.18 |

TABLE 11-continued
| | | | | |
|---|---|---|---|---|
| 16gn | 12a | 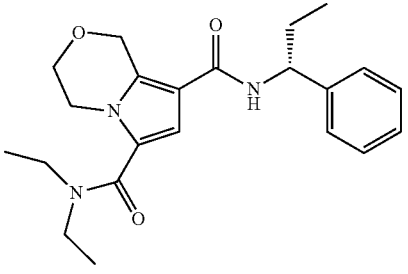 [SMILES: CC[C@@H](NC(=O)c1cc(C(=O)N(CC)CC)n2c1COCC2)c1ccccc1] | 1.11 (4) | 384.16 |
| 16gp | 12a | 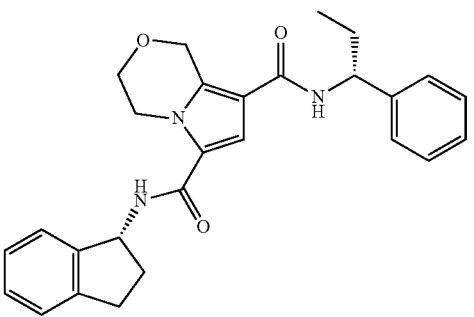 [SMILES: CC[C@@H](NC(=O)c1cc(C(=O)N[C@@H]2CCc3ccccc32)n2c1COCC2)c1ccccc1] | 1.3 (4) | 444.22 |
| 16lt | 12b | 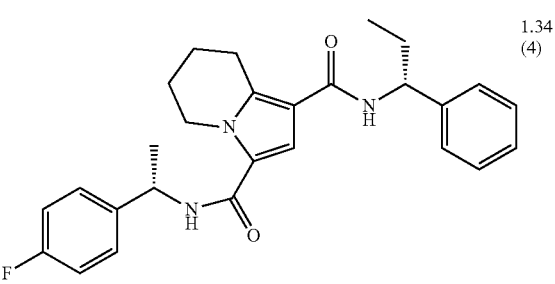 | 1.34 (4) | 448.35 |
| 16mb | 12b | 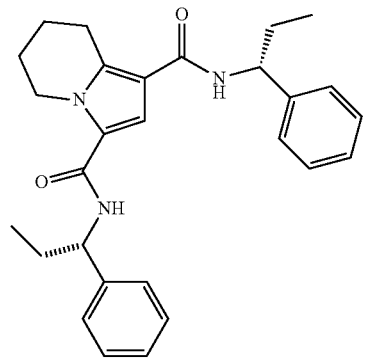 [SMILES: CC[C@H](NC(=O)c1cc(C(=O)N[C@H](CC)c2ccccc2)c2n1CCCC2)c1ccccc1] | 1.24 (4) | 444.23 |
| 16mf | 12b | 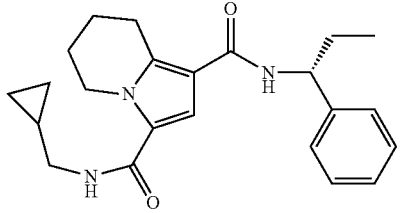 [SMILES: CC[C@@H](NC(=O)c1cc(C(=O)NCC2CC2)n2c1CCCC2)c1ccccc1] | 4.43 (5) | 380.35 |

TABLE 11-continued
| 16mg | 12b | 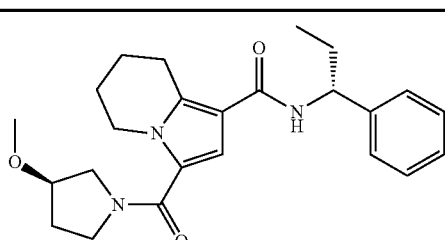 | 1.22 (4) | 410.33 |
| --- | --- | --- | --- | --- |
| 16mh | 12b | 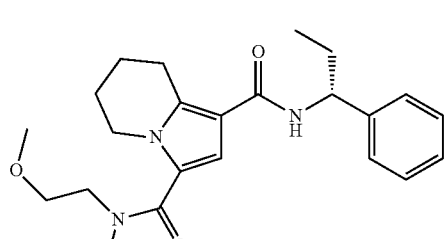 | 1.21 (4) | 398.32 |
| 16mi | 12b | 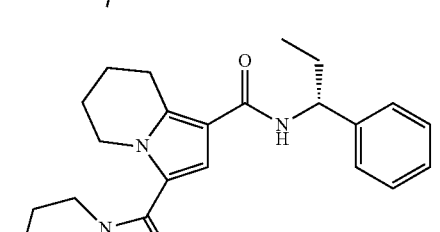 | 1.29 (4) | 394.33 |
| 16mk | 12b | 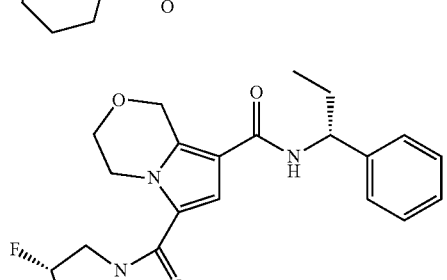 | 1.24 (4) | 398.23 |
| 16ml | 12b | 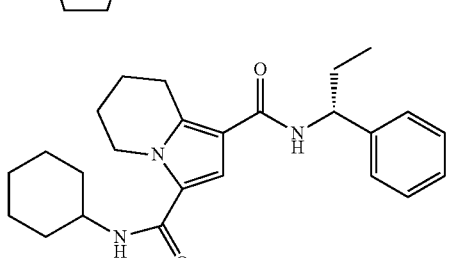 | 1.35 (4) | 408.29 |
| 16mm | 12b | 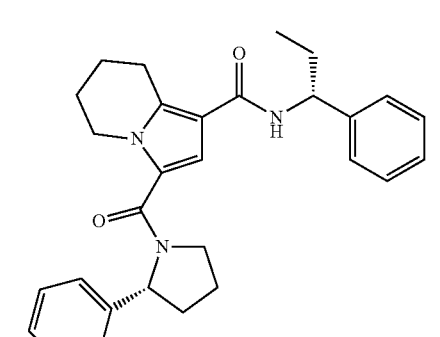 | 1.34 (4) | 456.39 |

TABLE 11-continued
| 16mn | 12b | 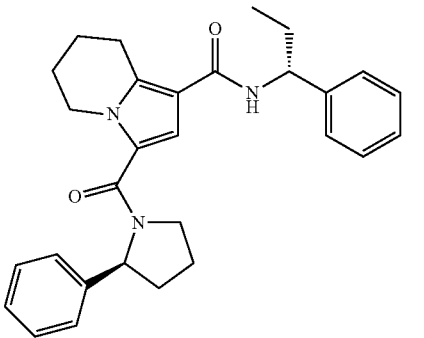 [SMILES: CC[C@@H](NC(=O)c1cc(C(=O)N2CCC[C@H]2c2ccccc2)n2c1CCCC2)c1ccccc1] | 1.22 (4) | 456.25 |
| --- | --- | --- | --- | --- |
| 16mo | 12b | 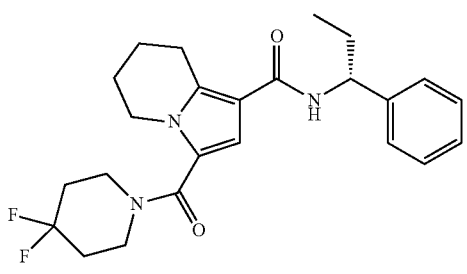 [SMILES: CC[C@@H](NC(=O)c1cc(C(=O)N2CCC(F)(F)CC2)n2c1CCCC2)c1ccccc1] | 1.17 (4) | 430.23 |
| 16mp | 12b | 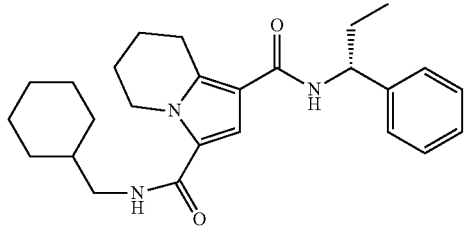 [SMILES: CC[C@@H](NC(=O)c1cc(C(=O)NCC2CCCCC2)n2c1CCCC2)c1ccccc1] | 1.25 (4) | 422.27 |
| 16mq | 12b | 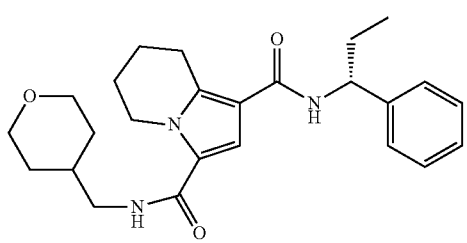 [SMILES: CC[C@@H](NC(=O)c1cc(C(=O)NCC2CCOCC2)n2c1CCCC2)c1ccccc1] | 1.1 (4) | 424.25 |
| 16mr | 12b | 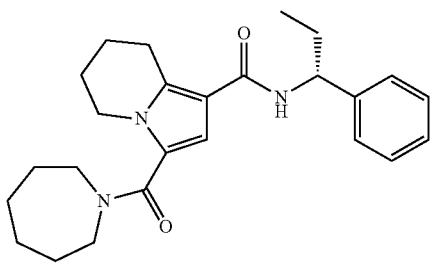 [SMILES: CC[C@@H](NC(=O)c1cc(C(=O)N2CCCCCC2)n2c1CCCC2)c1ccccc1] | 1.19 (4) | 408.25 |

TABLE 11-continued
| | | | | |
|---|---|---|---|---|
| 16ms | 12b | 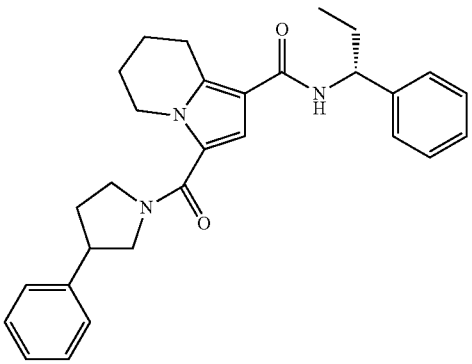 [SMILES: CC[C@@H](NC(=O)c1cc(C(=O)N2CCC(c3ccccc3)C2)n2c1CCCC2)c1ccccc1] | 4.75 (5) | 456.45 |
| 16mt | 12b | 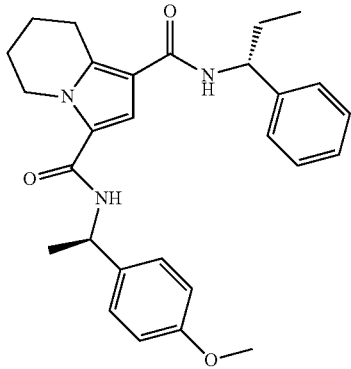 [SMILES: CC[C@@H](NC(=O)c1cc(C(=O)N[C@H](C)c2ccc(OC)cc2)n2c1CCCC2)c1ccccc1] | 1.21 (4) | 460.16 |
| 16mu | 12b | 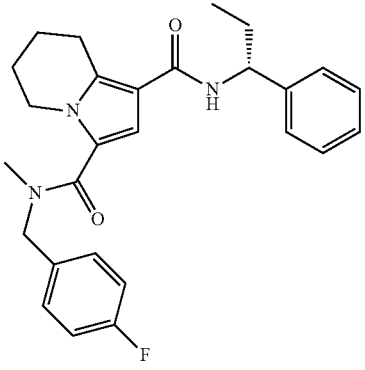 [SMILES: CC[C@@H](NC(=O)c1cc(C(=O)N(C)Cc2ccc(F)cc2)n2c1CCCC2)c1ccccc1] | 1.32 (4) | 448.29 |
| 16mv | 12b | 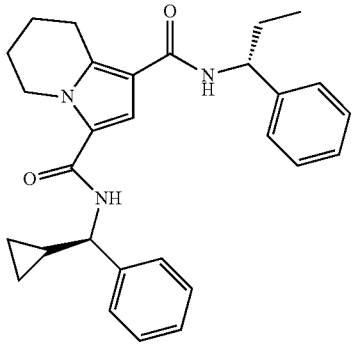 [SMILES: CC[C@@H](NC(=O)c1cc(C(=O)N[C@@H](c2ccccc2)C2CC2)n2c1CCCC2)c1ccccc1] | 1.24 (4) | 456.22 |

TABLE 11-continued

| Comp. no. | | Structure | | |
|---|---|---|---|---|
| 16mw | 12b | 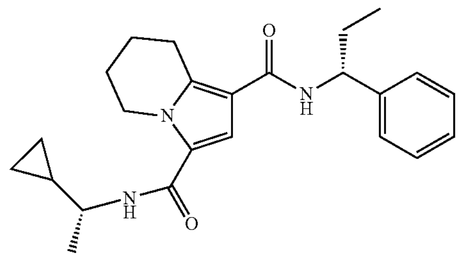 [SMILES: CC[C@@H](NC(=O)c1cc(C(=O)N(C)[C@H](C)C2CC2)n2c1CCCC2)c1ccccc1] | 1.28 (4) | 394.36 |
| 16mx | 12b | 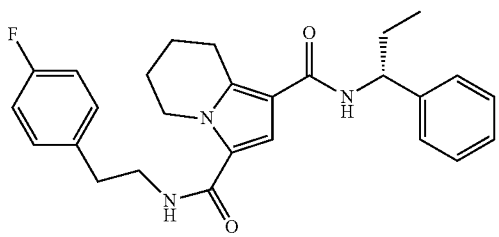 [SMILES: CC[C@@H](NC(=O)c1cc(C(=O)NCCc2ccc(F)cc2)n2c1CCCC2)c1ccccc1] | 1.3 (4) | 448.36 |
| 16my | 12b | 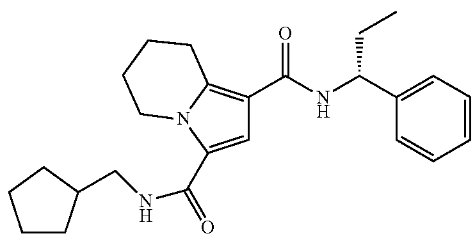 [SMILES: CC[C@@H](NC(=O)c1cc(C(=O)NCC2CCCC2)n2c1CCCC2)c1ccccc1] | 4.74 (5) | 408.43 |
| 16mz | 12b | 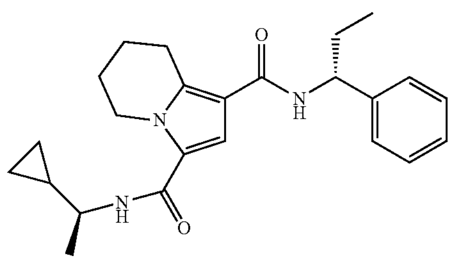 [SMILES: CC[C@@H](NC(=O)c1cc(C(=O)N[C@@H](C)C2CC2)n2c1CCCC2)c1ccccc1] | 4.59 (5) | 394.39 |
| 16na | 12b | 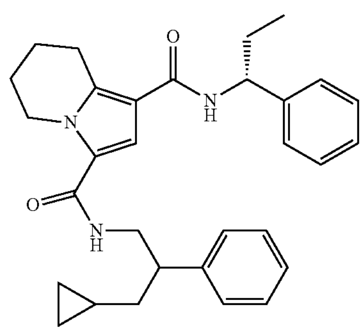 [SMILES: CC[C@@H](NC(=O)c1cc(C(=O)NCC(CC2CC2)c2ccccc2)n2c1CCCC2)c1ccccc1] | 1.39 (4) | 484.43 |

| Comp. no. | Chemical name |
|---|---|
| 16cx | 6-(Pyrrolidine-1-carbonyl)-3,4-dihydro-1H-pyrrolo[2,1-c][1,4]oxazine-8-carboxylic acid ((R)-1-phenyl-propyl)-amide |
| 16eh | 6-(Morpholine-4-carbonyl)-3,4-dihydro-1H-pyrrolo[2,1-c][1,4]oxazine-8-carboxylic acid ((R)-1-phenyl-propyl)-amide |
| 16ei | 6-((R)-2-Hydroxymethyl-pyrrolidine-1-carbonyl)-3,4-dihydro-1H-pyrrolo[2,1-c][1,4]oxazine-8-carboxylic acid ((R)-1-phenyl-propyl)-amide |
| 16ej | 6-((R)-2-Methyl-pyrrolidine-1-carbonyl)-3,4-dihydro-1H-pyrrolo[2,1-c][1,4]oxazine-8-carboxylic acid ((R)-1-phenyl-propyl)-amide |
| 16ek | 6-((S)-2-Methoxy-pyrrolidine-1-carbonyl)-3,4-dihydro-1H-pyrrolo[2,1-c][1,4]oxazine-8-carboxylic acid ((R)-1-phenyl-propyl)-amide |

TABLE 11-continued

| | |
|---|---|
| 16gd | 3,4-Dihydro-1H-pyrrolo[2,1-c][1,4]oxazine-6,8-dicarboxylic acid 6-[methyl-(tetrahydro-pyran-4-ylmethyl)-amide] 8-[((R)-1-phenyl-propyl)-amide] |
| 16ge | 3,4-Dihydro-1H-pyrrolo[2,1-c][1,4]oxazine-6,8-dicarboxylic acid 6-isopropylamide 8-[((R)-1-phenyl-propyl)-amide] |
| 16gf | 3,4-Dihydro-1H-pyrrolo[2,1-c][1,4]oxazine-6,8-dicarboxylic acid 6-isobutylamide 8-[((R)-1-phenyl-propyl)-amide] |
| 16gg | 3,4-Dihydro-1H-pyrrolo[2,1-c][1,4]oxazine-6,8-dicarboxylic acid 6-[(2-methoxy-1-methyl-ethyl)-amide] 8-[((R)-1-phenyl-propyl)-amide] |
| 16gh | 3,4-Dihydro-1H-pyrrolo[2,1-c][1,4]oxazine-6,8-dicarboxylic acid 6-[(2-methoxy-ethyl)-amide] 8-[((R)-1-phenyl-propyl)-amide] |
| 16gi | 3,4-Dihydro-1H-pyrrolo[2,1-c][1,4]oxazine-6,8-dicarboxylic acid 6-cyclopropylamide 8-[((R)-1-phenyl-propyl)-amide] |
| 16gj | 3,4-Dihydro-1H-pyrrolo[2,1-c][1,4]oxazine-6,8-dicarboxylic acid 6-(S)-indan-1-ylamide 8-[((R)-1-phenyl-propyl)-amide] |
| 16gk | 3,4-Dihydro-1H-pyrrolo[2,1-c][1,4]oxazine-6,8-dicarboxylic acid 6-[(2-cyclopropyl-ethyl)-amide] 8-[((R)-1-phenyl-propyl)-amide] |
| 16gm | 3,4-Dihydro-1H-pyrrolo[2,1-c][1,4]oxazine-6,8-dicarboxylic acid 8-[((R)-1-phenyl-propyl)-amide] 6-[(2-pyridin-2-yl-ethyl)-amide] |
| 16gn | 3,4-Dihydro-1H-pyrrolo[2,1-c][1,4]oxazine-6,8-dicarboxylic acid 6-diethylamide 8-[((R)-1-phenyl-propyl)-amide] |
| 16gp | 3,4-Dihydro-1H-pyrrolo[2,1-c][1,4]oxazine-6,8-dicarboxylic acid 6-(R)-indan-1-ylamide 8-[((R)-1-phenyl-propyl)-amide] |
| 16lt | 5,6,7,8-Tetrahydro-indolizine-1,3-dicarboxylic acid 3-{[(S)-1-(4-fluoro-phenyl)-ethyl]amide} 1-[((R)-1-phenyl-propyl)-amide] |
| 16mb | 5,6,7,8-Tetrahydro-indolizine-1,3-dicarboxylic acid 3-[((S)-1-phenyl-propyl)-amide] 1-[((R)-1-phenyl-propyl)-amide] |
| 16mf | 5,6,7,8-Tetrahydro-indolizine-1,3-dicarboxylic acid 3-cyclopropylmethyl-amide 1-[((R)-1-phenyl-propyl)-amide] |
| 16mg | 3-((R)-3-Methoxy-pyrrolidine-1-carbonyl)-5,6,7,8-tetrahydro-indolizine-1-carboxylic acid ((R)-1-phenyl-propyl)-amide |
| 16mh | 5,6,7,8-Tetrahydro-indolizine-1,3-dicarboxylic acid 3-[(2-methoxy-ethyl)-methyl-amide] 1-[((R)-1-phenyl-propyl)-amide] |
| 16mi | 3-(Piperidine-1-carbonyl)-5,6,7,8-tetrahydro-indolizine-1-carboxylic acid ((R)-1-phenyl-propyl)-amide |
| 16mk | 3-((S)-3-Fluoro-pyrrolidine-1-carbonyl)-5,6,7,8-tetrahydro-indolizine-1-carboxylic acid ((R)-1-phenyl-propyl)-amide |
| 16ml | 5,6,7,8-Tetrahydro-indolizine-1,3-dicarboxylic acid 3-cyclohexylamide 1-[((R)-1-phenyl-propyl)-amide] |
| 16mm | 3-((R)-2-Phenyl-pyrrolidine-1-carbonyl)-5,6,7,8-tetrahydro-indolizine-1-carboxylic acid ((R)-1-phenyl-propyl)-amide |
| 16mn | 3-((S)-2-Phenyl-pyrrolidine-1-carbonyl)-5,6,7,8-tetrahydro-indolizine-1-carboxylic acid ((R)-1-phenyl-propyl)-amide |
| 16mo | 3-(4,4-Difluoro-piperidine-1-carbonyl)-5,6,7,8-tetrahydro-indolizine-1-carboxylic acid ((R)-1-phenyl-propyl)-amide |
| 16mp | 5,6,7,8-Tetrahydro-indolizine-1,3-dicarboxylic acid 3-cyclohexylmethyl-amide 1-[((R)-1-phenyl-propyl)-amide] |
| 16mq | 5,6,7,8-Tetrahydro-indolizine-1,3-dicarboxylic acid 1-[((R)-1-phenyl-propyl)-amide] 3-[(tetrahydro-pyran-4-ylmethyl)-amide] |
| 16mr | 3-(Azepane-1-carbonyl)-5,6,7,8-tetrahydro-indolizine-1-carboxylic acid ((R)-1-phenyl-propyl)-amide |
| 16ms | 3-(3-Phenyl-pyrrolidine-1-carbonyl)-5,6,7,8-tetrahydro-indolizine-1-carboxylic acid ((R)-1-phenyl-propyl)-amide |
| 16mt | 5,6,7,8-Tetrahydro-indolizine-1,3-dicarboxylic acid 3-{[(R)-1-(4-methoxy-phenyl-ethyl]-amide} 1-[((R)-1-phenyl-propyl)-amide] |
| 16mu | 5,6,7,8-Tetrahydro-indolizine-1,3-dicarboxylic acid 3-[(4-fluoro-benzyl)-methyl-amide] 1-[((R)-1-phenyl-propyl)-amide] |
| 16mv | 5,6,7,8-Tetrahydro-indolizine-1,3-dicarboxylic acid 3-[((R)-cyclopropyl-phenyl-methyl]-amide] 1-[((R)-1-phenyl-propyl)-amide] |
| 16mw | 5,6,7,8-Tetrahydro-indolizine-1,3-dicarboxylic acid 3-[((R)-1-cyclopropyl-ethyl]-amide] 1-[((R)-1-phenyl-propyl)-amide] |
| 16mx | 5,6,7,8-Tetrahydro-indolizine-1,3-dicarboxylic acid 3-{[2-(4-fluoro-phenyl-ethyl]-amide} 1-[((R)-1-phenyl-propyl)-amide] |
| 16my | 5,6,7,8-Tetrahydro-indolizine-1,3-dicarboxylic acid 3-[((S)-1-cyclopropylmethyl-amide 1-[((R)-1-phenyl-propyl)-amide] |
| 16mz | 5,6,7,8-Tetrahydro-indolizine-1,3-dicarboxylic acid 3-[((S)-1-cyclopropyl-ethyl]-amide] 1-[((R)-1-phenyl-propyl)-amide] |
| 16na | 5,6,7,8-Tetrahydro-indolizine-1,3-dicarboxylic acid 3-[(3-cyclopropyl-2-phenyl-propyl)-amide] 1-[((R)-1-phenyl-propyl)-amide] |

6-((S)-2-Methyl-pyrrolidine-1-carbonyl)-3,4-dihydro-1H-pyrrolo[2,1-c][1,4]oxazine-8-carboxylic acid [(R)-1-(6-methylsulfanyl-pyridin-3-yl)-propyl]-amide (comp. no. 16ra)

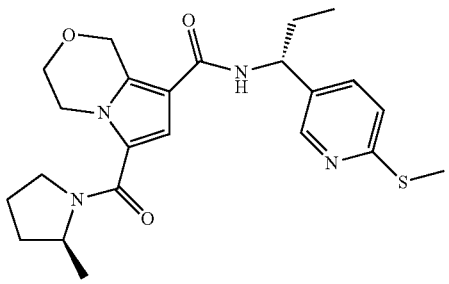 [SMILES: CC[C@@H](NC(=O)c1cc(C(=O)N2CCC[C@@H]2C)n2c1COCC2)c1ccc(SC)nc1]

A mixture of 6-((S)-2-methyl-pyrrolidine-1-carbonyl)-3,4-dihydro-1H-pyrrolo[2,1-c][1,4]oxazine-8-carboxylic acid [(R)-1-(6-bromo-pyridin-3-yl)-propyl]-amide (comp. no. 16al) (50 mg, 0.105 mmol) and sodium methylmercaptide (9 mg, 0.126 mmol) in N,N-dimethylformamide (1.5 ml) was heated at 120° C. for 7 h. After addition of a second portion of sodium methylmercaptide (9 mg) the mixture was heated for an additional 8 h at 120° C. After addition of 5 ml water, the mixture was extracted with dichloromethane, the organic layers were combined, solvents were evaporated and the residue was purified by reverse phase HPLC (acetonitrile/water gradient with 0.1% trifluoroacetic acid) to give 6-((S)-2-methyl-pyrrolidine-1-carbonyl)-3,4-dihydro-1H-pyrrolo[2,1-c][1,4]oxazine-8-carboxylic acid [(R)-1-(6-methylsulfanyl-pyridin-3-yl)-propyl]-amide (25 mg, 54%). LC/MS (method 4): Rt=1.18 min; m/z=443.23 (M+H$^+$).

6-((S)-2-Methyl-pyrrolidine-1-carbonyl)-3,4-dihydro-1H-pyrrolo[2,1-c][1,4]oxazine-8-carboxylic acid [(R)-1-(5-chloro-thiophen-2-yl)-propyl]-amide (comp. no. 16rb)

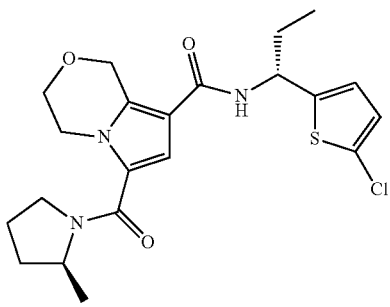 [SMILES: CC[C@@H](NC(=O)c1cc(C(=O)N2CCC[C@@H]2C)n2c1COCC2)c1ccc(Cl)s1]

A mixture of 6-((S)-2-methy-pyrrolidine-1-carbonyl)-3,4-dihydro-1H-pyrrolo[2,1-c][1,4]oxazine-8-carboxylic acid [(R)-1-(5-bromo-thiophen-2-yl)-propyl]-amide (comp. no. 16bg) (50 mg, 0.104 mmol) and copper(I) chloride (21 mg, 0.208 mmol) in dimethyl sulfoxide (0.7 ml) was heated at 130° C. for 90 min in a microwave reactor. The crude reaction mixture was purified by reverse phase HPLC (acetonitrile/water gradient with 0.1% trifluoroacetic acid) to give 6-((S)-2-methyl-pyrrolidine-1-carbonyl)-3,4-dihydro-1H-pyrrolo[2,1-c][1,4]oxazine-8-carboxylic acid [(R)-1-(5-chloro-thiophen-2-yl)-propyl]-amide (25 mg, 55%). LC/MS: Rt=1.28 min (method 2); m/z=436.03 (M+H$^+$).

6-((S)-2-Methyl-pyrrolidine-1-carbonyl)-3,4-dihydro-1H-pyrrolo[2,1-c][1,4]oxazine-8-carboxylic acid ((R)-1-thiophen-2-yl-propyl)amide (comp. no. 16rc)

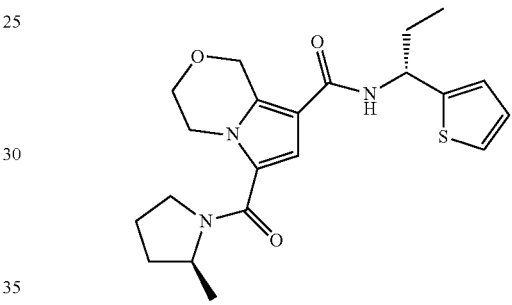

During the synthesis of comp. no. 16rb, 8 mg (18%) of 6-((S)2-methyl-pyrrolidine-1-carbonyl)-3,4-dihydro-1H-pyrrolo[2,1-c][1,4]oxazine-8-carboxylic acid ((R)-1-thiophen-2-yl-propyl)-amide) were obtained as side-product. LC/MS (method 2); Rt=1.21 min; m/z=402.1 (M+H$^+$).

The example compounds of the formula I in Table 12 were obtained in analogy to the synthesis of comp. no. 18rb. In some cases higher temperatures and longer reaction times were necessary (indicated in the Table).

TABLE 12

| Comp. no. | Starting comp. (no.) | Formula | Rt [min] (LC/MS method) | m/z (M + H$^+$) |
|---|---|---|---|---|
| 16rd | 16bg + CuCN | | 1.21 (2) | 427.11 |

TABLE 12-continued

| 16re | 16c + CuCN (160-170° C., 12 h) | | 1.93 (3) | 489.35 |
|---|---|---|---|---|
| 16rf | 16co + CuCN (160° C., 2 h) | | 1.82 (3) | 456.31 |

| Comp. no. | Chemical name |
|---|---|
| 16rd | 6-((S)-2-Methyl-pyrrolidine-1-carbonyl)-3,4-dihydro-1H-pyrrolo[2,1-c][1,4]oxazine-8-carboxylic acid [(R)-1-(5-cyano-thiophen-2-yl)-propyl]-amide |
| 16re | 6-((S)-2-Methyl-pyrrolidine-1-carbonyl)-3,4-dihydro-1H-pyrrolo[2,1-c][1,4]oxazine-8-carboxylic acid [(R)-1-(3-cyano-trifluoromethyl-phenyl)-propyl]-amide |
| 16rf | 6-((S)-2-Methyl-pyrrolidine-1-carbonyl)-3,4-dihydro-1H-pyrrolo[2,1-c][1,4]oxazine-8-carboxylic acid [(R)-1-(5-chloro-6-cyano-pyridin-3-yl)-propyl]-amide |

Acetic acid (R)-1-[8((R)-1-phenyl-propylcarbamoyl)-3,4-dihydro-1H-pyrrolo[2,1-c][1,4]oxazine-6-carbonyl]-pyrrolidin-2-ylmethyl ester (comp. no. 16rg)

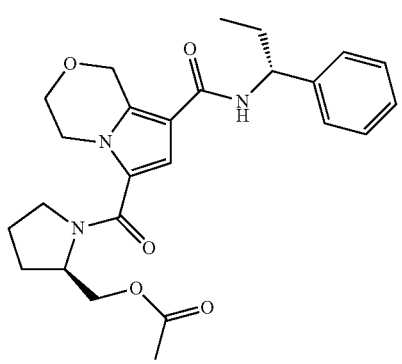 [SMILES: CC[C@@H](NC(=O)c1cc(C(=O)N2CCC[C@@H]2COC(C)=O)n2c1COCC2)c1ccccc1]

A mixture of 6-((R)-2-hydroxymethyl-pyrrolidine-1-carbonyl)-3,4-dihydro-1H-pyrrolo[2,1-c][1,4]oxazine-8-carboxylic acid ((R)-1-phenyl-propyl)-amide (comp. no. 16ei) (0.213 mmol), thethylamine (31 mg, 0.31 mmol), acetyl chloride (24 mg, 0.31 mmol) and 4-dimethylamino-pyridine (ca. 1 mg) in dry dichloromethane was stirred overnight. After addition of aqueous sodium hydrogencarbonate, extraction (3 times with dichloromethane), and drying of the combined organic layers over sodium sulfate, the solvents were evaporated and the residue was purified by reverse phase HPLC (acetonitrile/water gradient with 0.1% trifluoroacetic acid) to give acetic acid (R)-1-[8-((R)-1-phenyl-propylcarbamoyl)-3,4-dihydro-1H-pyrrolo[2,1-c][1,4]ox-azine-6-carbonyl]-pyrrolidin-2-ylmethyl ester (54 mg, 55%). LC/MS (method 4): Rt=1.23 min; m/z=454.31 (M+H$^+$).

3,4-Dihydro-1H-pyrrolo[2,1-c][1,4]oxazine-6,8-dicarboxylic acid 6-{[(R)-1-(6-hydroxy-pyridin-2-yl)-propyl]-amide} 8-[((R)-1-phenyl-propyl)-amide] (comp. no. 16rh)

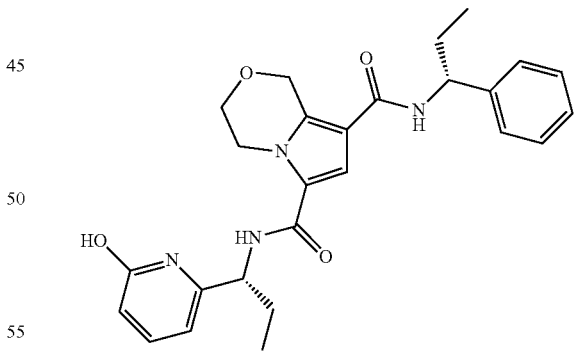

A solution of 3,4-dihydro-1H-pyrrolo[2,1-c][1,4]oxazine-6,8-dicarboxylic acid 6-{[(R)-1-(6-methoxy-pyridin-2-yl)-propyl]-amide} 8-[((R)-1-phenyl-propyl)-amide] (comp. no. 16ic) (50 mg, 0.105 mmol) and iodotrimethylsilane (32 mg, 0.157 mmol) in acetonitrile (3 ml) was heated at 80° C. After completion of the reaction solvents were evaporated and the residue was purified by reverse phase HPLC (acetonitrile/water gradient with 0.1% trifluoroacetic acid) to give 3,4-dihydro-1H-pyrrolo[2,1-c][1,4]oxazine-6,8-dicarboxylic acid 6-{[(R)-1-(6-hydroxy-pyridin-2-yl)-propyl]-amide}

8-[((R)-1-phenyl-propyl)-amide] (24 mg, 49%). LC/MS (method 2): Rt=1.02 mm: m/z=463.4 (M'H⁺).

3,4-Dihydro-1H-pyrrolo[2,1-c][1,4]oxazine-6,8-dicarboxylic acid 6-{[(R)-1-(3-methanesulfonylamino-phenyl)-propyl]-amide} 8-[((R)-1-phenyl-propyl)-amide] (comp. no. 16ri)

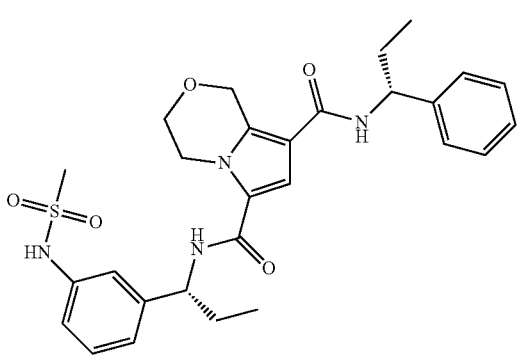 [SMILES: CC[C@@H](NC(=O)c1cc(C(=O)N[C@H](CC)c2cccc(NS(C)(=O)=O)c2)n2c1COCC2)c1ccccc1]

A solution of 3,4-dihydro-1H-pyrrolo[2,1-c][1,4]oxazine-6,8-dicarboxylic acid 6-{[(R)-1-(3-amino-phenyl)-propyl]-amide} 8-[((R)-1-phenyl-propyl)-amide] (obtained from comp. no. 11a and 3-((R)-1-amino-propyl)-phenylamine in analogy to comp. no. 16e) (50 mg, 0.105 mmol) and methanesulfonyl chloride (15 mg, 0.13 mmol) was stirred in pyridine (1.5 ml) at 25° C. for 1 h. After evaporation of all solvents the residue was purified by reverse phase HPLC (acetonitrile/water gradient with 0.1% trifluoroacetic aci) to give 13 mg (22%) of 3,4-dihydro-1H-pyrrolo[2,1-c][1,4]oxazine-6,8-dicarboxylic acid 6-{[(R)-1-(3-methanesulfonylamino-phenyl)-proply]-amide} 8-[((R)-1-phenyl-propyl)-amide]. LC/MS (method 4): Rt=1.23 min; m/z=539.41 (M+H⁺).

3,4-Dihydro-1H-pyrrolo[2,1-c][1,4]oxazine-6,8-dicarboxylic acid 6-{[1-(3-dimethylsulfamoyl-phenyl)-ethyl]-amide} 8-[((R)-1-phenyl-propyl)-amide] (comp. no. 16rj)

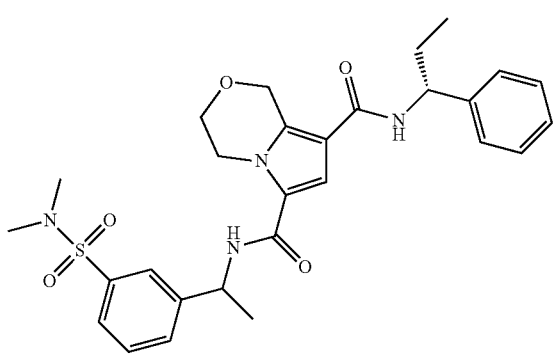 [SMILES: CC[C@@H](NC(=O)c1cc(C(=O)NC(C)c2cccc(S(=O)(=O)N(C)C)c2)n2c1COCC2)c1ccccc1]

A solution of 3,4-dihydro-1H-pyrrolo[2,1-c][1,4]oxazine-6,8-dicarboxylic acid 8-[((R)-1-phenyl-propyl)-amide] 6-{[1-(3-sulfamoyl-phenyl)-ethyl]-amide} (comp. no. 16ip) (50 mg, 0.100 mmol), iodomethane (21 mg, 0.15 mmol) and potassium carbonate (27 mg, 0.2 mmol) was stirred in acetonitrile at 50° C. overnight. After evaporation of all solvents the residue was purified by reverse phase HPLC (acetonitrile/water gradient with 0.1% trifluoroacetic acid) to give 11 mg (21%) of 3,4-dihydro-1H-pyrrolo[2,1-c][1,4]oxazine-6,8-dicarboxylic acid 6-{[1-(3-dimethylsulfamoyl-phenyl)ethyl]-amide} 8-[((R)-1-phenyl-propyl)-amide]. LC/MS (method 4): Rt=1.25 min; m/z=539.41 (M+H⁺).

3,4-Dihydro-1H-pyrrolo[2,1-c][1,4]oxazine-6,8-dicarboxylic acid 6-[((S)-1-dimethylcarbamoyl-ethyl)-methyl-amide] 8-[((R)-1-phenyl-propyl)-amide] (comp. no. 16rk)

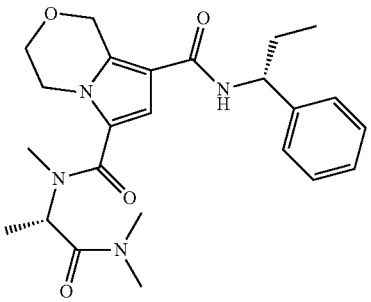 [SMILES: CC[C@@H](NC(=O)c1cc(C(=O)N(C)[C@@H](C)C(=O)N(C)C)n2c1COCC2)c1ccccc1]

To a solution of (S)-2-{methyl-[8-((R)-1-phenyl-propyl-carbamoyl)-3,4-dihydro-1H-pyrrolo[2,1-c][1,4]oxazine-6-carbonyl]-amino}-propionic acid (synthesized from comp. no. 16i by saponification with sodium hydroxide/water/methanol in analogy to the synthesis of comp. no. 7c) in dimethylformamide (2 ml) was added 1-hydroxybenzotriazole (18 mg, 0.133 mmol) and 1-ethyl-3-(3-dimethylamino-propyl)carbodiimide hydrochloride (26 mg; 0.133 mmol). The mixture was stirred for 45 min at 25° C., then 2 M dimethylamine in tetrahydrofuran (0.078 ml, 0.157 mmol) was added and the mixture was stirred at 25° C. overnight. The mixture was purified by reverse phase HPLC (acetonitrile/water gradient with 0.1% trifluoroacetic acid) to give 42 mg (79%) of 3,4-dihydro-1H-pyrrolo[2,1-c][1,4]oxazine-6,8-dicarboxylic acid 6-[((S)-1-dimethylcarbamoyl-ethyl)-methyl-amide] 8-[((R)-1-phenyl-propyl)-amide]. LC/MS (method 4); Rt=1.13 min; m/z=441.21 (M+H⁺).

3,4-Dihydro-1H-pyrrolo[2,1-c][1,4]oxazine-6,8-dicarboxylic acid 6-[((S)-1-isopropylcarbamoyl-ethyl)-methyl-amide] 8-[((R)-1-phenyl-propyl)-amide] (comp. no. 16rl)

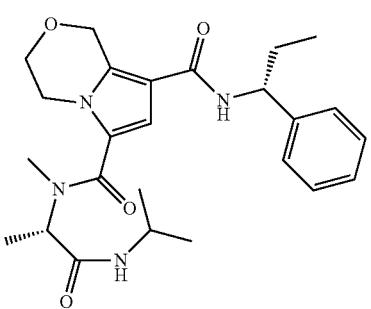 [SMILES: CC[C@@H](NC(=O)c1cc(C(=O)N(C)[C@@H](C)C(=O)NC(C)C)n2c1COCC2)c1ccccc1]

The compound was obtained from comp. no. 16l as starting compound and isopropylamine in analogy to the synthesis of comp. no. 16rk. LC/MS (method 4): Rt=1.18 min; m/z=455.22 (M+H)⁺.

3-((R)-1-{[8-((R)-1-Phenyl-propylcarbamoyl)-3,4-dihydro-1H-pyrrolo[2,1-c][1,4]oxazine-6-carbonyl]-amino}-propyl)-benzoic acid (comp. no. 16rm)

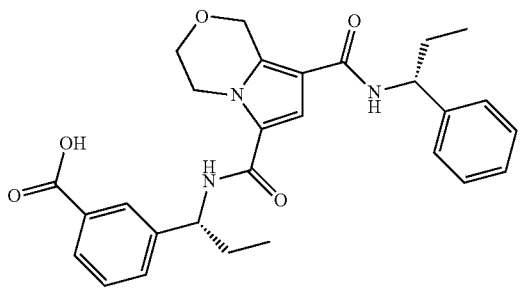 [SMILES: CC[C@@H](NC(=O)c1cc(C(=O)N[C@H](CC)c2cccc(C(=O)O)c2)n2c1COCC2)c1ccccc1]

A solution of 3-((R)-1-{[8-((R)-1-phenyl-propylcarbamoyl)-3,4-dihydro-1H-pyrrolo[2,1-c][1,4]oxazine-6-carbonyl]-amino}-propyl)-benzoic acid methyl ester (synthesized from comp. no. 11a and 3-((R)-1-amino-propyl)-benzoic acid methyl ester) in methanol (0.5 ml) and 2 N aqueous sodium hydroxide (0.5 ml) was stirred at reflux for 1 h, the solvents were evaporated, water was added and the solution was acidified with excess aqueous hydrochloric acid. The solid formed was filtered off, washed with water and dried in vacuo to give 41 mg (73%) of 3-((R)-1-{[8-((R)-1-phenyl-propylcarbamoyl)-3,4-dihydro-1H-pyrrolo[2,1-c][1,4]oxazine-6-carbonyl]-amino}-propyl)-benzoic acid. LC/MS (method 2): Rt=1.1 min; m/z=490.4 (M+H$^+$).

3,4-Dihydro-1H-pyrrolo[2,1-c][1,4]oxazine-6,8-dicarboxylic acid 6-{[1-(2-methyl-2H-tetrazol-5-yl)-ethyl]-amide} 8-[((R)-1-phenyl-propyl)-amide] (comp. no. 16m)

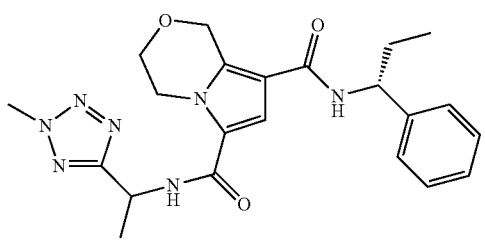 [SMILES: CC[C@@H](NC(=O)c1cc(C(=O)NC(C)c2nnn(C)n2)n2c1COCC2)c1ccccc1]

and 3,4-dihydro-1H-pyrrolo[2,1-c][1,4]oxazine-6,8-dicarboxylic acid 6-{[1-(1-methyl-1H-tetrazol-5-yl)-ethyl]-amide} 8-[((R)-1-phenyl-propyl)-amide] (comp. no. 16ro)

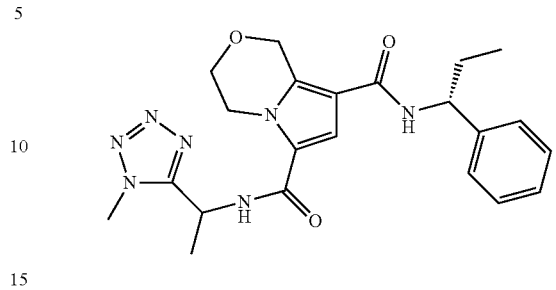

A mixture of 3,4-dihydro-1H-pyrrolo[2,1-c][1,4]oxazine-6,8-dicarboxylic acid 8-[((R)-1-phenyl-propyl)-amide] 6-{[1-(1H-tetrazol-5ly)-ethyl]-amide} (synthesized from comp. no. 11a and 1-(1H-tetrazol-5-yl)-ethylamine in analogy to comp. no. 16e) (152 mg, 0.360 mmol), iodomethane (77 mg, 0.54 mmol) and potassium carbonate (149 mg, 1.08 mmol) was stirred in acetonitrile at 50° C. overnight. After filtration through a short cartridge the residue was purified by reverse phase HPLC (acetonitrile/water gradient with 0.1% trifluoroacetic acid) to give 15 mg (10%) of 3,4-Dihydro-1H-pyrrolo[2,1-c][1,4]oxazine-6,8-dicarboxylic acid 6-{[1-(2-methyl-2H-tetrazol-5-yl)-ethyl]-amide} 88-[((R)-1-phenyl-propyl)-amide] (LC/MS (method 4): Rt=1.16 min; m/z=438.24 (M+H$^+$)) and 17 mg (11%) of 3,4-dihydro-1H-pyrrolo[2,1-c][1,4]oxazine-6,8-dicarboxylic acid 6-{[1-(1-methyl-1H-tetrazol-5-yl)-ethyl]-amide} 8-[((R)-1-phenyl-propyl)-amide] (LC/MS (method 4): Rt=1.14 min; m/z=438.23 (M+H$^+$)).

The example compounds of the formula I in Table 13 were obtained in analogy to the synthesis of comp no. 16m/16ro.

TABLE 13

| Comp. no. | Starting comp. no. | Formula | Rt [min] (LC/MS method) | m/z (M + H$^+$) |
| --- | --- | --- | --- | --- |
| 16rp | 11a + ethyl-(2H-tetrazol-5-ylmethyl)-amine + iodomethane | | 1.07 (2) | 452.24 |

TABLE 13-continued

| Comp. no. | | Structure | | |
|---|---|---|---|---|
| 16rq | 11a + 1-(1H-tetrazol-5-yl)-ethylamine + iodoethane | 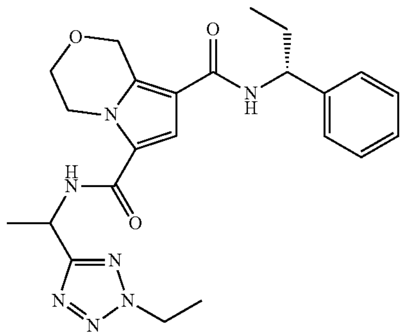 [SMILES: CC[C@@H](NC(=O)c1cc(C(=O)NC(C)c2nnn(CC)n2)n2c1COCC2)c1ccccc1] | 1.08 (2) | 452.26 |
| 16rr | 11a + 1-(1H-tetrazol-5-yl)-ethylamine + iodoethane | 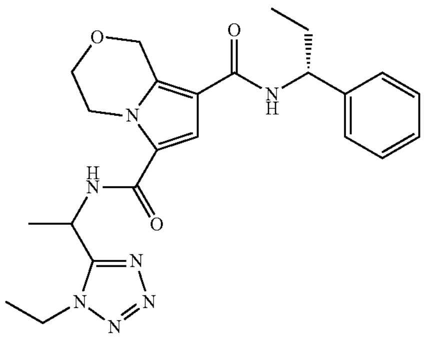 [SMILES: CC[C@@H](NC(=O)c1cc(C(=O)NC(C)c2nnnn2CC)n2c1COCC2)c1ccccc1] | 1.06 (2) | 452.28 |
| 16rs | 11a + C-(1H-tetrazol-5-yl)-methylamine + iodomethane | 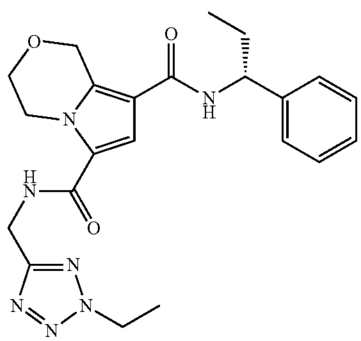 [SMILES: CC[C@@H](NC(=O)c1cc(C(=O)NCc2nnn(CC)n2)n2c1COCC2)c1ccccc1] | 1.01 (2) | 424.26 |
| 16rt | 7o + ethyl-(2H-tetrazol-5-ylmethyl)-amine + iodomethane | 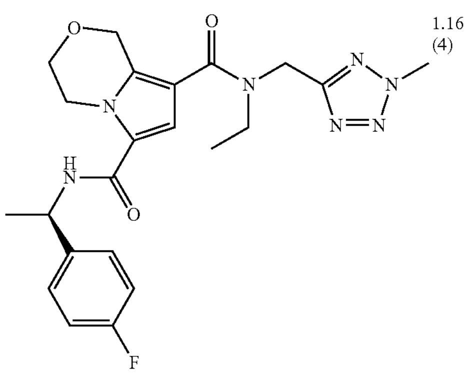 | 1.16 (4) | 456.15 |

| Comp. no. | Chemical name |
|---|---|
| 16rp | 3,4-Dihydro-1H-pyrrolo[2,1-c][1,4]oxazine-6,8-dicarboxylic acid 6-[ethyl-(2-methyl-2H-tetrazol-5-ylmethyl)-amide] 8-[((R)-1-phenyl-propyl)-amide] |
| 16rq | 3,4-Dihydro-1H-pyrrolo[2,1-c][1,4]oxazine-6,8-dicarboxylic acid 6-{[1-(2-ethyl-2H-tetrazol-5-yl)-ethyl]-amide} 8-[((R)-1-phenyl-propyl)-amide] |
| 16rr | 3,4-Dihydro-1H-pyrrolo[2,1-c][1,4]oxazine-6,8-dicarboxylic acid 6-{[1-(1-ethyl-1H-tetrazol-5-yl)-ethyl]-amide} 8-[((R)-1-phenyl-propyl)-amide] |
| 16rs | 3,4-Dihydro-1H-pyrrolo[2,1-c][1,4]oxazine-6,8-dicarboxylic acid 6-[(2-methyl-2H-tetrazol-5-ylmethyl)-amide] 8-[((R)-1-phenyl-propyl)-amide] |

| | |
|---|---|
| 16rt | 3,4-Dihydro-1H-pyrrolo[2,1-c][1,4]oxazine-6,8-dicarboxylic acid 8-[ethyl-(2-methyl-2H-tetrazol-5-ylmethyl)-amide] 6-{[(R)-1-(4-fluoro-phenyl)-ethyl]-amide} |

7-Bromo-6-((S)-2-methyl-pyrrolidine-1-carbonyl)-3,4-dihydro-1H-pyrrolo[2,1-c][1,4]oxazine-8-carboxylic acid [(R)-1-(6-trifluoromethyl-pyridin-3-yl)-propyl]-amide (comp. no. 16ru)

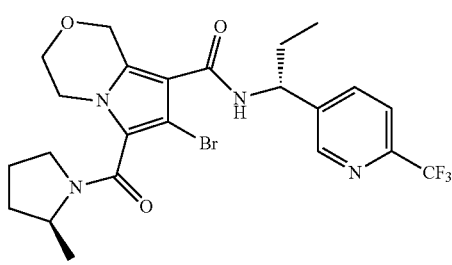 [SMILES: CC[C@@H](NC(=O)c1c(Br)c(C(=O)N2CCC[C@@H]2C)n2c1COCC2)c1ccc(C(F)(F)F)nc1]

To a solution of 6-((S)-2-methyl-pyrrolidine-1-carbonyl)-3,4-dihydro-1H-pyrrolo[2,1-c][1,4]oxazine-8-carboxylic acid [(R)-1-(6-trifluoromethyl-pyridin-3-yl)-propyl]-amide (comp. no. 16e) (200 mg, 0.43 mmol) in chloroform (5 ml) was added N-bromo-succinimide (76 mg, 0.43 mmol) and the mixture was stirred for 18 h at 25° C. Then excess dichloromethane was added and the mixture was washed consecutively with water, aqueous sodium hyorogencarbonate and brine. The organic layer was evaporated to dryness. The crude product was purified by reverse phase HPLC to give 200 mg (86%) of 7-bromo-6-((S)-2-methyl-pyrrolidine-1-carbonyl)-3,4-dihydro-1H-pyrrolo[2,1-c][1,4]oxazine-8-carboxylic acid [(R)-1-(6-trifluoromethyl-pyridin-3-yl)-propyl]-amide. LC/MS (method 3): Rt=1.81 min; m/z=543.1 (M+H⁺).

7-Chloro-6-((S)-2-methyl-pyrrolidine-1-carbonyl)-3,4-dihydro-1H-pyrrolo[2,1-c][1,4]oxazine-8-carboxylic acid [(R)-1-(6-trifluoromethyl-pyridin-3-yl)-propyl]-amide (comp. no. 16rv)

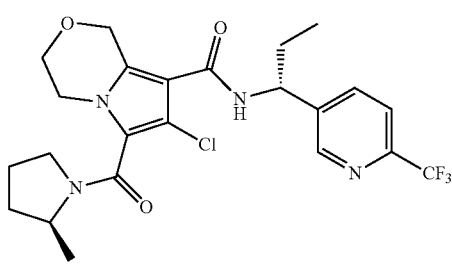 [SMILES: CC[C@@H](NC(=O)c1c(Cl)c(C(=O)N2CCC[C@@H]2C)n2c1COCC2)c1ccc(C(F)(F)F)nc1]

The compound was prepared from 6-((S)-2-methyl-pyrrolidine-1-carbonyl)-3,4-dihydro-1H-pyrrolo[2,1-c][1,4]oxazine-8-carboxylic acid [(R)-1-(6-trifluoromethyl-pyridin-3-yl)-propyl]-amide (comp. no. 16e) and N-chloro-succinimide in analogy to the synthesis of comp. no. 16ru. LC/MS (method 3): Rt=1.94 min; m/z=499.23 (M+H⁺).

7-Chloro-6-((S)-2-methyl-pyrrolidine-1-carbonyl)-3,4-dihydro-1H-pyrrolo[2,1-c][1,4]oxazine-8-carboxylic acid ((R)-1-phenyl-propyl)-amide (comp. no. 16rw)

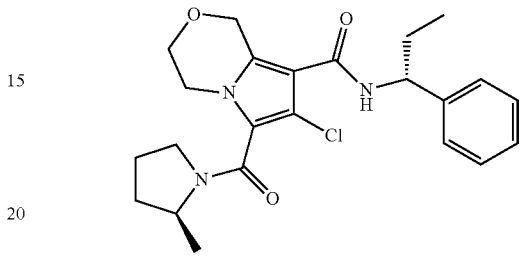

The compound was prepared from 6-((S)-2-methyl-pyrrolidine-1-carbonyl)-3,4-dihydro-1H-pyrrolo[2,1-c][1,4]oxazine-8-carboxylic acid ((R)-1-phenyl-propyl)-amide (comp. no. 16a) and N-chloro-succinimide in analogy to the synthesis of comp. no. 16 ru. LC/MS (method 3): Rt=1.86 min; m/z=430.22 (M+H⁺).

7-Methyl-6-((S)-2-methyl-pyrrolidine-1-carbonyl)-3,4-dihydro-1H-pyrrolo[2,1-c][1,4]oxazine-8-carboxylic acid [(R)-1-(6-trifluoromethyl-pyridin-3-yl)-propyl]-amide (comp. no. 16rx)

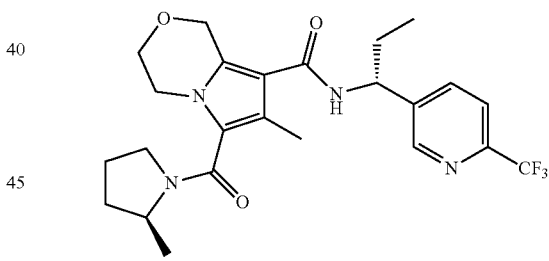

A solution of 7-bromo-6-((S)-2-methyl-pyrrolidine-1-carbonyl)-3,4-dihydro-1H-pyrrolo[2,1-c][1,4]oxazine-8-carboxylic acid [(R)-1-(6-trifluoromethyl-pyridin-3-yl)-propyl]-amide (comp. no. 16ru) (55 mg, 0.101 mmol), tetramethylstannane (101 mg, 0.50 mmol) and tetrakis(triphenylphosphino)palladium(O) (6 mg, 5 µmol) in dimethylformamide (2 ml) was heated at 110° C. under microwave irradiation for 1 h. The crude product was purified by reverse phase HPLC to give 45 mg (92%) of 7-methyl-6-((S)-2-methyl-pyrrolidine-1-carbonyl)-3,4-dihydro-1H-pyrrolo[2,1-c][1,4]oxazine-8-carboxylic acid [(R)-1-(6-trifluoromethyl-pyridin-3-yl)-propyl]-amide. LC/MS (method 3): Rt=1.85 min; m/z=479.32 (M+H⁺).

3,4-Dihydro-2H-pyrrolo[2,1-b][1,3]oxazine-6,8-dicarboxylic acid bis-[((R)-1-phenyl-propyl)-amide] (comp. no. 16ry)

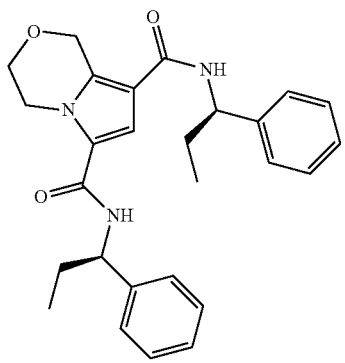 [SMILES: CC[C@@H](NC(=O)c1cc(C(=O)N[C@H](CC)c2ccccc2)n2c1COCC2)c1ccccc1]

A solution of 5-chloro-1H-pyrrole-2,4-dicarboxylic acid diethyl ester (500 mg, 2.035 mmol; prepared according to the procedure described in US 2004/0209886) in dry acetone (6 ml) was treated with (3-bromo-propoxy)tert-butyldimethylsilane (1.063 g, 0.973 ml, 4.070 mmol) and cesium carbonate (663 mg, 2.035 mmol) and stirred for 2.5 h at 65° C. The reaction mixture was concentrated in vacuo and dispersed between ethyl acetate and saturated aqueous sodium hydrogencarbonate-solution. The layers were separated and the aqueous layer extracted with ethyl acetate. The combined organic layers were dried over magnesium sulfate, filtered and evaporated.

Part of the obtained crude 1-[3-(tert-butyl-dimethyl-silanyloxy)-propyl]-5-chloro-1H-pyrrole-2,4-dicarboxylic acid diethyl ester (110 mg, 0.263 mmol) was dissolved in a 1:1 mixture of water and isopropanol (2 ml), sodium hydroxide (11.6 mg, 0.289 mmol) was added and the mixture was stirred at room temperature overnight. The reaction mixture was diluted with water, the pH was adjusted to pH 6 with 0.1 M aqueous hydrochloric acid and the solution was washed with a 3:1 mixture of dichloromethane and isopropanol before being freeze-dried. The resulting white solid was used in the next step without further purification.

The obtained crude 1-[3-(tert-butyl-dimethyl-silanyloxy)-propyl]-5-chloro-1H-pyrrole-2,4-dicarboxylic acid (50.0 mg, 0.138 mmol) was dissolved in dimethylformamide (2 ml) and, sequentially, 1-hydroxy-7-azabenzotriazole (39.5 mg, 0.290 mmol), 1-ethyl-3-(3-dimethylaminopropyl)carbodiimide hydrochloride (55.6 mg, 0.290 mmol) and, after 10 min, (R)-1-phenyl-propylamine (39.2 mg, 0.290 mmol) were added. After stirring for 48 h at room temperature, the reaction mixture was diluted with ethyl acetate, and washed with water, saturated aqueous sodium hydrogencarbonate solution and brine. The organic layer was dried over magnesium sulfate, filtered and concentrated in vacuo to yield 1-[3-(tert-butyl-dimethyl-silanyloxy)-propyl]-5-chloro-1H-pyrrole-2,4-dicarboxylic acid bis-[((R)-1-phenyl-propyl)-amide] as a white solid. The crude bis-amide was treated with a 4 M solution of hydrochloric acid in dioxane (2 ml), stirred for 3 h at room temperature, evaporated and freeze-dried from water (10 ml).

A mixture of the obtained crude 5-chloro-1-(3-hydroxy-propyl)-1H-pyrrole-2,4-dicarboxylic acid bis-[((R)-1-phenyl-propyl)-amide] (31.0 mg, 0.084 mmol) and cesium carbonate (21.0 mg, 0.064 mmol) in dimethylformamide (2 ml) was heated in a microwave reactor at 130° C. for a period of 5.5 h until all starting material was consumed. The resulting mixture was concentrated in vacuo and purified by reverse phase chromatography with a water/acetonitrile gradient. The fractions containing the product were evaporated and freeze-dried from water (10 ml). 2.5 mg of 3,4-dihydro-2H-pyrrolo[2,1-b][1,3]oxazine-6,8-dicarboxylic acid bis-[((R)-1-phenyl-propyl)-amide]were isolated as white powder. LC/MS (method 4): Rt=1.30 min; m/z=446.24 (M+H$^+$).

3,4-Dihydro-2H-pyrrolo[2,1-b][1,3]oxazine-6,8-dicarboxylic acid bis-[((S)-1-phenyl-propyl)-amide] (comp. no. 16rz)

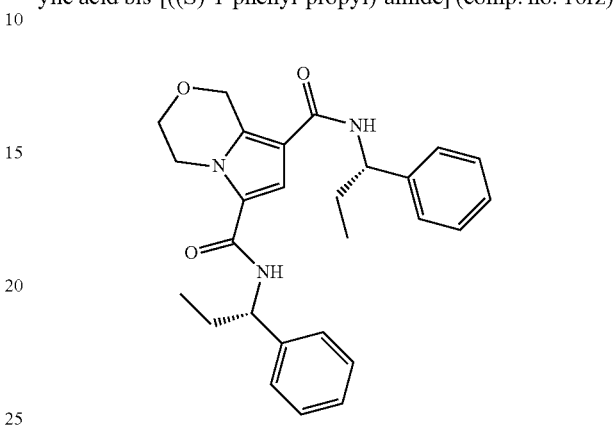

6.0 mg of 3,4-dihydro-2H-pyrmlo[2,1-b][1,3]oxazine-6,8-dicarboxylic acid bis-[((S)-1-phenyl-propyl)-amide] were prepared in analogy to the preparation of 3,4-dihydro-2H-pyrrolo[2,1-b][1,3]oxazine-6,8-dicarboxylic acid bis-[((R)-1-phenyl-propyl)-amide], starting from 5-bromo-1H-pyrrole-2,4-dicarboxylic acid diethyl ester (354 mg, 1.22 mmol; prepared according to the procedure described in US 2004/0209886), and (S)-1-phenyl-propylamine (284 mg, 2.10 mmol). LC/MS (method 4): Rt=1.31 min; m/z=446.24 (M+H$^+$).

Determination of the activity on the TASK-1 channel in *Xenopus oocytes*

Human TASK-1 channels were expressed in *Xenopus oocytes*. For this purpose, oocytes were isolated from *Xenopus laevis* and defoliculated. Subsequently, TASK-1-encoding RNA synthesized in vitro was injected into the oocytes. After two days of TASK-1 protein expression, TASK-1 currents were measured by two-microelectrode voltage clamp. Data were acquired and analyzed using a TEC-10cx amplifier (NPI Electronic, Tamm, Germany) connected to an ITC-16 interface (Instrutech Corp., Long island, USA) and Pulse software (HEKA Elektronik, Lambrecht, Germany). Oocytes were clamped to −90 mV and TASK-1 mediated currents were measured during 500 ms voltage pulses to 40 mV. Oocytes were continuously superfused with ND96 buffer containing 98 mM sodium chloride, 2 mM potassium chloride, 1.8 mM calcium chloride, 1 mM magnesium chloride, 5 mM 4-(2-hydroxyethyl)-piperazine-1-ethanesulfonic acid (HEPES: pH adjusted to 7.4 with sodium hydroxide). All experiments were performed at room temperature. Test compounds were consecutively added to the bath solution at rising concentrations. Compound effects were calculated as the percentage inhibition of TASK-1 control current before compound addition. $IC_{50}$ values were obtained by fitting the data to the general dose-response equation.

in Tables 14 and 15, activities determined in this assay with compounds of the formula I from the examples above are shown values in μM for TASK-1 inhibition in Table 14; TASK-1 inhibitions in percent at a compound concentration of 5 μM in Table 15).

TABLE 14

| Compound no. | IC$_{50}$ value [µM] for TASK-1 inhibition |
|---|---|
| 16a | 0.069 |
| 16aa | 2.4 |
| 16ab | 2.6 |
| 16ae | 0.67 |
| 16ah | 3.2 |
| 16ai | 1.4 |
| 16aj | 0.55 |
| 16ak | 1.3 |
| 16am | 0.92 |
| 16ap | 0.076 |
| 16aq | 0.46 |
| 16ar | 0.44 |
| 16at | 0.40 |
| 16au | 0.34 |
| 16av | 0.47 |
| 16aw | 0.28 |
| 16ax | 0.35 |
| 16ay | 0.91 |
| 16az | 0.12 |
| 16b | 0.061 |
| 16ba | 0.14 |
| 16bb | 0.79 |
| 16bc | 0.55 |
| 16bf | 0.74 |
| 16bg | 0.28 |
| 16bh | 0.92 |
| 16bi | 0.15 |
| 16bj | 4.1 |
| 16bl | 0.82 |
| 16bm | 0.093 |
| 16bo | 0.16 |
| 16br | 0.88 |
| 16bu | 0.21 |
| 16bv | 0.14 |
| 16bw | 1.2 |
| 16bx | 0.48 |
| 16by | 0.80 |
| 16bz | 0.20 |
| 16c | 0.013 |
| 16ca | 0.34 |
| 16cb | 0.14 |
| 16cc | 0.065 |
| 16ce | 0.28 |
| 16cf | 0.021 |
| 16cg | 0.015 |
| 16ch | 0.073 |
| 16ci | 0.03 |
| 16ck | 0.83 |
| 16cl | 0.05 |
| 16cn | 0.10 |
| 16co | 0.14 |
| 16cp | 0.97 |
| 16cq | 0.30 |
| 16cs | 0.29 |
| 16ct | 0.21 |
| 16cu | 9.0 |
| 16cv | 0.90 |
| 16cw | 2.4 |
| 16cx | 0.074 |
| 16cy | 0.21 |
| 16cz | 0.31 |
| 16d | 0.24 |
| 16da | 0.44 |
| 16db | 0.09 |
| 16de | 0.049 |
| 16df | 1.91 |
| 16dg | 0.30 |
| 16dh | 0.29 |
| 16di | 1.2 |
| 16dj | 1.9 |
| 16dk | 0.16 |
| 16dl | 0.062 |
| 16dm | 0.125 |
| 16dn | 0.050 |
| 16do | 0.19 |
| 16dq | 0.22 |
| 16dt | 1.0 |
| 16du | 0.22 |
| 16dv | 0.19 |
| 16dw | 0.048 |
| 16dx | 1.2 |
| 16dy | 1.5 |
| 16dz | 0.22 |
| 16e | 0.47 |
| 16eb | 0.25 |
| 16ec | 0.60 |
| 16ed | 0.30 |
| 16ee | 0.35 |
| 16ef | 0.82 |
| 16eg | 0.054 |
| 16eh | 1.7 |
| 16ei | 5.0 |
| 16ej | 0.26 |
| 16ek | 0.56 |
| 16el | 0.38 |
| 16em | 0.60 |
| 16en | 0.18 |
| 16eo | 0.38 |
| 16ep | 0.82 |
| 16eq | 0.48 |
| 16er | 0.32 |
| 16es | 1.8 |
| 16et | 1.3 |
| 16eu | 0.049 |
| 16ev | 0.33 |
| 16ew | 3.7 |
| 16ex | 0.18 |
| 16ey | 4.7 |
| 16ez | 0.50 |
| 16f | 0.068 |
| 16fb | 0.13 |
| 16fc | 0.025 |
| 16fd | 0.73 |
| 16fe | 0.15 |
| 16ff | 0.54 |
| 16fg | 1.3 |
| 16fh | 5.2 |
| 16fi | 0.13 |
| 16fk | 0.29 |
| 16fl | 0.24 |
| 16fm | 0.21 |
| 16fn | 0.16 |
| 16fo | 0.23 |
| 16fp | 1.9 |
| 16fq | 1.1 |
| 16fr | 1.3 |
| 16fs | 0.67 |
| 16ft | 3.6 |
| 16fu | 0.24 |
| 16fv | 0.92 |
| 16fw | 0.42 |
| 16fz | 5.1 |
| 16g | 0.29 |
| 16gb | 0.45 |
| 16gc | 0.10 |
| 16gd | 5.4 |
| 16ge | 0.69 |
| 16gf | 0.34 |
| 16gg | 0.23 |
| 16gh | 2.2 |
| 16gi | 1.3 |
| 16gj | 0.048 |
| 16gk | 0.036 |
| 16gl | 0.042 |
| 16gm | 0.49 |
| 16gn | 0.25 |
| 16go | 0.90 |
| 16gp | 0.57 |
| 16gq | 0.49 |
| 16gr | 0.31 |
| 16gs | 0.25 |
| 16gt | 0.31 |
| 16gu | 0.64 |
| 16gv | 1.31 |

TABLE 14-continued

| Compound no. | IC$_{50}$ value [μM] for TASK-1 inhibition |
|---|---|
| 16gw | 0.78 |
| 16gx | 0.43 |
| 16gy | 0.32 |
| 16gz | 2.2 |
| 16h | 0.24 |
| 16ha | 0.35 |
| 16hb | 0.013 |
| 16hc | 0.18 |
| 16hd | 0.56 |
| 16he | 0.49 |
| 16hf | 0.38 |
| 16hg | 0.60 |
| 16hh | 1.0 |
| 16hi | 1.1 |
| 16hj | 0.53 |
| 16hk | 1.4 |
| 16hl | 0.17 |
| 16hm | 0.66 |
| 16hn | 0.69 |
| 16ho | 0.73 |
| 16hp | 0.56 |
| 16hq | 0.32 |
| 16hr | 0.19 |
| 16hs | 0.10 |
| 16ht | 0.07 |
| 16hu | 0.62 |
| 16hv | 0.76 |
| 16hw | 0.36 |
| 16hx | 0.057 |
| 16hy | 0.041 |
| 16hz | 0.13 |
| 16i | 0.16 |
| 16ia | 0.12 |
| 16ib | 1.0 |
| 16ic | 0.04 |
| 16id | 0.53 |
| 16ie | 0.26 |
| 16if | 1.1 |
| 16ig | 0.24 |
| 16ih | 0.20 |
| 16ii | 0.65 |
| 16ij | 0.17 |
| 16ik | 0.71 |
| 16il | 0.17 |
| 16im | 0.14 |
| 16in | 0.37 |
| 16io | 0.94 |
| 16ip | 1.8 |
| 16iq | 0.33 |
| 16ir | 0.35 |
| 16is | 1.7 |
| 16it | 0.13 |
| 16iu | 0.12 |
| 16iv | 0.12 |
| 16iw | 0.62 |
| 16ix | 0.36 |
| 16iy | 0.27 |
| 16iz | 1.9 |
| 16j | 0.20 |
| 16ja | 0.10 |
| 16jc | 2.7 |
| 16jd | 2.5 |
| 16jh | 0.78 |
| 16ji | 1.9 |
| 16jj | 4.4 |
| 16jk | 0.62 |
| 16jl | 3.2 |
| 16jm | 1.5 |
| 16jn | 1.0 |
| 16jo | 0.25 |
| 16jp | 0.22 |
| 16jq | 0.067 |
| 16jr | 0.47 |
| 16js | 0.54 |
| 16jt | 0.15 |
| 16ju | 0.94 |
| 16jv | 0.21 |
| 16jw | 2.86 |
| 16jx | 0.22 |
| 16jy | 0.18 |
| 16jz | 0.30 |
| 16k | 0.18 |
| 16ka | 0.46 |
| 16kb | 0.62 |
| 16kc | 1.8 |
| 16kd | 0.14 |
| 16ke | 0.22 |
| 16kh | 0.99 |
| 16ki | 0.20 |
| 16kj | 0.27 |
| 16kk | 0.13 |
| 16kl | 0.21 |
| 16km | 0.39 |
| 16kn | 0.13 |
| 16ko | 0.31 |
| 16kp | 0.28 |
| 16kq | 0.046 |
| 16kr | 0.47 |
| 16ks | 0.037 |
| 16kt | 0.027 |
| 16ku | 0.087 |
| 16kv | 0.32 |
| 16kw | 0.095 |
| 16kx | 0.10 |
| 16ky | 0.033 |
| 16kz | 0.27 |
| 16l | 0.17 |
| 16la | 0.15 |
| 16lb | 0.065 |
| 16ld | 0.08 |
| 16le | 0.47 |
| 16lf | 0.11 |
| 16lg | 0.046 |
| 16lh | 0.19 |
| 16li | 0.90 |
| 16lj | 0.20 |
| 16lk | 0.31 |
| 16lm | 0.27 |
| 16ln | 0.14 |
| 16lo | 0.42 |
| 16lp | 0.55 |
| 16lq | 0.70 |
| 16lr | 0.36 |
| 16ls | 0.47 |
| 16lt | 0.058 |
| 16lu | 0.45 |
| 16lv | 2.1 |
| 16lw | 0.60 |
| 16lx | 0.20 |
| 16ly | 0.092 |
| 16m | 0.093 |
| 16m | 1.6 |
| 16ma | 0.051 |
| 16mb | 0.013 |
| 16mc | 0.62 |
| 16md | 0.080 |
| 16me | 0.34 |
| 16mf | 0.26 |
| 16mg | 0.84 |
| 16mh | 0.16 |
| 16mi | 0.59 |
| 16mk | 0.55 |
| 16ml | 0.13 |
| 16mm | 0.12 |
| 16mo | 1.9 |
| 16mp | 0.093 |
| 16mq | 0.31 |
| 16mr | 0.20 |
| 16ms | 0.55 |
| 16mt | 0.32 |
| 16mu | 0.075 |
| 16mv | 0.048 |
| 16mw | 0.074 |
| 16mx | 0.097 |

TABLE 14-continued

| Compound no. | IC$_{50}$ value [μM] for TASK-1 inhibition |
|---|---|
| 16my | 0.12 |
| 16mz | 0.042 |
| 16n | 0.14 |
| 16na | 1.7 |
| 16nb | 0.46 |
| 16nc | 2.0 |
| 16nd | 0.21 |
| 16nf | 0.11 |
| 16nh | 0.09 |
| 16ni | 0.29 |
| 16nj | 2.0 |
| 16nn | 0.27 |
| 16no | 0.17 |
| 16np | 0.17 |
| 16nq | 0.48 |
| 16nr | 0.31 |
| 16ns | 3.1 |
| 16nt | 0.67 |
| 16nu | 0.15 |
| 16nv | 0.17 |
| 16nw | 0.2 |
| 16nx | 0.37 |
| 16ny | 2.8 |
| 16nz | 2.2 |
| 16o | 0.41 |
| 16p | 0.38 |
| 16pa | 1.5 |
| 16pb | 0.52 |
| 16pf | 0.099 |
| 16pg | 0.19 |
| 16ph | 0.65 |
| 16pi | 0.85 |
| 16pj | 1.1 |
| 16pk | 0.19 |
| 16pl | 0.43 |
| 16pq | 0.65 |
| 16q | 0.064 |
| 16r | 1.9 |
| 16rb | 0.23 |
| 16rc | 0.15 |
| 16rd | 0.45 |
| 16rf | 1.0 |
| 16rg | 0.11 |
| 16rh | 0.24 |
| 16ri | 4.3 |
| 16rj | 1.1 |
| 16rl | 4.5 |
| 16rm | 4.9 |
| 16rn | 0.18 |
| 16ro | 2.8 |
| 16rp | 0.45 |
| 16rq | 0.75 |
| 16rs | 2.5 |
| 16ru | 0.82 |
| 16rv | 0.87 |
| 16rw | 0.47 |
| 16rx | 4.7 |
| 16ry | 0.87 |
| 16s | 0.25 |
| 16t | 0.044 |
| 16u | 0.049 |
| 16v | 0.11 |
| 16w | 0.04 |
| 16x | 0.19 |
| 16y | 1.0 |
| 16z | 0.27 |

TABLE 15

| Compound no. | TASK-1 inhibition [%] at 5 μM |
|---|---|
| 16af | 78 |
| 16ag | 84 |
| 16an | 81 |
| 16ao | 83 |
| 16as | 87 |
| 16bd | 47 |
| 16be | 85 |
| 16bk | 53 |
| 16bn | 63 |
| 16bp | 90 |
| 16bs | 80 |
| 16bt | 47 |
| 16cj | 69 |
| 16cm | 85 |
| 16dr | 84 |
| 16ds | 89 |
| 16ea | 72 |
| 16fj | 89 |
| 16fx | 90 |
| 16fy | 59 |
| 16ga | 67 |
| 16je | 91 |
| 16jf | 36 |
| 16jg | 80 |
| 16kf | 90 |
| 16kg | 70 |
| 16ll | 86 |
| 16lz | 76 |
| 16mn | 92 |
| 16ne | 83 |
| 16ng | 55 |
| 16nk | 62 |
| 16nl | 70 |
| 16nm | 77 |
| 16pc | 53 |
| 16pd | 82 |
| 16pe | 69 |
| 16po | 71 |
| 16ra | 60 |
| 16rk | 70 (a) |
| 16rr | 71 |
| 16rt | 72 |

(a) at 10 μM

Investigation of the refractory period and the left-atrial vulnerability in the pig The compounds were tested for prolongation of the refractory period and antiarrhythmic activity or the atrium of the anesthetized pig as described in Knobloch K. et al., Naunyn-Schmiedeberg's Arch. Pharmacol. 2002, 366, 482-487. Here the anti-arrhythmic action relates to the inhibition of the occurrence of episodes of atrial arrhythmias which are induced by a prematurely placed extra-stimulus (S2) in the left athum (=left-atrial vulnerability). The prolongation of the refractory period (refractoriness) is expressed as the increase in percent of the value of the refractory period 15 min after the end of administration of the test compound vs. the basal value before administration. Mean values of the prolongation of the refractory period are shown from three rates (150/min, 200/min and 250/min). The values for the inhibition of left atrial vulnerability (inhibition of episodes of arrhythmias) in percent refer to three measurements (three time points) before administration of the test compound vs. at least three measurements during the first hour after administration.

in Table 16, the action of compounds of the formula I from the examples above on the refractory period of the left atrium and their antiarrhythmic activity in the anesthetized pig after intravenous (i.v.) administration of the described dose is shown.

TABLE 16

| Compound no. | % Prolongation of left atrial refractory period | % Inhibition of left atrial vulnerability | Dose | Mode of i.v. administration |
|---|---|---|---|---|
| 16a | 40 | 91 | 0.3 mg/kg | infusion over 1 h |
| 16b | 21 | 91 | 0.3 mg/kg | bolus injection |
| 16c | 12 | 65 | 0.03 mg/kg | bolus injection |
| 16d | 24 | 100 | 0.3 mg/kg | bolus injection |
| 16e | 38 | 84 | 0.3 mg/kg | infusion over 1 h |
| 16f | 19 | 73 | 1.0 mg/kg | bolus injection |
| 16g | 19 | 100 | 0.3 mg/kg | bolus injection |
| 16h | 42 | 97 | 0.1 mg/kg | infusion over 1 h |
| 16o | 45 | 71 | 0.3 mg/kg | bolus injection |

Effect on upper airway collapsibility in the pig

Pharmacoiogicai efficacy against obstructive apneas was investigated in chloralose-urethane anesthetized pigs (weight range 20 to 35 kg), a large-animal model for obstructive apneas. Negative pressure generated by a negative pressure device was applied with a cannula to the upper part of the trachea for at least three breaths so that the upper airway was exposed to the negative pressure generated by the device. This caused an upper airway collapse as in an obstructive apnea in control animals treated with vehicle only, and in animals of the treatment group before the test compound was administered (baseline situation). Different levels of negative pressure were used to cause a collapse of the upper airway (−50 mbar, −100 mbar and −150 mbar). These negative pressure challenges were repeated several times before vehicle or test compound was given, and at regular intervals after administration of vehicle or test compound. Whether the upper airway was collapsed or open, was judged by airflow measurement and by the tracheal pressure in the cannula inserted into the upper trachea. In case the upper airway was collapsed by the negative pressure, airflow to the negative pressure device was close to zero. As a second parameter tracheal pressure approached the negative pressure generated by the device during upper airway collapse. Test compounds were administered by intravenous bolus injection. After administration of an effective test compound the upper airway was open during the negative pressure challenges, i.e. not collapsed, as indicated by airflow to the negative pressure device and the fact that tracheal pressure now approached atmospheric pressure in the inspiratory phase where upper airway muscles are activated. In vehicle-treated controls upper airway collapse occurred at every negative pressure challenge at −50 mbar, −100 mbar and −150 mbar.

In Table 17, the time after administration of compounds of the formula I from the examples above is shown during which no upper airway collapse occurred dime of inhibition of collapsibility) at a negative pressure of −150 mbar. The data show the efficacy of the compounds for inhibiting collapsibility.

TABLE 17

| Compound no. | Time of inhibition of collapsibility (at −150 mbar) | Dose | Number of animals |
|---|---|---|---|
| 16i | for 90 min | 10 µg/kg | 2 |
| 16j | for 120 min | 100 µg/kg | 2 |
| 16k | for >240 min | 100 µg/kg | 2 |
| 16l | for >120 min | 100 µg/kg | 2 |
| 16n | for 120 min | 100 µg/kg | 2 |

Determination of the effect on the hERG channel in CHO cells

An inhibition of the hERG (human Ether-a-go-go-Related Gene) potassium channel is unwanted because it can lead to dangerous arrhythmias. The effect of compounds of the formula I on the cloned human cardiac hERG channel was evaluated in an in vitro model using a whole-cell patch-clamping technique. CHO (Chinese hamster ovary) cells stably expressing hERG, the potassium channel underlying $I_{Kr}$ currents in human hearts, were grown in HAM's F-12 media supplemented with 10% fetal bovine serum, 1×penicillin/streptomycin and 500 µg/ml G418 (Invitrogen, Carlsbad, Calif., USA) in an atmosphere of 95% air and 5% carbon dioxide. Cells used for patch-clamping were seeded on glass or plastic coverslips 12 to 36 hours before use. hERG channel currents were recorded at room temperature using the whole-cell configuration of the patch clamp technique with an Axopatch 200B amplifier (Axon Instruments, Foster City, Calif., USA). Briefly, electrodes (3 to 6 MΩ resistance) were fashioned from TW150F glass capillary tubes (World Precision instruments, Sarasota, Fla., USA) and filled with pipette solution (containing 120 mM potassium aspartate, 20 mM potassium chloride, 4 mM adenosine triphosphate disodium salt, 5 mM HEPES, 1 mM magnesium chloride; pH adjusted to 7.2 with potassium hydroxide). hERG currents were initiated by a positive voltage pulse (20 mV) followed by a negative pulse (−40 mV) and were recorded for off-line analyses. Once hERG current from a cell perfused with external solution (containing 130 mM sodium chloride, 5 mM potassium chloride, 2.8 mM sodium acetate, 1 mM magnesium chloride, 10 mM HEPES, 10 mM glucose, 1 mM calcium chloride; pH adjusted to 7.4 with sodium hydroxide) without the test compound, i.e. control solution, was stabilized, the cell was perfused with external solution containing the test compound at specific concentrations. For each concentration from each cell, peak amplitude of the steady-state hERG tail current at −40 mV was measured in picoAmpere (pA). The peak amplitude in pA for each concentration (up to a maximum concentration of 10 µM) was compared with that for the control solution from the same cell and expressed as percent value of the control. From the percent values at multiple concentrations, $IC_{50}$ values for inhibition of hERG can be determined.

in Table 18, $IC_{50}$ values in µM for hERG inhibition are shown which result from measurements with compounds of the formula I from the examples above. The data show that the compounds are substantially devoid of the unwanted inhibition of hERG channels or have significant selectivity for TASK-1 inhibition vs. hERG inhibition.

TABLE 18

| Compound no. | $IC_{50}$ value [µM] for hERG inhibition |
|---|---|
| 16a | >10 |
| 16b | >10 |
| 16c | >10 |
| 16ci | ca. 10 |
| 16d | >10 |
| 16e | >10 |
| 16eb | >1 |
| 16f | >10 |
| 16g | >10 |
| 16h | >10 |
| 16i | >10 |
| 16j | >10 |
| 16k | >10 |
| 16l | >10 |

TABLE 18-continued

| Compound no. | IC$_{50}$ value [μM] for hERG inhibition |
|---|---|
| 16n | >10 |
| 16o | >10 |

The invention claimed is:

1. A method for the treatment of arrhythmia, atrial arrhythmia, atrial tachyarrhythmia, atrial fibrillation or atrial flutter, the method comprising administering to a patient in need thereof a compound of the formula I, in any of its stereoisomeric forms or a mixture of stereoisomeric forms in any ratio, or a pharmaceutically acceptable salt thereof,

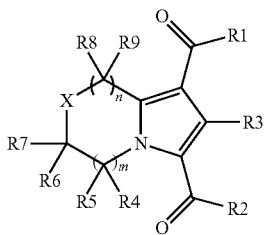

wherein n is selected from the series consisting of 0 and 1;

m is selected from the series consisting of 0, 1 and 2, with the proviso that m and n cannot simultaneously be 0;

X is selected from the series consisting of oxygen, sulfur and (R10)(R11)C;

one of the groups R1 and R2 is the group R20-NH— and the other of the groups R1 and R2 is the group (R30)(R31)N—;

R3 is selected from the series consisting of hydrogen, halogen and (C$_1$-C$_4$)-alkyl;

R4, R5, R6, R7, R8, R9, R10 and R11 are independently of one another selected from the series consisting of hydrogen and (C$_1$-C$_4$)-alkyl;

R20 is selected from the series consisting of (C$_5$-C$_7$)-cycloalkyl to which a benzene ring or a Het1 ring is fused, and (R21)(R22)(R23)C;

R21 is selected from the series consisting of phenyl and Het1, which are all unsubstituted or substituted by one or more identical or different substituents R24;

R22 is selected from the series consisting of hydrogen, (C$_1$-C$_4$)-alkyl, (C$_3$-C$_7$)-cycloalkyl and phenyl;

R23 is selected from the series consisting of hydrogen and (C$_1$-C$_4$)-alkyl;

R24 is selected from the series consisting of halogen, (C$_1$-C$_4$)-alkyl, (C$_3$-C$_7$)-cycloalkyl, HO—, (C$_1$-C$_4$)-alkyl-O—, (C$_1$-C$_4$)-alkyl-S(O)$_p$—, F$_5$S—, NC—, (C$_1$-C$_4$)-alkyl-O—C(O)—, —(C$_3$-C$_5$)-alkanediyl-, —O—(C$_1$-C$_4$)-alkanediyl-O— and —(C$_1$-C$_4$)-alkanediyl-O—C(O)—;

R30 is selected from the series consisting of hydrogen, (C$_1$-C$_4$)-alkyl, (C$_3$-C$_7$)-cycloalkyl-(C$_1$-C$_4$)-alkyl-, HO—(C$_1$-C$_4$)-alkyl- and (C$_1$-C$_4$)-alkyl-O—(C$_1$-C$_4$)-alkyl-;

R31 is selected from the series consisting of (C$_3$-C$_7$)-cycloalkyl, (C$_5$-C$_7$)-cycloalkyl to which a benzene ring is fused, phenyl, Het2 and (R32)(R33)(R34)C—, or the groups R30 and R31, together with the nitrogen atom carrying them, form a 4-membered to 10-membered, monocyclic or bicyclic, saturated or partially unsaturated heterocycle which, in addition to the nitrogen atom carrying R30 and R31, comprises 0 or 1 further ring heteroatom selected from the series consisting of nitrogen, oxygen and sulfur, and which is unsubstituted or substituted by one or more identical or different substituents R36;

R32 is selected from the series consisting of hydrogen and (C$_1$-C$_4$)-alkyl;

R33 is selected from the series consisting of hydrogen, (C$_1$-C$_4$)-alkyl, (C$_3$-C$_7$)-cycloalkyl and (C$_1$-C$_4$)-alkyl-O—C(O)—;

R34 is selected from the series consisting of (C$_1$-C$_6$)-alkyl, (C$_3$-C$_7$)-cycloalkyl, R38-(C$_3$-C$_7$)-cycloalkyl-, (C$_1$-C$_4$)-alkyl-O—C(O)—, (R39)(R40)N—C(O)—, phenyl and Het2, wherein the (C$_1$-C6)-alkyl is unsubstituted or substituted by one or more identical or different substituents R41, and the phenyl is unsubstituted or substituted by one or more identical or different substituents R35;

R35 is selected from the series consisting of halogen, (C$_1$-C$_4$)-alkyl, HO—(C$_1$-C$_4$)-alkyl-, (C$_1$-C$_4$)-alkyl-O—(C$_1$-C$_4$)-alkyl-, (C$_1$-C$_4$)-alkyl-O—C(O)—(C$_1$-C$_4$)-alkyl-, NC—, HO—, (C$_1$-C$_4$)-alkyl-O—, (C$_1$-C$_4$)-alkyl-S(O)$_p$—, (C$_1$-C$_4$)-alkyl-S(O)$_2$—NH—, R42-O—C(O)—, (R43)(R44)N—C(O)— and (R45)(R46)N—S(O)$_2$—;

R36 is selected from the series consisting of fluorine, (C$_1$-C$_6$)-alkyl, (C$_2$-C$_4$)-alkenyl, (C$_2$-C$_4$)-alkynyl, (C$_3$-C$_7$)-cycloalkyl, phenyl, Het3, HO—, (C$_1$-C$_4$)-alkyl-O—, (C$_3$-C$_7$)-cycloalkyl-O—, (C$_3$-C$_7$)-cycloalkyl-(C$_1$-C$_4$)-alkyl-O—, phenyl-O—, (C$_1$-C$_4$)-alkyl-S(O)$_p$—, NC— and R47-O—C(O)—, wherein the (C$_1$-C$_6$)-alkyl is unsubstituted or substituted by one or more identical or different substituents R48;

R38 is selected from the series consisting of phenyl, HO— and (C$_1$-C$_4$)-alkyl-O—;

R39, R40, R42, R47, R49, R50 and R51 are independently of one another selected from the series consisting of hydrogen and (C$_1$-C$_4$)-alkyl;

R41 is selected from the series consisting of (C$_3$-C$_7$)-cycloalkyl, phenyl, Het1, HO—, (C$_1$-C$_4$)-alkyl-O— and (C$_1$-C$_4$)-alkyl-S—;

R43, R44, R45 and R46 are independently of one another selected from the series consisting of hydrogen and (C$_1$-C$_4$)-alkyl;

R48 is selected from the series consisting of (C$_3$-C$_7$)-cycloalkyl, phenyl, Het3, HO—, (C$_1$-C$_4$)-alkyl-O—, (C$_1$-C$_4$)-alkyl-C(O)—O—, (C$_1$-C$_4$)-alkyl-S(O)$_p$—, (C$_1$-C$_4$)-alkyl-C(O)—(R49)N—, (R50)(R51)N—C(O)— and (C$_1$-C$_4$)-alkyl-O—C(O)—;

p is selected from the series consisting of 0, 1 and 2, wherein all numbers p are independent of one another;

Het1 is a 5-membered or 6-membered, monocyclic, aromatic heterocycle comprising 1 or 2 identical or different ring heteroatoms selected from the series consisting of nitrogen, oxygen and sulfur, which is bonded via a ring carbon atom and which is unsubstituted or substituted by one or more identical or different substituents selected from the series consisting of halogen, (C$_1$-C$_4$)-alkyl, (C$_3$-C$_7$)-cycloalkyl, NC—, HO—, (C$_1$-C$_4$)-alkyl-O— and (C$_1$-C$_4$)-alkyl-S(O)$_p$—, unless specified otherwise;

Het2 is a 4-membered to 10-membered, monocyclic or bicyclic, saturated, partially unsaturated or aromatic heterocycle comprising 1, 2, 3 or 4 identical or different ring heteroatoms selected from the series consisting of nitrogen, oxygen and sulfur, which is bonded via a ring carbon atom and which is unsubstituted or substituted by one or more identical or different substituents selected from the series consisting of halogen, $(C_1-C_4)$-alkyl, NC—, HO— and $(C_1-C_4)$-alkyl-O—;

Het3 is a 4-membered to 7-membered, monocyclic, saturated, partially unsaturated or aromatic heterocycle comprising 1, 2 or 3 identical or different ring heteroatoms selected from the series consisting of nitrogen, oxygen and sulfur, which is unsubstituted or substituted by one or more identical or different substituents selected from the series consisting of halogen, $(C_1-C_4)$-alkyl, $(C_3-C_7)$-cycloalkyl, NC—, HO—, $(C_1-C_4)$-alkyl-O— and $(C_1-C_4)$-alkyl-S(O)$_p$—;

wherein all phenyl groups are unsubstituted or substituted by one or more identical or different substituents selected from the series consisting of halogen, $(C_1-C_4)$-alkyl, NC—, HO— and $(C_1-C_4)$-alkyl-O—, unless specified otherwise;

wherein all alkyl groups, independently of any other substituents which can be present on an alkyl group, can be substituted by one or more fluorine substituents.

2. The method of claim 1, for the treatment of arrhythmia.

3. The method of claim 1, for the treatment of atrial arrhythmia or atrial tachyarrhythmia.

4. The method of claim 1, for the treatment of atrial fibrillation or atrial flutter.

5. The method of claim 1, wherein n is 1;

m is selected from the series consisting of 0 and 1 if X is sulfur or (R10)(R11)C, and m is 1 if X is oxygen;

R3 is selected from the series consisting of hydrogen, fluorine, chlorine, bromine and $(C_1-C_4)$-alkyl;

R4, R5, R6, R7, R8, R9, R10 and R11 are independently of one another selected from the series consisting of hydrogen and $(C_1-C_4)$-alkyl, with the proviso that at least six of these groups are hydrogen.

6. The method of claim 1, wherein n is 1;

m is 1;

X is selected from the series consisting of oxygen, sulfur and (R10)(R11)C;

one of the groups R1 and R2 is the group R20-NH— and the other of the groups R1 and R2 is the group (R30)(R31)N—;

R3, R4, R5, R6, R7, R8, R9, R10 and R11 are hydrogen;

R20 is (R21)(R22)(R23)C—;

R21 is selected from the series consisting of phenyl and Het1, which are all unsubstituted or substituted by one, two or three identical or different substituents R24;

R22 is selected from the series consisting of hydrogen, $(C_1-C_4)$-alkyl and cyclopropyl;

R23 is hydrogen;

R24 is selected from the series consisting of fluorine, chlorine, bromine, $(C_1-C_4)$-alkyl, $(C_3-C_7)$-cycloalkyl-, HO—, $(C_1-C_4)$-alkyl-O—, $(C_1-C_4)$-alkyl-S(O)$_p$—, $F_5S$—, NC— and $(C_1-C_4)$-alkyl-O—C(O)—;

R30 is selected from the series consisting of hydrogen, $(C_1-C_4)$-alkyl, cyclopropyl-$(C_1-C_2)$-alkyl-, HO—$(C_1-C_2)$-alkyl- and $(C_1-C_2)$-alkyl-O—$(C_1-C_2)$-alkyl-;

R31 is selected from the series consisting of $(C_3-C_6)$-cycloalkyl, $(C_5-C_6)$-cycloalkyl to which a benzene ring is fused, phenyl, Het2 and (R32)(R33)(R34)C—;

or the groups R30 and R31, together with the nitrogen atom carrying them, form a 4-membered to 7-membered, monocyclic, saturated heterocycle which, in addition to the nitrogen atom carrying R30 and R31, comprises 0 or 1 further ring heteroatom selected from the series consisting of nitrogen, oxygen and sulfur, and which is unsubstituted or substituted by one or two identical or different substituents R36;

R32 is hydrogen;

R33 is selected from the series consisting of hydrogen, $(C_1-C_4)$-alkyl and cyclopropyl;

R34 is selected from the series consisting of $(C_1-C_6)$-alkyl, $(C_3-C_6)$-cycloalkyl, R38-$(C_3-C_6)$-cycloalkyl-, $(C_1-C_4)$-alkyl-O—C(O)—, (R39)(R40)N—C(O)—, phenyl and Het2, wherein the $(C_1-C_6)$-alkyl is unsubstituted or substituted by one or two identical or different substituents R41, and the phenyl is unsubstituted or substituted by one or more identical or different substituents R35;

R35 is selected from the series of fluorine, chlorine, bromine, $(C_1-C_4)$-alkyl, HO—$(C_1-C4)$-alkyl-, $(C_1-C_4)$-alkyl-O—$(C_1-C_4)$-alkyl-, $(C_1-C_4)$-alkyl-O—C(O)—$(C_1-C_4)$-alkyl-, NC—, HO—, $(C_1-C_4)$-alkyl-O—, $(C_1-C_4)$-alkyl-S(O)$_p$—, $(C_1-C_4)$-alkyl-S(O)$_2$—NH—, R42-O—C(O)—, (R43)(R44)N—C(O)— and (R45)(R46)N—S(O)$_2$—;

R36 is selected from the series consisting of fluorine, $(C_1-C_4)$-alkyl, ethenyl, ethynyl, $(C_3-C_6)$-cycloalkyl, phenyl, Het3, $(C_1-C_4)$-alkyl-O—, $(C_3-C_6)$-cycloalkyl-O—, $(C_3-C_6)$-cycloalkyl-$(C_1-C_2)$-alkyl-O—, phenyl-O—, $(C_1-C_2)$-alkyl-S(O)$_p$—, NC— and R47-O—C(O)—, wherein the $(C_1-C_4)$-alkyl is unsubstituted or substituted by one or two identical or different substituents R48;

R38 is selected from the series consisting of phenyl, HO— and $(C_1-C_2)$-alkyl-O—;

R39, R40, R42, R47, R49, R50 and R51 are independently of one another selected from the series consisting of hydrogen and $(C_1-C_4)$-alkyl;

R41 is selected from the series consisting of $(C_3-C_6)$-cycloalkyl, phenyl, Het1, HO—, $(C_1-C_4)$-alkyl-O— and $(C_1-C_4)$-alkyl-S—;

R43, R44, R45 and R46 are independently of one another selected from the series consisting of hydrogen, $(C_1-C_4)$-alkyl, HO—$(C_1-C_4)$-alkyl- and $(C_1-C_4)$-alkyl-O—$(C_1-C_4)$-alkyl-;

R48 is selected from the series consisting of $(C_3-C_6)$-cycloalkyl, phenyl, Het3, HO—, $(C_1-C_4)$-alkyl-O—, $(C_1-C_4)$-alkyl-C(O)—O—, $(C_1-C_4)$-alkyl-S(O)$_p$—, $(C_1-C_4)$-alkyl-C(O)—(R49)N—, (R50)(R51)N—C(O)— and $(C_1-C_4)$-alkyl-O—C(O)—;

p is selected from the series consisting of 0 and 2, wherein all numbers p are independent of one another;

Het1 is a 5-membered or 6-membered, monocyclic, aromatic heterocycle comprising one ring heteroatom selected from the series consisting of nitrogen, oxygen and sulfur or one ring nitrogen atom and one further ring heteroatom selected from the series consisting of nitrogen, oxygen and sulfur, which is bonded via a ring carbon atom and which is unsubstituted or substituted by one or more identical or different substituents selected from the series consisting of halogen, $(C_1-C_4)$-alkyl, $(C_3-C_7)$-cycloalkyl, NC—, HO—, $(C_1-C_4)$-alkyl-O— and $(C_1-C_4)$-alkyl-S(O)$_p$—, unless specified otherwise;

Het2 is a 5-membered to 10-membered, monocyclic or bicyclic, saturated, partially unsaturated or aromatic heterocycle comprising 1, 2, 3 or 4 nitrogen atoms, or 1 oxygen atom or sulfur atom, or 1 or 2 nitrogen atoms and 1 oxygen atom or sulfur atom, as ring heteroatoms, which is bonded via a ring carbon atom and which is unsubstituted or substituted by one or more identical or different substituents selected from the series consisting of halogen, ($C_1$-$C_4$)-alkyl, NC—, HO— and ($C_1$-$C_4$)-alkyl-O—;

Het3 is a 5-membered or 6-membered, monocyclic, saturated, partially unsaturated or aromatic heterocycle comprising 1, 2 or 3 nitrogen atoms, or 1 sulfur atom or oxygen atom, or one nitrogen atom and one oxygen atom or sulfur atom, as ring heteroatoms, which is unsubstituted or substituted by one or two identical or different substituents selected from the series consisting of halogen, ($C_1$-$C_4$)-alkyl and ($C_1$-$C_4$)-alkyl-O—;

wherein all phenyl groups are unsubstituted or substituted by one, two or three identical or different substituents selected from the series consisting of fluorine, chlorine, ($C_1$-$C_4$)-alkyl and ($C_1$-$C_2$)-alkyl-O—, unless specified otherwise;

wherein all alkyl groups, independently of any other substituents which can be present on an alkyl group, can be substituted by one or more fluorine substituents.

7. The method of claim 1, wherein n is 1;

m is 1;

X is selected from the series consisting of oxygen, sulfur and (R10)(R11)C;

one of the groups R1 and R2 is the group R20-NH— and the other of the groups R1 and R2 is the group (R30)(R31)N—;

R3, R4, R5, R6, R7, R8, R9, R10 and R11 are hydrogen;

R20 is (R21)(R22)(R23)C—;

R21 is selected from the series consisting of phenyl and Het1, which are all unsubstituted or substituted by one, two or three identical or different substituents R24;

R22 is selected from the series consisting of hydrogen, ($C_1$-$C_4$)-alkyl and cyclopropyl;

R23 is hydrogen;

R24 is selected from the series consisting of fluorine, chlorine, bromine, ($C_1$-$C_4$)-alkyl, ($C_3$-$C_7$)-cycloalkyl-, ($C_1$-$C_4$)-alkyl-O—, ($C_1$-$C_4$)-alkyl-S—, $F_5$S— and NC—;

R30 is selected from the series consisting of hydrogen and ($C_1$-$C_4$)-alkyl;

R31 is selected from the series consisting of ($C_3$-$C_6$)-cycloalkyl, ($C_5$-$C_6$)-cycloalkyl to which a benzene ring is fused, Het2 and (R32)(R33)(R34)C—, wherein the Het2, which is bonded via a ring carbon atom, is a 4-membered to 6-membered, monocyclic, saturated heterocycle which comprises one ring heteroatom which is an oxygen atom, or is ($C_5$-$C_6$)-cycloalkyl to which a pyridine, pyrazine or pyrimidine ring is fused, and wherein the fused, pyridine, pyrazine and pyrimidine rings all are unsubstituted or substituted by one or two identical or different substituents selected from the series consisting of halogen, ($C_1$-$C_4$)-alkyl, NC—, HO— and ($C_1$-$C_4$)-alkyl-O—;

or the groups R30 and R31, together with the nitrogen atom carrying them, form a 5-membered to 6-membered, monocyclic, saturated heterocycle which, in addition to the nitrogen atom carrying R30 and R31, comprises 0 or 1 further ring heteroatom selected from the series consisting of nitrogen, oxygen and sulfur, and which is unsubstituted or substituted by one or two identical or different substituents R36;

R32 is selected from the series consisting of hydrogen and ($C_1$-$C_4$)-alkyl;

R33 is selected from the series consisting of hydrogen, ($C_1$-$C_4$)-alkyl and cyclopropyl;

R34 is selected from the series consisting of ($C_1$-$C_6$)-alkyl, ($C_3$-$C_6$)-cycloalkyl, ($C_1$-$C_4$)-alkyl-O—C(O)—, (R39)(R40)N—C(O)—, phenyl and Het2, wherein the ($C_1$-$C_6$)-alkyl is unsubstituted or substituted by one or two identical or different substituents R41, and wherein the phenyl is unsubstituted or substituted by one or more identical or different substituents R35, and wherein the Het2, which is bonded via a ring carbon atom, is a 5-membered to 6-membered, monocyclic, saturated, partially unsaturated or aromatic heterocycle comprising 1, 2, 3 or 4 nitrogen atoms, or 1 oxygen atom or sulfur atom, or 1 or 2 nitrogen atoms and 1 oxygen atom or sulfur atom, as ring heteroatoms, and is unsubstituted or substituted by one or more identical or different substituents selected from the series consisting of halogen, ($C_1$-$C_4$)-alkyl, NC—, HO— and ($C_1$-$C_4$)-alkyl-O—;

R35 is selected from the series of fluorine, chlorine, bromine, ($C_1$-$C_4$)-alkyl, HO—($C_1$-$C_4$)-alkyl-, ($C_1$-$C_4$)-alkyl-O—($C_1$-$C_4$)-alkyl-, ($C_1$-$C_4$)-alkyl-O—C(O)—($C_1$-$C_4$)-alkyl-, NC—, HO—, ($C_1$-$C_4$)-alkyl-O—, ($C_1$-$C_4$)-alkyl-S(O)$_p$—, ($C_1$-$C_4$)-alkyl-S(O)$_2$—NH—, R42-O—C(O)—, (R43)(R44)N—C(O)— and (R45)(R46)N—S(O)$_2$—;

R36 is selected from the series consisting of fluorine, ($C_1$-$C_4$)-alkyl, ethenyl, ethynyl, ($C_3$-$C_6$)-cycloalkyl, phenyl, Het3, ($C_1$-$C_4$)-alkyl-O—, ($C_3$-$C_6$)-cycloalkyl-O—, ($C_3$-$C_6$)-cycloalkyl-($C_1$-$C_2$)-alkyl-O—, phenyl-O—, ($C_1$-$C_2$)-alkyl-S(O)$_p$—, NC— and R47-O—C(O)—, wherein the ($C_1$-$C_4$)-alkyl is unsubstituted or substituted by one or two identical or different substituents R48;

R39, R40, R42, R43, R44, R45, R46, R47, R49, R50 and R51 are independently of one another selected from the series consisting of hydrogen and ($C_1$-$C_4$)-alkyl;

R41 is selected from the series consisting of ($C_3$-$C_6$)-cycloalkyl, phenyl and Het1;

R48 is selected from the series consisting of ($C_3$-$C_6$)-cycloalkyl, phenyl, Het3, HO—, ($C_1$-$C_4$)-alkyl-O—, ($C_1$-$C_4$)-alkyl-C(O)—O—, ($C_1$-$C_4$)-alkyl-S(O)$_p$—, ($C_1$-$C_4$)-alkyl-C(O)—(R49)N—, (R50)(R51)N—C(O)— and ($C_1$-$C_4$)-alkyl-O—C(O)—;

p is selected from the series consisting of 0 and 2, wherein all numbers p are independent of one another;

Het1 is a 5-membered or 6-membered, monocyclic, aromatic heterocycle comprising one ring heteroatom selected from the series consisting of nitrogen, oxygen and sulfur or one ring nitrogen atom and one further ring heteroatom selected from the series consisting of nitrogen, oxygen and sulfur, which is bonded via a ring carbon atom and which is unsubstituted or substituted by one or more identical or different substituents selected from the series consisting of halogen, ($C_1$-$C_4$)-alkyl, ($C_3$-$C_7$)-cycloalkyl, NC—, HO—, ($C_1$-$C_4$)-alkyl-O— and ($C_1$-$C_4$)-alkyl-S(O)$_p$—, unless specified otherwise;

Het3 is a 5-membered or 6-membered, monocyclic, saturated, partially unsaturated or aromatic heterocycle comprising 1, 2 or 3 nitrogen atoms, or 1 sulfur atom or oxygen atom, or 1 nitrogen atom and 1 oxygen atom or sulfur atom, as ring heteroatoms, which is unsubstituted or substituted by one or two identical or different substituents selected from the series consisting of fluorine, chlorine, NC—, ($C_1$-$C_2$)-alkyl and ($C_1$-$C_2$)-alkyl-O—;

wherein all phenyl groups are unsubstituted or substituted by one, two or three identical or different substituents selected from the series consisting of fluorine, chlorine, ($C_1$-$C_2$)-alkyl and ($C_1$-$C_2$)-alkyl-O—, unless specified otherwise;

wherein all alkyl groups, independently of any other substituents which can be present on an alkyl group, can be substituted by one or more fluorine substituents.

8. The method of claim 1, wherein n is 1;

m is 1;

X is selected from the series consisting of oxygen and (R10)(R11)C;

one of the groups R1 and R2 is the group R20-NH— and the other of the groups R1 and R2 is the group (R30)(R31)N—;

R3, R4, R5, R6, R7, R8, R9, R10 and R11 are hydrogen;

R20 is (R21)(R22)(R23)C—;

R21 is selected from the series consisting of phenyl and Het1, wherein Het1 is selected from the series consisting of pyridinyl, pyrimidinyl, pyrazinyl, pyridazinyl, pyrazolyl, imidazolyl, thiazolyl, isothiazolyl, oxazolyl, isoxazolyl, pyrrolyl, furanyl and thiophenyl, which are all bonded via a ring carbon atom, and wherein the phenyl and Het1 are all unsubstituted or substituted by one, two or three identical or different substituents selected from the series consisting of fluorine, chlorine, cyano, ($C_1$-$C_4$)-alkyl and ($C_1$-$C_4$)-alkyl-O—, wherein the alkyl groups can be substituted by one or more fluorine substituents;

R22 is hydrogen, ($C_1$-$C_4$)-alkyl or cyclopropyl;

R23 is hydrogen;

R30 is hydrogen or ($C_1$-$C_4$)-alkyl;

R31 is (R32)(R33)(R34)C—;

or the groups R30 and R31, together with the nitrogen atom carrying them, form a pyrrolidine ring which is unsubstituted or substituted by one or two identical or different substituents R36, wherein one of the substituents R36 is selected from the series consisting of fluorine, cyano, ($C_1$-$C_4$)-alkyl, cyclopropyl, ($C_1$-$C_4$)-alkyl-O—, phenyl, Het3 and ($C_1$-$C_4$)-alkyl-O—C(O)—, and a second of the substituents R36, if present, is selected from the series consisting of fluorine and ($C_1$-$C_4$)-alkyl, and wherein the ($C_1$-$C_4$)-alkyl groups representing R36 are independently of one another unsubstituted or substituted by one or two identical or different substituents R48, and wherein the alkyl groups can independently of one another be substituted by one or more fluorine substituents, and wherein the phenyl is unsubstituted or substituted by one, two or three identical or different substituents selected from the series consisting of fluorine, chlorine, ($C_1$-$C_2$)-alkyl, ($C_1$-$C_2$)-alkyl-O— and trifluoromethyl, and wherein the Het3 is selected from the series consisting of pyridinyl, pyrimidinyl, pyrazinyl, oxazolyl, isoxazolyl, thiophenyl and thiazolyl, which are all unsubstituted or substituted by one or two identical or different substituents selected from the series consisting of fluorine, chlorine, cyano, ($C_1$-$C_2$)-alkyl, ($C_1$-$C_2$)-alkyl-O- and trifluoromethyl;

R32 is hydrogen;

R33 is selected from the series consisting of hydrogen, ($C_1$-$C_4$)-alkyl and cyclopropyl;

R34 is selected from the series consisting of ($C_1$-$C_4$)-alkyl-O—C(O)—, cyclopropyl, phenyl and Het2, wherein Het2 is selected from the series consisting of pyridinyl, pyrimidinyl, pyrazinyl, pyridazinyl, pyrazolyl, imidazolyl, thiazolyl, isothiazolyl, oxazolyl, isoxazolyl, pyrrolyl, furanyl and thiophenyl, which are all bonded via a ring carbon atom, and wherein the phenyl and Het2 groups are unsubstituted or substituted by one or two identical or different substituents selected from the series consisting of fluorine, chlorine, cyano, ($C_1$-$C_4$)-alkyl- and ($C_1$-$C_4$)-alkyl-O—, wherein the alkyl groups can be substituted by one or more fluorine substituents;

R48 is selected from the series consisting of cyclopropyl, ($C_1$-$C_4$)-alkyl-O—, ($C_1$-$C_4$)-alkyl-C(O)—O— and ($C_1$-$C_4$)-alkyl-O—C(O)—.

9. The method of claim 1, wherein n is 1;

m is 1;

X is oxygen;

one of the groups R1 and R2 is the group R20-NH— and the other of the groups R1 and R2 is the group (R30)(R31)N—;

R3, R4, R5, R6, R7, R8 and R9 are hydrogen;

R20 is (R21)(R22)(R23)C—;

R21 is selected from the series consisting of phenyl and Het1, wherein Het1 is selected from the series consisting of pyridinyl, pyrimidinyl, thiazolyl and thiophenyl, which are all bonded via a ring carbon atom, and wherein Het1 is unsubstituted or substituted by one or two identical or different substituents one substituent of which is selected from the series consisting of fluorine, chlorine, cyano, methyl, trifluoromethyl and methoxy and a second substituent is selected from the series consisting of fluorine, chlorine, methyl and trifluoromethyl, and wherein phenyl is unsubstituted or substituted by one, two or three identical or different substituents one substituent of which is selected from the series consisting of fluorine, chlorine, cyano, methyl, trifluoromethyl and methoxy, and a second and third substituent are selected from the series consisting of fluorine, chlorine, methyl and trifluoromethyl;

R22 is selected from the series consisting of methyl, ethyl, n-propyl, isopropyl and cyclopropyl;

R23 is hydrogen;

the groups R30 and R31, together with the nitrogen atom carrying them, form a pyrrolidine ring which is unsubstituted or substituted in ring position 2 by one substituent R36 selected from the series consisting of methyl, ethyl, isopropyl, cyclopropyl, ($C_1$-$C_4$)-alkyl-O—C(O)—, ($C_1$-$C_4$)-alkyl-O—C(O)—$CH_2$— and trifluoromethyl; or or R30 is hydrogen; and R31 is (R32)(R33)(R34)C—; and R34 is selected from the series consisting of phenyl and Het2, wherein Het2 is selected from the series consisting of pyridinyl, pyrimidinyl, pyrazinyl, oxazolyl, isoxazolyl, thiazolyl, isothiazolyl and thiophenyl, which are bonded via a ring carbon atom, and wherein phenyl and Het2 are unsubstituted or substituted by one or two identical or different substituents selected from the series consisting of fluorine, chlorine, cyano, methyl, trifluoromethyl and methoxy; or R30 is selected from the series consisting of hydrogen, methyl and ethyl; and R31 is (R32)(R33)(R34)C—; and R34 is ($C_1$-$C_4$)-alkyl-O—C(O)—.

R32 is hydrogen;

R33 is selected from the series consisting of hydrogen, methyl, ethyl, n-propyl and isopropyl.

10. The method of claim 1, wherein n is 1;

m is 1;

X is oxygen;

331 one of the groups R1 and R2 is the group R20-NH— and the other of the groups R1 and R2 is the group (R30)(R31)N—;
R3, R4, R5, R6, R7, R8 and R9 are hydrogen;
R20 is (R21)(R22)(R23)C—;
R21 is selected from the series consisting of phenyl and Het1, wherein Het1 is selected from the series consisting of pyridinyl, pyrimidinyl, thiazolyl and thiophenyl, which are all bonded via a ring carbon atom, and wherein Het1 is substituted by one or two identical or different substituents one substituent of which is selected from the series consisting of fluorine, chlorine, cyano, trifluoromethyl and methoxy and a second substituent is selected from the series consisting of fluorine, chlorine, methyl and trifluoromethyl, and wherein phenyl is unsubstituted or substituted by one, two or three identical or different substituents one substituent of which is selected from the series consisting of fluorine, chlorine, cyano, trifluoromethyl and methoxy and a second substituent is selected from the series consisting of fluorine, chlorine, methyl and trifluoromethyl and a third substituent is fluorine;
R22 is selected from the series consisting of methyl, ethyl, n-propyl and isopropyl;
R23 is hydrogen;
the groups R30 and R31, together with the nitrogen atom carrying them, form a pyrrolidine ring which is unsubstituted or substituted in ring position 2 by one substituent R36 selected from the series consisting of methyl, ethyl, isopropyl, cyclopropyl and trifluoromethyl.

11. The method of claim 1, wherein the compound has the structure of formula Ig:

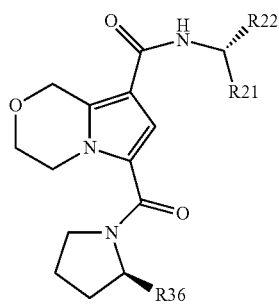

Ig or a pharmaceutically acceptable salt thereof, wherein
R21 is selected from the series consisting of phenyl and Het1, wherein Het1 is selected from the series consisting of pyridinyl, pyrimidinyl, thiazolyl and thiophenyl, which are bonded via a ring carbon atom, and Het1 is substituted by one or two identical or different substituents one substituent of which is selected from the series consisting of fluorine, chlorine, cyano, trifluoromethyl and methoxy and a second substituent is selected from the series consisting of fluorine, chlorine, methyl and trifluoromethyl, and phenyl is unsubstituted or substituted by one, two or three identical or different substituents one substituent of which is selected from the series consisting of fluorine, chlorine, cyano, trifluoromethyl and methoxy and a second substituent is selected from the series consisting of fluorine, chlorine, methyl and trifluoromethyl and a third substituent is fluorine;

332

R22 is selected from the series consisting of methyl, ethyl, n-propyl and isopropyl;
R36 is selected from the series consisting of methyl, ethyl, isopropyl, cyclopropyl and trifluoromethyl.

12. The method of claim 1, wherein
n is 1;
m is 1;
X is oxygen;
one of the groups R1 and R2 is the group R20-NH— and the other of the groups R1 and R2 is the group (R30)(R31)N—;
R3, R4, R5, R6, R7, R8 and R9 are hydrogen;
R20 is (R21)(R22)(R23)C—;
R21 is selected from the series consisting of phenyl and Het1, wherein Het1 is selected from the series consisting of pyridinyl, pyrimidinyl, thiazolyl and thiophenyl, which are bonded via a ring carbon atom, and wherein Het1 is substituted by one or two identical or different substituents one substituent of which is selected from the series consisting of fluorine, chlorine, cyano, trifluoromethyl and methoxy and a second substituent is selected from the series consisting of fluorine, chlorine, methyl and trifluoromethyl, and wherein phenyl is unsubstituted or substituted by one, two or three identical or different substituents one substituent of which is selected from the series consisting of fluorine, chlorine, cyano, trifluoromethyl and methoxy and a second substituent is selected from the series consisting of fluorine, chlorine, methyl and trifluoromethyl and a third substituent is fluorine;
R22 is selected from the series consisting of methyl, ethyl, n-propyl and isopropyl;
R23 is hydrogen;
R30 is hydrogen;
R31 is (R32)(R33)(R34)C—;
R32 is hydrogen;
R33 is selected from the series consisting of hydrogen, methyl, ethyl, n-propyl and isopropyl;
R34 is selected from the series consisting of phenyl and Het2, wherein Het2 is selected from the series consisting of pyridinyl, pyrimidinyl, pyrazinyl, oxazolyl, isoxazolyl, thiazolyl, isothiazolyl and thiophenyl, which are bonded via a ring carbon atom, and wherein the phenyl and Het2 are unsubstituted or substituted by one or two identical or different substituents selected from the series consisting of fluorine, chlorine, cyano, methyl, trifluoromethyl and methoxy.

13. The method of claim 1, wherein the compound is selected from the series consisting of:
6-(pyrrolidine-1-carbonyl)-3,4-dihydro-1H-pyrrolo[2,1-c][1,4]oxazine-8-carboxylic acid ((R)-1-phenyl-propyl)-amide,
6-((S)-2-methyl-pyrrolidine-1-carbonyl)-3,4-dihydro-1H-pyrrolo[2,1-c][1,4]oxazine-8-carboxylic acid[(R)-1-(2-chloro-phenyl)-propyl]-amide,
6-((S)-2-methyl-pyrrolidine-1-carbonyl)-3,4-dihydro-1H-pyrrolo[2,1-c][1,4]oxazine-8-carboxylic acid((R)-1-phenyl-propyl)-amide,
6-((S)-2-methyl-pyrrolidine-1-carbonyl)-3,4-dihydro-1H-pyrrolo[2,1-c][1,4]oxazine-8-carboxylic acid[(R)-1-(2,4-difluoro-phenyl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(6-cyano-pyridin-3-yl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(6-trifluoromethyl-pyridin-3-yl)-propyl]-amide, 6-((S)-2-methyl-pyrrolidine-1-carbonyl)-3,4-dihydro-1H-pyrrolo[2,1-c][1,4]oxazine-8-carboxylic acid[(R)-1-(4-cyano-2,6-difluoro-phenyl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(4-cyano-phenyl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(4-trifluoromethyl-phenyl)-propyl]-amide,
6-((S)-2-ethyl-pyrrolidine-1-carbonyl)-3,4-dihydro-1H-pyrrolo[2,1-c][1,4]oxazine-8-carboxylic acid[(R)-1-(6-trifluoromethyl-pyridin-3-yl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(3-fluoro-4-trifluoromethyl-phenyl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(6-trifluoromethyl-pyridin-3-yl)-butyl]-amide,
6-((R)-2-trifluoromethyl-pyrrolidine-1-carbonyl)-3,4-dihydro-1H-pyrrolo[2,1-c][1,4]oxazine-8-carboxylic acid[(R)-1-(6-trifluoromethyl-pyridin-3-yl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(3-chloro-4-cyano-phenyl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(5-trifluoromethyl-thiazol-2-yl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(5-chloro-6-methoxy-pyridin-3-yl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(2-chloro-6-trifluoromethyl-pyridin-3-yl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(5-trifluoromethyl-thiophen-2-yl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(3-chloro-4-trifluoromethyl-phenyl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(5-fluoro-6-trifluoromethyl-pyridin-3-yl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(3,4-dichloro-phenyl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(2,6-difluoro-4-trifluoromethyl-phenyl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(6-methoxy-5-trifluoromethyl-pyridin-3-yl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(3-chloro-4-fluoro-phenyl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(3-chloro-4-methoxy-phenyl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(5-chloro-6-cyano-pyridin-3-yl)-propyl]-amide,
6-((S)-2-methyl-pyrrolidine-1-carbonyl)-3,4-dihydro-1H-pyrrolo[2,1-c][1,4]oxazine-8-acid [(R)-1-(2-fluoro-4-trifluoromethyl-phenyl)-propyl]-amide,
6-((S)-2-ethyl-pyrrolidine-1-carbonyl)-3,4-dihydro-1H-pyrrolo[2,1-c][1,4]oxazine-8-carboxylic acid((R)-1-phenyl-propyl)-amide,
3-((S)-2-methyl-pyrrolidine-1-carbonyl)-5,6,7,8-tetrahydro-indolizine-1-carboxylic acid [(R)-1-(6-cyano-pyridin-3-yl)-propyl]-amide,
3-((S)-2-methyl-pyrrolidine-1-carbonyl)-5,6,7,8-tetrahydro-indolizine-1-carboxylic acid [(R)-1-(6-trifluoromethyl-pyridin-3-yl)-propyl]-amide,
6-((S)-2-methyl-pyrrolidine-1-carbonyl)-3,4-dihydro-1H-pyrrolo[2,1-c][1,4]oxazine-8-carboxylic acid[(R)-2-methyl-1-(6-trifluoromethyl-pyridin-3-yl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(4-chloro-phenyl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(4-fluoro-3-trifluoromethyl-phenyl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(3,5-dichloro-pyridin-4-yl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(2-chloro-5-fluoro-phenyl)-propyl]-amide,
6-((S)-2-methyl-pyrrolidine-1-carbonyl)-3,4-dihydro-1H-pyrrolo[2,1-c][1,4]oxazine-8-carboxylic acid[(R)-1-(2,6-difluoro-phenyl)-propyl]-amide,
6-(pyrrolidine-1-carbonyl)-3,4-dihydro-1H-pyrrolo[2,1-c][1,4]oxazine-8-carboxylic acid [(R)-1-(2,4-difluoro-phenyl)-propyl]-amide, and
6-(pyrrolidine-1-carbonyl)-3,4-dihydro-1H-pyrrolo[2,1-c][1,4]oxazine-8-carboxylic acid [(R)-1-(2-chloro-4-fluoro-phenyl)-propyl]-amide,
or a pharmaceutically acceptable salt thereof.

14. The method of claim 1, wherein the compound is selected from the series consisting of:
3,4-dihydro-1H-pyrrolo[2,1-c][1,4]oxazine-6,8-dicarboxylic acid bis-[((R)-1-phenyl-propyl)-amide],
3,4-dihydro-1H-pyrrolo[2,1-c][1,4]oxazine-6,8-dicarboxylic acid bis-{[(R)-1-(4-fluoro-phenyl)-ethyl]-amide},
3,4-dihydro-1H-pyrrolo[2,1-c][1,4]oxazine-6,8-dicarboxylic acid 6-{[(R)-1-(6-methoxy-pyridin-3-yl)-propyl]-amide}8-[((R)-1-phenyl-propyl)-amide],
3,4-dihydro-1H-pyrrolo[2,1-c][1,4]oxazine-6,8-dicarboxylic acid 8-[((R)-1-phenyl-propyl)-amide]6-[(pyrazin-2-ylmethyl)-amide],
3,4-dihydro-1H-pyrrolo[2,1-c][1,4]oxazine-6,8-dicarboxylic acid 6-{[(S)-1-(2-methoxy-pyrimidin-5-yl)-propyl]-amide}8-[((R)-1-phenyl-propyl)-amide],
3,4-dihydro-1H-pyrrolo[2,1-c][1,4]oxazine-6,8-dicarboxylic acid 6-{[(R)-1-(6-cyano-pyridin-3-yl)-propyl]-amide}8-[((R)-1-phenyl-propyl)-amide],
3,4-dihydro-1H-pyrrolo[2,1-c][1,4]oxazine-6,8-dicarboxylic acid 6-{[(R)-1-(5-methoxy-pyrazin-2-yl)-propyl]-amide}8-[((R)-1-phenyl-propyl)-amide],
3,4-dihydro-1H-pyrrolo[2,1-c][1,4]oxazine-6,8-dicarboxylic acid 8-[((R)-1-phenyl-propyl)-amide]6-[(1-pyrazin-2-yl-ethyl)-amide],
3,4-dihydro-1H-pyrrolo[2,1-c][1,4]oxazine-6,8-dicarboxylic acid 6-{[(R)-1-(4-fluoro-phenyl)-2-methyl-propyl]-amide}8-[(1-pyrimidin-2-yl-ethyl)-amide], 3,4-dihydro-1H-pyrrolo[2,1-c][1,4]oxazine-6,8-dicarboxylic acid 6-[(1-isoxazol-3-yl-ethyl)-amide]8-[((R)-1-phenyl-propyl)-amide], 3,4-dihydro-1H-pyrrolo[2,1-c][1,4]oxazine-6,8-dicarboxylic acid 8-[((R)-1-phenyl-propyl)-amide]6-[((S)-1-pyrazin-2-yl-propyl)-amide], 3,4-dihydro-1H-pyrrolo[2,1-c][1,4]oxazine-6,8-dicarboxylic acid 8-[((R)-1-phenyl-propyl)-amide]6-[((S)-1-pyrazin-2-yl-ethyl)-amide], 3,4-dihydro-1H-pyrrolo[2,1-c][1,4]oxazine-6,8-dicarboxylic acid 6-{[(R)-1-(2,4-difluoro-phenyl)-propyl]-amide}8-[((R)-1-pyrazin-2-yl-ethyl)-amide], 3,4-dihydro-1H-pyrrolo[2,1-c][1,4]oxazine-6,8-dicarboxylic acid 8-{[(R)-1-(2-chloro-4-fluoro-phenyl)-propyl]-amide}6-[(1-pyrimidin-2-yl-ethyl)-amide], 3,4-dihydro-1H-pyrrolo[2,1-c][1,4]oxazine-6,8-dicarboxylic acid 8-{[(R)-1-(2-chloro-phenyl)-propyl]-amide}6-[(1-pyrimidin-2-yl-ethyl)-amide], 3,4-dihydro-1H-pyrrolo[2,1-c][1,4]oxazine-6,8-dicarboxylic acid 6-{[(R)-1-(4-fluoro-phenyl)-2-methyl-propyl]-amide}8-[((S)-1-pyrimidin-2-yl-ethyl)-amide], 3,4-dihydro-1H-pyrrolo[2,1-c][1,4]oxazine-6,8-dicarboxylic acid 6-{[(R)-1-(4-fluoro-phenyl)-ethyl]-amide}8-[((S)-1-pyrimidin-2-yl-ethyl)-amide], 3,4-dihydro-1H-pyrrolo[2,1-c][1,4]oxazine-6,8-dicarboxylic acid 6-{[(R)-1-(2,4-difluoro-phenyl)-propyl]-amide}8-[((S)-1-pyrazin-2-yl-ethyl)-amide], 3,4-dihydro-1H-pyrrolo[2,1-c][1,4]oxazine-6,8-dicarboxylic acid 6-{[(R)-1-(4-fluoro-phenyl)-ethyl]-amide}8-[((R)-1-pyrimidin-2-yl-ethyl)-amide], 3,4-dihydro-1H-pyrrolo[2,1-c][1,4]oxazine-6,8-dicarboxylic acid 6-{[(R)-1-(4-fluoro-phenyl)-ethyl]-amide}8-[((R)-1-pyrimidin-2-yl-propyl)-amide], 3,4-dihydro-1H-pyrrolo[2,1-c][1,4]oxazine-6,8-dicarboxylic acid 8-[((R)-1-phenyl-propyl)-amide]6-{[(R)-1-(6-trifluoromethyl-pyridin-3-yl)-propyl]-amide}, 3,4-dihydro-1H-pyrrolo[2,1-c][1,4]oxazine-6,8-dicarboxylic acid 6-{[(R)-1-(4-fluoro-phenyl)-ethyl]-amide}8-{[(R)-1-(5-trifluoromethyl-pyrimidin-2-yl)-propyl]-amide}, 3,4-dihydro-1H-pyrrolo[2,1-c][1,4]oxazine-6,8-dicarboxylic acid 6-{[(R)-1-(4-fluoro-phenyl)-ethyl]-amide}8-{[(R)-1-(4-trifluoromethyl-phenyl)-propyl]-amide}, 3,4-dihydro-1H-pyrrolo[2,1-c][1,4]oxazine-6,8-dicarboxylic acid 6-{[(R)-1-(4-fluoro-phenyl)-ethyl]-amide}8-{[(R)-1-(6-trifluoromethyl-pyridin-3-yl)-propyl]-amide}, 3,4-dihydro-1H-pyrrolo[2,1-c][1,4]oxazine-6,8-dicarboxylic acid 6-{[(R)-1-(4-fluoro-phenyl)-ethyl]-amide}8-{[(R)-1-(5-trifluoromethyl-pyridin-2-yl)-propyl]-amide}, 3,4-dihydro-1H-pyrrolo[2,1-c][1,4]oxazine-6,8-dicarboxylic acid 8-[((R)-1-pyrimidin-2-yl-propyl)-amide]6-{[(R)-1-(4-trifluoromethyl-phenyl)-propyl]-amide}, 3,4-dihydro-1H-pyrrolo[2,1-c][1,4]oxazine-6,8-dicarboxylic acid 6-[((R)-1-phenyl-propyl)-amide]8-{[(R)-1-(6-trifluoromethyl-pyridin-3-yl)-propyl]-amide}, 3,4-dihydro-1H-pyrrolo[2,1-c][1,4]oxazine-6,8-dicarboxylic acid 6-{[(R)-1-(4-fluoro-phenyl)-ethyl]-amide}8-[((S)-1-pyrimidin-2-yl-propyl)-amide], 3,4-dihydro-1H-pyrrolo[2,1-c][1,4]oxazine-6,8-dicarboxylic acid 6-dicyclopropylmethyl-amide8-[((R)-1-phenyl-propyl)-amide], 5,6,7,8-tetrahydro-indolizine-1,3-dicarboxylic acid 3-[((S)-1-phenyl-propyl)-amide]1-[((R)-1-phenyl-propyl)-amide], 3,4-dihydro-1H-pyrrolo[2,1-c][1,4]oxazine-6,8-dicarboxylic acid 6-{[(R)-1-(6-methoxy-pyridin-2-yl)-propyl]-amide}8-[((R)-1-phenyl-propyl)-amide], 3,4-dihydro-1H-pyrrolo[2,1-c][1,4]oxazine-6,8-dicarboxylic acid 6-{[(R)-1-(4-fluoro-phenyl)-ethyl]-amide}8-[((R)-1-phenyl-propyl)-amide], 5,6,7,8-tetrahydro-indolizine-1,3-dicarboxylic acid 3-[((S)-1-cyclopropyl-ethyl)-amide]1-[((R)-1-phenyl-propyl)-amide], 3,4-dihydro-1H-pyrrolo[2,1-c][1,4]thiazine-6,8-dicarboxylic acid 8-{[(R)-1-(4-fluoro-phenyl)-ethyl]-amide}6-[((R)-1-phenyl-propyl)-amide], 3,4-dihydro-1H-pyrrolo[2,1-c][1,4]oxazine-6,8-dicarboxylic acid 6-{[(R)-1-(4-fluoro-phenyl)-ethyl]-amide}8-{[(R)-1-(5-methoxy-pyrazin-2-yl)-propyl]-amide}, 3,4-dihydro-1H-pyrrolo[2,1-c][1,4]oxazine-6,8-dicarboxylic acid 6-(S)-indan-1-ylamide 8-[((R)-1-phenyl-propyl)-amide], 5,6,7,8-tetrahydro-indolizine-1,3-dicarboxylic acid 3-[((R)-cyclopropyl-phenyl-methyl)-amide]1-[((R)-1-phenyl-propyl)-amide], 3,4-dihydro-1H-pyrrolo[2,1-c][1,4]oxazine-6,8-dicarboxylic acid 6-{[(R)-1-(4-fluoro-phenyl)-ethyl]-amide}8-[((R)-1-phenyl-ethyl)-amide], 5,6,7,8-tetrahydro-indolizine-1,3-dicarboxylic acid bis-[((R)-1-phenyl-propyl)-amide], 5,6,7,8-tetrahydro-indolizine-1,3-dicarboxylic acid 3-{[(S)-1-(4-fluoro-phenyl)-ethyl]-amide}1-[((R)-1-phenyl-propyl)-amide], 3,4-dihydro-1H-pyrrolo[2,1-c][1,4]oxazine-6,8-dicarboxylic acid 6-{[(S)-1-(4-fluoro-phenyl)-ethyl]-amide}8-[((R)-1-phenyl-propyl)-amide], 5,6,7,8-tetrahydro-indolizine-1,3-dicarboxylic acid 3-[((R)-1-cyclopropyl-ethyl)-amide]1-[((R)-1-phenyl-propyl)-amide], 5,6,7,8-tetrahydro-indolizine-1,3-dicarboxylic acid 3-[(4-fluoro-benzyl)-methyl-amide]1-[((R)-1-phenyl-propyl)-amide], 3,4-dihydro-1H-pyrrolo[2,1-c][1,4]oxazine-6,8-dicarboxylic acid 8-{[(R)-1-(2-chloro-phenyl)-propyl]-amide}6-cyclopropylmethyl-amide, and 5,6,7,8-tetrahydro-indolizine-1,3-dicarboxylic acid 3-[((R)-1-phenyl-propyl)-amide] 1-[(thiazol-2-ylmethyl)-amide], or a pharmaceutically acceptable salt thereof.

15. The method of claim 1, wherein the compound is selected from the series consisting of:

{[8-((R)-1-phenyl-propylcarbamoyl)-3,4-dihydro-1H-pyrrolo[2,1-c][1,4]oxazine-6-carbonyl]-amino}-acetic acid ethyl ester, (R)-1-[8-((R)-1-phenyl-propylcarbamoyl)-3,4-dihydro-1H-pyrrolo[2,1-c][1,4]oxazine-6-carbonyl]-pyrrolidine-2-carboxylic acid isopropyl ester, ((R)-1-{6-[(R)-1-(4-fluoro-phenyl)-ethylcarbamoyl]-3,4-dihydro-1H-pyrrolo[2,1-c][1,4]oxazine-8-carbonyl}-pyrrolidin-2-yl)-acetic acid ethyl ester, (R)-1-[8-((R)-1-phenyl-propylcarbamoyl)-3,4-dihydro-1H-pyrrolo[2,1-c][1,4]oxazine-6-carbonyl]-pyrrolidine-2-carboxylic acid ethyl ester, (S)-2-{ [8-((R)-1-phenyl-propylcarbamoyl)-3,4-dihydro-1H-pyrrolo[2,1-c][1,4]oxazine-6-carbonyl]-amino}-propionic acid isopropyl ester, {methyl-[8-((R)-1-phenyl-propylcarbamoyl)-3,4-dihydro-1H-pyrrolo[2,1-c][1,4]oxazine-6-carbonyl]-amino}-acetic acid isopropyl ester, {methyl-[8-((R)-1-phenyl-propylcarbamoyl)-3,4-dihydro-1H-pyrrolo[2,1-c][1,4]oxazine-6-carbonyl]-amino}-acetic acid ethyl ester, (S)-2-{methyl-[8-((R)-1-phenyl-propylcarbamoyl)-3,4-dihydro-1H-pyrrolo[2,1-c][1,4]oxazine-6-carbonyl]-amino}-propionic acid ethyl ester, (S)-2-{methyl-[8-((R)-1-phenyl-propylcarbamoyl)-3,4-dihydro-1H-pyrrolo[2,1-c][1,4]oxazine-6-carbonyl]-amino}-propionic acid isopropyl ester, {(R)-1-[8-((R)-1-phenyl-propylcarbamoyl)-3,4-dihydro-1H-pyrrolo[2,1-c][1,4]oxazine-6-carbonyl]-pyrrolidin-2-yl}-acetic acid ethyl ester, {(R)-1-[8-((R)-1-phenyl-propylcarbamoyl)-3,4-dihydro-1H-pyrrolo[2,1-c][1,4]oxazine-6-carbonyl]-pyrrolidin-2-yl}-acetic acid isopropyl ester, and (R)-1-{6-[(R)-1-(4-fluoro-phenyl)-2-methyl-propylcarbamoyl]-3,4-dihydro-1H-pyrrolo[2,1-c][1,4]oxazine-8-carbonyl}-pyrrolidine-2-carboxylic acid methyl ester, or a pharmaceutically acceptable salt thereof.

* * * * *